United States Patent [19]

Kimura et al.

[11] Patent Number: 4,748,161
[45] Date of Patent: May 31, 1988

[54] TRITERPENYL ESTERS OF ORGANIC ACIDS AND HYPOLIPIDEMIC AGENTS COMPOSED OF THEM

[75] Inventors: Goro Kimura, Kamakura; Yoshihiko Hirose, Ohgaki; Kumi Yoshida, Sayamachi; Fumio Kuzuya, Nagoya; Katsunari Fujita, Aichi, all of Japan

[73] Assignee: Amano Pharmaceutical Co., Ltd., Nagoya, Japan

[21] Appl. No.: 739,183

[22] Filed: May 30, 1985

[30] Foreign Application Priority Data

| Jun. 4, 1984 [JP] | Japan | 59-115306 |
| Jun. 4, 1984 [JP] | Japan | 59-115307 |
| Apr. 19, 1985 [JP] | Japan | 60-85254 |
| Apr. 19, 1985 [JP] | Japan | 60-85255 |

[51] Int. Cl.$^4$ ............ F61K 31/56; C07J 9/00
[52] U.S. Cl. .................. 514/182; 260/397.2
[58] Field of Search .............. 260/397.2; 514/182

[56] References Cited

U.S. PATENT DOCUMENTS 3,686,235  1/1972  Nicholas et al. ............ 260/397.2
4,393,044  7/1983  Takada et al. ............... 260/397.2

FOREIGN PATENT DOCUMENTS 149248  9/1982  Japan .

OTHER PUBLICATIONS

Chemical Abstracts, Vol. 85, No. 17, p. 668, No. 124202s, (Oct. 25, 1976).
Chemical Abstracts, vol. 98, No. 9, p. 506, No. 70637k, (Feb. 28, 1983).

Primary Examiner—Leonard Schenkman
Attorney, Agent, or Firm—Wegner & Bretschneider

[57] ABSTRACT

A triterpenyl ester of organic acid other than triterpenyl esters of ferulic acid and of monobasic and dibasic saturated fatty acids. A process for producing a triterpenyl ester of organic acid other than esters of ferulic acid and of monobasic and dibasic saturated fatty acids, which comprises the reaction of a triterpenyl alcohol with an acid halide of the corresponding organic acid. A pharmaceutical composition for treatment of hyperlipidemia comprising a pharmaceutical carrier and an effective amount of a triterpenyl ester of organic acid other than triterpenyl esters of dibasic saturated fatty acids. A pharmaceutical composition for treating hyperlipidemia which comprises a pharmaceutical carrier and an effective amount of cyclobranol as an active ingredient.

21 Claims, No Drawings

TRITERPENYL ESTERS OF ORGANIC ACIDS AND HYPOLIPIDEMIC AGENTS COMPOSED OF THEM

BACKGROUND OF THE INVENTION

1. Field of the Invention

The present invention relates to novel compounds having anti-hyperlipidemic activity and to processes for their production, and more particularly, is converned with novel triterpenyl esters of organic acids [except triterpenyl esters of ferulic acid (4-hydroxy-3-methoxycinnamic acid) and of monobasic and dibasic saturated fatty acids] having excellent anti-hyperlipidemic activity and low toxicity and with processes for the production of these esters.

The invention further relates to anti-atherosclerotic and hypolipidemic agents which contain the above-mentioned novel compounds and the known compounds (i.e. cycloartenyl, cyclobranyl, and 24-methylenecycloartanyl esters of ferulic acid, or monobasic saturated fatty acids, and cyclobranol).

More specifically, the present invention relates to excellently active and low toxic agents for treatment of hyperlipidemia or hyperlipoproteinemia, that is, safety and novel hypolipidemic and antiatherosclerotic agents which contain triterpenyl esters of organic acids, preferably, cycloartenyl, cyclobranyl, and 24-methylenecycloartanyl esters of organic acids including esters from triterpenyl alcohols and ferulic acid or monobasic saturated $C_4 \sim C_{20}$ fatty acids, and cyclobranol alone, as respective active ingredients.

2. Description of the Prior Art

It is well known that hyperlipidemia or hyperlipoproteinemia is one of the most serious factors causing atherosclerosic, a form of arteriosclerosis, especially coronary heart disease. Miller and Miller (G. J. Miller and N. E. Miller, Lancet Jan. 4, p. 16 (1975)) have observed a negative correlation between the concentration of high density lipoprotein choresterol (hereinafter referred to as HDL-C) in blood plasma and the cholesterol pool in the body, and no correlation between either the concentration of total cholesterol (hereinafter referred to as TC) for the concentration of other lipoproteins, and the cholesterol pool, and therefrom proposed the theory that the reduction of cholesterol clearance from the arteries caused by a decrease in the HDL-C concentration in blood promotes arteriosclerosis. Since the proposal of this theory, a number of epidemiological studies (e.g. T. Gordon et al., Am. J. Med., 62. 707 (1977)) have proved the presence of a reverse correlation between the onset of ischemic heart disease and the concentration of HDL-C, and comfirmed that a decrease in the HDL-C concentration in blood is one of the most serious factors causing ischemic heart disease regardless of the presence or absence of an anti-hyperlipidemic agent.

It has so far been known that phytosterols reduce the content of cholesterol in serum. For example, a mixture of β-sitosterol and dihydro-β-sitosterol (supplied by Lilly Co., U.S.A. under the tradename of Cytellin) and a mixture of soysterol, phytosterol, and tocopherol (supplied by Morishita Pharaceutical Co., Ltd. Japan, under the trandename of Moristerol) are on the market as anti-hyperlipedemic agents.

On the other hand, the following is reported on triterpenyl alcohols.

Japanese Patent Application Laid-Open No. 18617/1982 describes that when a phytosterol (1 part) was used jointly with a cycloartenol or 24-methylenecycloartanol (0.01–0.1 part), a stronger action of lowering serum cholesterol than that of phytosterol singly was exhibited by synergism.

Japanese Patent Application Laid-Open No. 116415/1983 also describes that a considerably stronger action depressing serum cholesterol due to synergistic effect was observed in the case of joint use of a phytosterol (100 parts) with cycloartenol, 24-methylencycloartanol, or cyclolandenol (1–20 parts, particularly about 5 parts) than in the case of single use of the phytosterol. In particular, cycloartenol has synergistic effect on the serum cholesterol lowering action of phytosterol, while 24-methylenecycloartanol and cyclolandenol have weaker effect than that of cycloartenol.

Japanese Patent Application Laid-Open No. 27824/1984 reports that when 1% of cycloartenol or 24-methylenecycloartanol was added to a diet containing 0.5% of cholesterol, the respective percentages of TC lowering were 13.7% and 10.2% based on a control with high cholesterol diet (calculated by the present inventors from the data shown in Table 2 of the above patent Laid-Open Gazette).

However, these three patent applications described none of triglyceride (hereinafter referred to as TG), total phospholipid (hereinafter referred to as PL), HDL-C, atherogenic index [(TC - HDL-C)/(HDL-C), hereinafter referred to as AI: some Japanese medical scientists designate the AI as cholesterol ratio or arteriosclerosis index], and lipid peroxide (hereinafter referred to as LPO), though reporting on the action of TC lowering in serum.

From the fact that cycloartenol, 24-methylenecycloartanol, and cyclolaudenol, alone or in combination with a phytosterol, depressed TC in serum, it is not obvious that these triterpenyl alcohols have also the action of lowering the other items of serum lipids TG, PL, and LPO which are important for treating or diagnosing hyperlipidemic conditions, and that these alcohols have the effect of increasing HDL-C, which is currently considered as particularly significant for treating hyperlipidemia, and in addition the effect of lowering AI. It is impossible to predict such overall pharmacological activity from analogy.

The γ-orizanol on the market today in Japan as a therapeutic agent for treating whiplash syndrome (head or cervical damage) is not composed of a single component but mixtures of various phytosteryl and triterpenyl esters of ferulic acid. An example of the γ-organol is composed of campesteryl (14%), stigmasteryl (1%), β-sitosteryl (4%), cycloartanyl (2%), cycloartenyl (35%), and 24-methylenecycloartonyl (44%) esters of ferulic acid but little cyclobranyl ester of ferulic acid.

Recently the following report on the influence of γ-orizanol upon cholesterol metabolism in hyperlipidemic rats was published by F. Kuzuya et al. (Geriatric Medicine 18, pp 519–524 (1980)). According to the report; TC was explicitly depressed in rats fed with a high cholesterol diet containing 0.1, 0.5, and 1% of γ-orizanol, as compared with TC in control rats fed with the same diet but containing no γ-orizanol, while the degree of the lowering depended on the dosage; the degree of TC lowering was greater than that of PL and comparable to that of HDL-C depression; γ-orizanol showed no activity an AI, but a tendency to increasing TG and the distinct action lowering LPO.

According to K. Mitani et al. [Domyaku Koka, 11, No. 2, June, pp 411–416 (1983)], the serum TC values in rats fed with a high chloresterol diet with 0.5, 1.0, and 2.0% of γ-orizanol were lower by 8.1, 23.4, and 30.9%, respectively, than control rats fed with the same diet but containing no γ-orizanol, while no significant depression was observed in the serum TG and PL values.

According to the study of the influence on hyperlipidemia of hypothalamic obesity rats, by S. Inoue et al. [Domyaku Koka, 11, No. 2, June, pp 417–428 (1983)]γ-orizanol exhibited the action of lowering TC but not TG in blood and no effect on PL and HDL-C in blood.

As regards organic acids, R. D. Sharma [Atherosclerosis, 37, pp. 463–468 (1980)] describes; that in rats fed with a high cholesterol diet containing 0.2% of an organic acid, TC level was lowered significantly by 10.8% when the acid was ferulic acid, and by 9.4% when the acid was p-coumaric acid, based on TC level in control rats fed with the same diet but containing none of such organic acids; that the degree of TG level lowering was 18.7% with ferulic acid and 19.8% with p-coumaric acid, but these values were not significant; that the PL level lowering was scarcely observed with both the acids; and that no decrease of TC, TG, or PL level was shown with vanillic acid, caffeic acid, or cinnamic acid.

Although an organic acid was not used singly, the following reports on the anti-hyperlipidemic effect of α-methylcinnamic acid derivatives was presented. K. Takashima et al. [Biochemical Pharmacology, 27, 2631 (1978)] describe the antihyperlipidemic effect of α-mono-p-myristyloxy-α'-methylcinnamoyl glycerol. T. Watanabe et al. [Journal of Medicinal Chemistry, 23, 50 (1980)] describe in detail synthetic methods of p-alkoxycinnamic acids, p-alkoxy-α-methylcinnamic acids wherein the alkyl moiety in the alkoxy substituent is 2-propenyl, $C_8$–$C_{18}$ alkyl, or phenyl; o-, p-, and m-myristyloxycinnamic acids; m-methoxy-p-alkoxy-α-methylcinnamic acids wherein the alkyl moiety of the alkoxy substituent is $C_{12}$ or $C_{14}$ alkyl; p-alkoxycinnamates, and p-alkoxyl-α-methylcinnamates wherein the alkyl moiety of the alkoxy substituent is 2-propenyl, methyl, butyl, or $C_8$–$C_{18}$ alkyl and the alcohlic residue of the ester is chloroethyl, metharyloxyethyl, monoglyceride residue, diglyceride residue, etc; and anti-hyperlipidemic activities of these compounds. T. Watanabe et al described also a process for producing p-alkoxy-α-methylcinnamic acids wherein the alkyl moiety of the alkoxy is $C_8$–$C_{16}$ alkyl) (Japanese Patent Publication No. 45582/1976). T. Ota et al. (Japanese patent application Laid-Open No. 80370/1982) describes α-methyl-p-pyridyloxycinnamic and α-methyl-p-pyridylalkyloxycinnamic acids and ($C_1$–$C_3$ alkyl) esters thereof, processes for producing these compounds, and anti-hyperlipidemic compositions containing these compounds.

Recently, Grill, H. et al. [Japanese patent application Laid-Open No. 25953/1985); DE, App. No. 3326164.4 (1983, July, 20)] desribe p-aloxybenzoic acid derivatives such as N-carboxymethyl-4-(2-hydroxy-4-phenyl-butoxy) benzamide and 4-[4-(4'-tert-butylphenyl)-2-oxobutoxy] benzoic acid, processes for producing these derivatives, and anti-hyperlipidemic compositions containing these derivatives.

Also, in the past, attempts have been made to lower the levels of cholesterol, phospholipids, an triglycerides in the blood by the oral feeding of various substances which have been generally referred to in the art as hypalipidemic agents or hypocholesteremic adjuvants. Several synthetic hypolipidemic agents are now available, namely, clofibrate, D-thyroxine, cholestyramine, and various nicotinic acid-derivatives.

The development of agents capable of reducing elevated blood lipids and of favorably altering blood-lipoprotein patterns is considered by medical authorities to be extremely important for the treatment and prevention of atherosclerosis.

The present inventors tested the known compounds cycloartenol, 24-methylenecycloartanol, and cyclobranol to ascertain the anti-hyperlipidemic effect thereof. The tests were carried out according to method A (male Wistar strain rats weighing initially 100±1 g were fed for 2 weeks with the diet limited to 10 g/day for each animal but with water given ad libitum) and method B (male Wistar strain rats weighing initially 100±1 g were fed for 4 weeks with the diet and water given ad libitum). Details of these test methods will be described later. Results of these tests shown in Tables 1 and 2 (method A) and Tables 15 and 16 (method B) were as follows: The hypolipidemic effects according to both methods were fundamentally identical. The decrease of TC in serum was observed in the both group given a hyperlipidemic diet containing cycloartenol and given a hyperlipidemic diet containing cyclobranol, at significance levels ($P<0.05$ according to method A, $P<0.01$ according to method B), as compared with that in the control group given only a hyperlipidemic diet. The TC lowering due to 24-methylenecycloartanol was slight and not significant according to method A but significant ($p<0.05$) according to method B). As to HDL-C; cycloartenol depressed it at significant levels ($p<0.05$ according to method A, $p<0.01$ according to method B), 24-methylenecycloartanol lowered it slightly with both method so it was not significant. On the contrary, cyclobranol showed a tendency to increasing HDL-C according to both methods though these increases were not significant. Needless to say, HDL-C level is desired to increase significantly, as shown in the foregoing literature.

One of the purposes of the invention is to develop a hypolipidemic agent which significantly lowers TC and increases HDL-C in serum. As stated above, it was confirmed that one of the triterpenyl alcohols, for instance, cycloartenol, cyclobranol, or 24-methylenecycloartanol singly depress TC level in serum significantly. However, no increase in HDL-C content was ascertained in the present inventors' test for hypolipidemic effect according to either methods A or B.

As to AI, cycloartenol and cyclobranol showed tendencies to decrease it according to method A, while 24-methylenecycloartanol showed only a slight tendency to increase. According to method B, the three triterpenyl alcohols showed tendencies to decrease AI. As to TG, PL, and LPO, no significant change was shown with these triterpenyl alcohols according to both methods.

Comparing these three triterpenyl alcohols, cyclobranol tended to lower TC, AI, TG, PL, and LPO but to increase HDL-C, and consequently it was different in the action from cycloartenol and 24-methylenecycloartanol. That is, it has proved that cyclobranol is superior to cycloartenol and 24-methylenecyloartanol in hypolipidemic effect.

Thus, the present inventors have studied aiming at the production of an hypolipidemic agent which will decrease the TC, PL, and TG, contents in serum while the HDL-C content is increased, furthermore an agent which lower AI and LPO contents simultaneously. So our studies have been concentrated on the development of a hypolipidemic agent which has distinctly greater effect in at least 2-3 of 6 items noted above than known triterpenyl alcohols and γ-orizanol. As a result, we discovered a number of novel triterpenyl esters of organic acids having excellent hypolipidemic activity. Further we found that each of the three known triterpenyl esters of ferulic acid, certain esters of monobasic saturated fatty acids, and cyclobranol have high hypolipidemic activity singly. It is difficult to predict these facts from properties of each of the known triterpenyl alcohols, organic acids, and γ-orizanol.

SUMMARY OF THE INVENTION

It is an object of the present invention to provide novel triterpenyl esters of organic acids except triterpenyl esters of ferulic acid (4-hydroxy-3-methoxycinnamic acid), and of monobasic and dibasic saturated fatty acids. More particularly, the novel triterpenyl esters of organic acids are organic esters derived from the following alcohols: cycloartenol 24-methylenecycloartanol, lanosterol, lanostenol agnosterol, cyclosadol (3β-hydroxy-24-methylene-9, 19-cyclo-9β-lanosta-23-ene), dihydroagnosterol, cyclolaudenol, cycloartanol, cycloeucalenol, euphol, butyrospermol, tirucallol, euphorbol and dammerradienol, except esters of ferulic acid, and monobasic and dibasic saturated fatty acids.

Of these esters, preferred are those derived from cycloartenol, 24-methylenecycloartanol, and cyclobranol. Favorable organic acids for the esters are; cinnamic acid, benzoic acid, and α-($C_1$-$C_4$ alkyl) cinnamic acid wherein one substituent group on the benzene ring is selected from amino, nitro, hydroxyl, $C_2$-$C_5$ acylamino, $C_1$-$C_4$ alkoxy, and $C_2$-$C_6$ alkylcarboxyl groups; cinnamic acid, benzoic acid, and α-($C_1$-$C_4$ alkyl) cinnamic acid wherein two substituent groups on the benzene ring are selected from these pairs hydroxyl and $C_1$-$C_4$ alkoxy, hydroxyl and $C_2$-$C_6$ alkylcarboxyl, $C_1$-$C_4$ alkoxy and $C_2$-$C_6$ alkylcarboxyl, $C_1$-$C_4$ alkoxy and nitro, $C_1$-$C_4$ alkoxy and amino, $C_1$-$C_4$ alkoxy and $C_2$-$C_5$ acylamino, two $C_1$-$C_4$ alkoxy, two $C_2$-$C_6$ alkylcarboxyl, and two hydroxyl groups; nicotinic acid; and unsaturared fatty acids such as linoleic acid, linolenic acid, arachidonic acid, and eicosapentaenoic acid.

It is another object of the present invention to provide processes for the production of the above-mentioned esters of organic acids.

It is still another object of the present invention to provide a hypolipridemic agent which significantly depresses TC and increases HDL-C in serum.

It is still further object of the present invention to provide a pharmaceutical composition for treating hyperlipidemia, comprising a pharmaceutical carrier and an effective amount of cyclobranol or a triterpenyl ester of organic acid other than dibasic saturated fatty acid.

It is still further object of the present invention to provide a method of treating hyperlipidemia comprising administering to a patient in need of such treatment, a therapeutically effective amount of cyclobranol or a triterpenyl ester of organic acid other than dibasic saturated fatty acid.

According to one aspect of the present invention, there is provided a triterpenyl ester of organic acid other than triterpenyl esters of ferulic acid and of monobasic and dibasic saturated fatty acids.

According to another aspect of the present invention, there is provided a process for producing a triterpenyl ester of organic acid ester other than esters of ferulic acid and of monobasic and dibasic saturated fatty acids, which comprises the reaction of a triterpenyl alcohol with an acid halide of the corresponding organic acid.

According to still another aspect of the present invention, there is provided a pharmaceutical composition for treatment of hyperlipidemia comprising a pharmaceutical carrier and an effective amount of a triterpenyl ester of organic acid other than triterpenyl esters of dibasic saturated fatty acids.

According to still another aspect of the present invention, there is provided a phermaceutical composition for treating hyperlipidemia which comprises a pharmaceutical carrier and an effective amount of cyclobranol as an active ingredient.

According to still another aspect of the present invention, there is provided a method of treating hyperlipidemia comprising administrating to a patient in need of such treatment, a therapentically effective amount of cyclobranol, or of a triterpenyl ester of organic acid other than dibasic saturated fatty acid.

DESCRIPTION OF THE PREFERRED EMBODIMENTS

The novel compounds of the present invention are, in general, white crystalline solids having characteristic melting points and specific rotation, and stable compounds which, as can be seen from later examples of preparation, that those are not hydrolyzed at all even heated at 60°-70° C. for 3 hours in a strongly acidic aqueous solution of pH 0.5-1.5 with stirring.

Structural formulae of three preferred triterpenyl compounds are shown below.

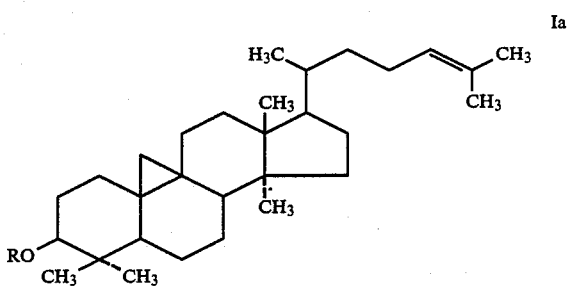

Ia

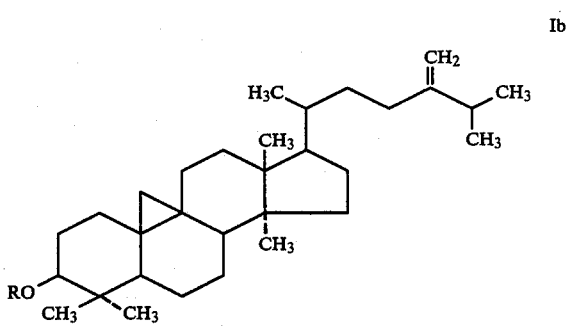

Ib

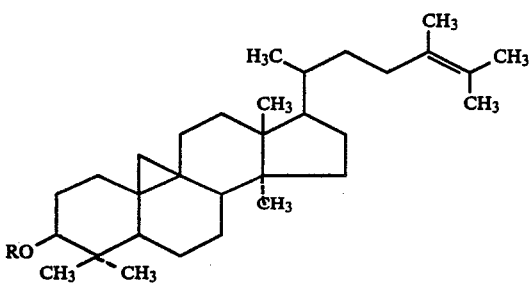

Ic

When R is H in the general formulae Ia, Ib, and Ic, formula Ia represents cycloartenol, formula Ib 24-methylenecycloartanol, and formula Ic cyclobranol. These three triterpenyl alcohols are publicly known.

In the present invention, R of formulae Ia, Ib, and Ic herein represents a residue of the above-mentioned various monobasic organic acids. The following general formulae II and IIIa–IIId represent the compounds of the present invention which have, in the molecule, one of these organic acid residues except nicotinic acid, linoleic acid, linolenic acid, arachidonic acid, and eicosanpentaenoic acid residues.

General formula

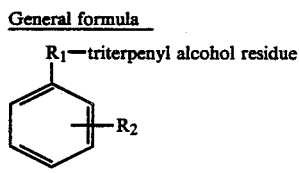

II.

In formula II, $R_1$ denotes $\alpha,\beta$-unsaturated carbonyl group (—CH=CH—CO—), carbonyl group (—CO—), or $\alpha$-($C_1$–$C_4$ alkyl) $\alpha,\beta$-unsaturated carbonyl group (—CH=CR$_3$—CO—), and $R_2$ denotes amino (—NH$_2$), acylamino (—NHCOR$_3$), nitro (—NO$_2$), hydroxyl (—OH), $C_1$–$C_4$ alkoxy (—OR$_3$), or $C_2$–$C_6$ alkylcarboxyl (—OCOR$_4$). $R_3$ is $C_1$–$C_4$ alkyl, i.e. methyl, ethyl, propyl, isopropyl, butyl, isobutyl, sec-butyl or tert-butyl, and $R_4$ is $C_1$–$C_5$ alkyl, that is, any of the above alkyls denoted by $R_3$ and of the $C_5$ alkyls, i.e. pentyl iso-pentyl, sec-pentyl, 3-pentyl, and tert-pentyl.

General formula (II) represents any of the triterpenyl esters of cinnamic acid, benzoic acid, and $\alpha$-($C_1$–$C_4$ alkyl) cinnamic acid which have the substituent $R_2$ on the ortho-, meta-, or para- position of the benzene ring.

General formula

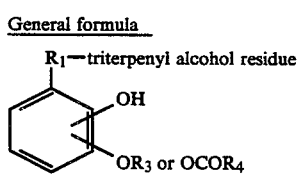

IIIa

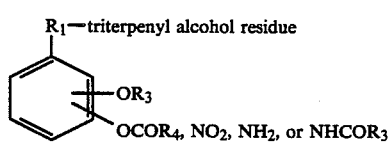

IIIb

General formula

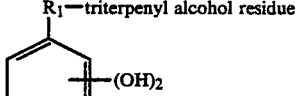

IIIc

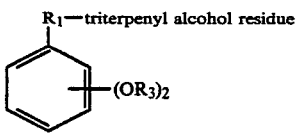

IIId

In general formulae IIIa–d, $R_1$, $R_3$, and $R_4$ are as defined above.

The compound of general formula IIIa is a triterpenyl ester of cinnamic acid, benzoic acid, or $\alpha$-($C_1$–$C_4$ alkyl)-cinnamic acid each having, on the benzene ring, two different substituents OH and OR$_3$ groups, or OH and OCOR$_4$ groups. The compound of general formula IIIb is the same ester but the acid residue of which has on the benzene ring, two different substituents OR$_3$ and OCOR$_4$ groups, OR$_3$ and NO$_2$ groups, OR$_3$ and NH$_2$ groupos, or OR$_3$ and NHCOR$_3$ groups.

Referring to the compounds of formula IIIa or IIIb, detailed description is given below.

The compound of formula IIIa, when an OH group is attached to the benzene ring at the o-position (2-position), is an ester having an OR$_3$ or OCOR$_4$ group at the 3-, 4-, 5- or 6-position. When an OH group is attached to the benzene ring at the m-position (3-position), the compound is an ester having an OR$_3$ or OCOR$_4$ group at the 2-, 4-, 5-or 6-position. When an OH group is attached to the benzene ring at the p-position (4-position), the compound is an ester having an OR$_3$ or OCOR$_4$ group at the 2- or 3-position (hereinafter these compounds are referred to as compounds of formula IIIa). Such bond-structures of the compounds of formula IIIa are shown by the following general formulae IIIa$_1$–IIIa$_{10}$:

General formula

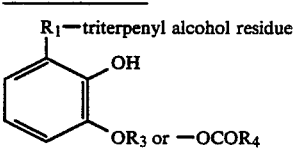

IIIa1

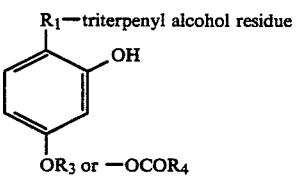

IIIa2

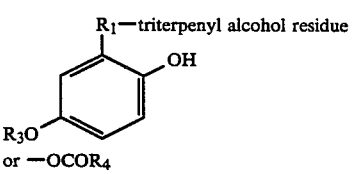

IIIa3

General formula -continued

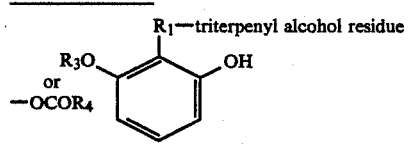 IIIa4

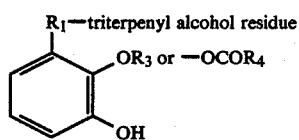 IIIa5

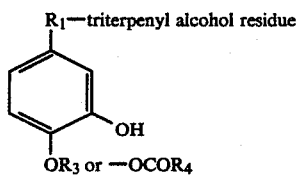 IIIa6

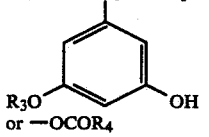 IIIa7

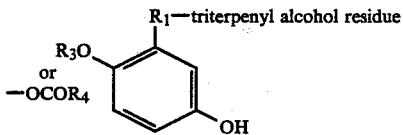 IIIa8

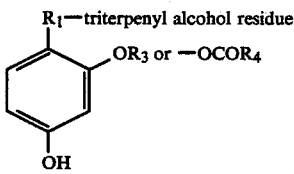 IIIa9

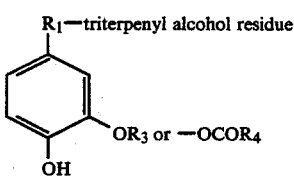 IIIa10

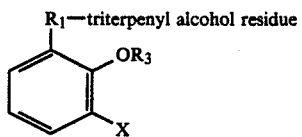 IIIb1

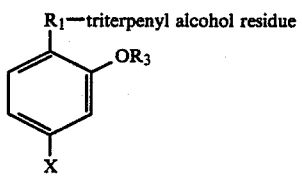 IIIb2

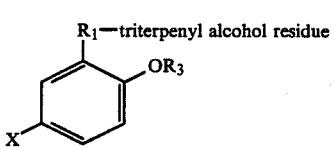 IIIb3

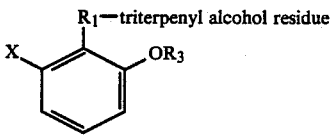 IIIb4

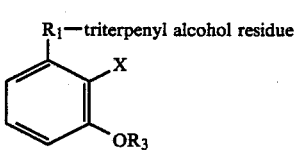 IIIb5

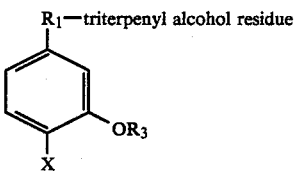 IIIb6

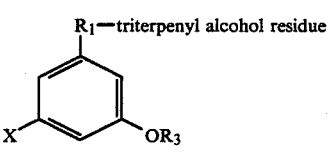 IIIb7

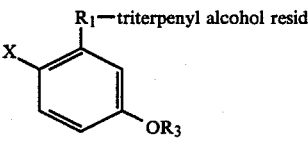 IIIb8

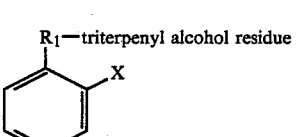 IIIb9

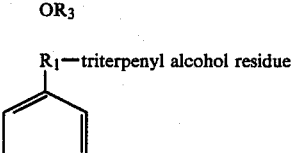 IIIb10

In formulae IIIa1–IIIa10, $R_1$, $R_3$, and $R_4$ are as defined above.

The compound of general formula IIIb is a triterpenyl ester of cinnamic acid, benzoic acid, or α-($C_1$–$C_4$ alkyl) cinnamic acid each having, on the benzene ring, two different groups, i.e. an $OR_3$ group, in place of the OH group of the compounds of formula IIIa, and any of $OCOR_4$, $NO_2$, $NH_2$, and $NHCOR_3$ groups. Consequently, the compound of formula IIIb1 shown below is a compound resulting from the substitution of an $OR_3$ group for the OH group of the compound of formula IIIa1 and the substitution of an $OCOR_4$, $NO_2$, $H_2$, or $NHCOR_3$ group for the $OR_3$ or $OCOR_4$ group of the compound of formula IIIa1.

The compounds of the following formulae IIIb-2–IIIb10 have similar bond-structures. In these formulae, X denotes $OCOR_4$, $NO_2$, $NH_2$, or $NHCOR_3$ group.

In formulae IIIb1–IIIb10, $R_1$ and $R_3$ are as defined above.

The compound of general formula IIIc and the compound of general formula IIId are triterpenyl esters of cinnamic acid, benzoic acid, or α-($C_1$-$C_4$ alkyl) cinnamic acid having, on the benzene ring, two OH groups and two $OR_3$ groups, respectively. That is, the compound of formula IIIc has two OH groups at the 2- and 3-positions, 2- and 4-positions, 2- and 5-positions, 2- and 6-positions, 3- and 4-positions, or 3- and 5-positions, that is, the following six bond-structures are present for the compounds of formula IIIc.

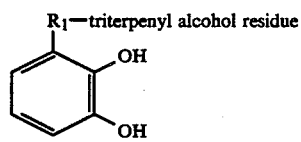
IIIc1

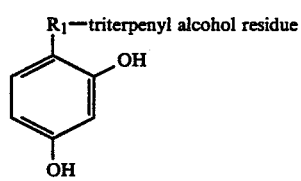
IIIc2

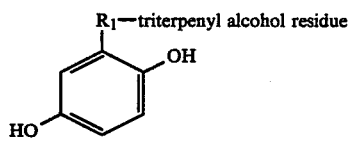
IIIc3

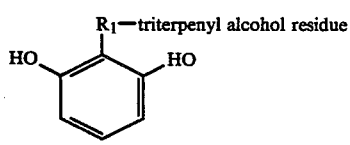
IIIc4

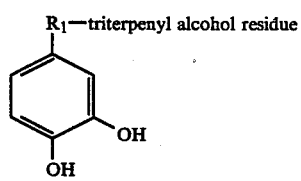
IIIc5

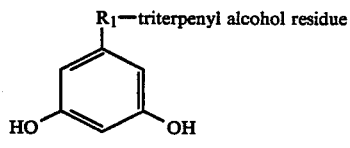
IIIc6

The compound of formula IIId has two $OR_3$ groups in place of the two OH groups of the compound of formula IIIc, thus including six compounds of formulae IIId1–IIId6 similarly to formulae IIIc1–IIIc6.

In the next place, the process for producing the compound of the invention is described.

The aforementioned γ-orizanol is a suitable raw material for cycloartenol, 24-methylenecycloartanol, and cyclobranol. The γ-orizanol, as stated before, is not a single compound but a mixture of various steryl and triterpenyl esters of ferulic acid. The mixture, for example, is composed of campesteryl (14%), stigmasteryl (1%), β-sitosteryl (4%), cycloartanyl (2%), cycloartenyl (35%), and of 24-methylenecycloartanyl (44%) esters of ferulic acid. With reference to the method of Endo et al. (Yukagaku, 18, pp. 63–67 (1969)), γ-orizanol was recrystallized repeatedly by using acetone-methanol (methanol content 2–7%), acetone, and ethyl acetate to give cycloartenyl ester of ferulic acid, which was then saponified to separate cycloartenol, m.p. 101°–102° C., specific rotation $[\alpha]_D^{21.5} +49.7°$ (c 1.01, $CHCl_3$). This cycloartenol, on gas chromatography, gave a single peak.

Method for isolating 24-methylenecycloartanol

According to the above method of Endo et al., crystals obtained from the mother liquor after separating cycloartenol from γ-orizanol were acetylated with phridine-acetic anhydride, the acetylated product was recrystallized repeatedly by using chloroform-ethyl acetate-ethanol (4:3:2) and then deacetylated, and the product was recrystallized from acetone-methanol to give 24-methylenecycloartanyl ester of ferulic acid, which was then saponified to isolate 24-methylenecycloartanol, m.p. 123°–124° C., specific rotation $[\alpha]_D^{24} +48.1°$ (c 1.00, $CHCl_3$). This substance, on gas chromatography, gave a single peak.

Method for isolating cyclobranol

γ-Orizanol (1.1 Kg, cyclobranol content 0%) was dissolved in acetone (8 l). After dissolution of iodine (40 g) therein, the mixture was heated for 1.5 hours under reflux. The mixture was then allowed to cool, a 10% aqueous solution (500 ml) of sodium thiosulfate was added, the mixture was stirred for 30 minutes, and further water (550 ml) was added. The formed crystals were filtered, washed with a 2% aqueous solution (700 ml) of sodium thiosulfate and then with water (4 l), and dried to give a γ-orizanol (1 Kg), which was found by gas chromatography to contain about 23% cyclobranol. This crystalline product (1 Kg) was suspended in a 4% ethanolic KOH solution, and the suspension was heated for 3 hours under reflux. After cooling the resulting mixture, the precipitated potassium salt of γ-orizanol was filtered, and suspended in methanol (8 l), and the suspension was refluxed for 2 hours. After cooling the resulting mixture, the precipitated yellow crystals were filtered and dried to give the potassium salt of a γ-orizanol (260 g). This crystalline product was treated similarly with 3% and 2% ethanolic KOH solutions to give yellow crystals (130 g). This product was found to contain 88% cyclobranol. Further this yellow crystalline product (130 g) was saponified in a 2N ethanolic KOH solution (2.6 l), and the residue was extracted with chloroform (1.2 l). The extract was dried and evaporated under reduced pressure to give crude cyclobranol (80 g, 88% purity), which was then recrystallized 3 times from acetone (1.6 l), thus giving crystalline cyclobranol (28 g), m.p. 165°–166° C., specific rotation $[\alpha]_D^{25} +47.0°$ (C 1.00, $CHCl_3$). This cyclobranol, on gas chromatography, gave a single peak.

The triterpenyl esters of organic acids according to the present invention can be readily obtained by known methods of esterification from the above defined alcohols and organic acids. That is, the ester can be prepared by the esterification of the organic acid and the triterpenyl alcohol through dehydration in the presence of a catalyst such as sulfuric acid, p-toluenesulfonic acid, or boron trifluoride ($BF_3$), the reaction of the anhydride of the organic acid with the triterpenyl alcohol in the presence of a catalyst such as sulfuric acid or zinc chloride, or the reaction of a halide of the organic acid (the corresponding acyl halide; hereinafter referred to as organic acid halide), with the triterpenyl alcohol. Of these methods, the most favorable is the method of reacting the organic acid halide with the triterpenyl alcohol. That is, when the starting organic acid is a monobasic acid such as nicotinic acid, linoleic acid, linolenic acid, arachidonic acid, eicosanpentaenoic acid, $C_6 \sim C_{14}$ saturated fatty acids, or an organic acid corresponding to an ester of formula II, IIIB, or IIId, i.e. a mono- or di-substituted cinnamic, benzoic, or $\alpha$-($C_1$-$C_4$ alkyl) cinnamic acid having; one substituent selected from $NO_2$, $OR_3$, $OCOR_4$, and $NHCOR_3$ groups (formula II); two different substituents $OR_3$ group and any of $OCOR_4$, $NO_2$, $NH_2$, and $NHCOR_3$ groups (formula IIIb); or two $OR_3$ groups (formula IIId); on the benzene ring; the intended triterpenyl esters of organic acid can be obtained with ease and in a high yield by converting the COOH group of the starting organic acid with a halogenating reagent into the CO-halogen group, followed by esterifying the resulting acid halide with the triterpenyl alcohol in the presence of a dehydrohalogenating agent in a solvent at a temperature of 10° to 100° C. Favorable halogenating reagents for this purpose are thionyl chloride, sulfuryl chloride, phosphorus pentachloride, phosphorus oxychloride, benzoyl chloride, phthaloyl chloride, hydrogen chloride, and hydrogen bromide. Suitable dehydrohalogenating agents for use in the esterification are pyridine, quinoline, trimethylamine, triethylamine, tripropylamine, tributylamine, magnesium, and dimethylaniline.

When the starting organic acid is one corresponding to an ester of formula II, IIIa, or IIIc [i.e. a mono- or di-substituted cinnamic, benzoic, or $\alpha$-($C_1$-$C_4$ alkyl) cinnamic acid having one substituent OH or $NH_2$ group (formula II), two different substituents OH and $OR_3$ groups or OH and $OCOR_4$ groups (formula IIIa), or two OH groups (formula IIIc), on the benzene ring], the acylated derivative of triterpenyl esters of organic acids can be obtained with ease and in a high yield by acylating the OH or $NH_2$ group of the organic acid in advance, followed by halogenation and esterification of the resulting acid as stated above. Then each ester of formula II, IIIa, or IIIc having OH or $NH_2$ group on the benzene ring can be prepared by deacylating the above acylated derivative, that is, by heating it in a concentrated aqueous solution of ammonia, caustic alkali (NaOH or KOH), or inorganic acid (HCl, $H_2SO_4$, or $H_3PO_4$).

The acylation can be readily accomplished by using an acylating agent such as an acid anhydride or acid halide of such a lower fatty acid as acetic acid, propionic acid, butyric acid or caproic acid.

Further an ester of formula II or IIIb having one substituent $NH_2$ group or two different substituents $NH_2$ and $OR_3$ groups or $NH_2$ and $OCOR_4$ groups on the benzene ring can be prepared by reducing the corresponding triterpenyl esters of substituted cinnamic, benzoic, or $\alpha$-($C_1$-$C_4$ alkyl) cinnamic acid having one $NO_2$ group, $NO_2$ and $OR_3$ groups, or $NO_2$ and $OCOR_4$ groups, on the benzene ring of the acid portion, with iron (or zinc) and acid (HCl, $H_2SO_4$, or acetic acid), or with tin (or tin chloride) and conc. $H_2SO_4$ to convert the $NO_2$ group selectively into $NH_2$ group. This reduction method using metal and acid is best suited since the unsaturated group present in the triterpenyl alcohol portion is not reduced.

The acylation of the above amino derivatives in the usual manner gives readily the corresponding esters of the invention having one $NHCOR_3$ group or two groups of $NHCOR_3$ and either $OR_3$ or $OCOR_4$ on the benzene ring of the acid portion.

Pharmacological action

In the next place, detailed description is given on the results of pharmacological tests of compounds according to the present invention for toxicity and anti-hyperlipidemic activity.

Acute toxicity test

Acute toxicity tests were conducted using 5 male ddy strain mice ($30\pm2$ g) and 5 male Wistar strain rats ($100\pm2$ g) for each compound by oral administration.

Examples of the compounds according to the present invention subjected to the acute toxicity tests were as follows:

Example 29, Cycloartenyl ester of 4-hydroxy-3-methoxybenzoic acid,

Example 37, Cyclobranyl ester of 4-hydroxy-3-methoxybenzoic acid,

Example 86, 24-Methylenecycloartanyl ester of 4-hydroxy-3-methoxybenzoic acid,

Example 60, Cycloartenyl ester of 3-ethoxy-4-hydroxybenzoic acid,

Example 62, Cyclobranyl ester of 3-ethoxy-4-hydroxybenzoic acid,

Example 74, Cycloartenyl ester of 4-hydroxy-4-propoxycinnamic acid,

Example 71, Cyclobranyl ester of 3-ethoxy-4-hydroxycinnamic acid,

Example 27, Cycloartenyl ester of 3,4-dihydroxybenzoic acid,

Example 39, Cyclobranyl ester of 3,4-dihydroxybenzoic acid,

Example 83, 24-Methylenecycloartanyl ester of p-acetoxycinnamic acid,

Example 2, Cycloartenyl ester of 3,4-dihydroxycinnamic acid,

Example 32, Cyclobranyl ester of 3,4-dihydroxycinnamic acid,

Example 82, 24-Methylenecycloartanyl ester of 3,4-dihydroxycinnamic acid,

Example 8, Cycloartenyl ester of o-hydroxybenzoic acid,

Example 41, Cyclobranyl ester of o-hydroxybenzoic acid,

Example 72, 24-Methylenecycloartanyl ester of 4-acetoxy-3-ethoxycinnamic acid,

Example 10, Cycloartenyl ester of p-hydroxybenzoic acid,

Example 58, Cyclobranyl ester of p-hydroxybenzoic acid,

Example 13, Cycloartenyl ester of o-methoxybenzoic acid,

Example 14, Cycloartenyl ester of p-methoxybenzoic acid,

Example 24, Cycloartenyl ester of nicotinic acid,

Example 50, Cyclobranyl ester of nicotinic acid,

Example 20, Cycloartenyl ester of p-acetamidobenzoic acid,

Example 19, Cycloartenyl ester of p-aminobenzoic acid,

Example 43, Cyclobranyl ester of p-aminobenzoic acid,

Example 100, 24-Methylenecyloartanyl ester of m-aminobenzoic acid,

Example 25, Cycloartenyl ester of linoleic acid,

Example 51, Cyclobranyl ester of linoleic acid,

Example 93, 24-Methylenecyloartanyl ester of linoleic acid,

Example 12, Cycloartenyl ester of m-hydroxybenzoic acid,
Example 54, Cyclobranyl ester of m-hydroxybenzoic acid,
Example 16, Cycloartenyl ester of o-nitrobenzoic acid,
Example 47, Cyclobranyl ester of o-aminobenzoic acid,
Example 23, Cycloartenyl ester of m-aminobenzoic acid,
Example 49, Cyclobranyl ester of m-aminobenzoic acid,
Example 100-1, Cycloartenyl ester of 4-hydroxy-3-methoxycinnamic acid (another name: cycloartenyl ester of ferulic acid),
Example 100-2, Cyclobranyl ester of 4-hydroxy-3-methoxycinnamic acid,
Example 100-3, 24-Methylenecycloartanyl ester of 4-hydroxy-3-methoxycinnamic acid,
Example 101, Cycloartenyl ester of p-nitrocinnamic acid,
Example 102, Cycloartenyl ester of p-aminocinnamic acid,
Example 104, Cyclobranyl ester of p-aminocinnamic acid,
Example 108, Cycloartenyl ester of m-aminocinnamic acid,
Example 112, 24-Methylenecyloartanyl ester of m-aminocinnamic acid,
Example 114, Cycloartenyl ester of 4-hydroxy-3-methoxy-α-methylcinnamic acid,
Example 116, Cyclobranyl ester of 4-hydroxy-3-methoxy-α-methylcinnamic acid,
Example 118, 24-Methylenecycloartanyl ester of 4-hydroxy-3-methoxy-α-methylcinnamic acid,
Example 120, Cycloartenyl ester of 4-hydroxy-3-methoxy-α-ethylcinnamic acid,
Example 140, Cyclobranyl ester of 3-ethoxy-4-hydroxy-α-methylcinnamic acid,
Example 130, Cycloartenyl ester of 4-hydroxy-α-ethylcinnamic acid,
Example 146, Cycloartenyl ester of 4-hydroxy-3-propoxy-α-methylcinnamic acid,
Example 167, Cycloartenyl ester of 4-amino-3-methoxybenzoic acid,
Example 173, Cyclobranyl ester of 5-amino-2-methoxybenzoic acid,
Example 189, Cycloartenyl ester of 4-amino-3-methoxy-α-methylcinnamic acid,
Example 177, Cycloartenyl ester of 4-amino-3-methoxycinnamic acid,
Example 205, Cycloartenyl ester of p-amino-α-methylcinnamic acid,
Example 183, Cycloartenyl ester of 5-amino-2-ethoxycinnamic acid,
Example 212, Cyclobranyl ester of m-amino-α-methylcinnamic acid,
Example 191, 24-Methylenecycloartanyl ester of 4-amino-3-methoxy-α-methylcinnamic acid,
Example 197, 24-Methylenecycloartanyl ester of 5-amino-2-propoxy-α-methylcinnamic acid,
Example 171, Cycloartenyl ester of 5-amino-2-methoxybenzoic acid,
Example 170, Cycloartenyl ester of 2-methoxy-5-nitrobenzoic acid,
Example 178, Cyclobranyl ester of 4-amino-3-methoxycinnamic acid,
EXAMPLE 195, Cycloartenyl ester of 5-amino-2-propoxy-α-methylcinnamic acid,
EXAMPLE 213, 24-Methylenecycloartanyl ester of m-amino-α-methylcinnamic acid,
EXAMPLE 113, Cycloartenyl ester of 3-methoxy-4-propionyloxy-α-methylcinnamic acid,
EXAMPLE 117, 24-Methylenecycloartanyl ester of 3-methoxy-4-propionyloxy-α-methylcinnamic acid.

The above 66 compounds of esters, and as control drugs, cycloartenol, 24-methylenecycloartanol, cyclobranol, and γ-orizanol were given forcibly to the above-mentioned mice and rats by means of a throat explorer rod in doses of 0.1 to 5 g/Kg for mice and 2 to 6 g/Kg for rats. During the test, the temperature of the animal room was kept at 22° to 23 ° C. After administration, the animals were observed for 2 weeks. With these doses none of the animals died. During the observation, no symptom of toxicosis appeared and no difference in behavior as well as in body weight was found between the animals given the test and the normal animals not given the compound. In the inspection conducted after 2-week observation, no macroscopic lesion was found in any part of main organs. Thus the compound of the invention has very low toxicity, so that the $LD_{50}$ value could not determined.

Pharmacological test method A for anti-hyper lipidemic activity (the term "method A" is used in the present specification)

Male Wistar strain rats (100±1g, each 10 rats were formed into a group) were used as test animals. Diet for the control group was prepared by thorough mixing of 20% casein, 62.5% glucose, 10% hydrogenated coconut oil, 2% agar powder, 4% vitamin-containing salt mixture, 1% cholesterol, and 0.5% cholic acid (this composition is described by Fukushima et al, in "Yakugaku Zassi", 89, No. 6, pp. 857–862 (1962)). Diet for the test groups was prepared by good mixing of 1% each of cycloartenol, 24-methylenecycloartanol, and cyclobranol with the control group's diet. Each rat was kept in a cage at a constant temperature of 23±1° C. and a constant R.H. of 55±5% for 2 weeks, during which 10 g/day of the prescribed was given. Finally the rats were fasted from food except water for 16 hours (from 4 p.m. of the 14th test day to 8 a.m. of the 15th test day), and under anesthesia with pentbarbital sodium (tradename: Nembutal), blood was taken from each rat through the descending abdominal arota. Then, TC, HDL-C, TG, PL, and LPO in the serum were measured in the manner that will be described below.

Pharmacological test method B for anti-hyper-lipidemic acitivity (the term "method B" was used in the present specification)

Male Wistar strain rats (100±1 g, each 8 rats were formed into a group except that the control group fed with a hyperlipidemic diet was formed of 16 rats) were used as test animals. A powdery diet (CE-2, supplied by Clea Japan, Inc.) was used as ordinary diet. The hyperlipidemic diet was prepared by fortifying the ordinary diet with cholesterol (1%) and cholic acid (0.5%). Each test compound (1%) for administration was admixed with the hyperlipidemic diet. Each two rats were kept in a cage and given the prescribed diet and water ad libitum. Thus the rats were fed for 4 weeks at a constant temperature of 23±1° C. and a constant R.H. of 55±5%. Finally, the rats were fasted from food except water for 16 hours (from 4 p.m. of the 28th test day to 8 a.m. of the 29th test day), and under anesthesia with pentbarbital sodium (tradename: Nembutal), blood was taken from each rat through the descending abdominal arota. Then, TC, HDL-C, TG, PL, and LPO in the serum were measured in the following manner.

Method for determination of serum TC

A TC kit-K (supplied by Nippon Shoji Kaisha, Ltd.) was used. The principle of this determination is as follows: The ester of cholesterol in the serum is hydrolyzed with cholesterol-ester hydrolase into free cholesterol and fatty acids. All the free cholesterol is oxidized with cholesterol oxydase to form $\Delta^4$-cholestenone and hydrogen peroxide. Phenol and 4-aminoantipyrin are oxidatively condensed together by the formed hydrogen peroxide and peroxydase. The produced red quinone coloring matter is measured by colorimetry for absorbance at 500 nm using a spectrophotometer, thereby determining the TC:

Preparation of color-developing liquid:

Color-developing reagent: One bial (components: cholesterol esterase 25,000μ, cholesterol oxydase 25μ, peroxydase 3,554μ, 4-aminoantipyrin 20 mg)

Buffer solution: 100 ml of the solution contains phenol (33.3 mg), potassium dihydrogenphosphate (489.9 mg), and anhydrous disodium hydrogenphosphate (908.5 mg) in purified water.

Standard solution: 100 ml of the solution contains cholesterol (300 mg).

A solution of one bial of the above color-developing reagent in 160 ml of the buffer solution is referred to as color-developing liquid.

The color-developing liquid (3.0 ml) is well mixed with the sample serum (0.02 ml). The mixture once heated at 37° C. for 15 minutes, is measured for absorbance at 500 nm with a spectrophotometer. The found absorbance is denoted by EA. On the other hand, the color-developing liquid (3.0 ml) is well mixed with the standard solution. The mixture is treated and measured for absorbance at 500 nm in the same manner as the above. This found absorbance is denoted by ES. Both EA and ES are determined with reference to the value of the blank test conducted using the color-developing liquid (3.0 ml) alone.

$$TC \text{ value (mg/dl)} = \frac{EA}{ES} \times 300 \text{ mg/dl}$$

Method for determination of serum HDL-C

An HDL-C kit-N (supplied by Nippon Shoji Kaisha, Ltd.) was used. Ultra-high density lipoprotein (VLDL) and lo density lipoprotein (LDL) in the serum is precipitated by the action of heparin. The precipitate is separated by centrifugation. High density lipoprotein (HDL) is dissolved in the separated supernatant. Esters of cholesterol in this fraction is hydrolyzed with cholesterol-ester hydrolase into free cholesterol and fatty acids. All the free cholesterol is oxidized with cholesterol oxydase to form $\Delta^4$-cholestenone and hydrogen peroxide. Phenol and 4-aminoantipyrine are oxidatively condensed together by the formed hydrogen peroxide and peroxydase. The produced red quinone coloring matter is measured by colorimetry for absorbance at 500 nm using a spectrophotometer, thereby determining the HDL-C.

Method for determination of serum PL

A PL kit-K (supplied by Nippon Shoji Kaisha, Ltd.) was used for the determination. Lecithin, sphingomyelin, and lysolecithin are decomposed by phospholipase D into choline and phosphatidic acid, N-acylsphingosyl phosphate, or lysophosphatidic acid, respectively. The resulting choline is quantitatively decomposed by choline oxydase into hydrogen peroxide and betaine. With this hydrogen peroxide, and aid of peroxydase, phenol and 4-aminoantipyrin are condensed into red quinone pigment, then the absorbance at 500 nm of which is measured with a spectrophotometer, thereby determining the PL.

Method for determination of serum TG

Serum TG level was determined by means of a triglyceride test kit (supplied by Wako Pure Chemical Industries, Ltd.) in which acetylacetone is used for a reagent, in the following manner: Serum proteins are precipitated, when isopropyl alcohol and the sample serum are mixed. Thereby serum lipids and sacchalides are extracted into the isopropyl alcohol layer. An adsorbent is added to the isopropyl alcohol solution to adsorb coloration-interferring materials. After centrifugation of the mixture, potassium hydroxide is added to a portion of the supernatant, thereby saponifying the triglyceride to liberate glycerol. Then the pH of the mixture is adjusted to 6 by adding a buffer solution, and a sodium metaperiodate solution is added to oxidize the glycerol into formic acid (1 mole from mole of gylcerol) and formaldehyde (2 moles from mole of glycerol). The resulting form aldehyde is allowed to react with acetylacetone and with the ammonia in the buffer solution, forming a cyclic compound 3,5-diacetyl-1,4-dihydrobutidine. This yellow pigment is determined by measuring the absorbance at 410 nm with a spectrophotometer, thus determining the TG content.

Method for determination of serum LPO

A lipoperoxide test kit (supplied by Wako Pure Chemical Industries, Ltd.) according to the Yagi's thiobarbituric acid method [K. Yagi, Biochem. Med. 15, p 212 (1976), Vitamin 49, p 403 (1975)] was used for this determination. Physiological saline (1.0 ml) is added to the sample serum (0.05 ml) and the mixture is stirred gently. After centrifugation (3,000 r.p.m., 10 minutes) of the mixture, $1/12N-H_2SO_4$ (4.0 ml) is added and well mixed with the supernatant (0.5 ml). A 10% aqueous phosphotungstic acid solution (0.5 ml) is added thereto and the mixture is stirred well, allowed to stand for 5 minutes, and centrifuged at 3,000 r.p.m. for 10 minutes. The resulting precipitate is suspended thoroughly in a mixture of $1/12 \text{ NH}_2SO_4$ (2.0 ml) and a 10% aqueous phosphotungstic acid solution by means of a mixer. The suspension is then centrifuged at 3000 r.p.m. for 10 minutes, then the obtained precipitate is suspended in distilled water (4.0 ml) by means of a mixer. Then a TBA reagent (1.0 ml; 50% acetic acid solution containing thiobarbituric acid) is well mixed with the suspension. The mixture is charged in a centrifuge tube, and heated in a boiling water bath for 60 minutes with a glass ball placed on the top of the tube. After 5-minute cooling of the tube in a running water, butanol (5.0 ml) is added to the mixture, and well mixed for 20 seconds by means of a mixer with the tube being stoppered, thereby extracting the reaction product in the butanol. The mixture is centrifuged at 3000 r.p.m. for 10 minutes. The butanol layer is measured for fluorescence. After adjustment of the zero point by a blank test, the fluorescence intensity (F) of 0.1 ml of a standard solution (1,1,3,3-tetraethoxypropane 5 n mole/ml) and that of the sample (f) are measured at 553 nm with an excitation wavelength of 515 nm. That is, in this method, the product of the reaction of LPO with thiobarbituric acid is identical with that of malondialdehyde with thiobarbituric acid. Accordingly, the LPO concentration is determined as the amount of malondialdehyde in 1 ml of the serum. The standard solution is a 5n mole/ml aqueous solution of 1,1,3,3-tetraethoxypropane, which is converted quantitatively into malondialdehyde. Since 0.1 ml of the standard solution is used in this method, the quantity of 1,1,3,3-tetraethoxypropane used is 0.5 n mole. Consequently the LPO content is calculated according to the following equation:

LPO content (n mole/ml serum) =

$$0.5 \times \frac{f}{F} \times \frac{1.0}{0.05} \times \frac{1.05}{0.5} = \frac{f}{F} \times 21$$

Results of phamacological tests for hypolipidemic activity

The hypolipidemic action of typical compounds among the present invention on serum lipids and on serum lipid hydroperoxide are described below. The compound selected here are the same as selected in the description of the acute toxicity. The tests were carried according to the above methods wherein rats were fed with high cholesterol diet.

Results of the tests for hypolipidemic activities of cycloartenol, cyclobranol, and 24-methylenecycloartanol, which are used as control drugs, are shown in Tables 1 and 2 (according to method A) and Tables 15 and 16 (according to method B). Effects of these compounds were described already.

Hypolipidemic effects of compounds of the present invention, tested according to method A are shown in Tables 3 to 14, 23, and 24. The effects of compounds according to the present invention and those of cycloartenol, cyclobranol, 24-methylenecycloartanol, and γ-orizanol as control drugs, with method B are shown in Tables 17 to 20. Tables 17 to 20 indicate that TC, PL, and LPO of the normal diet feeding group (denoted by N) were depressed at high significance levels (p<0.001, marked with ***) without exception while the HDL-C was raised at high significance levels (p<0.001), in contrast with those of the control group fed with the hyperlipidemic diet (denoted by C). On the TG in N tendency to depress was shown in C, but this difference between values of TG in N and C was not significant.

Hypolipidemic effects of improving serum lipids' components were clearly observed in the groups given the hyperlipidemic diet containing each of compounds according to the present invention, or each of the control drugs, as compared with those in the group given the hyperlipidemic diet only. In particular, compounds according to the present invention brought about distinctly better effects on two or more serum lipids components of TC, HDL-C, PL, and LPO than did the control compounds.

According to method A, the TC level were changed by compounds of the present invention as follows: The compound of Example 49 depressed the TC levels at a high significance level (p<0.001). The compounds of Examples 37, 62, 71, 27, 39, 8, 41, 10, 58, 13, 14, 19, 43, 100, 25, 51, 93, 100-1, 100-2, 101, 105, and 109 depressed the TC levels at medium significance levels. The compounds of Examples 29, 86, 60, 74, 83, 32, 72, 24, 50, 20, 12, 16, and 23 depressed the TC levels at low significance levels (p<0.05). The compounds of Examples 2, 82, and 47 didn't depress the TC significantly, but tended to depress apparently.

According to method B, the TC levels were 5 depressed by the control drugs, i.e. the three triterpenyl alcohols and γ-orizanol, at medium significance levels (p<0.01), as compared with the TC levels in the control group given the hyperlipidemic diet only. In contrast, the compounds of Examples 114, 116, 118, 189, 205, 212, 191, 197, 171, 178, 195, and 213 depressed the TC levels at high significance levels (p<0.001). The compounds of Examples 120, 140, 130, 146, 167, 173, 177, 183, 170, 113 and 117 depressed the TC levels at medium significance levels (p<0.01).

The HLD-C contents, according to method A, were affected by compounds of the invention as follows: The compound of Example 8 raised the HLD-C contents at a high significance level (p<0.001), the compounds of Examples 37, 62, and 39 at medium significance levels (p<0.01), and the compounds of Examples 71, 27, 83, 41, 51, 100-1, 105, and 109 at low significance levels (p<0.05). The compounds of Examples 86, 74, 10, 12, 47, and 49 scarcely varied or slight depressed the HLD-C contents while the compounds of other Examples showed tendencies to raise them but insignificantly.

According to method B, effects of test compounds on the HLD-C were as follows: The control drug cycloartenol caused the depression at a significance level (p<0.01), while the other control drugs cyclobranol, 24-methylenecycloartanol, and γ-orizanol showed tendencies to the raise or the depression but insignificantly. In contrast, the compounds of Examples 114, 116, 118, 140, 146, 167, 173, 189, 177, 205, 212, and 213 raised HDL-C levels at high significance levels (p<0.001) and the compounds of Examples 120, 130, 183, 191, 197, 171, 178, 195, 113, and 117 increased at significance levels (p<0.01). The compound of Example 170 caused the rise at a low significance level (p<0.05). In particular, the compounds of Examples 116, 118, 140, 167, 173, 170, 178, 195, and 213 caused remarkable rises in the HDL-C contents in comparison with that in the group given the normal diet.

As to the AI, all the compounds tended evidently to depress the AI levels without exception according to method A or B.

The TG, according to method A, was not depressed at the significance level but unvaried or slightly depressed by any compound tested, except that the depression was caused by the compound of Example 49 at a medium significance level (p<0.01) and by the compounds of Examples 100-1, 100-2, and 101 at low significance levels (p<0.05). According to method B, compounds of the present invention as well as control drugs showed tendencies to slight or some degree depression of the TG but insignificantly.

As to the PL, according to method A, the compounds of Examples 62, 71, 27, 39, 8, 41, 72, 24, 50, 20, 19, 43, 25, 51, 93, 49, and 100-2 depressed the PL levels at significance levels (p<0.001), the compounds of Examples 29, 37, 60, 74, 83, 58, 13, 14, 100, and 101 at significance levels (p<0.01), and the compounds of Examples 86, 32, 10, 23, 100-1, 105, and 109 at significance levels (p<0.05). The compounds of Examples 2, 82, 12, 16 and 47 showed apparent tendencies to the depression but insignificantly.

According to method B, the control drugs showed tendencies to slight depression of the PL but insignificantly. In contrast, the compounds of Examples 114, 116, 118, 140, 146, 171, 195, and 213 depressed the PL levels at significance levels (p<0.001), the compounds of Examples 120, 130, 189, 205, 212, 191, 197, 170, 178, 113, and 117 at significance levels (p<0.01), and the compounds of Examples 167, 173, 177, and 183 at significance levels (p<0.05).

As to LPO, according to method A, the compounds of Examples 10, 58, 13, 14, 19, 43, 100, 25, 51, 93, 101, 102, 104, and 112 depressed the LPO levels at significance levels (p<0.001), the compound of Example 50 at a significance level, and the compounds of Examples 29, 37, 60, 62, 71, 24, 12, 16, 47, 23, and 49 at significance levels (p<0.05). Other compounds of the invention showed distinct tendencies to the depression but insignificantly. According to method B, the control drug γ-orizanol depressed the LPO at a significance level (p<0.01) and the control drugs triterpenyl alcohols showed apparent tendencies to the depression but insignificantly. In contrast, the compounds of Examples 114, 116, 118, 120, 140, 130, 146, 189, 205, 212, 183, 191, 197, 171, 178, 195, and 213 depressed the LPO at significance levels (p<0.001) and the compounds of Examples 167, 173, 177, 170, 113, and 117 at significance levels (p<0.01).

As described above, most of the compounds according to the present invention, in the tests according to method A or B, tended obviously to raise the HDL-C contents and depress the TC, AI, PL, and LPO levels. In comparison with effects obtained by the administration of the free triterpenyl alcohols alone, it is evident that these hypolipidemic activities of the compounds of the invention are synergistic effects.

Increases of the body weights of rats used for the hypolipidemic activity tests according to method B are shown in Tables 21 and 22. These tables shows that the body weights of the rats given the normal diet were increased at significance levels (p<0.001) as compared with those of the control group rats given the hyperlipidemic diet. The group of rats given the hyperlipidemic diet containing each of typical compounds according to the present invention and the groups of rats given the hyperlipidemic diet containing each of the control drugs showed slight increases in body weight but insignificantly, as compared with the control group of rats given the hyperlipidemic diet alone.

TABLE 1

| Sample | TC mg/dl | SD | HDL-C mg/dl | SD | AI | TG mg/dl | SD | PL mg/dl | SD | LPO n mol/ml | SD |
|---|---|---|---|---|---|---|---|---|---|---|---|
| C | 205.1 | ±27.4 | 81.5 | ±10.1 | 1.517 | 34.3 | ±4.8 | 173.6 | ±11.0 | 2.27 | ±0.38 |
| 1 | 173.5* | ±32.1 | 72.0* | ±9.4 | 1.410 | 38.0 | ±5.2 | 173.7 | ±12.1 | 2.03 | ±0.23 |
| 2 | 168.0* | ±30.4 | 90.3 | ±9.3 | 0.860 | 30.6 | ±4.9 | 168.2 | ±10.8 | 1.98 | ±0.27 |
| 3 | 200.1 | ±33.5 | 76.8 | ±8.9 | 1.605 | 33.3 | ±6.5 | 167.0 | ±13.0 | 2.40 | ±0.25 |

[Notes]
In Sample column,
C: Serum of the control group of 10 rats given the hyperlipidemic diet in Tables 1 to 24.
1: Serum of the group of 10 rats given the hyperlipidemic diet containing 1% of cycloartenol as a control drug in Tables 1 to 2.
2: Serum of the group of 10 rats given the hyperlipidemic diet containing 1% of cyclobranol as a control drug in Tables 1 to 2.
3: Serum of the group of 10 rats given the hyperlipidemic diet containing 1% of 24-methylenecycloartanol as a control drug in Tables 1 to 2.
Mark*: Signicicance level (p < 0.05)
SD: Standard deviation.
These notations are applied to the following tables.

TABLE 2

| Sample | TC Diff. mg/dl | % of diff. | HDL-C Diff. mg/dl | % of diff. | AI Diff. mg/dl | % of diff. | TG Diff mg/dl | % of diff. | PL Diff. mg/dl | % of diff. | LPO Diff. n mol/ml | % of diff. |
|---|---|---|---|---|---|---|---|---|---|---|---|---|
| 1 | −31.6 | −15.4 | −9.5 | −11.6 | −1.107 | −7.1 | +3.7 | +10.9 | +0.1 | +0.06 | −0.24 | −10.6 |
| 2 | −37.1 | −18.1 | +8.8 | +10.8 | −0.657 | −43.3 | −3.7 | −10.9 | −5.4 | −3.1 | −0.29 | −12.8 |
| 3 | −5.0 | −2.4 | −4.7 | −5.8 | +0.088 | +5.8 | −1.0 | −2.9 | −6.6 | −3.8 | +0.13 | +5.8 |

[Notes]
"Diff." means the difference between Q-Qc and "% of diff." means (Q-Qc) × 100/Qc, wherein
Q: Concentration of the component lipid in the sample serum,
Qc: Concentration of the component lipid in the serum of the control group.
These notations apply in the following tables.

TABLE 3

| Sample (Example No.) | TC mg/dl | SD | HDL-C mg/dl | SD | AI | TG mg/dl | SD | PL mg/dl | SD | LPO nmol/ml | SD |
|---|---|---|---|---|---|---|---|---|---|---|---|
| C | 192.6 | ±24.3 | 96.2 | ±8.2 | 1.002 | 33.2 | ±8.1 | 180.9 | ±14.7 | 2.33 | ±0.35 |
| 29 | 162.7* | ±23.4 | 101.0 | ±8.2 | 0.611 | 32.7 | ±8.5 | 160.6** | ±14.9 | 1.95* | ±0.30 |
| 37 | 161.2** | ±22.8 | 110.4** | ±9.4 | 0.460 | 31.0 | ±7.8 | 155.4** | ±14.7 | 1.91* | ±0.32 |
| 86 | 165.6* | ±25.0 | 91.9 | ±9.7 | 0.802 | 33.1 | ±8.3 | 163.2* | ±17.2 | 2.06 | ±0.28 |
| 60 | 164.9* | ±24.0 | 102.5 | ±9.2 | 0.609 | 32.8 | ±8.8 | 161.4** | ±15.2 | 1.98* | ±0.33 |
| 62 | 159.5** | ±23.2 | 108.2** | ±9.3 | 0.474 | 32.0 | ±9.2 | 156.5*** | ±13.8 | 1.94* | ±0.32 |
| 74 | 165.1* | ±23.3 | 92.4 | ±8.9 | 0.787 | 33.1 | ±7.4 | 162.1** | ±14.5 | 2.09 | ±0.33 |
| 71 | 161.4** | ±23.6 | 106.0* | ±9.4 | 0.523 | 32.9 | ±8.3 | 157.7*** | ±15.6 | 1.96* | ±0.30 |

[Notes]
Mark**: Significance level (p < 0.01)
***: Significance level (p < 0.001)
Example No.: Serum of the group of 10 rats given the hyperipidemic diet containing 1% of compounds of example number each in Tables 3 to 24.
These notations apply in the following tables.

TABLE 4

| Sample (Example No.) | TC Diff. mg/dl | TC % of diff. | HDL-C Diff. mg/dl | HDL-C % of diff. | AI Diff. | AI % of diff. | TG Diff. mg/dl | TG % of diff. | PL Diff. mg/dl | PL % of diff. | LPO Diff. nmol/ml | LPO % of diff. |
|---|---|---|---|---|---|---|---|---|---|---|---|---|
| 29 | −29.9 | −15.5 | +4.8 | +5.0 | −0.391 | −39.0 | −0.5 | −1.5 | −20.3 | −11.2 | −0.38 | −16.3 |
| 37 | −31.4 | −16.3 | +14.2 | +14.8 | −0.542 | −54.1 | −2.2 | −6.6 | −25.5 | −14.1 | −0.42 | −18.0 |
| 86 | −27.0 | −14.0 | −4.3 | −4.5 | −0.200 | −20.0 | −0.1 | −0.3 | −17.7 | −9.8 | −0.27 | −11.6 |
| 60 | −27.7 | 14.4 | +6.3 | +6.5 | −0.393 | −39.2 | −0.4 | −1.2 | −19.5 | −10.8 | −0.35 | −15.0 |
| 62 | −33.1 | 17.2 | +12.0 | +12.5 | −0.528 | −52.7 | −1.2 | −3.6 | −24.4 | −13.5 | −0.39 | −16.8 |
| 74 | −27.5 | 14.3 | −3.8 | −4.0 | −0.215 | −21.5 | −0.1 | −0.3 | −18.8 | −10.4 | −0.24 | −10.4 |
| 71 | −31.2 | 16.2 | +9.8 | +10.2 | −0.479 | −47.8 | −0.9 | −2.8 | −23.2 | −12.8 | −0.37 | −15.9 |

TABLE 5

| Sample (Example No.) | TC mg/dl | TC SD | HDL-C mg/dl | HDL-C SD | AI | TG mg/dl | TG SD | PL mg/dl | PL SD | LPO nmol/ml | LPO SD |
|---|---|---|---|---|---|---|---|---|---|---|---|
| C | 217.1 | ±25.2 | 80.9 | ±10.2 | 1.684 | 42.8 | ±6.4 | 179.7 | ±10.9 | 2.31 | ±0.40 |
| 27 | 186.1** | ±22.7 | 95.2* | ±12.3 | 0.955 | 40.4 | ±5.7 | 160.3*** | ±11.0 | 1.99 | ±0.38 |
| 39 | 176.9** | ±23.3 | 98.1** | ±11.4 | 0.803 | 39.8 | ±7.2 | 155.1*** | ±12.2 | 1.99 | ±0.35 |
| 83 | 192.1* | ±23.1 | 93.3* | ±10.8 | 1.059 | 41.1 | ±6.5 | 162.1** | ±9.7 | 2.02 | ±0.27 |
| 2 | 194.5 | ±23.1 | 89.2 | ±10.7 | 1.180 | 41.3 | ±7.1 | 170.2 | ±10.3 | 2.05 | ±0.34 |
| 32 | 190.4* | ±23.2 | 89.2 | ±11.2 | 1.135 | 40.7 | ±5.5 | 168.2* | ±11.4 | 2.06 | ±0.29 |
| 82 | 195.8 | ±25.0 | 87.9 | ±11.3 | 1.228 | 42.3 | ±5.3 | 173.9 | ±12.7 | 2.08 | ±0.29 |
| 8 | 177.8** | ±24.5 | 101.1*** | ±10.8 | 0.759 | 41.3 | ±6.6 | 148.8*** | ±11.8 | 2.01 | ±0.29 |
| 41 | 175.6** | ±23.8 | 92.9* | ±10.6 | 0.890 | 41.5 | ±6.3 | 156.7*** | ±10.9 | 2.01 | ±0.35 |
| 72 | 186.5* | ±22.7 | 89.2 | ±10.2 | 1.091 | 41.8 | ±6.1 | 160.3*** | ±9.8 | 2.07 | ±0.44 |

TABLE 6

| Sample (Example No.) | TC Diff. mg/dl | TC % of diff. | HDL-C Diff. mg/dl | HDL-C % of diff. | AI Diff. | AI % of diff. | TG Diff. mg/dl | TG % of diff. | PL Diff. mg/dl | PL % of diff. | LPO Diff. nmol/ml | LPO % of diff. |
|---|---|---|---|---|---|---|---|---|---|---|---|---|
| 27 | −31.0 | −14.3 | +14.3 | +17.7 | −0.729 | −43.3 | −2.4 | −5.5 | −19.4 | −10.8 | −0.32 | −14.0 |
| 39 | −40.2 | −18.5 | +17.2 | +21.2 | −0.881 | −52.3 | −3.0 | −6.9 | −24.6 | −13.7 | −0.32 | −14.0 |
| 83 | −25.0 | −11.5 | +12.4 | +15.3 | −0.625 | −37.1 | −1.7 | −4.0 | −17.6 | −9.8 | −0.29 | −12.7 |
| 2 | −22.6 | −10.4 | +8.3 | +10.2 | −0.504 | −29.9 | −1.5 | −3.5 | −9.0 | −5.0 | −0.26 | −11.2 |
| 32 | −26.7 | −12.3 | '+8.3 | +10.2 | −0.549 | −32.6 | −2.1 | −4.8 | −11.5 | −6.4 | −0.25 | −10.7 |
| 82 | −21.3 | −9.8 | +7.0 | +8.7 | −0.456 | −27.1 | −0.5 | −1.2 | −5.8 | −3.2 | −0.23 | −9.8 |
| 8 | −39.3 | −18.1 | +20.2 | +25.0 | −0.925 | −54.9 | −1.5 | −3.5 | −30.9 | −17.2 | −0.30 | −13.0 |
| 41 | −41.5 | 19.1 | +12.0 | +14.8 | −0.794 | −47.1 | −1.3 | −3.0 | −23.0 | −12.8 | −0.30 | −13.0 |
| 72 | −30.6 | −14.1 | +8.3 | +10.2 | −0.593 | −35.2 | −1.0 | −2.4 | −19.4 | −10.8 | −0.24 | −10.4 |

TABLE 7

| Sample (Example No.) | TC mg/dl | TC SD | HDL-C mg/dl | HDL-C SD | AI | TG mg/dl | TG SD | PL mg/dl | PL SD | LPO nmol/ml | LPO SD |
|---|---|---|---|---|---|---|---|---|---|---|---|
| C | 166.6 | ±14.1 | 60.2 | ±8.5 | 1.767 | 27.2 | ±4.2 | 136.7 | ±12.0 | 2.53 | ±0.31 |
| 10 | 146.5** | ±15.3 | 57.6 | ±9.4 | 1.543 | 27.3 | ±4.1 | 123.3* | ±11.9 | 1.73*** | ±0.24 |
| 58 | 143.7** | ±17.9 | 62.0 | ±9.6 | 1.318 | 26.8 | ±4.0 | 121.3** | ±11.8 | 1.82*** | ±0.13 |
| 13 | 144.5** | ±16.8 | 60.5 | ±8.6 | 1.388 | 26.2 | ±3.8 | 122.8** | ±12.7 | 1.94*** | ±0.25 |
| 14 | 145.8** | ±15.2 | 64.1 | ±9.2 | 1.275 | 25.4 | ±3.1 | 120.9** | ±11.3 | 1.81*** | ±0.18 |

TABLE 8

| Sample (Example No.) | TC Diff. mg/dl | TC % of diff. | HDL-C Diff. mg/dl | HDL-C % of diff. | AI DIff. | AI % of diff. | TG Diff. mg/dl | TG % of diff. | PL Diff. mg/dl | PL % of diff. | LPO Diff. nmol/ml | LPO % of diff. |
|---|---|---|---|---|---|---|---|---|---|---|---|---|
| 10 | −20.1 | −12.1 | −2.6 | −4.3 | −0.224 | −12.7 | +0.1 | +0.4 | −13.4 | −9.8 | −0.80 | −31.6 |
| 58 | −22.9 | −13.7 | +1.8 | +3.0 | −0.449 | −25.4 | −0.4 | −1.5 | −15.4 | −11.3 | −0.71 | −28.1 |
| 13 | −22.1 | −13.3 | +0.3 | +0.5 | −0.379 | −21.4 | −1.0 | −3.7 | −13.9 | −10.2 | −0.59 | −23.3 |
| 14 | −20.8 | −12.5 | +3.9 | +6.5 | −0.492 | −27.8 | −1.8 | −6.6 | −15.8 | −11.6 | −0.72 | −28.5 |

TABLE 9

| Sample (Example No.) | TC mg/dl | TC SD | HDL-C mg/dl | HDL-C SD | AI | TG mg/dl | TG SD | PL mg/dl | PL SD | LPO nmol/ml | LPO SD |
|---|---|---|---|---|---|---|---|---|---|---|---|
| C | 192.2 | ±24.0 | 86.5 | ±9.7 | 1.232 | 36.3 | ±5.3 | 172.6 | ±10.5 | 2.24 | ±0.26 |
| 24 | 164.3* | ±23.1 | 94.0 | ±9.8 | 0.748 | 34.7 | ±6.4 | 133.8*** | ±10.1 | 1.93* | ±0.30 |
| 50 | 162.4** | ±22.4 | 95.7 | ±10.4 | 0.697 | 34.7 | ±5.1 | 138.8*** | ±11.3 | 1.87** | ±0.31 |
| 20 | 168.8* | ±24.5 | 90.4 | ±10.8 | 0.867 | 35.2 | ±5.8 | 143.3*** | ±11.4 | 2.02 | ±0.35 |
| 19 | 156.1** | ±24.5 | 91.9 | ±9.4 | 0.699 | 31.6 | ±5.6 | 153.6*** | ±10.2 | 1.63*** | ±0.21 |
| 43 | 157.4** | ±23.6 | 91.9 | ±9.6 | 0.713 | 33.3 | ±6.4 | 146.0*** | ±10.1 | 1.54*** | ±0.24 |
| 100 | 159.1** | ±22.6 | 90.1 | ±10.3 | 0.766 | 34.3 | ±6.2 | 155.6** | ±11.4 | 1.68** | ±0.23 |
| 25 | 157.4** | ±23.4 | 92.3 | ±9.6 | 0.705 | 34.0 | ±5.4 | 144.6*** | ±11.5 | 1.67*** | ±0.30 |

TABLE 9-continued

| Sample (Example No.) | TC mg/dl | SD | HDL-C mg/dl | SD | AI | TG mg/dl | SD | PL mg/dl | SD | LPO nmol/ml | SD |
|---|---|---|---|---|---|---|---|---|---|---|---|
| 51 | 156.5** | ±23.5 | 96.4* | ±9.8 | 0.623 | 34.7 | ±4.9 | 146.0*** | ±12.0 | 1.69*** | ±0.27 |
| 93 | 161.1** | ±23.3 | 91.5 | ±9.5 | 0.761 | 35.1 | ±5.0 | 150.2*** | ±11.0 | 1.70*** | ±0.28 |

TABLE 10

| Sample (Example No.) | TC Diff. mg/dl | % of diff. | HDL—C Diff. mg/dl | % of diff. | AI Diff. | % of diff. | TG Diff. mg/dl | % of diff. | PL Diff. mg/dl | % of diff. | LPO Diff. nmol/ml | % of diff. |
|---|---|---|---|---|---|---|---|---|---|---|---|---|
| 24 | −27.9 | −14.5 | +7.5 | +8.7 | −0.474 | −38.8 | −1.6 | 4.3 | −38.8 | −22.5 | −0.31 | −13.7 |
| 50 | −29.8 | −15.5 | +9.2 | 10.6 | −0.525 | −43.0 | −1.6 | −4.3 | −33.8 | −19.6 | −0.37 | −16.7 |
| 20 | −23.4 | −12.2 | +3.9 | +4.5 | −0.355 | −29.1 | −1.1 | −3.0 | −29.3 | −17.0 | −0.22 | −9.7 |
| 19 | −36.1 | −18.8 | +5.4 | +6.2 | −0.523 | −42.8 | −4.7 | −12.9 | −19.0 | −11.0 | −0.61 | −27.2 |
| 43 | −34.8 | −18.1 | +5.4 | +6.2 | −0.509 | −41.7 | −3.0 | −8.2 | −26.6 | −15.4 | −0.70 | −31.3 |
| 100 | −33.1 | −17.2 | +3.6 | +4.2 | −0.456 | −37.3 | −2.0 | −5.5 | −17.6 | −10.2 | −0.56 | −25.2 |
| 25 | −34.8 | −18.1 | +5.8 | +6.7 | −0.517 | −42.3 | −2.3 | −6.2 | −28.0 | −16.2 | −0.57 | −25.6 |
| 51 | −35.7 | −18.6 | +9.9 | +11.5 | −0.599 | −49.0 | −1.6 | −4.3 | −26.6 | −15.4 | −0.55 | −24.4 |
| 93 | −31.1 | −16.2 | +5.0 | +5.8 | −0.461 | −37.7 | −1.2 | −3.3 | −22.4 | −13.0 | −0.54 | −24.3 |

TABLE 11

| Sample (Example No.) | TC mg/dl | SD | HDL—C mg/dl | SD | AI | TG mg/dl | SD | PL mg/dl | SD | LPO nmol/ml | SD |
|---|---|---|---|---|---|---|---|---|---|---|---|
| C | 167.1 | ±16.4 | 58.7 | ±6.7 | 1.847 | 24.8 | ±4.7 | 148.4 | ±13.6 | 2.34 | ±0.29 |
| 12 | 150.4* | ±15.2 | 58.5 | ±5.8 | 1.571 | 24.0 | ±5.5 | 140.4 | ±12.8 | 2.03* | ±0.22 |
| 16 | 150.2* | ±15.3 | 59.4 | ±5.7 | 1.529 | 22.0 | ±5.3 | 140.1 | ±12.7 | 2.04* | ±0.23 |
| 47 | 150.1 | ±15.4 | 53.4 | ±6.4 | 1.811 | 20.4 | ±5.1 | 140.3 | ±12.3 | 2.03* | ±0.22 |
| 23 | 147.6* | ±15.0 | 58.9 | ±6.2 | 1.506 | 20.2 | ±5.1 | 133.1* | ±12.6 | 2.06* | ±0.27 |
| 49 | 132.7*** | ±17.0 | 58.0 | ±5.2 | 1.288 | 18.3** | ±4.9 | 128.4*** | ±13.0 | 2.02* | ±0.26 |

TABLE 12

| Sample (Example No.) | TC Diff. mg/dl | % of diff. | HDL—C Diff. mg/dl | % of diff. | AI Diff. | % of diff. | TG Diff. mg/dl | % of diff. | PL Diff. mg/dl | % of diff. | LPO Diff. nmol/ml | % of diff. |
|---|---|---|---|---|---|---|---|---|---|---|---|---|
| 12 | −16.7 | −10.0 | −0.2 | −0.3 | −0.276 | −14.9 | −0.8 | −3.2 | −8.0 | −5.4 | −0.31 | −13.2 |
| 16 | −16.9 | −10.1 | +0.7 | +1.2 | −0.318 | −17.2 | −2.8 | −11.3 | −8.3 | −5.6 | −0.30 | −12.8 |
| 47 | −17.0 | −10.2 | −5.3 | −9.0 | −0.036 | −1.9 | −4.4 | −17.7 | −8.1 | −5.5 | −0.31 | −13.2 |
| 23 | −19.5 | −11.7 | +0.2 | +0.3 | −0.341 | −18.5 | −4.6 | −18.5 | −15.3 | −10.3 | −0.28 | −12.0 |
| 49 | −34.4 | −20.6 | −0.7 | −1.2 | −0.559 | −30.3 | −6.5 | −26.2 | −20.0 | −13.5 | −0.32 | −13.7 |

TABLE 13

| Sample (Example No.) | TC mg/dl | SD | HDL—C mg/dl | SD | AI | TG mg/dl | SD | PL mg/dl | SD | LPO nmol/ml | SD |
|---|---|---|---|---|---|---|---|---|---|---|---|
| C | 205.1 | ±27.4 | 81.5 | ±10.1 | 1.517 | 34.3 | ±4.8 | 173.6 | ±11.0 | 2.27 | ±0.38 |
| 100-1 | 174.3* | ±30.4 | 79.1 | ±9.4 | 1.204 | 28.3* | ±6.0 | 150.0*** | ±11.4 | 1.51*** | ±0.30 |
| 100-2 | 166.7** | ±28.1 | 94.1** | ±9.3 | 0.772 | 21.6*** | ±5.6 | 143.0*** | ±10.6 | 1.59*** | ±0.33 |
| 100-3 | 176.6* | ±32.3 | 73.8 | ±10.3 | 1.393 | 35.1 | ±7.3 | 152.9*** | ±10.6 | 1.89* | ±0.26 |

TABLE 14

| Sample (Example No.) | TC Diff. mg/dl | % of diff. | HDL—C Diff. mg/dl | % of diff. | AI Diff. | % of diff. | TG Diff. mg/dl | % of diff. | PL Diff. mg/dl | % of diff. | LPO Diff. nmol/ml | % of diff. |
|---|---|---|---|---|---|---|---|---|---|---|---|---|
| 100-1 | −30.8 | −15.0 | −2.4 | −3.0 | −0.313 | −20.6 | −6.0 | −17.6 | −23.1 | −13.3 | −0.76 | −33.5 |
| 100-2 | −38.4 | −18.7 | +15.1 | +18.5 | −0.745 | −49.1 | −12.7 | −37.0 | −30.6 | −17.6 | −0.68 | −29.8 |
| 100-3 | −28.5 | −13.9 | −7.7 | −9.4 | −0.124 | −8.2 | +0.8 | +2.3 | −20.7 | −11.9 | −0.38 | −16.7 |

TABLE 15

| Sample | TC mg/dl | SD | HDL—C mg/dl | SD | AI | TG mg/dl | SD | PL mg/dl | SD | LPO nmol/ml | SD |
|---|---|---|---|---|---|---|---|---|---|---|---|
| C | 307.3 | ±95.9 | 13.5 | ±3.8 | 21.8 | 56.5 | ±20.6 | 142.5 | ±30.9 | 2.80 | ±0.38 |
| 1 | 190.1** | ±51.3 | 10.3** | ±1.4 | 17.5 | 55.1 | ±12.4 | 140.2 | ±40.2 | 2.68 | ±0.45 |
| 2 | 191.5** | ±46.8 | 15.0 | ±5.0 | 12.0 | 53.4 | ±17.4 | 138.6 | ±38.2 | 2.60 | ±0.40 |

TABLE 15-continued

| | TC | | HDL—C | | | TG | | PL | | LPO | |
|---|---|---|---|---|---|---|---|---|---|---|---|
| Sample | mg/dl | SD | mg/dl | SD | AI | mg/dl | SD | mg/dl | SD | nmol/ml | SD |
| 3 | 191.2** | ±48.4 | 12.8 | ±3.2 | 14.8 | 53.3 | ±19.2 | 133.3 | ±25.2 | 2.71 | ±0.32 |

[Notes]
In Sample column,
C: Serum of the control group of 16 rats given the hyperlipidemic diet in Tables 15 to 22.
1: Serum of the group of 8 rats given the hyperlipidemic diet containing 1% of cycloartenol as a control drug in Tables 15 to 18 and 21.
2: Serum of the group of 8 rats given the hyperlipidemic diet containing 1% of cyclobranol as a control drug in Tables 15 to 18 and 21.
3: Serum of the group of 8 rats given the hyperlipidemic diet containing 1% of 24-methylencycloartanol as a control drug in Tables 15 to 18 and 21.

TABLE 16

| | TC | | HDL—C | | AI | | TG | | PL | | LPO | |
|---|---|---|---|---|---|---|---|---|---|---|---|---|
| Sample (Example No.) | Diff. mg/dl | % of diff. | Diff. mg/dl | % of diff. | Diff. | % of diff. | Diff. mg/dl | % of diff. | Diff. mg/dl | % of diff. | Diff. nmol/ml | % of diff. |
| 1 | −117.2 | −38.1 | −3.2 | −23.7 | −4.3 | −19.7 | −1.4 | −2.5 | −2.3 | −1.6 | −0.12 | −4.3 |
| 2 | −115.8 | −37.7 | +1.5 | +11.1 | −9.8 | −45.0 | −3.1 | −5.5 | −3.9 | −2.7 | −0.20 | −7.1 |
| 3 | −116.1 | −37.8 | −0.7 | −5.2 | −7.0 | −32.1 | −3.2 | −5.7 | −9.2 | −6.5 | −0.09 | −3.2 |

TABLE 17

| | TC | | HDL—C | | | TG | | PL | | LPO | |
|---|---|---|---|---|---|---|---|---|---|---|---|
| | mg/dl | SD | mg/dl | SD | AI | mg/dl | SD | mg/dl | SD | nmol/ml | SD |
| Sample | | | | | | | | | | | |
| C | 307.3 | ±95.9 | 13.5 | ±3.8 | 21.76 | 56.5 | ±20.6 | 140.1 | ±28.5 | 2.82 | ±0.40 |
| N | 43.4*** | ±8.3 | 29.9*** | ±6.7 | 0.452 | 54.0 | ±12.1 | 67.3*** | ±10.0 | 1.82*** | ±0.25 |
| 1 | 202.4*** | ±48.3 | 10.3** | ±1.4 | 18.65 | 54.2 | ±14.4 | 127.6 | ±25.8 | 2.62 | ±0.35 |
| 2 | 197.5** | ±45.7 | 15.2 | ±5.6 | 11.99 | 53.3 | ±13.6 | 130.3 | ±25.2 | 2.60 | ±0.32 |
| 3 | 198.3** | ±45.6 | 15.1 | ±5.0 | 12.13 | 54.2 | ±15.2 | 128.4 | ±24.8 | 2.58 | ±0.34 |
| 4 | 190.3** | ±45.0 | 15.3 | ±4.8 | 11.44 | 52.8 | ±18.4 | 127.6 | ±26.0 | 2.25** | ±0.35 |
| Example | | | | | | | | | | | |
| 114 | 138.2*** | ±40.3 | 24.2*** | ±5.6 | 4.711 | 39.0* | ±14.6 | 96.7*** | ±20.0 | 2.04*** | ±0.22 |
| 116 | 140.1*** | ±38.3 | 61.4*** | ±16.4 | 1.282 | 54.0 | ±19.0 | 97.4*** | ±19.1 | 2.11*** | ±0.20 |
| 118 | 139.5*** | ±39.3 | 47.4*** | ±17.0 | 1.943 | 51.4 | ±19.4 | 98.3*** | ±16.9 | 2.08*** | ±0.18 |
| 120 | 203.2** | ±47.4 | 24.6** | ±8.7 | 7.260 | 53.0 | ±18.0 | 105.3** | ±20.1 | 2.06*** | ±0.20 |
| 140 | 197.4** | ±45.2 | 54.8*** | ±17.0 | 2.602 | 52.4 | ±18.4 | 98.0*** | ±17.3 | 2.02*** | ±0.21 |
| 130 | 201.3** | ±44.2 | 21.0** | ±6.8 | 8.586 | 53.4 | ±18.0 | 107.2** | ±19.0 | 2.07*** | ±0.23 |
| 146 | 198.4** | ±47.5 | 23.4*** | ±5.8 | 7.479 | 51.4 | ±17.4 | 97.6*** | ±18.2 | 2.02*** | ±0.20 |

[Notes]
N: Serum of the group of 8 rats given the ordinary diet. The same applies in the following tables.
4: Serum of the group of 8 rats given the hyperlipidemic diet containing 1% of γ-orizanol.
Example No.: Serum of the group of 8 rats given the hyperlipidemic diet containing 1% of compounds of example numbers each in Tables 17 to 22.
These notations are applied to the following tables.

TABLE 18

| | TC | | HDL—C | | AI | | TG | | PL | | LPO | |
|---|---|---|---|---|---|---|---|---|---|---|---|---|
| | Diff. mg/dl | % of diff. | Diff. mg/dl | % of diff. | Diff. | % of diff. | Diff. mg/dl | % of diff. | Diff. mg/dl | % of diff. | Diff. nmol/ml | % of diff. |
| Sample | | | | | | | | | | | | |
| N | −263.9 | −85.9 | +16.4 | +121.5 | −21.31 | −97.9 | −2.5 | −4.4 | −72.8 | −52.0 | −1.0 | −35.5 |
| 1 | −104.9 | −34.1 | −3.2 | −23.7 | −3.11 | −14.3 | −4.1 | −7.1 | −12.5 | −8.9 | −0.2 | −7.1 |
| 2 | −109.8 | −35.7 | +1.7 | +12.6 | −9.77 | −44.9 | −3.2 | −5.7 | −9.8 | −7.0 | −0.22 | −7.8 |
| 3 | −109.0 | −35.5 | +1.6 | +11.9 | −9.63 | −44.3 | −2.3 | −4.1 | −11.7 | −8.4 | −0.24 | −8.5 |
| 4 | −117.0 | −38.1 | +1.8 | +13.3 | −10.32 | −47.4 | −3.7 | −6.5 | −12.5 | −8.9 | −0.57 | −20.2 |
| Example | | | | | | | | | | | | |
| 114 | −169.1 | −55.0 | +10.7 | +79.3 | −17.05 | −78.4 | −17.5 | −31.0 | −43.4 | −31.0 | −0.78 | −27.7 |
| 116 | −167.2 | −54.4 | +47.9 | +354.8 | −20.48 | −94.1 | −6.1 | −10.8 | −42.7 | −30.5 | −0.71 | −25.2 |
| 118 | −168.2 | −54.6 | +33.9 | +251.1 | −19.82 | −91.9 | −5.1 | −9.0 | −41.8 | −29.8 | −0.74 | −26.2 |
| 120 | −104.1 | −33.9 | +11.1 | +82.2 | −14.5 | −66.6 | −3.5 | −6.2 | −34.8 | −24.8 | −0.76 | −27.0 |
| 140 | −109.9 | −35.8 | +41.3 | +305.9 | −19.16 | −88.0 | −4.1 | −7.3 | −42.1 | −30.0 | −0.80 | −28.4 |
| 130 | −106.0 | −34.5 | +7.5 | +55.6 | −13.17 | −60.5 | −3.1 | −5.5 | −32.9 | −23.5 | −0.75 | −26.6 |
| 146 | −108.9 | −38.1 | +9.9 | +73.3 | −14.28 | −65.6 | −5.1 | −9.0 | −42.5 | −30.3 | −0.80 | −28.4 |

TABLE 19

| | TC | | HDL-C | | | TG | | PL | | LPO | |
|---|---|---|---|---|---|---|---|---|---|---|---|
| Sample | mg/dl | SD | mg/dl | SD | AI | mg/dl | SD | mg/dl | SD | nmol/ml | SD |
| C | 364.6 | ±113.8 | 19.6 | ±5.4 | 17.60 | 71.4 | ±29.5 | 158.7 | ±31.7 | 2.84 | ±0.41 |
| N | 73.13*** | ±24.6 | 39.7*** | ±9.3 | 0.842 | 71.5 | ±19.4 | 90.3*** | ±9.4 | 1.75*** | ±0.20 |
| Example | | | | | | | | | | | |
| 167 | 271.0** | ±43.4 | 79.6*** | ±16.5 | 2.405 | 67.1 | ±18.6 | 126.4* | ±16.4 | 2.28** | ±0.29 |

TABLE 19-continued

| | TC | | HDL-C | | | TG | | PL | | LPO | |
|---|---|---|---|---|---|---|---|---|---|---|---|
| Sample | mg/dl | SD | mg/dl | SD | AI | mg/dl | SD | mg/dl | SD | nmol/ml | SD |
| 173 | 272.8** | ±40.5 | 58.4*** | ±9.0 | 3.671 | 65.2 | ±27.5 | 127.2* | ±16.3 | 2.23** | ±0.28 |
| 189 | 179.5*** | ±45.5 | 35.4*** | ±7.3 | 4.071 | 58.4 | ±17.5 | 115.0** | ±15.6 | 2.05*** | ±0.22 |
| 177 | 245.5** | ±43.0 | 32.5*** | ±6.0 | 6.554 | 63.1 | ±26.4 | 125.8* | ±16.5 | 2.29** | ±0.30 |
| 205 | 192.4*** | ±41.3 | 37.4*** | ±9.4 | 4.144 | 60.3 | ±21.2 | 113.1** | ±17.0 | 2.02*** | ±0.20 |
| 212 | 195.0*** | ±41.9 | 37.2** | ±9.0 | 4.242 | 59.7 | ±18.9 | 112.9** | ±17.2 | 2.01*** | ±0.21 |
| 183 | 244.0** | ±42.0 | 29.2** | ±8.5 | 7.356 | 65.2 | ±22.5 | 125.7* | ±18.1 | 2.08*** | ±0.22 |
| 191 | 188.4*** | ±32.6 | 28.4** | ±8.0 | 5.634 | 60.4 | ±23.4 | 117.3** | ±16.9 | 2.08*** | ±0.23 |
| 197 | 221.6*** | ±38.5 | 27.1** | ±6.4 | 7.177 | 61.2 | ±24.4 | 115.5** | ±14.9 | 2.05*** | ±0.21 |

TABLE 20

| | TG | | HDL-C | | AI | | TG | | PL | | LPO | |
|---|---|---|---|---|---|---|---|---|---|---|---|---|
| Sample | Diff. mg/dl | % of diff. | Diff. mg/dl | % of diff. | Diff. | % of diff. | Diff. mg/dl | % of diff. | Diff. mg/dl | % of diff. | Diff. n mol/ml | % of diff. |
| N | −365.4 | −8.7 | +11.4 | +71.3 | −24.22 | −96.3 | −28.1 | −34.6 | −82.4 | −46.6 | −2.32 | −66.9 |
| Sample | | | | | | | | | | | | |
| 171 | −221.6 | −53.0 | +8.2 | +51.3 | −18.02 | −71.6 | −15.7 | −19.3 | −58.4 | −33.0 | −1.25 | −36.0 |
| 170 | −157.0 | −37.5 | +19.7 | +123.1 | −18.83 | −74.9 | −17.8 | −21.9 | −51.1 | −28.9 | −0.49 | −14.1 |
| 178 | −226.9 | −54.2 | +34.4 | +215.0 | −22.35 | −88.9 | −22.8 | −28.0 | −49.8 | −28.2 | −1.27 | −36.6 |
| 195 | −223.1 | −53.3 | +33.7 | +210.6 | −22.22 | −88.3 | −23.5 | −28.9 | −60.4 | −34.2 | −1.29 | −37.2 |
| 213 | −229.0 | −54.7 | +52.4 | +327.5 | −23.38 | −93.0 | −23.7 | −29.2 | −61.5 | −34.8 | −1.35 | −38.9 |
| 113 | −164.7 | −39.4 | +8.9 | +55.6 | −15.96 | −63.5 | −20.9 | −25.7 | −52.5 | −29.7 | −0.42 | −12.1 |
| 117 | −157.9 | −37.7 | +10.1 | +63.1 | −16.17 | −64.3 | −17.6 | −21.6 | −50.0 | −28.3 | −0.85 | −24.5 |

TABLE 21

| | Body weight during feed period (g ± SD) | | | | | Body weight just before blood sampling (g ± SD) |
|---|---|---|---|---|---|---|
| Sample | 1st day | 8th day | 15th day | 22nd day | 28th day | 29th day |
| C | 105 ± 4.0 | 143 ± 9.0 | 181 ± 20.8 | 231 ± 21.8 | 266 ± 22.2 | 252 ± 21.7 |
| N | 106 ± 3.9 | 162*** ± 5.5 | 226*** ± 9.0 | 284*** ± 14.7 | 319*** ± 15.2 | 297*** ± 17.4 |
| 1 | 105 ± 3.6 | 144 ± 9.8 | 191 ± 18.0 | 241 ± 20.4 | 272 ± 20.7 | 258 ± 20.2 |
| 2 | 104 ± 3.7 | 147 ± 8.4 | 191 ± 12.8 | 240 ± 16.9 | 268 ± 20.4 | 258 ± 20.4 |
| 3 | 106 ± 4.2 | 147 ± 9.6 | 192 ± 16.2 | 240 ± 16.7 | 267 ± 13.2 | 258 ± 19.2 |
| 4 | 104 ± 3.1 | 147 ± 8.1 | 191 ± 12.8 | 241 ± 16.8 | 269 ± 13.4 | 258 ± 18.4 |
| Example | | | | | | |
| 114 | 105 ± 3.3 | 145 ± 9.5 | 194 ± 18.0 | 247 ± 16.6 | 277 ± 14.9 | 265 ± 14.5 |
| 116 | 106 ± 5.9 | 146 ± 10.0 | 193 ± 17.5 | 244 ± 15.8 | 273 ± 20.4 | 260 ± 19.0 |
| 118 | 106 ± 3.4 | 147 ± 9.2 | 192 ± 17.8 | 243 ± 15.4 | 274 ± 18.4 | 259 ± 20.4 |
| 120 | 105 ± 3.2 | 144 ± 9.4 | 191 ± 18.2 | 242 ± 15.7 | 272 ± 20.1 | 258 ± 23.0 |
| 140 | 105 ± 3.6 | 147 ± 9.5 | 194 ± 17.2 | 246 ± 15.8 | 273 ± 18.7 | 261 ± 15.6 |
| 130 | 105 ± 3.3 | 144 ± 9.3 | 194 ± 18.1 | 245 ± 15.7 | 271 ± 18.0 | 258 ± 20.2 |
| 146 | 106 ± 5.9 | 149 ± 11.0 | 193 ± 17.5 | 243 ± 15.8 | 271 ± 20.2 | 258 ± 19.1 |

TABLE 22

| | Body weight during feed period (g ± SD) | | | | | Body weight just before blood sampling (g ± SD) |
|---|---|---|---|---|---|---|
| Sample | 1st day | 8th day | 15th day | 22nd day | 28th day | 29th day |
| C | 105 ± 4.0 | 144 ± 9.5 | 182 ± 20.9 | 233 ± 22.4 | 268 ± 22.3 | 253 ± 22.0 |
| N | 106 ± 4.0 | 163*** ± 5.8 | 227*** ± 8.9 | 286*** ± 14.0 | 320*** ± 14.8 | 298*** ± 16.8 |
| Example | | | | | | |
| 167 | 105 ± 3.4 | 143 ± 10.4 | 191 ± 18.4 | 241 ± 21.7 | 272 ± 20.8 | 259 ± 20.6 |
| 173 | 105 ± 3.6 | 142 ± 10.5 | 190 ± 18.2 | 240 ± 23.5 | 271 ± 24.2 | 258 ± 23.6 |
| 189 | 104 ± 3.8 | 142 ± 8.1 | 188 ± 12.6 | 239 ± 20.6 | 268 ± 22.7 | 256 ± 20.2 |
| 177 | 104 ± 3.9 | 142 ± 9.6 | 187 ± 12.8 | 238 ± 21.2 | 267 ± 25.2 | 256 ± 27.1 |
| 205 | 105 ± 3.7 | 142 ± 9.8 | 188 ± 13.2 | 238 ± 19.8 | 267 ± 20.4 | 256 ± 19.2 |
| 212 | 104 ± 3.3 | 143 ± 9.2 | 190 ± 18.6 | 239 ± 15.8 | 268 ± 21.4 | 257 ± 19.0 |
| 183 | 105 ± 3.9 | 142 ± 8.8 | 189 ± 11.9 | 239 ± 16.5 | 268 ± 20.9 | 257 ± 18.8 |
| 191 | 104 ± 3.7 | 142 ± 9.6 | 188 ± 12.9 | 239 ± 14.9 | 268 ± 21.7 | 257 ± 20.6 |
| 197 | 104 ± 3.4 | 142 ± 8.4 | 188 ± 13.6 | 239 ± 16.2 | 268 ± 20.8 | 257 ± 20.4 |

TABLE 23

| Sample | TC | | HDL-C | | | TG | | PL | | LPO | |
|---|---|---|---|---|---|---|---|---|---|---|---|
| (Example No.) | mg/dl | SD | mg/dl | SD | AI | mg/dl | SD | mg/dl | SD | nmol/ml | SD |
| C | 326.2 | ±101.4 | 36.9 | ±8.0 | 7.840 | 34.0 | ±6.4 | 165.6 | ±13.9 | 2.80 | ±0.42 |
| 101 | 216.6** | ±63.3 | 46.4* | ±7.5 | 3.668 | 28.2* | ±5.7 | 150.7* | ±15.7 | 2.12*** | ±0.25 |

TABLE 23-continued

| Sample | TC | | HDL-C | | | TG | | PL | | LPO | |
|---|---|---|---|---|---|---|---|---|---|---|---|
| (Example No.) | mg/dl | SD | mg/dl | SD | AI | mg/dl | SD | mg/dl | SD | nmol/ml | SD |
| 102 | 205.0** | ±58.4 | 48.1** | ±7.2 | 3.262 | 26.7* ±5.9 | | 140.9*** | ±11.2 | 2.02*** | ±0.18 |
| 104 | 204.8** | ±57.8 | 48.7** | ±7.3 | 3.205 | 27.4* ±6.2 | | 143.7** | ±12.0 | 2.01*** | ±0.20 |
| 108 | 215.6** | ±59.5 | 46.6* | ±9.0 | 3.627 | 29.0 ±6.6 | | 151.4* | ±15.4 | 2.20** | ±0.18 |
| 112 | 216.4*** | ±60.4 | 46.8* | ±8.5 | 3.624 | 28.5 ±6.3 | | 150.4* | ±15.7 | 2.16*** | ±0.20 |

TABLE 24

| Sample | TC | | HDL-C | | AI | | TG | | PL | | LPO | |
|---|---|---|---|---|---|---|---|---|---|---|---|---|
| (Example No.) | Diff. mg/dl | % of diff. | Diff. mg/dl | % of diff. | Diff. | % of diff. | Diff. mg/dl | % of diff. | Diff. mg/dl | % of diff. | Diff. nmol/ml | % of diff. |
| 101 | −109.6 | −33.6 | +9.5 | +25.7 | −4.172 | −53.2 | −5.8 | −17.1 | −14.9 | −9.0 | −0.68 | −24.3 |
| 102 | −121.2 | −37.2 | +11.2 | +30.4 | −4.578 | −58.4 | −7.3 | −21.5 | −24.7 | −14.9 | −0.78 | −27.9 |
| 104 | −121.4 | −37.2 | +11.8 | +32.0 | −4.635 | −59.1 | −6.6 | −19.4 | −21.9 | −13.2 | −0.79 | −28.2 |
| 108 | −110.6 | −33.9 | +9.7 | +26.3 | −4.213 | −53.7 | −5.0 | −14.7 | −14.2 | −8.6 | −0.60 | −21.4 |
| 112 | −109.8 | −33.7 | +9.9 | +26.8 | −4.216 | −53.8 | −5.5 | −16.2 | −15.2 | −9.2 | −0.64 | −22.9 |

In the anti-hyperlipidemic assay according to method A, the daily dosage of each compound according to the present invention was 1% of 10 g/day of the hyperlipidemic diet, i.e. 100 mg. For instance, cyclobranyl esters of m-, o-, and p-aminobenzoic acid (Examples 49, 47, and 43), cyclobranyl ester of linoleic acid (Example 51), and cyclobranyl ester of nicotinic acid (Example 50) (100 mg each) contain the bound m-, o-, and p-aminobenzoic acids (24.5 mg each), linoleic acid (39.9 mg), and nicotinic acid (22.6 mg), respectively.

These organic acids in free form were added each to the hyperlipidemic diet, and the resulting diets (10 g/day each) were administered to rats in the same manner as in the above anti-hyperlipidemic assay, but the anti-hyperlipidemic effect was not observed with the above doses (22.6–39.9 mg/day) of the free acids. Thus, it has been confirmed that the effect of the compounds of Examples 49, 47, 43, 51, and 50 is not attributable to the m-, o-, or p-aminobenzoic acid, linoleic acid, or nicotinic acid combining with cyclobranol.

In method B, the dosage of each compound according to the present invention is roughtly calculated as 210 mg/day for each rat at most from the amount of the fed diet containing the compound. For example, cycloartenyl ester of 4-hydroxy-3 -methoxy-α-methylcinnamic acid (Example 114), cyclobranyl ester of 3-ethoxy-4-hydroxy-α-methylcinnamic acid (Example 140), cylobranyl ester of 5-amino-2-methoxybenzoic acid (Example 173), cycloartenyl ester of p-amino-α-methylcinnamic acid (Example 205), and cyclobranonyl ester of m-amino-α-methylcinnamic acid (Example 212) (210 mg each) contain the bound 4-hydroxy-3-methoxy-α-methylcinnamic acid (70.8 mg), 3-ethoxy-4-hydroxy-α-methylcinnamic acid (72.5 mg), 5-amino-2-methoxybenzoic acid (59.4 mg), p-amino-α-methylcinnamic acid (63.4 mg), and m-amino-α-methylcinnamic acid (62.0 mg), respectively.

These organic acids in free form were added each to the hyperlipidemic diet, and the resulting diets were administered to rats in the same manner as in the above anti-hyperlipidemic assay, but the anti-hyperlipidemic effect was not observed with the above doses (59.4–72.5 mg/day) of the free acids. Thus, it has been proved that the effect of the compound according to the present invention is not attributable to the organic acid liberated by the hydrolysis of the triterpeny ester of organic acid.

Of the compounds according to the present invention, the most favorable as anti-hyperlipidemic agents are esters from combinations of the triterpenyl alcohols with substituted cinnamic, α-($C_1$-$C_4$ alkyl) cinnamic, and benzoic acid which have one or two substituents on the benzene ring, the one substituent being a hydroxyl or amino group and the two being $C_1$-$C_4$ alkoxy and hydroxyl groups or $C_1$-$C_4$ alkoxy and amino groups.

For clinical use, the compounds of the invention can be administered parenterally or preferably orally. Suitable forms of the compounds for oral dosage are of tablets (uncoated or coated with sugar or the like), granules, powders, coated tablets, sugar-coated tablets, capsules, emulsions, etc. which additionally contain pharmaceutically acceptable carriers. For example, the carriers include lactose, white sugar, mannitol, anhydrous dextrose, starch, sorbitol, glycine, potassium phosphate, and microcrystalline cellulose as excipients; starch, gelatin, gum arabic, anhydrous dextrose, white sugar, sorbitol, mannitol, traganth, hydroxypropylcellulose, hydroxypropoxymethylcellulose, carboxymethylcellulose, 2-methyl-5-vinylpyridinemethacrylic acid-methyl acrylate copolymer, polyvinylpyrrolidone, and sodium aliginate as binders; stearic acid, hardened oil, magnesium stearate, calcium stearate, polyoxyethylene monostearate, talc, silicon oxide, and polyethylene glycol as lubricants; potato starch and starch containing a surfactant or the like, as disintegrating agents; and sodium laurylsulfate as a wetting agent. For parenteral dosage, the present compounds can be used in the form of intramuscular-injectable or suppository composition. Base materials for the suppository include cacao butter, Witepsol, Subanal, polyethylene glycol, polypropylene glycol, glycerogelatin, gelatin capsules, etc. In addition, the suppository may contain a known safety preservative such as methyl p-hydroxybenzoate, propyl p-hydroxybenzoate, butyl p-hydroxybenzoate, or butylhydroxyanisole, and pharmaceutically acceptable coloring matter.

While depending upon the mode of administration, the age, weight, and conditions of the patient, and the kind of disease, daily doses of the present compounds for man are generally from 0.01 to 5 g, preferably from 0.02 to 1.5 g.

Triterpenyl alcohols for the novel esters of the present invention include also lanosterol, lanostenol, agnosterol, cyclosadol (3β-hydroxy-24-methylene-9,19-cylo-9β-lanosta-23-ene), dihydroagnosterol, cyclolaudenol, cycloartanol, cycloeucalenol, euphol, butyrospermol, tirucallol, euphorbol, and dammerrdienol, besides cycloartenol, cyclobranol, and 24-methylenecycloartanol mentioned above. Further, anti-hyperlipidemic effect can also be expected for the esters of the organic acids, defined above, combined with sterols, e.g. dihydro-β-sitosterol, dihydro-γ-sitosterol, campesterol, β-sitosterol, γ-sitosterol, stigmasterol, 24-methylenecholesterol, episterol, and 22-dihydroergosterol, which are analogous in structure to triterpenyl alcohols.

EXAMPLE 1

Preparation of cycloartenyl-3,4-diacetoxycinnamate

Toluene (20 ml) was added to 3,4-diacetoxycinnamic acid (4.65 g, 0.018 mole) and cooled to 0° C. Thionyl chloride (10.0 ml, 10 equivalents) was added dropwise thereto and further pyridine (0.5 ml) was added. The reaction mixture was conducted at 60° C. for 3 hours. Then, the resulting mixture was evaporated to dryness under reduced pressure and cycloartenol (5.0 g, 0.012 mole) and pyrydine (50 ml) were added thereto and the mixture was stirred at 60° C. for 1 hour. Thereafter, the solvent was removed by distillation under diminished pressure. The residue was dissolved in chloroform, and the solution was washed with saturated aqueous solution of sodium bicarbonate. The aqueous layer was extracted with chloroform (3×50 ml). The combined chloroform layer was dried, concentrated under reduced pressure, and purified by silica gel column chromatography (solvent:ethyl acetate-hexane (1:9, V/V)), giving cycloartenyl-3,4-diacetoxycinnamate (5.6 g) in a 71% yeild, m.p. 125.5°–126.5° C.

Specific rotation $[\alpha]_D^{24}$ +36.6° (C 1.00, CHCl$_3$).

Analysis, Calcd. for $C_{43}H_{60}O_6$ (M.W. 672.91): C, 76.75; H, 8.99. Found: C, 76.82; H, 9.04.

IR$\nu$, KBr (cm$^{-1}$): 2930, 2860, 1773, 1710, 1637, 1502, 1370, 1257, 1205, 1176.

PMR (CDCl$_3$)δ: 0.39 (1H, ½ ABq, 4.2 Hz), 0.60 (1H, ½ ABq, 4.2 Hz), 0.70–2.40 (27H, m), 0.90 (6H, s), 0.96 (6H, s), 1.61 (3H, bs), 1.68 (3H, bs), 2.31 (6H, s), 4.40–5.40 (2H, m), 6.40 (1H, ½ ABq, 16 Hz), 7.00–7.60 (3H, m), 7.58 (1H, ½ ABq, 16 Hz).

EXAMPLE 2

Preparation of cycloartenyl-3,4-dihydroxycinnamate

Dioxane (540 ml) was added to cycloartenyl-3,4-diactoxycinnamate (27.0 g, 0.040 mole) prepared according to the procedure of Example 1. To the mixture cooled to 0° C. was added dropwise 25% aqueous ammonia (27 ml), and this reaction mixture was stirred at 20° C. for 1 hour. Then the resulting mixture was evaporated to dryness under reduced pressure to give crude crystals, which were then washed with water and recrystallized from acetone-water (1:1, V/V), thereby giving cycloartenyl-3,4-dihydroxycinnamate (21.1 g) in a 89% yield m.p. 230°–231° C.

Specific rotation $[\alpha]_D^{23}$ +44.7° (C 0.19, CHDCl$_3$).

Analysis, Calcd. for $C_{39}H_{56}O_4$ (M.W. 588.84): C, 79.54; H, 9.59. Found: C, 79.62; H, 9.52.

IR$\nu$, KBr (cm$^{-1}$): 3470, 3300, 2910, 2850, 1680, 1602, 1525, 1440, 1275, 1180, 972.

PMR (CDCl$_3$-DMSO-d$_6$)δ: 0.20–0.70 (2H, m), 0.40–2.40 (27H, m), 0.90 (6H, s), 0.94 (6H, s), 1.58 (3H, bs), 1.65 (3H, bs), 4.30–4.80 (1H, m), 4.80–5.30 (1H, m), 6.17 (1H, ½ ABq, 15 Hz), 6.60–7.20 (2H, m), 6.99 (1H, bs), 7.40 (1H, ½ ABq, 15 Hz), 8.87 (1H, bs), 9.25 (1H, bs).

EXAMPLE 3

Preparation of Cycloartenyl-3,4-dipropionyloxycinnamate

Toluene (26 ml) and thionyl chloride (34ml, 4.6 equivalents) were added to 3,4-dipropionyloxycinnamic acid (29.0 g) at 0° C. This reaction mixture was stirred at 60° C. for 20 minutes. Then, the resulting mixture was evaporated to dryness under reduced pressure, and the residue was dissolved again in toluene (50 ml). To the mixture cooled to 0° C. was added a solution of cycloartenol (30.0 g, 0.070 mole) in pyridine (60 ml) and the whole was stirred at 20° C. for 1 hour. Then, the solvent was removed by distillation under diminished pressure. The resulting residue was dissolved in chloroform, and the solution was washed with saturated aqueous solution of sodium bicarbonate. The aqueous layer was extracted with chloroform (3×500 ml). The combined chloroform layer was dried and evaporated to dryness under reduced pressure. The residue was purified by silica gel column chromatography (solvent: methylenechloride), giving cycloartenyl-3,4-dipropionyloxycinnamate (35.7 g) in a 72% yield.

EXAMPLE 4

Preparation of cycloartenyl-3,4-dihydroxycinnamate

Dioxane (20 ml) was added to cycloartenyl-3,4-dipropionyloxycinnamate (1.0 g, 1.43 mmoles) prepared according to the procedure of Example 3 and was stirred at 0° C. Thereto was added dropwise 25% aqueous ammonia (2.0 ml) and the whole was stirred at 20° C for 1 hour. The resulting mixture was evaporated to dryness under reduced pressure. The crude crystals were washed with water and recrystallized from acetone-water (1:1, V/V) giving cycloartenyl-3,4-dihydroxycinnamate (756 mg) in a 90% yield, m.p. 230°–231° C.

Specific rotation $[\alpha]_D^{23}$ +44.7° (C 0.19, CHCl$_3$)

Analysis, Calcd. for $C_{39}H_{56}O_4$ (M.W. 588.84): C, 79.54; H, 9.59. Found: C, 79.59; H, 9.63.

IR$\nu$, KBr (cm$^{-1}$): 3470, 3300, 2910, 2850, 1680, 1602, 1525, 1440, 1275, 1180, 972.

PMR (CDCl$_3$-DMSO-d$_6$)δ: 0.20–0.70 (2H, m), 0.40–2.40 (27H, m), 0.90 (6H, s), 0.94 (6H, s), 1.58 (3H, bs), 1.65 (3H, bs), 4.30–4.80 (1H, m), 4.80–5.30 (1H, m), 6.17 (1H, ½ ABq, 15 Hz), 6.60–7.20 (2H,m), 6.99 (1H, bs), 7.40 (1H, ½ ABq, 15 Hz), 8.87 (1H, bs), 9.25 (1H, bs).

EXAMPLE 5

Preparation of Cycloartenyl-p-Acetoxycinnam

Toluene (18 ml) was added to p-acetoxycinnamic acid (18.1 g, 0.088 mole) and the mixture was cooled to 0° C. Thionyl chloride (31 ml, 5 equivalents) and pyridine (1.0 ml) were added dropwise thereto, and the whole was heated at 60° C. for 15 minutes. After concentration of the resulting mixture, toluene (35 ml) and pyridine (50 ml) were added, and the whole was cooled to 0° C. Thereto was added dropwise a solution of cycloartenol (25.0 g, 0.059 mole) in pyridine (50 ml). The mixture was refluxed for 40 minutes and then evaporated to dryness under reduced pressure. The resulting residue was dissolved in chloroform, and the solution was washed with saturated aqueous solution of Sodium bicarbonate. The aqueous layer was extracted with chloroform (3×500 ml). The combined extracts was dried, and concentrated under reduced pressure. The residue was purified by silica gel column chromatography (solvent: methylene chloridehexane, (1:1, V/V)), giving cycloartenyl-p-acetoxycinnamate (32.0 g) in a 89% yield, m.p. 153°–156° C.

Specific rotation $[\alpha]_D^{21.5}+42.6°$ (C 1.02, CHCl$_3$)

Analysis, Calcd. for C$_{41}$H$_{58}$O$_4$ (M.W 614.87): C, 80.08; H, 9.51. Found: C, 80.13; H, 9.42.

IR$\nu$, KBr (cm$^{-1}$) 2920, 2850, 1765, 1695, 1500, 1370, 1270, 1195, 1160.

PMR (CDCl$_3$)δ: 0.39 (1H, ½ ABq, 4.2 Hz), 0.60 (1H, ½ ABq, 4.2 Hz), 0.70–2.40 (27H, m), 0.90 (6H, s), 0.96 (6H, s), 1.60 (3H, bs), 1.67 (3H, bs), 2.30 (3H, s), 4.50–5.30 (2H, m), 6 40 (1H, ½ ABq, 15 Hz), 6.90–7.80 (4H, m), 7.60 (1H, ½ ABq, 15 Hz).

EXAMPLE 6

Preparation of Cycloartenyl-p-Hydroxycinnamate

Cycloartenyl-p-acetoxycinnamate (28.0 g, 0.046 mole) prepared according to the procedure of Example 5 was dissolved in dioxane (280 ml). Then 25% aqueous ammonia (28 ml) was added dropwise to the solution at 0° C. The reaction mixture was stirred at 50° C. for 2 hours, and then evaporated to dryness under reduced pressure. The residue was recrystallized from acetone-water (1:1, V/V), giving cycloartenyl-p-hydroxycinnamate (23.4 g) in a 90% yield, m.p. 248°–248.5° C.

Specific rotation $[\alpha]_D^{26}+45.9°$ (C 0.98, CHCl$_3$)

IR$\nu$, KBr (cm$^{-1}$): 3190, 2930, 2850, 1705, 1670, 6105, 1582, 1512, 1440, 1280, 1170, 830.

PMR (CDCl$_3$-DMSO-d$_6$)δ: 0.20–0.80 (2H, m), 0.50–2.40 (27H, m), 0.88 (6H, s), 0.95 (6H, s), 1.57 (3H, bs), 1.64 (3H, bs), 4.30–4.84 (1H, m), 4.84–5.30 (1H, m), 6.28 (1H, ½ ABq, 15 Hz), 6.60–7.00 (2H, m), 7.20–7.60 (2H, m), 7.44 (1H, ½ ABq, 15 Hz), 9.75 (1H, bs).

EXAMPLE 7

Preparation of Cycloartenyl-o-Acetoxybenzoate

Thionyl chloride (39.0 ml, 5 equivalents) and pyridine (2.0 ml) were added dropwise to acetylsalicylic acid (19.0 g, 0.106 mole) in benzene (95 ml) with stirring at 20° C. This reaction mixture was stirred at 50° C. for 1 hour, and then evaporated to dryness under reduced pressure. Benzene (100 ml) was added thereto and the whole was stirred at 0° C., and cycloartenol (30.0 g, 0.070 mole) dissolved in pyridine (100 ml) was added and the whole was stirred at 50° for 20 minutes. After the reaction mixture was concentrated under reduced pressure, the residue was dissolved in methylene chloride, and the solution was washed with saturated aqueous solution of Sodium binarbonate. The aqueous layer was extracted with methylene chloride (3×500 ml). The combined extracts were dried, evaporated under reduced pressure to remove methylene chloride, and the residue was purified by silica gel column chromatography (solvent: toluene-methylene chloride, (1:1, V/V)), giving cycloartenyl-o-acetoxybenzoate (30.9 g) in a 75% yield, m.p. 138°–139° C.

Specific rotation $[\alpha]_D^{25}+61.4$(C 0.99, CHCl$_3$)

Analysis, Calcd. for C$_{39}$H$_{56}$O$_4$ (M.W. 588.84): C, 79.54; H, 9.59. Found: C, 79.47; H, 9.63.

IR$\nu$, KBr (cm$^{-1}$): 2993, 2850, 1768, 1715, 1605, 1447, 1288, 1260, 1190, 1120.

PMR (CDCl$_3$)δ:0.38 (1H, ½ ABq, 4.2 Hz), 0.59 (1H, ½ ABq, 4.2 Hz), 0.70–2.30 (27H, m), 0.81 (6H, s), 0.97 (3H, s), 1.00 (3H, s), 1.60 (3H, bs), 1.67 (3H, bs), 2.35 (3H, s), 4.50–5.30 (2H, m), 6.90–8.20 (4H, m).

EXAMPLE 8

Preparation of cycloartenyl-o-hydroxybenzoate

Sixty milliliter of 25% aqueous ammonia was added dropwise to cycloartenyl-o-acetoxybenzoate (30.0 g, 0.051 mole) in dioxane (600 ml) with stirring at 0° C. The reaction mixture was stirred at 55° C. for 4 hours. Then the solvent was removed by distillation under reduced pressure, the residue was dissolved in methylene chloride, and the solution was washed with saturated aqueous solution of Sodium bicarbonate. The aqueous layer was extracted with methylene chloride (3×500 ml). The combined extracts were dried and evaporated to dryness under reduced pressure. The residue was recrystallized from methylene chloridemethanol (1:5, V/V), giving cycloartenyl-o-hydroxybenzoate (26.2 g) in a 95% yield, m.p. 132°–133° C.

Specific rotation $[\alpha]_D^{25}+72.9°$ (C 1.01, CHCl$_3$)

Analysis, Calcd. for C$_{37}$H$_{54}$O$_3$ (M.W. 546.80): C, 81.27; H, 9.95. Found: C, 81.36; H, 9.90.

IR$\nu$KBr (cm$^{-1}$): 3130, 2910, 2850, 1663, 1610, 1480, 1295, 1245, 1210, 1155, 1090, 965, 760.

PMR (CDCl$_3$)δ: 0.39 (1H, ½ ABq, 4.2 Hz), 0.61 (1H, ½ ABq, 4.2 Hz), 0.60–2.30 (27H, m), 0.91 (6H, s), 0.98 (3H, s), 1.04 (3H, s), 1.60 (3H, bs), 1.68 (3H, bs), 4.60–5.30 (2H, m), 6.60–8.00 (5H, m).

EXAMPLE 9

Preparation of Cycloartenyl-p-Acetoxybenzoate

Thionyl chloride (52 ml, 5 equivalents) and Pyridine (1.0 ml) was added to p-acetoxybenzoic acid (25.4 g, 0.141 mole) in benzene (100 ml) with stirring at 0° C. The reaction mixture was stirred at 55° C. for 30 minutes, and evaporated under reduced pressure, then the residue was cooled to 5° C. After addition of benzene (200 ml) thereto, cycloartenol (40.0 g, 0.094 mole) dissolved in pyridine (200 ml) was added and the mixture was stirred at 60° C. for 30 minutes. Then the resulting mixture was concentrated under reduced pressure to remove the solvents. The residue was dissolved in chloroform, and the solution was washed with saturated aqueous solution of Sodium bicarbonate. The aqueous layer was extracted with chloroform (3×600 ml). The combined chloroform layer was dried and evaporated to dryness. The crude crystals were recrystallized from methylene chloride-methanol (1:5, V/V) giving cycloartenyl-p-acetoxybenzoate (52.5 g) in a 95% yield, m.p. 141°–142° C.

Specific rotation $[\alpha]_D^{25}+58.6°$ (C 1.00, CHCl$_3$)

Analysis, Calcd. for C$_{39}$H$_{56}$O$_4$ (M.W. 588.84): C, 79.54; H, 9.59. Found: C, 79.52; H, 9.68.

IR$\nu$, KBr (cm$^{-1}$): 2930, 2850, 1760, 1720, 1600, 1360, 1272, 1189, 1159, 1120.

PMR (CDCl$_3$)δ: 6: 0.40 (1H, ½ ABq, 4.2 Hz), 0.61 (1H, ½ ABq, 4.2 Hz), 0.60–2.30 (27H, m), 0.91 (6H, s), 0.98 (3H, s), 1.03 (3H, s), 1.60 (3H, bs), 1.69 (3H, bs), 2.32 (3H, s), 4.60–5.30 (2H, m), 6.96–7.40 (2H, m), 7.80–8.22 (2H, m).

EXAMPLE 10

Preparation of cycloartenyl-p-hydroxybenzoate

Dioxane (500 ml) was added to cycloartenyl-p-acetoxybenzoate (27.0 g, 0.046 mole) prepared according to the procedure of Example 1. Then 25% aqueous ammonia (50 ml) was added dropwise to the solution, and the reaction mixture was stirred at 20° C. for 2.5 hours. Then the mixture was evaporated under reduced pressure to remove the solvent. The resulting residue was purified by silica gel column chromatography (solvent: methylene chloride-ethanol, (98:2, V/V)), giving cycloartenyl-p-hydroxybenzoate containing a molecular ethanol in a 96% yield, m.p. 180°–182° C.

Specific rotation $[\alpha]_D^{25} + 66.1°$ (C 1.00, CHCl$_3$)

Analysis, Calcd. for C$_{37}$H$_{54}$O$_3$.C$_2$H$_5$OH (M.W. 592.87): C, 79.00; H, 10.20. Found: C, 79.11; H, 10.14.

IR$\nu$, KBr (cm$^{-1}$) 3450, 3150, 2950, 2850, 1715, 1689, 1612, 1600, 1515, 1310, 1280, 1160.

PMR (CDCl$_3$)δ: 0.39 (1H, ½ABq, 4.2 Hz), 0.60 (1H, ½ABq, 4.2 Hz), 0.60–2.30 (27H, m), 0.91 (6H, s), 0.97 (3H, s), 1.03 (3H, s), 1.60 (3H, bs), 1.68 (3H, bs), 4.50–5.30 (2H, m), 6.60–7.05 (2H, m), 6.88 (2H, ½ABq, 8.1 Hz), 7.11 (1H, bs), 7.60–8.20 (2H, m), 7.82 (2H, ½ABq, 8.1 Hz).

EXAMPLE 11

Preparation of cycloartenyl-m-acetoxybenzoate

Thionyl Chloride (52 ml, 5 equivalents) and Pyridine (0.5 ml) were added to m-acetoxybenzoic acid (25.0 g, 0.139 mole) in benzene (100 ml) with stirring at 0° C. The reaction mixture was stirred at 60° C. for 30 minutes and evaporated under reduced pressure. Benzene (200 ml) was added to the concentrate and the solution was stirred at 0° C. Cycloartenol (40.0 g, 0.094 mole) dissolved in pyridine (200 ml) was added dropwise thereto, and the reaction mixture was stirred at 60° C. for 1 hour. The resulting mixture was evaporated under reduced pressure, to give a crystalline residue. This residue was dissolved in chloroform, and the solution was washed with saturated aqueous solution of sodium bicarbonate. The aqueous layer was extracted with chloroform (3×500 ml). The combined extracts were dried, concentrated under reduced pressure and the residue was purified by silica gel column chromatography (solvent: methylene chloride-hexane, (2:1, V/V)) giving cycloartenyl-m-acetoxybenzoate (49.0 g) in a 89% yield, m.p. 122°–123° C.

Specific rotation $[\alpha]_D^{25.5} + 60.8°$ (C,0.99, CHCl$_3$)

Analysis, Calcd. for C$_{39}$H$_{56}$O$_4$ (M.W 588.84): C, 79.54; H, 9.59. Found: C, 79.60; H, 9.55.

IR$\nu$, KBr (cm$^{-1}$) 2930, 2850, 1769, 1715, 1585, 1440, 1370, 1280, 1275, 1212.

PMR (CDCl$_3$)δ: 0.39 (1H, ½ABq, 4.2 Hz), 0.61 (1H, ½ABq, 4.2 Hz), 0.60–2.30 (27H, m), 0.91 (6H, s), 0.98 (3H, s), 1.03 (3H, s), 1.60 (3H, bs), 1.68 (3H, bs), 2.32 (3H, s), 4.60–5.30 (2H, m), 7.10–8.05 (4H, m).

EXAMPLE 12

Preparation of cycloartenyl-m-hydroxybenzoate

Dioxane (400 ml) was added to cycloartenyl-m-acetoxybenzoate (27.0 g, 0.036 mole) prepared according to the procedure of Example 11. While stirring the mixture at 0° C., 25% aqueous ammonia (40 ml) was added dropwise. Then the reaction mixture was stirred at 40° C. for 1.5 hours. The resulting mixture was evaporated to dryness under reduced pressure. Then the residual crystals were dissolved in chloroform, and the solution was washed with saturated aqueous solution of Sodium bicarbonate. The aqueous layer was extracted with chloroform (3×300 ml). The combined extracts were dried and evaporated under reduced pressure, separating out crude crystals which were then recrystallized from methylene chloride-hexane (1:4, V/V), giving cycloartenyl-m-hydroxy benzoate (22.7 g) in a 91% yeild. m.p. 176°–177.5° C.

Specific rotation $[\alpha]_D^{25.5} + 65.4°$ (C 1.01, CHCl$_3$)

Analysis Calcd. for C$_{37}$H$_{54}$O$_3$ (M.W. 546.80): C, 81.27; H, 9.95. Found: C, 81.21; H, 9.99.

IR$\nu$, KBr (cm$^{-1}$) 3380, 2950, 2930, 2850, 1710, 1692, 1600, 1450, 1310, 1290, 1110, 970, 758.

PMR (CDCl$_3$)δ: 0.38 (1H, ½ABq, 4.2 Hz), 0.60 (1H, ½ABq, 4.2 Hz), 0.60–2.30 (27H, m), 0.90 (6H, s), 0.97 (3H, s), 1.02 (3H, s), 1.60 (3H, bs), 1.68 (3H, bs), 4.52–5.30 (2H, m), 6.90–7.70 (4H, m).

EXAMPLE 13

Preparation of cycloartenyl-o-methoxybenzoate

Cycloartenol (16.0 g, 0.038 ml) was dissolved in pyridine (160 ml). While the solution was stirred at 0° C., o-methoxybenzoyl chloride (7.0 ml, 1.2 equivalents) was added dropwise thereto and the mixture was allowed to react at 40° C. for 1 hour. Then the resulting mixture was evaporated under reduced pressure, and the crystalline residue was dissolved in chloroform, and the solution was washed with saturated aqueous solution of Sodium bicarbonate. The aqueous layer was extracted with chloroform (3×100 ml). The combined extracts were dried and evaporated to dryness under reduced pressure. The resulting crude crystals were recrystallized from methylene chloride-methanol (1:6, V/V), giving cycloartenyl-o-methoxybenzoate (18.0 g) in a 86% yield. m.p. 141°–142° C.

Specific rotation $[\alpha]_D^{25} + 47.5°$ (C 1.02, CHCl$_3$)

Analysis, Calcd. for C$_{38}$H$_{56}$O$_3$ (M.W. 560.83): C, 81.38; H, 10.07. Found: C, 81.33; H, 10.15.

IR$\nu$, KBr (cm$^{-1}$) 2930, 2850, 1720, 1696, 1598, 1460, 1298, 1250, 1130.

PMR (CDCl$_3$)δ: 0.38 (1H, ½ABq, 4.2 Hz), 0.60 (1H, ½ABq, 4.2 Hz), 0.60–2.30 (27H, m), 0.91 (3H, s), 0.96 (6H, s), 1.00 (3H, s), 1.60 (3H, bs), 1.67 (3H, bs), 3.88 (3H, s), 4.50–5.30 (2H, m), 6.70–8.00 (4H, m).

EXAMPLE 14

Preparation of cycloartenyl-p-methoxybenzoate

To a solution of cycloartenol (20.0 g, 0.047 mole) in pyridine (150 ml) cooled to 0° C., there was added dropwise p-methoxybenzoic chloride (9.5 ml, 1.2 equivalents), and the whole was stirred at 50° C. for 3 hours. The resulting mixture was evaporated to dryness under reduced pressure. The residual crystals were dissolved in chloroform, and the solution was washed with saturated aqueous solution of sodium bicarbonate. The aqueous layer was extracted with chloroform (3×200 ml). The combined extracts were dried and evaporated to dryness under reduced pressure. The crude crystals were recrystallized from methylene chloride-methanol (1:7, V/V), giving cycloroartenyl-p-methoxybenzoate (25.0 g) in a 95% yield. m.p. 129.5°–130° C.

Specific rotation $[\alpha]_D^{25} + 62.9°$ (C 0.99 CHCl$_3$)

Analysis, Calcd. for C$_{38}$H$_{56}$O$_3$ (M.W. 560.83): C, 81.38; H, 10.07. Found: C, 81.31; H, 10.15.

IR$\nu$, KBr (cm$^{-1}$): 2910, 2850, 1711, 1605, 1508, 1270, 1250, 1165, 1115, 1100.

PMR (CDCl$_3$)δ: 0.39 (1H, ½ABq, 4.2 Hz), 0.61 (1H, ½ABq, 4.2 Hz), 0.70–2.30 (27H, m), 0.91 (6H, s), 0.98 (3H, s), 1.03 (3H, s), 1.60 (3H, bs), 1.68 (3H, bs), 3.84 (3H, s), 6.70–7.05 (2H, m), 7.80–8.12 (2H, m).

EXAMPLE 15

Preparation of cycloartenyl-m-methoxybenzoate

Thionyl Chloride (24 ml, 5 equivalents) and pyridine (0.5 ml) were added to m-methoxybenzoic acid (9.6 g, 0.063 mole) in benzene (50 ml) with stirring at 0° C. The reaction mixture was stirred at 40° C. for 30 minutes. The resulting mixture was evaporated under reduced pressure and benzene (100 ml) was added to the residue. Cycloartenol (18.0 g, 0.042 mole) dissolved in pyridine (100 ml) was added dropwise thereto at 0° C. and the whole was stirred at 40° C. for 1 hour and at 50° C. for 1 additional hour. Then the solvent was removed by distillation under reduced pressure. The residue was dissolved in chloroform, and the solution was washed with saturated aqueous solution of Sodium bicarbonate. The aqueous layer was extracted with chloroform (3×200 ml). The combined extracts were dried, and evaporated under reduced pressure. The crude crystals were recrystallized from methylene chloride-methanol (1:5, V/V), giving cycloartenyl-m-methoxybenzoate (23.0 g) in an almost quantitative yield. m.p. 127°–128° C.

Specific rotation $[\alpha]_D^{25.5} +63.7°$ (C 1.00, CHCl$_3$)

Analysis, Calcd. for $C_{38}H_{56}O_3$ (M.W. 560.83): C, 81.38; H, 10.07. Found: C, 81.44; H, 10.01.

IR$\nu$, KBr (cm$^{-1}$) 2930, 2850, 1715, 1700, 1584, 1450, 1285, 1275, 1100, 1045, 755.

PMR (CDCl$_3$)δ: 0.39 (1H, ½ABq, 4.2 Hz), 0 60 (1H, ½ABq, 4.2 Hz), 0.60–2.30 (27H, m), 0.91 (6H, s), 0.98 (3H, s), 1.04 (3H, s), 1.60 (3H, bs), 1.68 (3H, bs), 3.84 (3H, s), 4.60–5.30 (2H, m), 6.90–7.80 (4H, m).

EXAMPLE 16

Preparation of cycloartenyl-o-nitrobenzoate o-Nitrobenzoic acid (4.7 g, 0.028 mole) was dissolved in dioxane (50 ml). Thionyl chloride (10.0 ml, 5 equivalents) and dimethylformamide (0.2 ml) was added dropwise to the former solution with stirring at 0° C. The whole was stirred at 50° C. for 30 minutes. The resulting mixture was concentrated under reduced pressure to remove the excess thionyl chloride. Dioxane (50 ml) was added to the residue and the solution was stirred at 0° C. Cycloartenol (10.0 g, 0.023 mole) dissolved in pyridine (50 ml) was added dropwise thereto, and the mixture was stirred at 70° C. for 30 minutes. The resulting mixture was concentrated under reduced pressure, and dissolved in chloroform (100 ml). The solution was washed with saturated aqueous solution of Sodium bicarbonate. The aqueous layer was extracted with chloroform (3×100 ml). The combined extracts were dried and concentrated under reduced pressure. The residue was purified by silica gel column chromatography (solvent:chloroform-hexane (1:2, V/V)), giving cycloartenyl-o-nitrobenzoate (13.0 g) in a 96% yield. m.p. 166°–167° C.

Specific rotation $[\alpha]_D^{22} +94.8°$ (C 1.01, CHCl$_3$)

Analysis, Calcd. for $C_{37}H_{53}O_4N$ (M.W. 575.80): C, 77.17; H, 9.28; N, 2.43. Found: C, 77.28; H, 9.21; N, 2.42.

IR$\nu$, KBr (cm$^{-1}$); 2930, 2850, 1710, 1535, 1375, 1300, 1130.

PMR (CDCl$_3$)δ: 0.38 (1H, ½ABq, 4.2 Hz), 0.59 (1H, ½ABq, 4.2 Hz), 0.60–2.30 (27H, m), 0.89 (3H, s), 0.91 (3H, s), 0.94 (3H, s), 0.97 (3H, s), 1.60 (3H, bs), 1.68 (3H, bs), 4.60–5.30 (2H, m), 7.50–8.00 (4H, m).

EXAMPLE 17

Preparation of cycloartenyl-o-aminobenzoate

Cycloartenyl-o-nitrobenzoate (20.0 g, 0.035 mole) prepared according to the procecure of Example 16 was suspended in acetic acid (800 ml). By adding zinc powder (20.0 g), the mixture was stirred at 50° C. for 3 hours. Then, zinc powder was removed by filtration and the filtrate was concentrated under reduced pressure. The residue was dissolved in chloroform, and the solution was washed with saturated aqueous solution of Sodium bicarbonate. The aqueous layer was extracted with chloroform (3×500 ml). The combined extracts were dried, concentrated under reduced pressure and the residue was purified by silica gel chromatography (solvent: methylene chloride-hexane, (1:2, V/V)), giving cycloartenyl-o-aminobenzoate (15.0 g) in a 80% yield. m.p. 185°–186° C.

Specific rotation $[\alpha]_D^{25.5} +77.5°$ (C 1.02, CHCl$_3$)

Analysis, Calcd. for $C_{37}H_{55}O_2N$ (M.W. 545.82): C, 81.41; H, 10.16; N, 2.57. Found: C, 81.48; H, 10.18; N, 2.53.

IR$\nu$, KBr (cm$^{-1}$) 3470, 3350, 2930, 2850, 1670, 1620, 1290, 1248, 1155, 760.

PMR (CDCl$_3$)δ: 0.40 (1H, ½ABq, 4.2 Hz), 0.61 (1H, ½ABq, 4.2 Hz), 0.60–2.30 (27H, m), 0.91 (6H, s), 0.97 (3H, s), 1.03 (3H, s), 1.60 (3H, bs), 1.67 (3H, bs), 4.60–5.32 (2H, m), 5.50 (2H, bs), 6.40–8.00 (4H, m).

EXAMPLE 18

Preparation of cycloartenyl-p-nitrobenzoate

Dioxane (30 ml) was added to p-nitrobenzoic acid (2.95 g, 0.018 mole). Thionyl chloride (6.5 ml, 5 equivalents) and dimethylformamide (0.3 ml) were added dropwise to the former solution at 20° C. and the reaction mixture was continued to stir at 50° C. for 30 minutes. Then, the resulting mixture was distilled under reduced pressure to remove the excess thionyl chlorice completely. Dioxane (25 ml) was added to the resulting acid-chloride and cycloartenol (5.0 g, 0.012 mole) dissolved in pyridine (25 ml) was added thereto at 0° C. The mixture was stirred at 60° C. for 20 minutes, then the resulting mixture was concentrated under reduced pressure, the residue was dissolved in chloroform (50 ml), and the solution was washed with saturated aqueous solution of Sodium bicarbonate. The aqueous layer was extracted with chloroform (3×50 ml). The combined extracts were dried and concentrated under reduced pressure, and the residue was purified by silica gel column chromatography (solvent:chloroform-hexane (1:3, V/V)), giving cycloartenyl-p-nitrobenzoate (6.3 g) in a 93% yield. m.p. 221°–222° C.

Specific rotation $[\alpha]_D^{22.5} +62.3°$ (C 1.01, CHCl$_3$)

Analysis, Calcd. for $C_{37}H_{53}O_4N$ (M.W. 575.80): C, 77.17; H, 9.28; N, 2.43. Found: C, 77.25; H, 9.21; N, 2.50.

IR$\nu$, KBr (cm$^{-1}$): 2930, 2850, 1715, 1520, 1350, 1290, 1120, 1100.

PMR (CDCl$_3$)δ: 0.41 (1H, ½ABq, 4.2 Hz), 0.61 (1H, ½ABq, 4.2 Hz), 0.70–2.40 (27H, m), 0.91 (3H, s), 0.98 (3H, s), 1.05 (3H, s), 1.60 (3H, bs), 1.68 (3H, bs), 4.60–5.30 (2H,m), 8.00–8.50 (4H, m).

EXAMPLE 19

Preparation of cycloartenyl-p-aminobenzoate

Cycloartenyl-p-nitrobenzoate (5.0 g, 8.70 mmoles) prepared according to the procedure of Example 18 was suspended in acetic acid (250 ml). By adding zinc powder (10.0 g), the mixture was stirred at 20°–25° C. for 2.5 hours. Then, zinc powder was removed by filtration and the filtrate was concentrated under reduced pressure. The residual solid was dissolved in chloroform, and the solution was washed with saturated aqueous solution of sodium bicarbonate. The aqueous layer was extracted with chloroform. The combined extracts were dried, and distilled to remove the solvent. The resulting residue was purified by silica gel column chromatography (solvent: methylene chloride), giving cycloartenyl-p-aminobenzoate (4.0 g) in a 84% yield. m.p. 168°–169° C.

Specific rotation $[\alpha]_D^{25}+62.2°$ (C 1.00, CHCl$_3$)

Analysis, Calcd. for $C_{37}H_{55}O_2N$ (M.W. 545.82): C, 81.41; H, 10.16, N, 2.57. Found: C, 81.52; H, 10.12; N, 2.53.

IR$\nu$, KBr (cm$^{-1}$): 3470, 3350, 2930, 2850, 1705, 1685, 1625, 1600, 1515, 1310, 1275, 1170, 1115.

PMR (CDCl$_3$)$\delta$: 0.36 (1H, ½ABq, 4 Hz), 0.58 (1H, ½ABq, 4 Hz), 0.70–2.30 (27H, m), 0.95 (3H, s), 0.98 (6H, s), 1.00 (3H, s), 1.59 (3H, bs), 1.66 (3H, bs), 4.50 (2H, bs), 4.50–5.30 (2H, m), 6.40–6.80 (2H, m), 7.60–8.10 (2H, m).

EXAMPLE 20

Preparation of cycloartenyl-p-acetamidobenzoate

Dioxane (110 ml) was added to p-acetamidobenzoic acid (5.5 g, 0.031 mole). Thionyl chloride (21.0 ml, 0 equivalents) and pyridine (0.5 ml) were added dropwise to the former solution at 20° C. and the reaction mixture was stirred at 50° C. for 5 minutes. The resulting mixture was concentrated under reduced pressure to remove the unreacted thionyl chloride. Dioxane (50 ml) and a solution of cycloartenol (10.0 g, 0.023 mole) in benzene (50 ml) were added to the concentrate and then pyridine (20 ml) was added at 20° C. This reaction mixture was heated at 70° C. for 3 hours. Then the solvent was removed by distillation under reduced pressure the resulting residue was dissolved in chloroform (100 ml), and the solution was washed with saturated aqueous solution of sodium bicarbonate. The aqueous layer was extracted with chloroform (5×100 ml). The combined extracts were dried, concentrated under reduced pressure and the residue was purified by silica gel column chromatography (solvent:chloroformethyl acetate, (7:1, V/V)) giving cycloartenyl-p-acetamidobenzoate (11.0 g) in a 80% yield. m.p. 202°–204° C.

Specific rotation $[\alpha]_D^{24}+59.6°$ (C 0.99, CHCl$_3$)

Analysis, Calcd. for $C_{39}H_{57}O_3N$ (M.W. 587.85): C, 79.68; H, 9.77; N, 2.38. Found: C, 79.59; H, 9.82; N, 2.34.

IR$\nu$, KBr (cm$^{-1}$): 3310, 2930, 2850, 1705, 1680, 1598, 1520, 1310, 1285, 1260, 1180, 1135.

PMR (CDCl$_3$)$\delta$: 0.39 (1H, ½ABq, 4 Hz), 0.60 (1H, ½ABq, 4 Hz), 0.60–2.30 (27H, m), 0.91 (6H, s), 0.98 (3H, s), 1.03 (3H, s), 1.60 (3H, bs), 1.68 (3H, bs), 2.20 (3H, s), 4.50–5.30 (2H, m), 7.51 (1H, bs), 7.59 (2H, ½ABq, 8.4 Hz), 7.97 (2H, ½ABq, 8.4 Hz).

EXAMPLE 21

Preparation of cycloartenyl-p-aminobenzoate

Tetrahydrofuran (200 ml) and 30% hydrochloric acid (100 ml) were added to cycloartenyl-p-acetamidobenzoate (10.0 g, 0.017 mole) prepared according to the procedure of Example 20. The mixture was refluxed for 2 hours. Then the solvent was removed by distillation under reduced pressure The residue was dissolved in chloroform (300 ml), and washed with 1N aqueous sodium hydroxide (200 ml) followed by saturated brine.

The aqueous layer and brine were extracted with chloroform (3×200 ml). The combined extracts were dried and concentrated under reduced pressure, and the residue was purified by silica gel column chromatography (solvent: ethyl acetate-hexane, (1:4, V/V)) giving cycloartenyl-p-aminobenzoate (3.2 g) in a 34% yield. m.p. 168°–169° C.

Specific rotation $[\alpha]_D^{25}+62.2°$

Analysis, Calcd. for $C_{37}H_{55}O_2N$ (M.W. 545.82): C, 81.41; H, 10.16; N, 2.57. Found: C, 81.48; H, 10.23; N, 2.54.

EXAMPLE 22

Preparation of cycloartenyl-m-nitrobenzoate

Cycloartenol (15.0 g, 0.035 mole) was dissolved in pyridine (150 ml). m-Nitrobenzoyl chloride (8.5 g, 1.3 equivalents) was added dropwise to the solution at 0° C. and the mixture was stirred at 40° C. for 30 minutes. Then, the resulting mixture was concentrated under reduced pressure and the residue was dissolved in methylene chloride (100 ml). The solution was washed with saturated aqueous solution of sodium bicarbonate. The aqueous layer was extracted with methylene chloride (3×100 ml). The combined extracts were dried and concentrated under reduced pressure. The concentrate was dissolved in methylene chloride (50 ml), and crystals separated out by adding methanol (100 ml), giving cycloartenyl-m-nitrobenzoate (19.5 g) in a 96% yield. m.p. 162.5°–163.5° C.

Specific rotation $[\alpha]_D^{22}+60.8°$ (C 0.99, CHCl$_3$)

Analysis, Calcd. for $C_{37}H_{53}O_4N$ (M.W. 575.80): C 77.17; H, 9.28; N, 2.43. Found: C, 77.10; H, 9.33; N, 2.37.

IR$\nu$, KBr (cm$^{-1}$) 2920, 2850, 1712, 1532, 1350, 1290, 1145, 980, 715.

PMR (CDCl$_3$)$\delta$: 0.42 (1H, ½ABq, 4.2 Hz), 0.64 (1H, ½ABq, 4.2 Hz), 0.60–2.40 (27H, m), 0.92 (6H, s), 0.98 (3H, s), 1.07 (3H, s), 1.60 (3H, bs), 1.67 (3H, bs), 4.60–5.30 (2H, m), 7.50–8.50 (4H, m).

EXAMPLE 23

Preparation of cycloartenyl-m-aminobenzoate

Cycloartenyl-m-nitrobenzoate (15.0 g, 0.026 mole) prepared according to procedure of Example 22 was suspended in acetic acid (750 ml). By adding zinc powder (30.0 g), the mixture was stirred at 40° C. for 2 hours. Then, stirred the zinc powder was removed by filtration and the filtrate was concentrated under reduced pressure. The residue was dissolved in chloroform, and the solution was washed with saturated aqueous solution of sodium bicarbonate. The aqueous layer was extracted with chloroform (5×300 ml). The combined extracts were dried and concentrated under reduced pressure, and the residue was purified by silica gel column chromatography (solvent:chloroform), giving cycloartenyl-m-aminobenzoate (12.6 g) in a 89% yield. m.p. 172.5°–173.5° C.

Specific rotation $[\alpha]_D^{25.5}+62.6°$ (C 0.99, CHCl$_3$)

Analysis. Calcd. for $C_{37}H_{55}O_2N$ (M.W. 545.82): C 81.41; H 10.16; N 2.57. Found: C 81.53; H 10.11; N 2.53.

IR$\nu$, KBr (cm$^{-1}$) 3450, 3350, 2900, 2850, 1700, 1627, 1460, 1287, 1240, 1100, 975, 755.

PMR (CDCl$_3$)$\delta$: 0.40 (1H, ½ABq, 4.2 Hz), 0.61 (1H, ½ABq, 4.2 Hz), 0.60–2.30 (27H, m), 0.91 (6H, s), 0.98 (3H, s), 1.03 (3H, s), 1.61 (3H, bs), 1.68 (3H, bs), 3.70 (2H, bs), 4.60–5.30 (2H, m), 6.70–7.50 (4H, m).

EXAMPLE 24

Preparation of cycloartenyl nicotinate

Toluene (10 ml) was thionyl chloride (50 ml, 10 equivalents) were added to nicotinic acid (8.7 g, 0.071 mole) at 0° C., and the whole was stirred at 60° C. for 30 minutes. The reaction mixture was concentrated under reduced pressure, and cycloartenol (20.0 g, 0.047 mole), pyridine (100 ml) and toluene (50 ml) were added thereto at 0° C., and the reaction mixture was stirred at 100° C. for 30 minutes. Then, the solvent was removed by distillation under reduced pressure, the resulting residue was dissolved in methylene chloride and the solution was washed with saturated aqueous solution of sodium bicarbonate. The aqueous layer was extracted with methylene (3×300 ml). The combined extracts was concentrated to dryness under reduced pressure, and the crude crystals were recrystallized from methylene chloride-methanol (1:4, V/V), giving cycloartenyl-nicotinate (24.4 g) in a 98% yield. m.p. 170.5°–171° C.

Specific rotation $[\alpha]_D^{25} + 67.8°$ (C 1.00, CHCl$_3$)

Analysis, Calcd. for $C_{36}H_{53}O_2N$ (M.W. 531.79): C 81.30; H 10.05; N 2.63. Found: C 81.22, H 10.09, N 2.57.

IR$\nu$, KBr (cm$^{-1}$): 2920, 2850, 1718, 1590, 1282, 1122, 965, 740.

PMR (CDCl$_3$)δ: 0.40 (1H, ½ ABq, 4.2 Hz), 0.62 (1H, ½ ABq, 4.2 Hz), 0.60–2.40 (27H, m), 0.91 (6H, s), 0.98 (3H, s), 1.04 (3H, s), 1.60 (3H, bs), 1.67 (3H, bs), 4.50–5.30 (2H, m), 7.20–9.30 (4H, m).

EXAMPLE 25

Preparation of cycloartenyl linolate

Benzene (61 ml) was added to linoleic acid (23.0 g, 0.082 mole) and the solution was stirred at 0° C. Thionyl chloride (61 ml, 10 equivalents) was added dropwise thereto, and the reaction mixture was stirred at 40° C. for 30 minutes. Then the resulting mixture was concentrated under reduced pressure, and benzene (125 ml) was added with stirring at 0° C. Cycloartenol (25.0 g, 0.059 ml) dissolved in pyridine (125 ml) was added thereto and the whole was stirred at 40° C. for 10 minutes. Then the solvent was removed by distillation under reduced pressure. The resulting residue was dissolved in methylene chloride, and the solution was washed with saturated aqueous solution of sodium bicarbonate, and the aqueous layer was extracted with methylene chloride (3×500 ml). The combined extracts were dried over anhydrous sodium sulfate and concentrated under reduced pressure. The resulting oily material was purified by silica gel column chromatography (solvent: methylene chloride-hexane (1:1, V/V)), giving cycloartenyl linolate (36.1 g) in a 90% yield. m.p. (oily matter).

Specific rotation $[\alpha]_D^{21.5} + 39.3°$

Analysis, Calcd. for $C_{48}H_{80}O_2$ (M.W. 689.12): C 83.65; H 11.70. Found: C 83.52; H 11.83.

IR$\nu$, neat (cm$^{-1}$): 2910, 2850, 1730, 1460, 1373, 1170, 980.

PMR (CDCl$_3$)δ: 0.33 (1H, ½ ABq, 4.2 Hz), 0.56 (1H, ½ ABq, 4.2 Hz), 0.60–2.50 (52H, m), 0.84 (3H, s), 0.87 (6H, s), 0.96 (3H, s), 1.60 (3H, bs), 1.67 (3H, bs), 2.76 (2H, bt, 5.0 Hz), 4.40–4.80 (1H, m), 4.90–5.64 (5H, m).

EXAMPLE 26

Preparation of cycloartenyl-3,4-diacetoxybenzoate

Toluene (50 ml) was added to 3,4-diacetoxybenzoic acid (20.9 g, 0.088 mole) and stirred at 0° C. Thionyl chloride (33 ml, 5 equivalents) was added dropwise to 3,4-diacetoxybenzoic acid (20.9 g, 0.088 mole) and the mixture was stirred at 70° for 10 minutes. The resulting mixture was concentrated under reduced pressure. Toluene (125 ml) was added to the concentrate at 0° C. Cycloartenol (25.0 g, 0.059 mole) dissolved in pyridine (60 ml) was added thereto and the mixture was stirred at 22° C. for 1 hour. Then the solvent was removed by distillation under reduced pressure. The resulting residue was dissolved in methylene chloride, and the solution was washed with saturated aqueous solution of sodium bicarbonate. The aqueous layer was extracted with methylene chloride (3×400 ml). The combined extracts were dried and concentrated to dryness under reduced pressure. The residue was recrystallized from chloroform-methanol (1:5, V/V), giving cycloartenyl-3,4-diacetoxybenzoate (33.8 g) in a 89% yield. m.p. 148°–148.5° C.

Specific rotation $[\alpha]_D^{23} + 53.3°$ (C 0.99, CHCl$_3$)

Analysis, Calcd. for $C_{41}H_{58}O_6$ (M.W 646.87): C 76.12, H 9.04. Found: C76.01, H 9.17.

IR$\nu$, KBr (cm$^{-1}$): 2910, 2850, 1775, 1710, 1610, 1498, 1420, 1370, 1280, 1195, 1160.

PMR (CDCl$_3$)δ: 0.39 (1H, ½ ABq, 4.2 Hz), 0.61 (1H, ½ ABq, 4.2 Hz), 0.70–2.40 (27H, m), 0.90 (6H, s), 0.97 (3H, s), 1.02 (3H, s), 1.60 (3H, s), 1.68 (3H, bs), 2.29 (6H, s), 4.60–5.30 (2H, m), 7.10–7.50 (2H, m), 7.78–8.20 (3H, m).

EXAMPLE 27

Preparation of cycloartenyl-3,4-dihydroxybenzoate

Dioxane (460 ml) was added to cycloartenyl-3,4-diacetoxybenzoate (23.0 g, 0.036 mole) prepared according to procedure of Example 26 and the solution was cooled to 0° C. After addition of 25% aqueous ammonia (46 ml) dropwise thereto, the mixture was stirred at 20° C. for 30 minutes and at 40° C. for 15 minutes to complete the reaction. Then the solvent was removed by distillation under reduced pressure. The resulting residue was recrystallized from chloroform-hexane (1:6, V/V), giving cycloartenyl-3,4-dihydroxybenzoate (18.6 g) in a 93% yield. m.p. 199°–199.5° C.

Specific rotation $[\alpha]_D^{26} + 63.7°$ (C 0.97, CHCl$_3$)

Analysis, Calcd. for $C_{37}H_{54}O_4$ (M.W. 562.80): C 78.96; H 9.67. Found: C 78.82; H 9.63.

IR$\nu$, KBr (cm$^{-1}$): 3470, 3330, 2900, 2850, 1705, 1679, 1605, 1525, 1435, 1280, 1230, 1098, 975.

PMR (CDCl$_3$)δ: 0.38 (1H, ½ABq, 4.2 Hz), 0.50 (1H, ½ABq, 4.2 Hz), 0.50–2.40 (27H, m), 0.88 (6H, s), 0.96 (3H, s), 1.00 (3H, s), 1.60 (3H, bs), 1.67 (3H, bs), 4.50–5.30 (2H, m), 5.80–6.80 (1H, bs), 6.70–7.90 (3H, m).

EXAMPLE 28

Preparation of cycloartenyl-4-acetoxy-3-methoxybenzoate

Toluene (26 ml) and thionyl chloride (23 ml) were added to 4-acetoxy-3-methoxybenzoic acid (13.0 g, 0.062 mole). The reaction mixture was stirred at 60° C. for 20 minutes. Then the resulting mixture was concentrated to dryness under reduced pressure. To the residue were added pyridine (25 ml) and toluene (25 ml), and the mixture was stirred at 0° C. Cycloartenol (20.0 g, 0.047 mole) dissolved in pyridine (25 ml) was added dropwise thereto, and the mixture was heated with stirring at 60° C. for 1.5 hours, at 80° C. for 1 hour, and at 100° C. for 2 hour to complete the reaction. The resulting mixture was concentrated under reduced pressure, and the residue was dissolved in chloroform (300 ml). The solution was washed with saturated aqueous solution of sodium bicarbonate. The aqueous layer was extracted with chloroform (3×300 ml). The combined extracts was dried and concentrated under reduced pressure and the residue was purified by silica gel column chromatography (solvent: ethyl acetatehexane, (1:8, V/V)), giving cycloartenyl-4-acetoxy-3-methoxybenzoate (26.0 g) in a 90% yield. m.p. 157°–158° C.

Specific roatation $[\alpha]_D^{23} +58.9°$ (C 0.99, CHCl$_3$)

Analysis, Calcd. for C$_{40}$H$_{58}$O$_5$ (M.W. 618.86): C 77.63; H 9.45. Found: C 77.75; H 9.40.

IR$\nu$, KBr (cm$^{-1}$): 2920, 2850, 1770, 1710, 1600, 1500, 1410, 1280, 1210, 1195, 1170, 1100, 1030.

PMR (CDCl$_3$)δ: 0.39 (1H, ½ ABq, 4.2 Hz), 0.60 (1H, ½ ABq, 4.2 Hz), 0.60–2.40 (27H, m), 0.89 (6H, s), 0.96 (3H, s), 1.02 (3H, s), 1.60 (3H, bs), 1.68 (3H, bs), 2.32 (3H, s), 3.86 (3H, s), 4.60–5.30 (2H, m), 6.80–7.90 (3H, m).

EXAMPLE 29

Preparation of cycloartenyl-4-hydroxy-3-methoxybenzoate

Dioxane (480 ml) was added to cycloartenyl-4-acetoxy-3-methoxybenzoate (24.0 g, 0.039 mole) prepared according to the procedure of Example 28. Thereto was added dropwise 25% aqueous ammonia (48 ml) at 0° C. and the whole was stirred at 35° C. for 1 hour. Then the resulting mixture was concentrated under reduced pressure and the residue was dissolved in chloroform (200 ml), and the solution was washed with saturated aqueous solution of sodium bicarbonate. The aqueous layer was extracted with chloroform (3×200 ml). The combined extracts was dried and concentrated, and crystallized by adding ethanol, giving cycloartenyl-4-hydroxy-3-methoxybenzoate containing a molecular ethanol (21.0 g) in a 87% yield. m.p. 132°–133° C.

Specific rotation $[\alpha]_D^{26} +61.3°$ (C 1.00, CH$_3$Cl)

Analysis, Calcd. for C$_{38}$H$_{56}$O$_4$·C$_2$H$_5$OH (M.W. 622.90): C 77.12; H 10.03. Found: C 77.21; H 10.12.

IR$\nu$, KBr (cm$^{-1}$): 3380, 2920, 2850, 1705, 1683, 1607, 1590, 1510, 1280, 1225.

PMR (CDCl$_3$)δ: 0.39 (1H, ½ ABq, 4.2 Hz), 0.60 (1H, ½ ABq, 4.2 Hz), 0.70–2.40 (27H, m), 0.91 (6H, s), 0.97 (3H, s), 1.03 (3H, s), 1.60 (3H, bs), 1.68 (3H, bs), 3.93 (3H, s), 4.60–5.30 (2H, m), 6.08 (1H, bs), 6.78–7.80 (3H, m).

EXAMPLE 30

Preparation of cyclobranyl-3,4-diacetoxycinnamate

Thionyl chloride (30 ml) was added to a suspension of 3,4-diacetylcaffeic acid (21.44 g, 0.081 mole) in toluene (100 ml). The mixture was stirred at 60° C. for 3 hours. The resulting mixture was distilled under reduced pressure to remove the solvent. The residue was suspended in a mixture of toluene (150 ml) and pyridine (30 ml). Cyclobranol (25 g, 0.0567 mole) was added to the suspension, and the mixture was stirred at 60° C. for 2 hours. Then the solvents were removed by distillation under reduced pressure. The residue was extracted with chloroform (300 ml). The extract was washed, dried, and evaporated to remove the chloroform. The residue was purified by silica gel column chromatography (solvent: toluene), giving cyclobranyl-3,4-diacetoxycinnamate (23.7 g) in a 61% yield. m.p. 174°–175° C.

Specific rotation $[\alpha]_D^{21.5} +37.0°$ (C 1.00, CHCl$_3$)

Analysis, Calcd. for C$_{44}$H$_{62}$O$_6$ (M.W. 686.94): C 76.93; H 9.10. Found: C 76.87; H 9.15.

IR$\nu$, KBr (cm$^{-1}$): 3400, 2850, 1775, 1705, 1200, 1170.

PMR (CDCl$_3$)δ: 0.36 (1H, ½ ABq, 4.8 Hz), 0.62 (1H, ½ ABq, 4.8 Hz), 0.70–2.50 (27H, m), 0.88 (6H, s), 0.96 (6H, s), 1.62 (9H, s), 1.28 (3H, s), 4.50–4.88 (1H, m), 6.39 (1H, ½ ABq, 15.6 Hz), 7.08–7.43 (3H, m), 7.62 (1H, ½ ABq, 15.6 Hz).

EXAMPLE 31

Preparation of cyclobranyl-3,4-dipropionyloxycinnamate

Thionyl chloride (17.43 ml, 2 equivalents) was added to a suspension of 3,4-dipropionylcaffeic acid (35.07 g, 0.12 mole) in toluene (150 ml), and the reaction mixture was stirred at 60° C. for 2 hours. The resulting mixture was distilled under reduced pressure to remove the solvent. The residue was suspended in a mixture of toluene (240 ml) and pyridine (50 ml). Cyclobranol (40 g, 0.0908 mole) was added to the suspension, and the mixture was stirred at 60° C. for 2 hours. Then the solvents were removed by distillation under reduced pressure. The residue was extracted with chloroform (300 ml). The extract was dried and evaporated to remove the chloroform. The resulting residue was purified by silica gel column chromatography (solvent: toluene), giving cyclobranyl-3,4-dipropionyloxycinnamate (41.9 g) in a 64% yield. m.p. 163°–165° C.

Specific rotation $[\alpha]_D^{21.5} +34.7°$ (C 1.00, CHCl$_3$)

Analysis, Calcd. for C$_{46}$H$_{66}$O$_6$ (M.W. 714.99): C 77.27; H 9.30. Found: C 77.34; H 9.23.

IR$\nu$, KBr (cm$^{-1}$): 2920, 2850, 1770, 1710, 1250, 1170.

PMR (CDCl$_3$)δ: 0.36 (1H, ½ ABq, 4.8 Hz), 0.62 (1H, ½ ABq, 4.8 Hz), 0.70–2.20 (27H, m), 0.90 (6H, s), 0.96 (6H, s), 1.25 (6H, t, 7.2 Hz), 1.62 (9H, s), 2.57 (4H, q, 7.2 Hz), 4.50–4.88 (1H, m), 6.36 (1H, ½ABq, 15.6 Hz), 7.05 (3H, m), 7.60 (1H, ½ ABq, 15.6 Hz).

EXAMPLE 32

Preparation of cyclobranyl-3,4-dihydroxycinnamate

Cyclobranyl-3,4-dipropionyloxycinnamate (35 g, 0.049 mole) prepared according to the procedure of Example 31 was dissolved in dioxane (600 ml). To the solution was added 25% aqueous ammonia (70 ml) and the mixture was stirred at 50° C. for 2 hours. Then the solvent was removed by distillation under reduced pressure. The crude crystals were recrystallized from acetone-water (4:1, V/V), giving cyclobranyl-3,4-dihydroxycinnamate (22.3 g) in a 75% yield. m.p. 246°–247.5° C.

Specific rotation $[\alpha]_D^{25} +33.6°$ (C 1.10, CHCl$_3$)

Analysis, Calcd. for C$_{40}$H$_{58}$O$_4$ (M.W. 602.86): C 79.69; H 9.70. Found: C 79.62, H 9.68.

IR$\nu$, KBr (cm$^{-1}$): 3400, 2920, 2850, 1680, 1600, 1520, 1440, 1275, 1180, 970.

PMR (CDCl$_3$)δ: 0.36 (1H, ½ ABq, 4.8 Hz), 0.59 (1H, ½ ABq, 4.8 Hz), 0.69–2.20 (27H, m), 0.85 (3H, s), 0.90 (3H, s), 0.96 (6H, s), 1.60 (9H, s), 4.36–4.80 (1H, m), 6.16 (1H, ½ ABq, 15.6 Hz), 6.60–7.16 (5H, m), 7.74 (1H, ½ ABq, 15.6 Hz).

EXAMPLE 33

Preparation of cyclobranyl-3,4-dihydroxycinnamate

The title compound was prepared according to following the procedure of Example 32 where cyclobranyl-3,4-diacetoxycinnamate (35 g, 0.051 mole) was used in place of cyclobranyl-3,4-dipropionyloxycinnamate. The yield was 22.1 g (64%). m.p. 246°–247° C.

Specific rotation $[\alpha]_D^{25} + 33.6°$ (C 0.11, CHCl$_3$)

Analysis, Calcd. for C$_{40}$H$_{58}$O$_4$ (M.W. 602.86): C79.69; H 9.70. Found: C 77.78; H 9.62.

EXAMPLE 34

Preparation of cyclobranyl-p-acetoxycinnamate p-Acetyl coumaric acid (18.2 g, 0.0885 mole) suspended in toluene (100 ml) and thionyl chloride (12.82 ml, 2 equivalents) was heated at 60° C. for 2 hours with stirring. The resulting mixture was distilled under reduced pressure to remove the solvent. The residue was dissolved in a mixture of toluene (150 ml) and pyridine (30 ml), and to the mixture was added cyclobranol (30 g, 0.068 mole). The whole was heated at 60° C. for 2 hours with stirring. Then the solvents were removed by distillation under reduced pressure, and the residue was extracted with chloroform (250 ml). The extract was dried and evaporated to remove the chloroform. The residue was purified by silica gel column chromatography (solvent: toluene), giving cyclobranyl-p-acetoxycinnamate (32.1 g) in a 75% yield. m.p. 164°–165° C.

Specific rotation $[\alpha]_D^{21.5} + 40.8°$ (C 1.00, CHCl$_3$)

Analysis, Calcd. for C$_{42}$H$_{60}$O$_4$ (M.W. 628.90): C 80.21; H 9.62. Found: C 80.14; H 9.67.

IR$\nu$, KBr (cm$^{-1}$): 2920, 2850, 1765, 1700, 1630, 1370, 1200, 1165.

PMR (CDCl$_3$)$\delta$: 0.35 (1H, ½ ABq, 4.8 Hz), 0.60 (1H, ½ ABq, 4.8 Hz), 0.70–2.40 (27H, m), 0.90 (6H, s), 0.98 (6H, s), 1.62 (9H, s), 2.28 (3H, s), 4.50–4.88 (1H, m), 6.37 (1H, ½ ABq, 15.6 Hz), 6.90–7.20 (2H, m), 7.35–7.64 (2H, m), 7.62 (1H, ½ ABq, 15.6 Hz).

EXAMPLE 35

Preparation of cyclobranyl-p-hydroxycinnamate

Cyclobranyl-p-acetoxycinnamate (27 g, 0.043 mole) prepared according to the procedure of Example 34 was dissolved in tetrahydrofuran (400 ml), and heated with 25% aqueous ammonia (50 ml) at 40° C. for 2 hours with stirring. The resulting mixture was evaporated to dryness under reduced pressure to remove the solvent. The crystals separating out were recrystallized from acetone-water (5:1, V/V), giving cyclobranyl-p-hydroxycinnamate (22.2 g) in a 88% yield, m.p. 243°–244° C.

Specific rotation $[\alpha]_D^{25} + 41.3°$ (C 1.09, CHCl$_3$)

Analysis, Calcd. for C$_{40}$H$_{58}$O$_3$ (M.W. 586.86): C 81.86; H 9.96. Found: C 81.77; H 9.99

IR$\nu$, KBr (cm$^{-1}$): 3370, 2920, 2850, 1670, 1605, 1585, 1510, 1280, 1170, 830.

PMR (CDCl$_3$)$\delta$: 0.37 (1H, ½ ABq, 4.8 Hz), 0.62 (1H, ½ ABq, 4.8 Hz), 0.68–2.15 (27H, m), 0.88 (3H, s), 0.90 (3H, s), 0.97 (6H, s), 1.59 (9H, s), 4.39–4.78 (1H, m), 6.11 (1H, ½ ABq, 15.6 Hz), 6.55–6.83 (2H, m), 7.10–7.41 (3H, m), 7.42 (1H, ½ ABq, 15.6 Hz).

EXAMPLE 36

Preparation of cyclobranyl-4-acetoxy-3-methoxybenzoate

To 4-acetylvanillic acid (18.60 g, 0.0885 mole) dissolved in toluene (100 ml) was added thionyl chloride (12.86 ml, 2 equivalents) and the mixture was stirred at 60° C. for 2 hours. The resulting mixture was evaporated under reduced pressure and the residue was dissolved in toluene (150 ml) and pyridine (30 ml). To the solution was added cyclobranol (30 g 0.068 mole) and the mixture was stirred at 60° C. for 2 hours. Then the mixture was evaporated under the reduced pressure, and the residue was extracted with chloroform (300 ml). The extract was dried, concentrated in vacuo, and purified by silica gel column chromatography (solvent: ethylacetatehexane, (1:6, V/V)), giving cyclobranyl-4-acetoxy-3-methoxybenzoate ester (33.38g) in a 77% yield. m.p. 177°–178° C.

Specific rotation $[\alpha]_D^{21.5} + 54.1°$ (C 1.02, CHCl$_3$)

Analysis, Calcd. for C$_{41}$H$_{60}$O$_5$ (M.W. 632.89): C 77.80; H 9.56. Found: C 77.71; H 9.64.

IR$\nu$, KBr (cm$^{-1}$): 2920, 2850, 1770, 1710, 1285, 1190, 1170.

PMR (CDCl$_3$)$\delta$: 0.38 (1H, ½ ABq, 4.8 Hz), 0.63 (1H, ½ ABq, 4.8 Hz), 0.70–2.40 (27H, m), 0.92 (6H, s), 0.98 (3H, s), 1.04 (3H, s), 1.62 (9H, s), 2.32 (3H, s), 3.88 (3H, s), 4.60–5.00 (1H, m), 6.92–7.20 (1H, m), 7.51–7.80 (2H, m).

EXAMPLE 37

Preparation of cyclobranyl-4-hydroxy-3-methoxybenzoate

Cyclobranyl-4-acetoxy-3-methoxybenzoate (30 g, 0.0474 mole) prepared according to the procedure of Example 36 was dissolved in tetrahydrofuran (300 ml), and to the solution was added 25% aqueous ammonia (60 ml). The mixture was stirred at 50° C. for 2 hours, then the resulting mixture was evaporated to dryness under reduced pressure. The residual crystals were recrystallized from acetone-water (5:1. V/V), giving cyclobranyl-4-hydroxy-3-methoxybenzoate (23.1 g), in a 82% yield. m.p. 191°–193° C.

Specific rotation $[\alpha]_D^{26} + 55.8°$ (C 1.02, CHCl$_3$)

Analysis, Calcd. for C$_{39}$H$_{58}$O$_4$ (M.W. 590.85): C 79.27; H 9.89. Found: C 79.35; H 9.80.

IR$\nu$, KBr (cm$^{-1}$): 3400, 2920, 2850, 1700, 1590, 1510, 1275, 1220.

PMR (CDCl$_3$)$\delta$: 0.38 (1H, ½ ABq, 4.8 Hz), 0.64 (1H, ½ ABq, 4.8 Hz), 0.70–2.2 (27H, m), 0.92 (6H, s), 1.0 (3H, s), 1.05 (3H, s), 1.64 (9H, s), 3.95 (3H, s), 4.6–5.0 (1H, m), 6.06 (1H, bs), 6.74–7.04 (1H, m), 7.44–7.77 (2H, s).

EXAMPLE 38

Preparation of cyclobranyl-3,4-diacetoxybenzoate

To diacetylprotocatechuic acid (21.08 g, 0.0885 mole) suspended in toluene (100 ml) was added thionyl chloride (12.86 ml, 2 equivalents), and the mixture was stirred at 60° C. for 2 hours. Then the resulting mixture was evaporated under reduced pressure. The residue was suspended in toluene (150 ml) and pyridine (30 ml), and to the suspension was added cyclobranol (30 g, 0.068 mole). The mixture was stirred at 60° C. for 2 hours. Then the solution was evaporated under reduced pressure. The residue was extracted with chloroform (300 ml). And the extract was dried, concentrated in vacuo, and purified by silica gel column chromatography (solvent: toluene), giving cyclobranyl-3,4-diacetoxybenzoate (24.2 g) in a 54% yield. m.p. 165°–166° C.

Specific rotation $[\alpha]_D^{21.5} + 51.3°$ (C 1.01, CHCl$_3$)

Analysis, Calcd. for C$_{42}$H$_{60}$O$_6$ (M.W. 660.90): C 76.32; H 9.15. Found: C 76.45; H 9.10.

IR$\nu$, KBr (cm$^{-1}$): 2920, 2850, 1770, 1715, 1280, 1195, 1160.

PMR (CDCl$_3$)$\delta$: 0.36 (1H, ½ ABq, 4.8 Hz), 0.62 (1H, ½ ABq, 4.8 Hz), 0.70–2.40 (27H, m), 0.90 (6H, s), 0.96 (3H, s), 1.00 (3H, s), 1.60 (9H, s), 2.26 (6H, s), 4.60–4.98 (1H, m), 7.08–7.40 (1H, m), 7.73–8.06 (2H, m).

EXAMPLE 39

Preparation of cyclobranyl-3,4-dihydroxybenzoate

Cyclobranyl-3,4-diacetoxybenzoate (24.0 g, 0.0363 mole) prepared according to the procedure of Example 38 was dissolved in dioxane (480 ml) and to the solution was added 25% aqueous ammonia (48 ml). The mixture was stirred at 40° C. for 1 hour, then the resulting mixture was evaporated to dryness under reduced pressure. The residual crystals were recrystallized from ethanol, giving cyclobranyl-3,4-dihydroxybenzoate (17.5 g), in a 84% yield. m.p. 215°–216° C.

Specific rotation $[\alpha]_D^{26}+59.4°$ (C 0.98, CHCl$_3$)

Analysis, Calcd. for $C_{38}H_{56}O_4$ (M.W. 576.83): C 79.12; H 9.79. Found: C 79.03; H 9.87.

IR$\nu$, KBr (cm$^{-1}$) 3350, 2920, 2850, 1680, 1605, 1440, 1280, 1230, 1100, 975.

PMR (CDCl$_3$)$\delta$: 0.38 (1H, ½ ABq, 4.8 Hz), 0.61 (1H, ½ ABq, 4.8 Hz), 0.70–2.20 (27H, m), 0.90 (6H, s), 0.98 (3H, s), 1.02 (3H, s), 1.62 (9H, s), 2.72–3.20 (2H, bs), 4.60–4.90 (1H, m), 6.70–6.96 (1H, m), 7.40–7.64 (2H, m).

EXAMPLE 40

Preparation of cyclobranyl-o-acetoxybenzoate

To acetylsalicylic acid (15.94 g, 0.088 mole) suspended in toluene (100 ml) was added thionyl chloride (40 ml, 6.3 equivalents) and the mixture was stirred at 80° C. for 3 hours. The resulting mixture was evaporated under reduced pressure, and the residue was dissolved in toluene (180 ml) and pyridine (40 ml), followed by addition of cyclobranol (30 g, 0.068 mole). The mixture was continued to stir at 60° C. for 2 hours, then the resulting mixture was evaporated under reduced pressure. The residue was extracted with chloroform (300 ml), and the extract was washed with 3% aqueous sodium bicarbonate, water, and saturated brine. The extract was dried, concentrated in vacuo, and the residue was purified by silica gel column chromatography (solvent: hexane-toluene, (1:1, V/V)), giving cyclobranyl-o-acetoxybenzoate (29.6 g), in a 72% yield. m.p. 165°–166° C.

Specific rotation $[\alpha]_D^{23}+58.4°$ (C 1.01, CHCl$_3$)

Analysis, Calcd. for $C_{40}H_{58}O_4$ (M.W. 602.86): C 79.69; H 9.70. Found: C 79.64; H 9.78.

IR$\nu$, KBr (cm$^{-1}$): 2920, 2850, 1770, 1720, 1260, 1190, 1080

PMR (CDCl$_3$)$\delta$: 0.36 (1H, ½ ABq, 4.8 Hz), 0.60 (1H, ½ ABq, 4.8 Hz), 0.70–2.40 (27H, m), 0.89 (6H, s), 0.96 (3H, s), 1.00 (3H, s), 1.62 (9H, s), 2.33 (3H, s), 4.60–4.95 (1H, m), 6.88–7.68 (3H, m), 7.82–8.10 (1H, m).

EXAMPLE 41

Preparation of cyclobranyl-o-hydroxybenzoate

Cyclobranyl-o-acetoxybenzoate (24 g, 0.0398 mole) prepared according to the procedure of Example 40 was dissolved in dioxane (400 ml) and to the solution was added 25% aqueous ammonia (60 ml) dropwise. The mixture was stirred at 50° C. for 2 hours and evaporated to dryness under reduced pressure. The residual crystals were recrystallized from acetone-water (1:1, V/V), giving cyclobranyl-o-hydroxybenzoate ester (20.2 g), in a 90% yield. m.p. 200°–201° C.

Specific rotation $[\alpha]_D^{23}+69.3°$ (C 1.00, CHCl$_3$)

Analysis, Calcd. for $C_{38}H_{56}O_3$ (M.W. 560.83): C 81.38; H 10.07. Found: C 81.29; H 10.02.

IR$\nu$, KBr (cm$^{-1}$): 3120, 2920, 2850, 1670, 1615, 1300, 1250, 1220, 1165, 1095.

PMR (CDCl$_3$)$\delta$: 0.37 (1H, ½ ABq, 4.8 Hz), 0.62 (1H, ½ ABq, 4.8 Hz), 0.7–2.20 (27H, m), 1.05 (3H, s), 0.90 (6H, s), 0.97 (3H, s), 1.60 (9H, s), 4.60–5.00 (1H, m), 6.67–7.93 (4H, s), 10.92 (1H, s).

EXAMPLE 42

Preparation of cyclobranyl-p-nitrobenzoate

To p-nitrobenzoic acid (1 g, 0.006 mole) dissolved in dioxane (20 ml) was added thionyl chloride (3 ml, 7 equivalents) and the mixture was stirred at 60° C. for 2 hours. The resulting mixture was evaporated under reduced pressure, then dioxane (20 ml) and pyridine (3 ml) were added to the resulting residue. Cyclobranol (2 g, 0.0045 mole) was added to the solution and the mixture was stirred at 60° C. for 2 hours to complete the reaction. The mixture was evaporated under reduced pressure, and the residue was extracted with chloroform (30 ml). The extract was washed successively with 3% aqueous sodium carbonate, water, and saturated brine, dried, and evaporated to dryness under reduced pressure. The crude crystals were washed with ethanol (50 ml), and recrystallized from ethyl acetate, giving cyclobranol-p-nitrobenzoate (2.28 g) in a 90% yield. m.p. 244°–245° C.

Specific rotation $[\alpha]_D^{24}+60.1°$ (C 1.00, CHCl$_3$)

Analysis, Calcd. for $C_{38}H_{55}O_4N$ (M.W. 589.83): C 77.37; H 9.40; N 2.37. Found: C 77.45; H 9.33; N 2.42.

IR$\nu$, KBr (cm$^{-1}$): 2920, 2850, 1715, 1525, 1350, 1290, 1120, 1100, 720.

PMR (CDCl$_3$)$\delta$: 0.39 (1H, ½ ABq, 4.8 Hz), 0.64 (1H, ½ ABq, 4.8 Hz), 0.72–2.20 (27H, m), 0.92 (6H, s), 0.98 (3H, s), 1.06 (3H, s), 1.62 (9H, s), 4.59–5.02 (1H, m), 8.00–8.43 (4H, m).

EXAMPLE 43

Preparation of cyclobranyl-p-aminobenzoate

Cyclobranyl-p-nitrobenzoate (2 g, 0.0034 mole) prepared according to the procedure of Example 42 was suspended in acetic acid (80 ml), and was added zinc powder (2 g, 9 equivalents). The mixture was refluxed for 4 hours, then cooled and the zinc powder was separated by filtration. The filtrate was evaporated under reduced pressure, and extracted with chloroform (50 ml). The extract was dried, concentrated in vacuo, and the purified by silica gel column chromatography (solvent: chloroform). The thus obtained crystals were recrystallized from ethanol, giving cyclobranyl-p-aminobenzoic acid ester (1.37 g), in a 72% yield. m.p. 190°–191° C.

Specific rotation $[\alpha]_D^{26}+58.4°$ (C 1.01, CHCl$_3$)

Analysis, Calcd. for $C_{38}H_{57}O_2N$ (M.W. 559.84): C 81.52; H 10.26; N 2.50. Found: C 81.49; H 10.21; N 2.57.

IR$\nu$, KBr (cm$^{-1}$): 3450, 3350, 2920, 2850, 1685, 1620, 1600, 1510, 1275, 1170, 1110.

PMR (CDCl$_3$)$\delta$: 0.37 (1H, ½ ABq, 4.8 Hz), 0.61 (1H, ½ ABq, 4.8 Hz), 0.72–2.30 (27H, m), 0.89 (6H, s), 0.96 (3H, s), 1.00 (3H, s), 1.60 (9H, s), 3.60–4.40 (2H, b), 4.50–4.90 (1H, m), 6.44–6.76 (2H, m), 7.64–8.00 (2H,m).

EXAMPLE 44

Preparation of cyclobranyl-p-acetamidobenzoate

To p-acetamidobenzoic acid (15.85 g, 0.088 mole) dissolved in dioxane (150 ml) was added thionyl chloride (25.7 ml, 4 equivalents) and the mixture was stirred at 60° C. for 2 hours. The resulting mixture was evaporated under reduced pressure and dioxane (150 ml) and pyridine (50 ml) were added to the residue. Cyclobranol (30 g, 0.068 mole) was added to the solution, and the mixture was stirred at 60° C. for hours. The reactioh mixture was evaporated under reduced pressure, and to the residue was added ethyl acetate (300 ml). The crude crystals which separated out were filtered, and purified by silica gel column chromatography (solvent: chloroform). The resulting crystals were further recrystallized from ethanol, giving cyclobranyl-p-acetamidobenzoate (32 g), in a 78% yield. m.p. 197°-198° C.

Specific rotation $[\alpha]_D^{24} + 54.7°$ (C 1.01, CHCl$_3$)

Analysis, Calcd. for C$_{40}$H$_{59}$O$_3$N (M.W. 601.88): C 79.82; H 9.88; N 2.33. Found: C 79.75; H 9.83; N 2.41.

IR$\nu$, KBr (cm$^{-1}$) 3420, 2920, 2850, 1710, 1690, 1680, 1600, 1535, 1280, 1175.

PMR (CDOD-CDCl$_3$)δ: 0.38 (1H, ½ ABq, 4.8 Hz), 0.62 (1H, ½ ABq, 4.8 Hz), 0.70-2.28 (27H, m), 0.90 (6H, s), 0.98 (3H, s), 1.04 (3H, s), 1.62 (9H, s), 2.16 (3H, s), 4.50-4.96 (1H, m), 7.37 (1H, b), 7.44-8.12 (4H, m).

EXAMPLE 45

Preparation of cyclobranyl-p-aminobenzoate

Cyclobranyl-p-acetamidobenzoate (32 g, 0.053 mole) prepared according to the procedure of Example 44 was dissolved in tetrahydrofuran (300 ml) and conc. hydrochloric acid (60 ml) was added to it, and stirred at 70° C. for 2 hours. Then the mixture was evaporated under reduced pressure. The residue was extracted with chloroform (400 ml), then the extract was dried and concentrated. The residue was purified twice by silica gel column chromatography (solvent: toluene-hexane-ethyl acetate, (5:3:1, V/V)), giving cyclobranyl-p-aminobenzoate (17 g) in a 57% yield. m.p. 190°-191° C.

Specific rotation $[\alpha]_D^{26} + 58.4°$ (C 1.01, CHCl$_3$)

Analysis, Calcd. for C$_{38}$H$_{57}$O$_2$N (M.W. 559.84): C 81.52; H 10.26; N 2.50. Found: C 81.57; H 10.34; N 2.44.

EXAMPLE 46

Preparation of cyclobranyl-o-nitrobenzoate

To o-nitrobenzoic acid (12.32 g, 0.074 mole) dissolved in dioxane (200 ml) was added thionyl chloride (30 ml, 5.6 equivalents) and the mixture was stirred at 60° C. for 2 hours. After the reaction is finished, the mixture was evaporated to dryness under reduced pressure. The resulting residue was dissolved in dioxane (150 ml) and pyridine (50 ml). To the solution was added cyclobranol (25 g, 0.0567 mole) and this mixture was stirred at 60° C. for 2 hours. Then the mixture was evaporated to dryness under reduced pressure, and the residue was extracted with chloroform (300 ml). The extract was washed successively with 3% aqueous sodium carbonate, water, and saturated brine, dried, and evaporated to dryness under reduced pressure. The crude crystals were washed with ethanol (100 ml), and recrystallized from acetone-water (1:1, V/V), giving cyclobranyl-o-nitrobenzoate (30.8 g), in a 92% yield. m.p. 217°-218° C.

Specific rotation $[\alpha]_D^{21} + 90.8°$ (C 0.98, CHCl$_3$)

Analysis, Calcd. for C$_{38}$H$_{55}$O$_4$N (M.W. 589.83): C 77.37; H 9.40; N 2.37. Found: C 77.42, H 9.34; N 2.47.

IR$\nu$, KBr (cm$^{-1}$): 2930, 2850, 1710, 1535, 1380, 1300.

PMR (CDCl$_3$)δ: 0.36 (1H, ½ ABq, 4.8 Hz), 0.62 (1H, ½ ABq, 4.8 Hz), 0.75-2.20 (27H, m), 0.90 (3H, s), 0.92 (6H, s), 0.98 (3H, s), 1.64 (9H, s), 4.63-5.00 (1H, m), 7.46-7.98 (4H, m).

EXAMPLE 47

Preparation of cyclobranyl-o-aminobenzoate

Cyclobranyl-o-nitrobenzoic acid ester (30 g, 0.05 mole) prepared according to the procedure of Example 46 was suspended in acetic acid (1.2 l). And to the suspension was added zinc powder (30 g, 9 equivalents) which was washed with dilute hydrochloric acid before it. The mixture was refluxed for 5 hours, then cooled and the zinc powder was removed by filtration. The filtrate was evaporated under reduced pressure and the residue was extracted with chloroform (300 ml). The extract was dried, concentrated to dryness in vacuo, and purified by silica gel column chromatography (solvent: chloroform), giving cyclobranyl-o-aminobenzoate (20 g) in a 68% yield. m.p. 207°-208° C.

Specific rotation $[\alpha]_D^{24} + 74.9°$ (C 1.00, CHCl$_3$)

Analysis, Calcd. for C$_{38}$H$_{57}$O$_2$N (M.W. 559.84): C 81.52; H 10.26; N 2.50. Found: C 81.59; H 10.28; N 2.43.

IR$\nu$, KBr (cm$^{-1}$) 3460, 3350, 2940, 2850, 1670, 1620, 1290, 1245, 1155, 755.

PMR (CDCl$_3$)δ: 0.37 (1H, ½ ABq, 4.8 Hz), 0.62 (1H, ½ ABq, 4.8 Hz), 0.7-2.20 (27H, m), 0.92 (6H, s), 0.98 (3H, s), 1.04 (3H, s), 1.64 (9H, s), 4.50-4.95 (1H, m), 5.73 (2H, bs), 6.40-6.78 (2H, m), 7.00-7.40 (1H, m), 7.61-7.98 (1H, m).

EXAMPLE 48

Preparation of cyclobranyl-m-nitrobenzoate

Cyclobranol (18 g, 0.04 mole) dissolved in pyridine (200 ml) was stirred and cooled in a bath of ice water, and to it was added m-nitrobenzoyl chloride (9.85 g, 0.053 mole). Then the mixture was warmed to 20° C. and continued to stir for 12 hours. After the reaction is complete the mixture was evaporated under reduced pressure. Ice cold water (200 ml) was added to the residue and crystals begans to appear. The crude crystals were separated by filtration and recrystallized from acetone-water (1:1, V/V), giving cyclobranol-m-nitrobenzoate (20.1 g), in a 83% yield. m.p. 206°-207° C.

Specific rotation $[\alpha]_D^{21} + 60.8°$ (C 0.99, CHCl$_3$)

Analysis, Calcd. for C$_{38}$H$_{55}$O$_4$N (M.W. 589.83): C 77.37; H 9.40; N 2.37. Found: C 77.44; H 9.33; N 2.45.

IR$\nu$, KBr (cm$^{-1}$): 2930, 2850, 1715, 1530, 1350, 1290, 1140, 715.

PMR (CDCl$_3$)δ: 0.40 (1H, ½ ABq, 4.8 Hz), 0.66 (1H, ½ ABq, 4.8 Hz), 0.80-2.20 (27H, m). 0.92 (6H, s), 0.98 (3H, s), 1.08 (3H, s), 1.64 (9H, s), 4.65-5.05 (1H, m), 7.44-7.80 (1H, m), 8.20-8.52 (2H, m), 8.72-8.89 (1H, m).

EXAMPLE 49

Preparation of cyclobranyl-m-aminobenzoate

Cyclobranyl-m-nitrobenzoate (24 g, 0.04 mole) prepared according to the procedure of Example 48 was suspended in acetic acid (1.3 l). Zinc powder (24 g, 9 equivalents) was added to the suspension, and the mixture was refluxed for 2 hours. After the reaction was finished mixture was cooled and the zinc powder was separated by filtration. The filtrate was evaporated under reduced pressure, and the residue was extracted with chloroform (300 ml). The extract was dried, evaporated to dryness under reduced pressure, and the residue was purified by silica gel column chromatography (solvent: chloroform), giving cyclobranyl-m-aminobenzoate (19 g) in a 83% yield. m.p. 187°-188° C.

Specific rotation $[\alpha]_D^{24} + 61.7°$ (C 1.03, CHCl$_3$)

Analysis, Calcd. for $C_{38}H_{57}O_2N$ (M.W. 559.84): C 81.52; H 10.26; N 2.50. Found: C 81.44; H 10.29; N 2.56.

IR$\nu$, KBr (cm$^{-1}$): 3450, 3350, 2940, 2850, 1700, 1460, 1320, 1290, 1245, 755.

PMR (CDCl$_3$)$\delta$: 0.36 (1H, ½ ABq, 4.8 Hz), 0.61 (1H, ½ ABq, 4.8 Hz), 0.70–2.28 (27H, m), 0.90 (6H, s), 0.98 (3H, s), 1.04 (3H, s), 1.64 (9H, s), 3.53 (2H, b), 4.59–4.90 (1H, m), 6.60–7.55 (4H, m).

EXAMPLE 50

Preparation of cyclobranylnicotinate

Thionyl chloride (30 ml, 4.6 equivalents) was added to nicotinic acid (10.9 g, 0.0885 mole) and the mixture was stirred at 80° C. for 2 hours to complete the reaction. Then the excess thionyl chloride was removed under reduced pressure. To the residue dissolved in a mixture of toluene (120 ml) and pyridine (50 ml) was added cyclobranol (30 g, 0.068 mole) and the mixture was stirred at 60° C. for 2 hours. Then the mixture was evaporated to dryness under reduced pressure, and the residue was extracted with chloroform (300 ml). The extract was dried, concentrated in vacuo, and the residue was purified by silica gel column chromatography (solvent: toluene), giving cyclobranylnicotinate (32.3 g), in a 87% yield. m.p. 176°–177° C.

Specific rotation $[\alpha]_D^{26}+63.4°$ (C 1.04, CHCl$_3$)

Analysis, Calcd. for $C_{37}H_{55}O_2N$ (M.W. 545.82): C 81.41; H 10.16; N 2.57. Found: C 81.49; H 10.13; N 2.64.

IR$\nu$, KBr (cm$^{-1}$): 2920, 2850, 1720, 1590, 1285, 1120, 965.

PMR (CDCl$_3$)$\delta$: 0.37 (1H, ½ ABq, 4.8 Hz), 0.62 (1H, ½ ABq, 4.8 Hz), 0.70–2.27 (27H, m), 0.90 (6H, s), 0.93 (3H, s), 1.03 (3H, s), 1.62 (9H, s), 4.60–5.00 (1H, m), 7.13–7.50 (1H, m), 8.06–8.40 (1H, m), 8.60–8.82 (1H, m), 9.07–9.27 (1H, m).

EXAMPLE 51

Preparation of cyclobranyllinolate

Thionyl chloride (20 ml, 4.8 equivalents) was added to linoleic acid (16.5 g, 0.0588 mole) and the mixture was stirred at 40° C. for 1.5 hours. After the reaction was completed excess thionyl chloride was removed under reduced pressure, and the residue was dissolved in a mixture of toluene (100 ml) and pyridine (20 ml). Cyclobranol (20 g, 0.0454 mole) was added to the solution and the mixture was stirred at 40° C. for 2 hours, then evaporated under reduced pressure. The oily residue was extracted with chloroform (300 ml), and the extract was dried and evaporated under reduced pressure. The crude product was purified by silica gel column chromatography (solvent: toluene-hexane, (2:1, V/V)), giving cyclobranyllinolate (22.2 g), in a 69% yield. m.p. oily matter.

Specific rotation $[\alpha]_D^{21.5}+36.5°$ (C 0.95, CHCl$_3$)

Analysis, Calcd. for $C_{49}H_{82}O_2$ (M.W. 703.15): C 83.69; H 11.76. Found: C 83.61; H 11.88.

IR$\nu$, KBr (cm$^{-1}$): 2910, 2850, 1730, 1460, 1372, 1175.

PMR (CDCl$_3$)$\delta$: 0.34 (1H, ½ ABq, 4.8 Hz), 0.58 (1H, ½ ABq, 4.8 Hz), 0.68–2.43 (52H, m), 0.83 (3H, s), 0.89 (6H, s), 0.95 (3H, s), 1.60 (9H, s), 2.52–2.91 (2H, m), 4.40–4.80 (1H, m), 5.04–5.62 (4H, m).

EXAMPLE 52

Preparation of cyclobranyl-m-methoxybenzoate m-Anisic acid (8.1 g, 0.053 mole) was added to thionyl chloride (20 ml), and the mixture was stirred at 60° C. for 2 hours. After the reaction is completed the excess thionyl chloride was removed under reduced pressure. The residue was dissolved in pyridine (80 ml) and cyclobranol (18 g, 0.041 mole) was added to the solution. The mixture was stirred at 60° C. for 2 hours, then evaporated to dryness under reduced pressure. The resulting residue was purified by silica gel column chromatography, and recrystallized from ethanol, giving cyclobranyl-m-methoxybenzoate (20.7 g), in a 88% yield. m.p. 163°–164° C.

Specific rotation $[\alpha]_D^{21.5}+61.6°$ (C 1.00, CHCl$_3$)

Analysis, Calcd. for $C_{39}H_{58}O_3$ (M.W. 574.85): C 81.48; H10.17. Found: C 81.40; H 10.25.

IR$\nu$, KBr (cm$^{-1}$): 2920, 2850, 1715, 1585, 1270, 1220, 1100, 750

PMR (CDCl$_3$)$\delta$: 0.36 (1H, ½ ABq, 4.8 Hz), 0.60 (1H, ½ ABq, 4.8 Hz), 0.70–2.20 (27H, m), 0.90 (6H, s), 0.98 (3H, s), 1.02 (3H, s), 1.61 (9H, s), 3.82 (3H, s), 4.60–4.95 (1H, m), 6.84–7.72 (4H, m).

EXAMPLE 53

Preparation of cyclobranyl-m-acetoxybenzoate m-Acetoxybenzoic acid (19 g, 0.105 mole) and thionyl chloride (40 ml) was mixed and stirred at 60° C. for 2 hours. After the reaction is complete, the excess thionyl chloride was removed by distillation, and the residue was dissolved in a mixture of toluene (220 ml) and pyridine (60 ml). Cyclobranol (35 g, 0.0794 mole) was added to the solution and the mixture was stirred at 60° C. for 2 hours. After that the solution was evaporated under reduced pressure, and the residue was extracted with chloroform (300 ml). The extract was dried, concentrated in vacuo, and the residue was purified by silica gel column chromatography (solvent: chloroform), giving cyclobranyl-m-acetoxybenzoate (46.3 g), in a 97% yield. m.p. 42°–143° C.

Specific rotation $[\alpha]_D^{21.5}+59.0°$ (C 0.97, CHCl$_3$)

Analysis, Calcd. for $C_{40}H_{58}O_4$ (M.W. 602.86): C 79.69; H 9.70. Found: C 79.58; H 9.73.

IR$\nu$KBr (cm$^{-1}$): 2920, 2850, 1770, 1720, 1290, 1270, 1200, 1100.

PMR (CDCl$_3$)$\delta$: 0.36 (1H, ½ ABq, 4.8 Hz), 0.61 (1H, ½ ABq, 4.8 Hz), 0.70–2.38 (27H, m), 0.90 (6H, s), 0.96 (3H, s), 1.02 (3H, s), 1.62 (9H, s), 2.31 (3H, s), 4.60–4.96 (1H, m), 7.11–8.02 (4H, m).

EXAMPLE 54

Preparation of cyclobranyl-m-hydroxybenzoate

Cyclobranyl-m-acetoxybenzoate (24.5 g, 0.0406 mole) prepared according to the procedure of Example 53 was dissolved in tetrahydrofuran (300 ml). To the solution was added 25% aqueous ammonia (40 ml) and the mixture was stirred at 40° C. for 2 hours. The reaction mixture was evaporated to dryness under reduced pressure, and the resulting residue was recrystallized from ethanol, giving cyclobranyl-m-hydroxybenzoate (20.3 g), in a 86% yield. m.p. 203°–204.5° C.

Specific rotation $[\alpha]_D^{21.5}+62.2°$ (C 0.95, CHCl$_3$)

Analysis, Calcd. for $C_{38}H_{56}O_4$ (M.W. 576.83): C 79.12; H 9.79. Found: C 79.23; H 9.72.

IR$\nu$, KBr (cm$^{-1}$): 3380, 2920, 2850, 1690, 1600, 1450, 1290, 1245, 1110, 760.

PMR (CDCl$_3$)$\delta$: 0.38 (1H, ½ ABq, 4.8 Hz), 0.61 (1H, ½ ABq, 4.8 Hz), 0.70–2.20 (27H, m), 0.93 (6H, s), 0.98 (3H, s), 1.04 (3H, s), 1.64 (9H, s), 3.54 (1H, bs), 4.58–4.90 (1H, m), 6.84–7.66 (4H, m).

EXAMPLE 55

Preparation of cyclobranyl-p-methoxybenzoate

Cyclobranol (18 g, 0.041 mole) dissolved in pyridine (80 ml) was stirred and cooled in a bath of ice water, and to it was added p-methoxybenzoyl chloride (9.1 g, 0.0533 mole). The mixture was warmed to 20° C. and continued to stir for 15 hours. Then the mixture was evaporated under reduced pressure, and the residue was extracted with chloroform (300 ml). The extract was concentrated in vacuo, and the resulting residue was purified by silica gel column chromatography (solvent: chloroform), giving cyclobranyl-p-methoxybenzoate (21.7 g), in a 92% yield. m.p. 202°–203° C.

Specific rotation $[\alpha]_D^{21.5} +60.2°$ (C 1.06, CHCl$_3$)

Analysis, Calcd. for $C_{39}H_{58}O_3$ (M.W. 574.85): C 81.48; H 10.17. Found: C 81.32; H 10.25.

IR$\nu$, KBr (cm$^{-1}$); 2920, 2850, 1705, 1605, 1510, 1270, 1255, 1170, 1110, 1100.

PMR (CDCl$_3$)$\delta$: 0.36 (1H, ½ ABq, 4.8 Hz), 0.61 (1H, ½ ABq, 4.8 Hz), 0.70–2.38 (27H, m), 0.90 (6H, s), 0.98 (3H, s), 1.02 (3H, s), 1.62 (9H, s), 3.84 (3H, s), 4.60–4.95 (1H, m), 6.72–7.04 (2H, m), 7.80–8.12 (2H, m).

EXAMPLE 56

Preparation of cyclobranyl-o-methoxybenzoate

Cyclobranol (18 g, 0.041 mole) dissolved in pyridine (80 ml) was stirred and cooled in a bath of ice water, then to it was added o-methoxybenzoyl chloride (9 g, 0.0527 mole). The mixture was warmed to 20° C. and continued to stir for 15 hours. The mixture was evaporated under reduced pressure, and the residue was extracted with chloroform (300 ml). The extract was dried and the resulting residue was purified by silica gel column chromatography (solvent: chloroform), giving cyclobranyl-o-methoxybenzoate (21.9 g), in a 93% yield. m.p. 176°–177° C.

Specific rotation $[\alpha]_D^{21.5} +46.3°$ (C 1.00, CHCl$_3$)

Analysis, Calcd. for $C_{39}H_{58}O_3$ (M.W. 574.85): C 81.48; H 10.17. Found: C 81.40; H 10.25.

IR$\nu$, KBr (cm$^{-1}$): 2920, 2850, 1695, 1600, 1460, 1300, 1250, 1130, 760.

PMR (CDCl$_3$)$\delta$: 0.35 (1H, ½ ABq, 4.8 Hz), 0.59 (1H, ½ ABq, 4.8 Hz), 0.70–2.20 (27H, m), 0.90 (3H, s), 0.96 (6H, s), 0.99 (3H, s), 1.61 (9H, s), 3.86 (3H, s), 4.60–5.00 (1H, m), 6.72–7.94 (4H, m).

EXAMPLE 57

Preparation of cyclobranyl-p-acetoxybenzoate p-Acetoxybenzoic acid (18.6 g, 0.103 mole) and thionyl chloride (40 ml) were mixed and stirred at 60° C. for 12 hours. Then, the excess thionyl chloride was removed by distillation under reduced pressure. And to the residue suspended in toluene (220 ml) and pyridine (60 ml) was added cyclobranol (35 g, 0.0794 mole) and the mixture was stirred at 60° C. for 2 hours. Then the solution was evaporated under reduced pressure, and the residue was extracted with chloroform (400 ml). The extract was dried and concentrated in vacuo, and the resulting product was purified by silica gel column chromatography (solvent: chloroform), giving cyclobranyl-p-acetoxybenzoate ester (44.1 g) in a 92% yield. m.p. 192°–193° C.

Specific rotation $[\alpha]_D^{22} +55.5°$ (C 0.93, CHCl$_3$)

Analysis, Calcd. for $C_{40}H_{58}O_4$ (M.W. 602.86): C 79.69; H 9.70. Found: C 79.61; H 9.79.

IR$\nu$, KBr (cm$^{-1}$): 2920, 2850, 1765, 1715, 1270, 1190, 1160, 1115.

PMR (CDCl$_3$)$\delta$: 0.36 (1H, ½ ABq, 4.8 Hz), 0.60 (1H, ½ ABq, 4.8 Hz), 0.68–2.40 (27H, m), 0.89 (6H, s), 0.96 (3H, s), 1.01 (3H, s), 1.60 (9H, s), 2.28 (3H, s), 4.60–5.00 (1H, m), 6.96–7.32 (2H, m), 7.90–8.25 (2H, m).

EXAMPLE 58

Preparation of cyclobranyl-p-hydroxybenzoate

Cyclobranyl-p-acetoxybenzoate (24 g, 0.0398 mole) prepared according to the procedure of Example 57 was dissolved in tetrahydrofuran (350 ml) and to that was added 25% aqueous ammonia (50 ml). The mixture was continued to stir at 40° C. for 1 hour, then, evaporated to dryness under reduced pressure. The residual crystals were recrystallized from ethanol, giving cyclobranyl-p-hydroxybenzoate (21.0 g), in a 94% yield. m.p. 174°–175° C.

Specific rotation $[\alpha]_D^{23} +57.7°$ (C 1.10, CHCl$_3$)

Analysis, Calcd. for $C_{38}H_{56}O_3 \cdot C_2H_5OH$ (M.W. 606.9): C 79.16; H 10.30. Found: C 79.13; H 10.42.

IR$\nu$, KBr (cm$^{-1}$): 3400, 2920, 2850, 1685, 1610, 1280, 1160.

PMR (CDCl$_3$)$\delta$: 0.38 (1H; ½ ABq, 4.8 Hz), 0.64 (1H, ½ ABq, 4.8 Hz), 0.70–2.42 (27H, m), 0.91 (6H, s), 0.98 (3H, s), 1.02 (3H, s), 1.28 (3H, t, 7.2 Hz), 1.62 (9H, s), 3.77 (2H, q. 7.2 Hz), 4.60–5.00 (1H, m), 6.72–7.18 (4H, m), 7.80–8.12 (2H, m).

EXAMPLE 59

Preparation of cycloartenyl-4-acetoxy-3-ethoxybenzoate

The title compound was prepared according to following the procedure of Example 28 where 4-acetoxy-3-ethoxybenzoic acid (13.9 g, 0.062 mole) was used in place of 4-acetoxy-3-methoxybenzoic acid (13.0 g); cycloartenyl-4-acetoxy-3-ethoxybenzoate was yielded 24.5 g (82%). m.p. 140°–141° C.

Specific rotation $[\alpha]_D^{24}$ 58.2° (C 1.00, CHCl$_3$)

Analysis, Calcd. for $C_{41}H_{60}O_5$ (M.W. 632.89): C 77.80; H 9.56. Found: C 77.91; H 9.43.

EXAMPLE 60

Preparation of cycloartenyl-3-ethoxy-4-hydroxybenzoate

Cycloartenyl-4-acetoxy-3-ethoxybenzoate (30 g, 0.047 mole) prepared according to the procedure of Example 59 was dissolved in tetrahydrofuran (300 ml), and to it was added 25% aqueous ammonia (60 ml). After the mixture was stirred at 50° C. for 2 hours, the mixture was evaporated to dryness under reduced pressure. The residual crystals were recrystallized from acetone-water (2:1, V/V), giving cycloartenyl-3-ethoxy-4-hydroxybenzoate ester (20.5 g), in a 74% yield. m.p. 128°–130° C.

Specific rotation $[\alpha]_D^{24} +59.5°$ (C 1.00, CHCl$_3$)

Analysis, Calcd. for $C_{39}H_{58}O_4$ (M.W. 590.85): C 79.27; H 9.89. Found: C 79.21; H 9.82.

EXAMPLE 61

Preparation of cyclobranyl-4-acetoxy-3-ethoxybenzoate

The title compound was prepared according to following the procedure of Example 28 where 4-acetoxy-3-ethoxybenzoic acid (13.9 g, 0.062 mole) and cyclobranol (20.0 g, 0.045 mole) were used respectively, in place of 4-acetoxy-3-methoxybenzoic acid (13.0 g) and cycloartenol (20.0 g); cyclobranyl-4-acetoxy-3-methoxybenzoate was yielded 23.4 g (80%). m.p. 161°–162° C.

Specific rotation $[\alpha]_D^{24}$ +56.5° (C 1.00, CHCl$_3$)

Analysis, Calcd. for C$_{42}$H$_{62}$O$_5$ (M.W. 646.92): C 77.97; H 9.66. Found: C 78.05; H 9.61.

EXAMPLE 62

Preparation of cyclobranyl-3-ethoxy-4-hydroxybenzoate

Cyclobranyl-4-acetoxy-3-ethoxybenzoate (30 g, 0.046 mole) prepared according to procedure of Example 61 was dissolved in tetrahydrofuran (300 ml) and to it was added 25% aqueous ammonia (60 ml). After the mixture was stirred at 50° C. for 3 hours, the mixture was evaporated to dryness under reduced pressure, and the residual crystals were recrystallized from acetone-water (2:1, V/V), giving cycloartenyl-3-ethoxy-4-hydroxybenzoate (20.8 g), in a 74% yield. m.p. 175°–176° C.

Specific rotation $[\alpha]_D^{24}$+57.5° (C 1.00, CHCl$_3$)

Analysis, Calcd. for C$_{40}$H$_{60}$O$_4$ (M.W. 604.88): C 79.42; H 10.00. Found: C 79.31; H 10.12.

EXAMPLE 63

Preparation of 24-methylenecycloartanyl-4-acetoxy-3-ethoxybenzoate

The title compound was prepared according to following the procedure of Example 28 where 4-acetoxy-3-ethoxybenzoic acid (13.9 g, 0.062 mole) and 24-methylenecycloartenol (20.0 g, 0.045 mole) were used in place of 4-acetoxy-3-methoxybenzoic acid (13.0 g) and cycloartenol (20.0 g), respectively; The yield was 23.1 g (79%). m.p. 152°–153° C.

Specific rotation $[\alpha]_D^{24}$+57.8° (C 1.00, CHCl$_3$)

Analysis, Calcd. for C$_{42}$H$_{62}$O$_5$ (M.W. 646.92): C 77.97; H 9.66. Found: C 77.92; H 9.54.

EXAMPLE 64

Preparation of 24-methylenecycloartanyl-3-ethoxy-4-hydroxybenzoate

The title compound was prepared according to following the procedure of Example 55 where 24-methylenecycloartanol-4-acetoxy-3-ethoxybenzoate (30 g, 0.046 mole) obtained by the procedure of Example 63 was used; The yield was 20.1 g (72%). m.p. 141°–142° C.

Specific rotation $[\alpha]_D^{24}$+58.4° (C 1.00, CHCl$_3$)

Analysis, Calcd. for C$_{40}$H$_{60}$O$_4$ (M.W. 604.88): C 79.42; H 10.00. Found: C 79.49 H 10.05.

EXAMPLE 65

Preparation of cyclobranyl-4-acetoxy-3-methoxycinnamate

To 4-acetoxy-3-methoxycinnamic acid (26.5 g, 0.112 mole) suspended in toluene (200 ml) was added thionyl chloride (16.3 ml, 3 equivalents) and the mixture was stirred at 60° C. for 2 hours. Then the mixture was evaporated under reduced pressure and the residue was suspended in toluene (150 ml) and pyridine (30 ml). Cyclobranol (33.1 g, 0.075 mole) was added to the suspension and the mixture was stirred at 60° C. for 2 hours. After the reaction was complete, the mixture was evaporated to dryness under reduced pressure, and the residue was extracted with chloroform (300 ml). The extract was washed, dried, and evaporated to dryness under reduced pressure. The residual crystals were recrystallized from ethanol, giving cyclobranyl-4-acetoxy-3-methoxycinnamate (44.9 g), in a 91% yield. m.p. 175°–176° C.

Specific rotation $[\alpha]_D^{25}$+37.0° (C 1.00, CHCl$_3$)

Analysis, Calcd. for C$_{43}$H$_{62}$O$_5$ (M.W. 658.93): C 78.38; H 9.48. Found: 78.44; H 9.43.

EXAMPLE 66

Preparation of cycloartenyl-4-acetoxy-3-methoxycinnamate

The title compound was prepared according to following the procedure of Example 65 where cycloartenol (33 g, 0.077 mole) was used in place of cyclobranol (33 g); the yield was 42.4 g (86%). m.p. 187°–188° C.

Specific rotation $[\alpha]_D^{24}$+40.7° (C 1.00, CHCl$_3$)

Analysis, Calcd. for C$_{42}$H$_{60}$O$_5$ (M.W. 644.90): C 78.22; H 9.38. Found: C78.34; H 9.30.

EXAMPLE 67

Preparation of 24-methylenecycloartanyl-4-acetoxy-3-methoxycinnamate

The title compound was prepared according to following the procedure of Example 65 where 24-methylenecycloartanol (33 g, 0.0749 mole) was used in place of cyclobranol; The yield was 43.7 g (88%). m.p. 216°–217° C.

Specific rotation $[\alpha]_D^{24}$+40.1° (C 1.00, CHCl$_3$)

Analysis, Calcd. for C$_{43}$H$_{62}$O$_5$ (M W. 658.93): C 78.38; H 9.48. Found: C 78.46; H 9.40.

IR$\nu$, KBr (cm$^{-1}$) 2920, 2850, 1765, 1710, 1635, 1510, 1275, 1258, 1200, 1170, 1155.

PMR (CDCl$_3$)δ: 0.39 (1H, ½ ABq, 4.2 Hz), 0.61 (1H, ½ ABq, 4.2 Hz), 0.60–2.40 (28H, m), 0.82 (6H, s), 0.96 (6H, s), 1.02 (6H, d, 7.2 Hz), 2.32 (3H, s), 3.86 (3H, s), 4.70 (2H, bs), 4.50–4.90 (1H, m), 6.40 (1H, ½ ABq, 16 Hz), 6.90–7.30 (3H, m), 7.58 (1H, ½ ABq, 16 Hz).

EXAMPLE 68

Preparation of cycloartenyl-4-acetoxy-3-ethoxycinnamate

The title compound was prepared according to following the procedure of Example 65 where 4-acetoxy3-ethoxycinnamic acid (27.0 g, 0.108 mole) and cycloartenol (25.2 g, 0.059 mole) was used in place of 4-acetoxy-3-methoxycinnamic acid (26.5 g) and cyclobranol (33 g), respectively; the yield was 32.6 g (83%). m.p. 165°–166° C.

Specific rotation $[\alpha]_D^{24}$+40.5° (C 1.00, CHCl$_3$)

Analysis, Calcd. for C$_{43}$H$_{62}$O$_5$ (M.W. 658.93): C 78.38; H 9.48. Found: C 78.27; H 9.53.

EXAMPLE 69

Preparation of cycloartenyl-3-ethoxy-4-hydroxycinnamate

Cycloartenyl-4-acetoxy-3-ethoxycinnamate (30.3 g, 0.046 mole) prepared according to procedure of Example 68 was dissolved in tetrahydrofuran (300 ml), followed by addition of 25% aqueous ammonia (60 ml). The mixture was stirred at 50° C. for 2 hours. After the reaction was complete, the mixture was evaporated to dryness under reduced pressure, and the residual crystals were recrystallized from acetone-water (2:1, V/V), giving cycloartenyl-3-ethoxy-4-hydroxycinnamate (19.7 g), in a 69% yield. m.p. 134°–135° C.

Specific rotation $[\alpha]_D^{24}+40.8°$ (C 1.00, $CHCl_3$)

Analysis, Calcd. for $C_{41}H_{60}O_4$ (M.w. 616.89): C 79.82; H 9.80. Found: C 79.89; H 9.73.

EXAMPLE 70

Preparation of cyclobranyl-4-acetoxy-3-ethoxycinnamate

The title compound was prepared according to following the procedure of Example 68 where cyclobranol (33.1 g, 0.075 mole) was used as starting material; the yield was 43.1 g (85%). m.p. 153°–154° C.

Specific rotation $[\alpha]_D^{24}+37.6°$ (C 1.00, $CHCl_3$)

Analysis, Calcd. for $C_{44}H_{64}O_5$ (M.W. 672.95): C 78.53; H 9.59. Found: C 78.48; H 9.64.

EXAMPLE 71

Preparation of cyclobranyl-3-ethoxy-4-hydroxycinnamate

The title compound was prepared according to following the procedure of Example 69 where cyclobranyl-4-acetoxy-3-ethoxycinnamate (30.9 g, 0.046 mole) obtained by the procedure of Example 70 was used; the yield was 22.8 g (78%). m.p. 181°–182° C.

Specific rotation $[\alpha]_D^{24}+38.0°$ (C 1.00, $CHCl_3$)

Analysis, Calcd. for $C_{42}H_{62}O_4$ (M.W. 630.92): C 79.95; H 9.91. Found: C 79.91; H 9.98.

EXAMPLE 72

Preparation of 24-methylenecycloartanyl-4-acetoxy-3-ethoxycinnamate

The title compound was prepared according to following the procedure of Example 68 where 24-methylenecycloartanol (33.1 g, 0.075 mole) was used as starting material; the yield was 42.7 g (84%). m.p. 184°–185° C.

Specific rotation $[\alpha]_D^{24}+39.9°$ (C 1.00, $CHCl_3$)

Analysis, Calcd. for $C_{44}H_{64}O_5$ (M.W. 672.95): C 78.53; H 9.59. Found: C 78.59; H 9.52.

EXAMPLE 73

Preparation of 24-methylenecycloartanyl-3-ethoxy-4-hydroxycinnamate

The title compound was prepared according to following the procedure of Example 69 where 24-methylenecycloartanyl-4-acetoxy-3-ethoxycinnamate (30.9 g, 0.046 mole) obtained according to the procedure of Example 72 was used; the yield was 23.4 g (80%). m.p. 146°–147° C.

Specific rotation $[\alpha]_D^{24}+40.1°$ (C 1.00, $CHCl_3$)

Analysis, Calcd. for $C_{42}H_{62}O_4$ (M.W. 630.92): C 79.95; H 9.91. Found: C 79.89; H 9.95.

EXAMPLE 74

Preparation of cycloartenyl-4-hydroxy-3-propoxycinnamate

The title compound was prepared according to following the procedure of Example 69 cycloartenyl-4-acetoxy-3-n-propoxycinnamate (31.0 g, 0.046 mole) obtained according to the procedure of Example 68; the yield was 20.5 g (70%). m.p. 144°–145° C.

Specific rotation $[\alpha]_D^{24}+40.2°$ (C 1.00, $CHCl_3$)

Analysis, Calcd. for $C_{42}H_{62}O_4$ (M.W. 630.92): C 79.95; H 9.91. Found: C 79.99; H 9.85.

EXAMPLE 75

Preparation of cyclobranyl-4-hydroxy-3-propoxycinnamate

The title compound was prepared according to following the procedure of Example 69 being used cyclobranyl-4-acetoxy-3-propoxycinnamate (31.6 g, 0.046 mole) obtained according to the procedure of Example 68; the yield was 22.8 g (76%). m.p. 187°–188° C.

Specific rotation $[\alpha]_D^{24}+37.4°$ (C 1.00, $CHCl_3$)

Analysis, Calcd. for $C_{43}H_{64}O_4$ (M.W. 644.94): C 80.07; H 10.00. Found: C 79.92; H 10.13.

EXAMPLE 76

Preparation of cycloartenyl-3,4-dimethoxycinnamate

Acetone (200 ml) and potassium carbonate (10.0 g) were added to cycloartenyl-4-hydroxy-3-methoxycinnamate (10.0 g, 0.017 mole) at 20° C. and the mixture was stirred. Thereto was added dimethyl sulfate (2.8 ml, 5 equivalents) and continued to stir at 50° C. for 3 hours. Then the potassium carbonate was separated by filtration, and the filtrate was evaporated under reduced pressure. The residue was dissolved in methylene chloride, and the methylene chloride layer washed with saturated aqueous solution of sodium bicarbonate. The aqueous layer was extracted with methylene chloride and the.combined extracts were dried, evaporated to dryness under reduced pressure, and the residue was recrystallized from methylene chloride-methanol (1:4, V/V), giving the title compound (9.6 g) in a 94% yield. m.p. 136°–137° C.

Specific rotation $[\alpha]_D^{23}+41.7°$ (C 1.03, $CHCl_3$)

Analysis, Calcd. for $C_{41}H_{60}O_4$ (M.W. 616.89): C 79.82; H 9.80. Found: C 79.90; H 9.88.

EXAMPLE 77

Preparation of cycloartenyl-3-methoxy-4-propionyloxycinnamate

Pyridine (160 ml) was added to cycloartenyl-4-hydroxy-3-methoxycinnamate (40.0 g, 0.066 mole) and the mixture was stirred at 0° C. Thereto was added propionic anhydride (80 ml) dropwise and the solution was continued to stir at 20° C. for 1 hour, then allowed to stand at 5° C. for 48 hours. After the reaction was completed water (250 ml) was added to the solution to precipitate crystals of the title compound, which were then filtered and washed with water and methanol. The yield was 42.3 g (95%). m.p. 156–157° C.

Specific rotation $[\alpha]_D^{25}+40.2°$ (C 1.04, $CHCl_3$)

Analysis, Calcd. for $C_{43}H_{62}O_5$ (M.W. 658.93): C 78.38; H 9.48. Found: C 78.45; H 9.42.

EXAMPLE 78

Preparation of cycloartenyl-3,4-dimethoxybenzoate

Toluene (10 ml), thionyl chloride (48 ml, 10 equivalents) and pyridine (1.0 ml) were added to 3,4-dimethoxybenzoic acid (11.8 g, 0.065 mole) at 0° C., and the mixture was stirred at 40° C. for 10 minutes. The reaction mixture was evaporated under reduced pressure, and to the residue were added cycloartenol (20.0 g, 0.043 mole) and pyridine (100 ml) at 0° C. The mixture was heated to 40° C. and stirred for 1 hour and furthermore continued to stir at 60° C. for 1 hour. The resulting mixture was evaporated under reduced pressure, and the residual crystals were dissolved in chloroform. The organic layer was washed with saturated aqueous solution of sodium bicarbonate, then aqueous layer was extracted with chloroform. The combined extracts were dried, and evaporated under reduced pressure. The resulting residue was purified by silica gel column chromatography (solvent: toluene-methylene chloride, (2:1, V/V)), giving cycloartenyl-3,4-dimethoxybenzoate (25.9 g), in a 88% yield. m.p. 147°–147.5° C.

Specific rotation $[\alpha]_D^{26}+63.8°$ (C 1.00, CHCl$_3$)

Analysis, Calcd. for C$_{39}$H$_{58}$O$_4$ (M.W. 590.85): C 79.27; H 9.89. Found: C 79.34; H 9.82.

EXAMPLE 79

Preparation of cyclobranyl-3,4-dimethoxycinnamate

To 3,4-dimethoxycinnamic acid (16.53 g, 0.0794 mole) suspended in toluene (200 ml) was added thionyl chloride (11.5 ml, 2 equivalents) and the mixture was stirred at 100° C. for 2.5 hours. The resulting mixture was evaporated under reduced pressure, and the residue was suspended in a toluene (100 ml) and pyridine (50 ml). To the suspension was added cyclobranol (17.5 g, 0.0397 mole) and the mixture was stirred at 100° C. for 3 hours. The solution was evaporated under reduced pressure, and the residue was extracted with chloroform (300 ml). The extract was dried, concentrated in vacuo, and purified by silica gel column chromatography (solvent: toluene), giving cyclobranyl-3,4-dimethoxycinnamate (22.3 g), in a 93% yield. m.p. 168°–169° C.

Specific rotation $[\alpha]_D^{25}+38.5°$ (C 1.00, CHCl$_3$)

Analysis, Calcd. for C$_{42}$H$_{62}$O$_4$ (M.W. 630.92): C 79.95; H 9.91. Found: C 80.02; H 9.84.

EXAMPLE 80

Preparation of cyclobranyl-3,4-dimethoxybenzoate

To veratric acid (15.5 g, 0.085 mole) dissolved in toluene (150 ml) was added thionyl chloride (12.4 ml, 2 equivalents) and the mixture was stirred at 100° C. for 1.5 hours. The solution was evaporated under reduced pressure and the residue was dissolved in toluene (100 ml) and pyridine (50 ml). To the solution was added cyclobranol (25 g, 0.057 mole) and the mixture was stirred at 60° C. for 2 hours. The reaction mixture was evaporated to dryness under reduced pressure, and the residue was extracted with chloroform (300 ml). The extract was dried, concentrated in vacuo, and purified by silica gel column chromatography (solvent: toluene), giving cyclobranyl-3,4-dimethoxybenzoate (25.6 g), in a 76% yield. m.p. 158°–159° C.

Specific rotation $[\alpha]_D^{26}+59.2°$ (C 0.89, CHCl$_3$)

Analysis, Calcd. for C$_{40}$H$_{60}$O$_4$ (M.W. 604.88): C 79.42; H 10.00. Found: C 79.34; H 10.12.

EXAMPLES 81–100

The esters of 24-methylenecycloartanol in Examples 81–100 were prepared according to following the corresponding procedures of the cyclobranol's mentioned above. In these procedures the same amounts (by mole) of 24-methylenecycloartanol, in place of cyclobranol, was used. Yields (%), melting points (°C.), and specific rotations (C1.00, CHCl$_3$) of these compounds are summarized in Table 25.

TABLE 25

| Example No. | Original organic acid of ester | Yield (%) | M.P. (°C.) | Specific rotation $[\alpha]_D^{24}$ |
|---|---|---|---|---|
| 81 | 3,4-Diacetoxycinnamic acid | 62 | 143–145 | +36.2° |
| 82 | 3,4-Dihydroxycinnamic acid | 73 | 236–237 | +42.5° |
| 83 | p-Acetoxycinnamic acid | 76 | 158–159 | +42.0° |
| 84 | p-Hydroxycinnamic acid | 87 | 240–241 | +43.5° |
| 85 | 4-Acetoxy-3-methoxybenzoic acid | 76 | 162–163 | +58.2° |
| 86 | 4-Hydroxy-3-methoxybenzoic acid | 80 | 155–156 | +60.2° |
| 87 | 3,4-Diacetoxybenzoic acid | 62 | 153–154 | +52.3° |
| 88 | 3,4-Dihydroxybenzoic acid | 85 | 205–206 | +61.4° |
| 89 | p-Nitrobenzoic acid | 89 | 229–230 | +61.8° |
| 90 | p-Aminobenzoic acid | 72 | 174–175 | +60.2° |
| 91 | Nicotinic acid | 86 | 173–174 | +66.5° |
| 92 | o-Hydroxybenzoic acid | 69 | 161–162 | |
| 93 | Linoleic acid | 69 | oily matter | +38.1° |
| 94 | p-Hydroxybenzoic acid | 92 | 177–178 | +64.4° |
| 95 | m-Acetoxybenzoic acid | 90 | 133–134 | +60.1° |
| 96 | m-Hydroxybenzoic acid | 85 | 185–186 | +64.2° |
| 97 | o-Nitrobenzoic acid | 89 | 190–191 | +92.5° |
| 98 | o-Aminobenzoic acid | 67 | 196–197 | +76.1° |
| 99 | m-Nitrobenzoic acid | 85 | 170–171 | +60.8° |
| 100 | m-Aminobenzoic acid | 82 | 178–179 | +62.0° |

EXAMPLE 100-1

Preparation of cycloartenyl-4-hydroxy-3-methoxycinnamate

Methanol (350 ml) was added to a solution or γ-oryzanol (1.0 kg, cycloartenol ester content 44%) in acetone (5.0 l) at an elevated temperature. Then the mixture was cooled and allowed to stand overnight at 20° C. The thus separated crystals were filtered, giving γ-oryzanol (680 g) in which the content of cycloartenyl ester was 60%. Similar recrystallization of this γ-oryzanol by using acetone (3.4 l) and methanol (68 ml) gave γ-oryzanol (450 g) of cycloartenyl ester content 75%. Further repeated recrystallizations the first time from acetone (2.25 l), the second ethyl acetate (1.25 l), the third acetone (1.29 l), and the fourth acetone (960 ml), respectively, yielded 250 g (88% purity on cycloartenyl ester), 184 g (92% purity), 120 g (97% purity) and 91 g (98% purity) of γ-oryzanol, and the final recrystallization from ethyl acetate (640 ml) gave cycloartenyl-4-hydroxy-3-methoxycinnamate (53 g), in a 5.3% yield. m.p. 153°–153.5° C.

Specific rotation $[\alpha]_D^{21.5}+41.2°$ (C 0.99, CHCl$_3$)

Analysis, Calcd. for C$_{40}$H$_{58}$O$_4$ (M.W. 602.86): C 79.69; H 9.70. Found: C 79.73; H 9.62.

IR$\nu$, KBr (cm$^{-1}$): 3400, 2910, 1700, 1672, 1599, 1510, 1270, 1155.

PMR (CDCl$_3$)δ: 0.38 (1H, ½ ABq, 4.2 Hz), 0.58 (1H, ½ ABq, 4.2 Hz), 0.70–2.40 (27H, m), 0.89 (6H, s), 0.96 (6H, s), 1.61 (3H, bs), 1.68 (3H, bs), 3.91 (3H, s), 4.50–4.90 (1H, m), 4.80–5.30 (1H, m), 5.87 (1H, s), 6.28 (1H, ½ ABq, 15 Hz), 6.76–7.10 (2H, m), 7.00 (1H, s), 7.55 (1H, ½ ABq, 15 Hz).

EXAMPLE 100-2

Preparation of cyclobranyl-4-hydroxy-3-methoxycinnamate

Cyclobranyl-4-actoxy-3-methoxycinnamate (44.9 g, 0.068 mole) prepared according to the procedure of Example 65 was dissolved in dioxane (900 ml), and to the solution was added 25% aqueous ammonia (90 ml) dropwise. After the mixture was stirred at 50° C. for 2 hours, the solution was evaporated to dryness under reduced pressure. The residual crystals were washed with ethanol, giving cyclobranyl-4-hydroxy-3-methoxycinnamate (40.0 g), in a 95.2% yield. m.p. 191°–192° C.

Specific rotation $[\alpha]_D^{23.5}+38.5°$ (C 0.99, CHCl$_3$)

Analysis, Calcd. for C$_{41}$H$_{60}$O$_4$ (M.W. 616.89): C 79.82; H 9.80. Found: C 79.77; H 9.88.

IR$\nu$, KBr (cm$^{-1}$): 3500, 2920, 2850, 1690, 1600, 1510, 1265, 1155.

PMR (CDCl$_3$)$\delta$: 0.36 (1H, ½ ABq, 4.8 Hz), 0.60 (1H, ½ ABq, 4.8 Hz), 0.68–2.20 (27H, m), 0.89 (6H, s), 0.96 (6H, s), 1.62 (9H, s), 3.90 (3H, s), 4.50–4.90 (1H, m), 5.97 (1H, b), 6.27 (1H, ½ ABq, 15.6 Hz), 6.75–7.20 (3H, m), 7.9 (1H, ½ ABq, 15.6 Hz).

EXAMPLE 100-3

Preparation of 24-methylenecycloartanyl-4-hydroxy-3-methoxycinnamate

Commercial available γ-oryzanol (100 g, 24-methylenecycloartanol content 45%) was acetylated with acetic anhydride in pyridine. This acetylated γ-oryzanol was recrystallized repeatedly from chloroform-ethyl acetate-ethanol (4:3:2, V/V), giving acetyl ferulate (18 g) of 24-methylenecycloartanol content 95%. This acetyl ferulate was completely saponified in the solution of 2N NaOH-ethanol, then the obtained alcohol was converted into the benzoate. This benzoate was recrystallized repeatedly, and completely saponified to give 24-methylenecycloartanol (5 g). A portion (2 g, 0.0045 mole) thereof wa converted into 24-methylenecycloartanol-4-acetoxy-3-methoxycinnamate according to following the procedure of Example 65. This ester was then deacetylated according to following the procedure of Example 100-2, giving 24-methylenecycloartanol-4-hydroxy-3-methoxycinnamate (2.58 g), in a 90% yield. m.p. 166°–167° C.

Specific rotation $[\alpha]_D^{24}+40.6°$ (C 1.00, CHCl$_3$)

Analysis, Calcd. for C$_{41}$H$_{60}$O$_4$·⅓C$_2$H$_5$OH (M.W. 632.25): C 79.15; H 9.88. Found: C 79.11; H 9.94.

IR$\nu$, KBr (cm$^{-1}$): 3400 2920, 2850, 1688, 1630, 1600, 1510, 1463, 1425, 1265, 1158

PMR (CDCl$_3$)$\delta$: 0.39 (1H, ½ ABq, 4.2 Hz), 0.59 (1H, ½ ABq, 4.2 Hz), 0.60–2.50 (28H, m), 0.82 (6H, s), 0.95 (6H, s), 1.02 (6H, d, 7.2 Hz), 3.91 (3H, s), 4.70 (2H, bs), 4.50–4.90 (1H, m), 5.95 (1H, s), 6.70–7.30 (3H, m), 6.32 (1H, ½ ABq, 16 Hz), 7.56 (1H, ½ ABq, 16 Hz).

EXAMPLE 101

Preparation of cycloartenyl ester of p-nitro cinnamic acid

Thionyl chloride (112 ml, 4 equivalents) and dimethylformamide (1 ml) were added to p-nitrocinnamic acid (73.0 g, 0.378 mole) and the mixture was stirred at 60° C. for 2 hours. Then the resulting mixture was concentrated under reduced pressure. Dioxane (250 ml), pyridine (250 ml), and then cycloartenyl (125 g, 0.293 mole) were added to the residue. After 2 hours' stirring at 60° C., the solvents were removed by distillation under reduced pressure, and the residue was extracted with chloroform. The extracts were washed successively with water and saturated aqueous NaHCO$_3$, then dried, and concentrated under reduced pressure. The residual crystals were recrystallized from methylene chloride-methanol (1:5,v/v),giving cycloartenyl ester of p-nitrocinnamic acid (158.0 g), in a 89.6% yield. m.p. 199°–200° C.

Specific rotation $[\alpha]_D^{26}+43.8°$ (C1.00, CHCl$_3$).

Analysis, Calcd. for C$_{39}$H$_{55}$NO$_4$ (M.W.601.83): C,77.83; H,9.21; N,2.33. Found: C,77.89; H,9.16; N,2.28.

IR$\nu$, KBr(cm$^{-1}$): 2930, 1708, 1640, 1600, 1520, 1345, 1205, 1175.

PMR(CDCl$_3$)$\delta$: 0.38(1H, ½ ABq, 4.2 Hz), 0.61(1H, ½ABq, 4.2 Hz), 0.52–2.36(27H, m), 0.91(6H, s), 0.98(6H, s), 1.61(3H, s), 1.63(3H, s), 4.83–4.90(1H, m), 4.90–5.31(1H, m), 6.55(1H, ½ ABq, 16.2 Hz), 7.65(2H, ABq, 8.7 Hz), 7.67 (1H, ½ABq, 16.2 Hz), 8.24(2H, ABq, 8.7 Hz).

EXAMPLE 102

Preparation of cycloartenyl ester of p-amino-cinnamic acid

Cycloartenyl ester of p-nitro cinnamic acid (160.0 g, 0.266 mole) prepared according to the procedure of Example 101 was suspended in a mixture of acetic acid (1.5 l) and dioxane (1.5 l). To the suspension were added 6N-HCl-dioxane (95 ml) and zinc powder (80 g) and the mixture was stirred at 40° C. for 3 hours. After the reaction, zinc powder was removed by filtration. The filtrate was concentrated under reduced pressure, and the residue was extracted with chloroform. The extracts were washed successively with water and saturated aqueous NaHCO3, then dried, and concentrated under reduced pressure. The residual crystals were recrystallized from chloroform-ethanol (1:5, v/v), giving cycloartenyl ester of p-aminocinnamic acid (140.0 g), in a 92.0% yield. m.p. 185°–187° C.

Specific rotation $[\alpha]_D^{26}+42.3$(C 1.00, CHCl$_3$)

Analysis, Calcd. for C$_{39}$H$_{57}$NO$_2$(M.W.571.85): C,81.91; H,10.05; N,2.45. Found: C,81.87; H, 10.03; N,2.53.

IR$\nu$, KBr(cm$^{-1}$): 3450, 3350, 2920, 1695, 1620, 1600, 1515, 1440, 1205, 1165.

PMR(CDCl$_3$)$\delta$: 0.38(1H, ½ABq, 4.2 Hz), 0.61(1H, ½ABq, 4.2 Hz), 0.72–2.80(27H, m), 0.91(6H, s), 0.96(6H s), 160(3H, s), 168(3H, s), 3.92(2H, bs), 4.48–4.88(1H, m), 4.88–5.32(1H, m), 6.22(1H, ½ABq, 15.8 Hz), 6.63(2H, ABq, 8.4 Hz), 7.35(2H, ABq, 8.4 Hz), 7.56(1H, ½ABq, 15.8 Hz).

EXAMPLE 103

Preparation of cyclobranyl ester of p-nitrocinnamic acid

Thionyl chloride (60 ml, 2 equivalents),dioxane (300 ml), and dimethylformamide (1 ml) were added to p-nitrocinnamic acid (75 g, 0.388 mole), and the mixture was stirred at 60° C. for 2 hours. Then the resulting mixture was concentrated under reduced pressure. To the residue were added dioxane (300 ml), pyridine (200 ml) and then cylobranol (130 g, 0.295 mole). After 2 hours' stirring at 60° C., the solvents were removed by distillation under reduced pressure, and the residue was extracted with chloroform. The extracts were washed successively with water and saturated aqueous NaHCO$_3$, then dried, and concentrated in vacuo. The residue was recrystallized from chloroform-ethanol (1:3, v/v), giving cyclobranyl ester of p-nitrocinnamic acid (168.4 g), in a 92.7% yield. m.p. 231°–232° C.

Specific rotation $[\alpha]_D^{26}+40.6°$(C 1.00, CHCl$_3$)

Analysis Calcd. for C$_{40}$H$_{57}$NO$_4$(M.W.615.86): C,78.01; H,9.33; N,2.27. Found: C,78.10; H,9.24; N,2.36.

IRν, KBr(cm⁻¹): 2930, 1710, 1635, 1600, 1520, 1345, 1300, 1175.

PMR(CDCl$_3$)δ: 0.36(1H, ½ABq, 4.8 Hz), 0.61(1H, ½ABq, 4.8 Hz), 0.68-2.20(27H, m), 0.91(6H, s), 0.97(6H, s), 1.62(9H, s), 4.48-4.92(1H, m), 6.55(1H, ½ABq, 15.6 Hz), 7.67(2H, ABq, 8.4 Hz), 7.69(1H, ½ABq, 15.6 Hz), 8.22(2H, ABq, 8.4 Hz).

EXAMPLE 104

Preparation of cyclobranyl ester of p-aminocinnamic acid

Cyclobranyl ester of p-nitrocinnamic acid (165.0 g, 0.268 mole) prepared according to the procedure of Example 103 was suspended in a mixture of acetic acid (1.5 l) and tetrahydrofuran (2 l). To the suspension were added 6N-HCl-dioxane (125 ml) and zinc powder (165 g) and the mixture was stirred at 20° C. for 2 hours. Then the reaction mixture was filtered to remove zinc powder. The filtrate was concentrated under reduced pressure, and the residue was extracted with chloroform. The extracts were washed successively with water and saturated aqueous NaHCO3, then dried, and concentrated in vacuo. The residual crystals were recrystallized from chloroform-ethanol (1:3, v/v), giving cyclobranyl ester of p-aminocinnamic acid (119.2 g), in a 75.9% yield. m.p. 206°-207° C.

Specific rotation $[\alpha]_D^{26}$+40.1°(C 1.00, CHCl$_3$)

Analysis Calcd. for C$_{40}$H$_{59}$NO$_2$(M.W.585.87): C,82.00; H,10.15; N,2.39. Found: C,81.92; H,10.14; N,2.43.

IRν, KBr(cm⁻¹): 3450, 3350, 2930, 1690, 1620, 1595, 1515, 1440, 1300, 1270, 1170.

PMR(CDCl$_3$)δ: 0.35(1H, ½ABq, 4.8 Hz), 0.59(1H, ½ABq, 4.8 Hz), 0.68-2.36(27H, m), 0.90(6H, s), 0.96(6H, s), 1.62(9H, s), 3.76-4.08(2H, m), 4.44-4.87(1H, m), 6.22(1H, ½ABq, 15.6 Hz), 6.62(2H, ABq, 8.4 Hz), 7.34(2H, ABq, 8.4 Hz), 7.57(1H, ½ABq, 15.6 Hz).

EXAMPLE 105

Preparation of 24-methylenecycloartanyl ester of p-nitrocinnamic acid

The title compound was prepared according to following the procedure of Example 103 where 24-methylenecycloartanol (130 g, 0.295 mole) was used as a starting material in place of cyclobranol. The yield was 164.8 g (90.7%). m.p. 223°-224° C.

Specific rotation $[\alpha]_D^{26}$+43.1°(C 1.00, CHCl$_3$)

Analysis Calcd. for C$_{40}$H$_{57}$NO$_4$(M.W.615.86): C,78.01; H,9.33; N,2.27. Found: C,78.08; H,9.25; N,2.34.

EXAMPLE 106

Preparation of 24-methylenecycloartanyl ester of p-aminocinnamic acid

The title compound was prepared according to following the procedure of Example 104 where 24-methylenecycloartanyl ester of p-nitrocinnamic acid (163.5 g, 0.265 mole) as a starting material. The yield was 118.3 g (76.2%). m.p. 201°-202° C.

Specific rotation $[\alpha]_D^{26}$+42.0°(C 1.00, CHCl$_3$)

Analysis, Calcd. for C$_{40}$H$_{59}$NO$_2$(M.W 585.87): C,82.00; H,10.15; N2.39. Found: C,81.95; H, 10.19; N2.42.

EXAMPLE 107

Preparation of cycloartenyl ester of m-nitrocinnamic acid

The title compound was prepared according to following the procedure of Example 101 but m-nitrocinnamic acid (73.0 g, 0.378 mole) was used as a starting material in place of p-nitrocinnamic acid. The yield was 156.8 g (88.9%). m.p. 181°-182° C.

Specific rotation $[\alpha]_D^{26}$+42.4°(C 1.00, CHCl$_3$)

Analysis, Calcd. for C$_{39}$H$_{55}$NO$_4$(M.W.601.83): C,77.83 H,9.21; N,2.33. Found: C,77.76; H,9.26; N,2.39.

EXAMPLE 108

Preparation of cycloartenyl ester of m-aminocinnamic acid

The title compound was prepared according to following the procedure of Example 102 but cycloartenyl ester of m-nitrocinnamic acid (160.0 g, 0.266 mole) obtained according to the procedure of Example 107 was used in place of cycloartenyl ester. The yield was 135.8 g (89.2%). m.p. 189°-190° C.

Specific rotation $[\alpha]_D^{26}$+43.1°(C 1.00, CHCl$_3$)

Analysis Calcd. for C$_{39}$H$_{57}$NO$_2$(M.W.571.85): C,81.91; H,10.05; N,2.45. Found: C,81.87; H,10.08; N,2.53.

EXAMPLE 109

Preparation of cyclobranyl ester of m-nitrocinnamic acid

The title compound was prepared according to following the procedure of Example 103 but m-nitrocinnamic acid (75 g, 0.388 mole) was used as a starting material. The yield was 167.6 g (92.2%). m.p.204°-205° C.

Specific rotation $[\alpha]_D^{26}$+40.5°(C 1.00, CHCl$_3$)

Analysis Calcd. for C$_{40}$H$_{57}$NO$_4$(M.W.615.86): C,78.01; H,9.33; N,2.27. Found: C,77.95; H,9.38; N,2.32.

EXAMPLE 110

Preparation of Cyclobranyl ester of m-aminocinnamic acid

The title compound was prepared according to following the procedure of Example 104 but cyclobranyl ester of m-nitrocinnamic acid (163.2 g, 0.265 mole) obtained according to the procedure of Example 109, was used as a starting material. The yield was 117.4 g (75.6%). m.p.211°-212° C.

Specific rotation $[\alpha]_D^{26}$+41.2°(C 1.00, CHCl$_3$)

Analysis Calcd. for C$_{40}$H$_{59}$NO$_2$(M.W.585.87): C,82.00; H,10.15; N,2.39. Found: C,82.07; H,10.08; N,2.43.

EXAMPLE 111

Preparation of 24-methylene cycloartanyl ester of m-nitrocinnamic acid

The title compound was prepared according to following the procedure of Example 103 but m-nitrocinnamic acid (75 g, 0.388 mole) and 24-methylenecycloartanol (130 g, 0.295 mole) was used in place of p-nitrocinnamic acid and cyclobranol, respectively. The yield was 167.2 g (92.0%). m.p.193°-194° C.

Specific rotation $[\alpha]_D^{26}$+42.3°(C 1.00, CHCl$_3$)

Analysis Calcd. for C$_{40}$H$_{57}$NO$_4$(M.W.615.86): C,78.01; H,9.33; N,2.27. Found: C,78.05; H,9.27; N,2.34.

EXAMPLE 112

Preparation of 24-methylenecycloartanyl ester of m-aminocinnamic acid

The title compound was prepared according to following the procedure of Example 104 but 24-methylenecycloartanyl ester of m-nitrocinnamic acid (160.4 g, 0.260 mole) obtained according to the procedure of Example 111 was used as a starting material. The yield was 114.8 g (75.3%). m.p. 197°–198° C.

Specific rotation $[\alpha]_D^{26}+42.7°$(C 1.00, CHCl$_3$)

Analysis Calcd. for $C_{40}H_{59}NO_2$(M W.585.87): C,82.00; H,110.15; N,2.39. Found: C,81.93; H,10.22; N,2.44.

EXAMPLE 113

Preparation of cycloartenyl ester of 3-methoxy-4-propionyloxy-α-methyl cinnamic acid To 3-Methoxy-4-propionyloxy-α-methylcinnamic acid (72.0 g, 0.272 mole) were added thionyl chloride (40.0 ml, 2 equivalents), toluene (400 ml) and dimethylformamide (0.5 ml) and the mixture was stirred at 60° C. for 1.5 hours. After concentration of the mixture under reduced pressure, thereto dioxane (100 ml) was added and the whole was stirred at 0° C. To the mixture was added cycloartenol (80.0 g, 0.187 mole) dissolved in pyridine (300 ml) and the whole was stirred at 60° C. for 3 hours. The reaction mixture was evaporated under reduced pressure and the residue was dissolved in chloroform (800 ml). The solution was washed with saturated aqueous NaHCO$_3$, and the aqueous layer was extracted with chloroform (500 ml×2). The combined chloroform layer was dried and evaporated under reduced pressure, and the residue was purified by silica gel column chromatography [solvent hexane-methylene chloride, (5:1, v/v)] giving cycloartanyl ester of 3-methoxy-4-propionyloxy-α-methylcinnamic acid (110 g), in a 87.1% yield. m.p. 130°–131° C.

Specific rotation $[\alpha]_D^{19}+41.4°$(C 1.00, CHCl$_3$)

Analysis Calcd. for $C_{44}H_{64}O_5$(M.W.672.95): C,78.53; H,9.59. Found: C,78.59; H,9.52.

IRν, KBr(cm$^{-1}$): 2920, 2850, 1765, 1710, 1630, 1600, 1510, 1240, 1140, 1110.

PMR(CDCl$_3$)δ: 0.39(1H, ½ABq, 4.2 Hz), 0.60(1H, ½ABq, 4.2 Hz), 0.60–2.20(27H, m), 0.90(6H, s), 0.98(6H, s), 1.27(3H, t, 7.2 Hz), 1.58(3H, bs), 1.68(3H, bs), 2.12(3H, d, 1.2 Hz), 2.62(2H, q, 7.2 Hz), 3.80(3H, s), 4.50–5.30(2H, m), 6.80–7.70(4H, m).

EXAMPLE 114

Preparation of cycloartenyl ester of 4-hydroxy-3-methoxy-α-methylcinnamic acid (another name: cycloartenyl ester of α-methylferulic acid)

To cycloartenyl ester of 3-methoxy-4-propionyloxy-α-methyl-cinnamic acid (84.0 g, 0.125 mole) prepared according to the procedure of Example 113 dissolved in dioxane (1000 ml) was added 25% aqueous ammonia (200 ml) and the solution was stirred at 50° C. for 2 hours. Then, the reaction mixture was concentrated under reduced pressure to remove the solvent, and the residue was dissolved in chloroform. The chloroform solution was washed with saturated brine (500 ml), and the aqueous layer were extracted with chloroform (300 ml×2). The combined chloroform layer was dried, concentrated under reduced pressure, and the residue was recrystallized from methylene chloride-methanol (1:4, v/v), giving cycloartenyl ester of 4-hydroxy-3-methoxy-α-methylcinnamic acid (73.0 g), in a yield 94.8%. m.p.143°–144° C.

Specific rotation $[\alpha]_D^{19}+44.1°$(C 1.00, CHCl$_3$)

Analysis Calcd. for $C_{41}H_{60}O_4$(M.W.616.93): C,79.82; H,9.80. Found: C,79.88; H,9.81.

IRν, KBr(cm$^{-1}$): 3400, 2900, 2850, 1695, 1690, 1625, 1600, 1510, 1250, 1110.

PMR(CDCl$_3$)δ: 0.38(1H, ½ABq, 4.2 Hz), 0.59(1H, ½ABq, 4.2 Hz), 0.60–2.30(27H, m), 0.88(6H, s), 0.97 (6H, s), 1.60(3H, bs), 1.66(3H, bs), 2.12(3H, d, 1.2 Hz), 3.88(3H, s), 4.50–5.30(2H, m), 5.80(1H, bs), 6.70–7.70(4H, m).

EXAMPLE 115

Preparation of cyclobranyl ester of 3-methoxy-4-propionyloxy-α-methylcinnamic acid To 3-Methoxy-4-propionyloxy-α-methylcinnamic acid (15.59 g, 0.059 mole) suspended in toluene (50 ml) was added thionyl chloride (20 ml, 4.6 equivalents) and dimethyl formamide (5 drops) and the mixture was stirred at 60° C. for 2 hours. Then the solvent was removed by distillation under reduced pressure. The residue was suspended in toluene (150 ml) and anhydrous pyridine (30 ml), and to the suspension was added cyclobranol (20 g, 0.045 mole). The mixture was stirred at 60° C. for 2 hours, then concentrated under reduced pressure. The residue was extracted with chloroform (300 ml), and the chloroform solution was washed, dried, and evaporated to dryness under reduced pressure. The crystalline residue was washed with ethanol (50 ml), and recrystallized from acetone-water (19:1, v/v), giving cyclobranyl ester of 3-methoxy-4-propionyloxy-α-methylcinnamic acid (24.69 g), in a 79.2% yield. m.p.146°–147° C.

Specific rotation $[\alpha]_D^{19}+39.2°$(C 1.00, CHCl$_3$)

Analysis Calcd. for $C_{45}H_{66}O_5$ (M.W.686.98): C,78.67; H,9.68. Found: C,78.75; H9.62.

IRν, KBr(cm$^{-1}$): 3400, 2590, 2850, 1760, 1710, 1630, 1600, 1240, 1150, 1120.

PMR(CDCl$_3$)δ: 0.37(1H, ½ABq, 4.8 Hz), 0.62(1H, ½ABq, 4.8 Hz), 0.70–2.22(27H, m), 0.92(6H, s), 0.99(6H, s), 1.29(3H, t, 7.2 Hz), 1.64(9H, s), 2.14(3H, d, 1.2 Hz), 2.63(2H, q, 7.2 Hz), 3.84(3H, s), 4.48–4.88(1H, m), 6.80–7.08(3H, m), 7.59(1H, q, 1.2 Hz).

EXAMPLE 116

Preparation of cyclobranyl ester of 4-hydroxy-3-methoxy-α-methylcinnamic acid

Cyclobranyl ester of 3-methoxy-4-propionyloxy-α-methyl cinnamic acid (24.69 g, 0.036 mole) obtained according to the procedure of Example 115 was dissolved in dioxane (400 ml) and to the solution was added 25% aqueous ammonia dropwise. The mixture was stirred at 50° C. for 2 hours, then the solvent was removed by distillation under reduced pressure. The crystalline residue was washed with ethanol, and recrystallized from acetone-water (19:1, v/v), giving cyclobranyl ester of 4-hydroxy-3-methoxy-α-methylcinnamic acid (21.72 g)in a 95.8% yield. m.p. 185°–186° C.

Specific rotation $[\alpha]_D^{20}+43.7°$(C 1.00, CHCL$_3$)

Analysis Calcd. for $C_{42}H_{62}O_4$(M.W.630.92): C,79.95; H,9.91. Found: C,79.90; H,9.98.

IVν, KBr(cm$^{-1}$): 3380, 2920, 2850, 1693, 1600, 1510, 1285, 1250, 1120.

PMR(CDCl$_3$)δ: 0.36(1H, ½ABq, 4.8 Hz), 0.61(1H, ½ABq, 4.8 Hz), 0.76–2.30(27H, m), 0.91(6H, s), 0.99(6H, s), 1.63(9H, s), 2.14(3H, d, 1.2 Hz), 3.90(3H, s), 4.48–4.84(1H, m), 5.84(1H, bs), 6.80–6.98(3H, m), 7.55(1H, q, 1.2 Hz).

EXAMPLE 117

Preparation of 24-methylenecycloartanyl ester of 3-methoxy-4-propionyloxy-α-methylcinnamic acid To 3-methoxy-4-propionyloxy-α-methylcinnamic acid (0.8 g, 0.003 mole) suspended in toluene (2 ml) was added thionyl chloride (0.5 ml, 2.2 equivalent) and dimethylformamide (2 drops), and the mixture was stirred at 60° C. for 2 hours. Then the solvent was removed by distillation under reduced pressure. The residue was suspended in toluene (2 ml) and anhydrous pyridine (1 ml), and to the suspension was added 24-methylene cycloartanyl (1g, 0.0023 mole). The mixture was stirred at 60° C. for 2 hours, then the solvents wer removed by distillation under reduced pressure. The residue was extracted with chloroform (20 ml) and the chloroform extract was washed with sodium bicarbonate, dried, and evaporated under reduced pressure. The crystalline residue was washed with ethanol (5 ml), and recrystallized from acetonemethanol (1:1, v/v), giving 24-methylenecycloartanyl ester of 3-methoxy-4-propionyloxy-α-methylcinnamic acid (1.35 g), in a 86.6% yield. m.p. 134°–135° C.

Specific rotation $[\alpha]_D^{19}$ +41.2°(C 1.00, CHCl$_3$)

Analysis Calcd. for C$_{45}$H$_{66}$O$_5$(M.W.686.98): C,78.67; H,9.68. Found: C,78.75; H,9.62.

IR$\nu$, KBr(cm$^{-1}$): 3400, 2920, 2850, 1760, 1700, 1240, 1115.

PMR(CDCl$_3$)δ: 0.36(1H, ½ABq, 4.2 Hz), 0.61(1H, ½ABq, 4.2 Hz), 0.70–2.22(34H, m), 0.88(6H, s), 0.96(6H, s), 1.26(3H, t, 7.2 Hz), 2.11(3H, d, 1.2 Hz), 2.60(2H, q, 7.2 Hz), 3.80(3H, s), 4.44–4.86(1H, m), 4.86–5.26(2H, m), 6.76–7.08 (3H, m), 7.55(1H, q, 1.2 Hz).

EXAMPLE 118

Preparation of 24-methylenecycloartanyl ester of 4-hydroxy-3-methoxy-α-methylcinnamic acid 24-Methylenecycloartanyl ester of 3-methoxy-4-propionyloxy-α-methylcinnamic acid (1.35 g, 0.002 mole) obtained according to the procedure of Example 117 was dissolved in dioxane (20 ml), and to the solution was added 25% aqueous ammonia (2 ml) dropwise. The mixture was stirred at 50° C. for 2 hours, then the solvents were removed by distillation under reduced pressure. The crystalline residue was washed with ethanol, and recrystallized from ethanol, giving 24-methylenecycloartanyl-ester of 4-hydroxy-3-methoxy-α-methylcinnamic acid (1.02 g), in a 82.2% yield. m.p. 144°–145° C.

Specific rotation $[\alpha]_D^{20}$ +44.8°(1.00, CHCl$_3$)

Analysis Calcd. for C$_{43}$H$_{62}$O$_4$(M.W.630.92): C,79.95; H,9.91. Found: C,79.99; H,9.84.

IR$\nu$, KBr(cm$^{-1}$): 3400, 2900, 2850, 1690, 1600, 1510, 1250, 1110.

PMR(CDCl$_3$)δ: 0.37(1H, ½ABq, 4.2 Hz), 0.61(1H, ½ABq, 4.2 Hz), 0.70–2.21(34H, m), 0.89(6H, s), 0.98 (6H, s), 2.14(3H, d, 1.2 Hz), 3.88(3H, s), 4.50–4.88(1H, m), 4.88–5.28(2H, m), 5.80(1H, bs), 6.82–7.10(3H, m), 7.59(1H, q, 1.2 Hz)

EXAMPLE 119

Preparation of cycloartenyl ester of 4-butyryloxy-3-methoxy-α-ethylcinnamic acid Thionyl chloride (15.0 ml, 3.3 equivalents) was added dropwise to a solution of 4-butyryloxy-3-methoxy-α-ethylcinnamic acid (18.0 g, 0.062 mole) in benzene (40 ml) at 0° C., and the mixture was heated to 60° C. and allowed to stirr for 2 hours. Then the excess thionyl chloride and the solvent were removed by distillation under reduced pressure. Pyridine (10 ml) and dioxane (40 ml) were added to the residue. While cooling the mixture at 0° C., a solution of cycloartenol (17.5 g, 0.041 mole) in pyridine (30 ml) was added dropwise. This reaction mixture was allowed to stir overnight at 20° C. Then the solvents were removed by distillation under reduced pressure. The residue was extracted with chloroform (200 ml) and the extract was concentrated in vacuo. The residue was recrystallized from acetone-methanol (1:1, v/v), giving cycloartenyl ester of 4-butyryloxy-3-methoxy-α-ethylcinnamic acid (22.4 g) in a 77.9% yield. m.p. 118.5°–119.5° C.

Specific rotation $[\alpha]_D^{20}$ +35.7°(C 1.00, CHCl$_3$)

Analysis Calcd. for C$_{46}$H$_{68}$O$_5$(M.W.701.00): C,78.81; H 9.78. Found: C,78.72; H 9.86.

IR$\nu$, KBr(cm$^{-1}$): 3400, 2920, 2800, 1700, 1600, 1510, 1230, 1120.

PMR(CDCl$_3$)δ: 0.36(1H, ½ABq, 4.2 Hz), 0.52–2.26(29H, m), 0.61(1H, ½ABq, 4.2 Hz), 0.90(6H, s), 0.96 (6H, s), 1.04(3H, t, 7.2 Hz), 1.18(3H, t, 7.2 Hz), 1.60(3H, s), 1.66(3H, s), 2.26–2.82(4H, m), 3.79(3H, s), 4.50–4.88(1H, m), 4.88–5.28(1H, m), 6.70–7.12(3H, m), 7.48–7.68(1H, m).

EXAMPLE 120

Preparation of cycloartenyl ester of 4-hydroxy-3-methoxy-α-ethylcinnamic acid

Cycloartenyl ester of 4-butyryloxy-3-methoxy-α-ethylcinnamic acid (22.0 g, 0.0314 mole) obtained according to the procedure of Example 119 was dissolved in dioxane (200 ml), and to the solution was added 25% aqueous ammonia (20 ml) dropwise. The mixture was heated at 50° C. for 5 hours. Then the solvent was removed by distillation under reduced pressure. The residue was extracted with chloroform (200 ml), and the extract was concentrated under in vacuo. The residue was recrystallized from acetone-methanol (1:1, v/v), giving cycloartenyl ester of 4-hydroxy-3-α-ethylcinnamic acid (17.2 g), in a 86.8% yield. m.p. 136°–137° C.

Specific rotation $[\alpha]_D^{20}$ +41.5°(C 1.00, CHCl$_3$)

Analysis Calcd. for C$_{42}$H$_{62}$O$_4$(M.W.630.92): C,79.95; H,9.96. Found: C,79.90; H,9.83.

IR$\nu$, KBr(cm$^{-1}$): 3400, 2830, 1700, 1595, 1510, 1240, 1120.

PMR(CDCl$_3$)δ: 0.35(1H, ½ABq, 4.2 Hz), 0.50–2.18(27H, m), 0.60(1H, ½ABq, 4.2 Hz), 0.89(6H, s), 0.95(6H, s), 1.19(3H, t, 7.2 Hz), 1.57(3H, s), 1.65(3H, s), 2.56(2H, bq, 7.2 Hz), 3.87(3H, s), 4.47–4.85(1H, m), 4.85–5.24(1H, m), 5.76(1H, bs), 6.96–7.09(3H, m), 7.24–7.64(1H, m).

EXAMPLE 121

Preparation of cyclobranyl ester of 4-butyryloxy-3-methoxy-α-ethylcinnamic acid

Thionyl chloride (15.0 ml, 3.3 equivalents) was added dropwise to a solution of 4-butyryloxy-3-methoxy-α-ethylcinnamic acid (18.0 g, 0.062 mole) in benzene (40 ml) at 0° C., and the mixture was heated at 60° C. for 2 hours. Then the excess thionyl chloride and the solvent were removed by distillation under reduced pressure. Pyridine (40 ml) and dioxane (40 ml) were added to the residue. While cooling the mixture at 0° C., cyclobranol (18.1 g, 0.041 mole) was added, then the mixture was warmed to 20° C. and allowed to stir overnight. The solvents were removed by distillation under reduced pressure and the residue was extracted with chloroform (200 ml). The extract was concentrated in vacuo, and the residue was recrystallized from acetone-ethanol (1:1, v/v), giving cyclobranyl ester of 4-butyryloxy-3-methoxy-α-ethyl-cinnamic acid (22.3 g), in a 76.0% yield. m.p. 138°-139° C.

Specific rotation $[\alpha]_D^{20} + 33.7°$ (C 1.00, CHCl$_3$)

Analysis Calcd. for C$_{47}$H$_{70}$O$_5$(M.W.715.03): C,78.94; H,9.87. Found: C,78.89; H,9.88.

IRν, KBr(cm$^{-1}$): 3400, 2920, 2850, 1760, 1710, 1625, 1510, 1230, 1120.

PMR(CDCl$_3$)δ: 0.36(1H, ½ABq, 4.8 Hz), 0.52-2.22(29H, m), 0.61(1H, ½ABq, 4.8 Hz), 0.92(6H, s), 0.97(6H, s), 1.03(3H, t, 7.2 Hz), 1.18(3H, t, 7.2 Hz), 1.60(9H, s), 2.22-2.82 (4H, m), 3.81(3H, s), 4.48-4.90(1H, m), 6.70-7.18(3H, m), 7.40-7.64(1H, m).

EXAMPLE 122

Preparation of cyclobranyl ester of 4-hydroxy-3-methoxy-α-ethylcinnamic acid

Cyclobranyl ester of 4-butyryloxy-3-methoxy-α-ethylcinnamic acid (21.3 g, 0.0298 mole) obtained according to the procedure of Example 121 was dissolved in dioxane (200 ml), and to the solution was added 25% aqueous ammonia (20 ml) by dropwise. The mixture was heated to 50° C. and stirred for 5 hours. Then the solvent was removed by distillation under reduced pressure and the residue was extracted with chloroform (200 ml). The extract was concentrated in vacuo, and the residue was recrystallized from ethanol to give cyclobranyl ester of 4-hydroxy-3-methoxy-α-ethylcinnamic acid (17.1 g), in a 88.9% yield. m.p. 156°-157° C.

Specific rotation $[\alpha]_D^{20} + 37.7°$ (C 1.00, CHCl$_3$)

Analysis Calcd. for C$_{43}$H$_{64}$O$_4$(M.W.644.94): C,80.07; H 10.00. Found: C,80.13; H 10.12.

IRν, KBr(cm$^{-1}$): 3400, 2930, 1696, 1235, 1130.

PMR(CDCl$_3$)δ: 0.38(1H, ½ABq, 4.8 Hz), 0.52-2.22(27H, m), 0.62(1H, ½ABq, 4.8 Hz), 0.91(6H, s), 0.97(6H, s), 1.21(3H, t, 7.2 Hz), 1.62(9H, s), 2.57(2H, bq, 7.2 Hz), 3.98(3H, s), 4.48-4.86(1H, m), 5.78(1H, bs), 6.70-7.00(3H, m), 7.53(1H, m).

EXAMPLE 123

Preparation of cycloartenyl ester of 4-propionyloxy-α-methylcinnamic acid

Thionyl chloride (18.1 ml, 3.3 equivalents) and dimethylformamide (0.5 ml) were added dropwise to a solution of 4-propionyloxy-α-methylcinnamic acid (17.6 g, 0.075 mole) in benzene (40 ml) at 0° C. The mixture was heated to 60° C. and allowed to stir for 2 hours. Then the excess thionyl chloride and the solvent were removed by distillation under reduced pressure. Dioxane (40 ml) and pyridine (10 ml) were added to the residue. While cooling the mixture at 0° C., a solution of cycloartenol (21.3 g, 0.050 mole) in pyridine (40 ml) was added dropwise. This reaction mixture was warmed to 20° C. and allowed to stir overnight. Then the solvents were removed by vacuum distillation, and the residue was extracted with chloroform (200 ml). The extract was concentrated under reduced pressure, and the residue was recrystallized from acetone-ethanol (1:2, v/v), giving cycloartenyl ester of 4-propionyloxy-α-methyl-cinnamic acid (27.0 g) in a 83.9% yield. m.p. 87°-88° C.

Specific rotation $[\alpha]_D^{19} + 45.9°$ (C 1.00, CHCl$_3$)

Analysis Calcd. for C$_{43}$H$_{62}$O$_4$(M.W.642.93): C,80.33; H 9.72. Found: C,80.31; H 9.79.

IRν, KBr(cm$^{-1}$): 3400, 2920, 2850, 1760, 1700, 1260, 1215, 1115.

PMR(CDCl$_3$)δ: 0.36(1H, ½ABq, 4.2 Hz), 0.52-2.20(27H, m), 0.61(1H, ½ABq, 4.2 Hz), 0.89(6H, s), 0.97(6H, s), 1.25(3H, t, 7.2 Hz), 1.57(3H, s), 1.65(3H, s), 2.10(3H, d, 1.2 Hz), 2.58(2H, q, 7.2 Hz), 4.28-4.84 (1H, m), 4.92-5.24(1H, m), 6.92-7.09(2H, m), 7.11-7.50(2H, m), 7.50-7.70(1H, m).

EXAMPLE 124

Preparation of cycloartenyl ester of 4-hydroxy-α-methylcinnamic acid

Cycloartenyl ester of 4-propionyloxy-α-methylcinnamic acid (27.0 g, 0.042 mole) obtained by the procedure of Example 123 was dissolved in dioxane (200 ml), and to the solution was added 25% aqueous ammonia dropwise. The mixture was heated to 50° C. and allowed to stir for 2 hours. Then the solvent was removed by distillation under reduced pressure, and the residue was extracted with chloroform (200 ml). The extract was concentrated in vacuo, and the residue was recrystallized from ethanol, giving cycloartenyl ester of 4-hydroxy-α-methylcinnamic acid (20.5 g), in a 83.1% yield. m.p. 190°-191° C.

Specific rotation $[\alpha]_D^{19} + 45.8°$ (C 1.00, CHCl$_3$)

Analysis Calcd. for C$_{40}$H$_{58}$O$_3$(M.W. 586.86): C,81.86; H 9.96. Found: C,81.77, H 9.99.

IRν, kBr(cm$^{-1}$): 3400, 2992, 2985, 1700, 1675, 1600, 1510, 1260, 1200, 1170.

PMR(CDCl$_3$)δ: 0.36(1H, ½ABq, 4.2 Hz), 0.52-2.24(27H, m), 0.61(1H, ½ABq, 4.2 Hz), 0.90(6H, s), 0.98(6H, s), 1.61(3H, s), 1.64(3H, s), 2.13(3H, d, 1.2 Hz), 4.50-4.88(1H, m), 4.88-5.24(1H, m), 5.88-6.60 (1H, m), 6.68-7.12(2H, m), 7.12-7.50(1H, m), 7.50-7.68(1H, m).

EXAMPLE 125

Preparation of cyclobranyl ester of 4-propionyloxy-α-methylcinnamic acid

Thionyl chloride (18.1 ml, 3.3 equivalents) and dimethylformamide (0.5 ml) were added dropwise to a solution of 4-propionyloxy-α-methylcinnamic acid (17.6 g, 0.075 mole) in benzene (40 ml) at 0° C. The mixture was heated to 60° C. and continued to stir for 2 hours. Then the excess thionyl chloride and the solvent were removed by distillation under reduced pressure. Dioxane (20 ml) and pyridine (40 ml) were added to the residue. While cooling the mixture at 0° C., cyclobranol (22.0 g, 0.050 mole) was added, then the mixture was warmed to 20° C. and continued to stir overnight. Then, the solvents were removed by distillation in vacuo, and the residue was extracted with chloroform (200 ml). The extract was concentrated under reduced pressure, and the residue was recrystallized from acetone-methanol (1:1, v/v), giving cyclobranyl ester of 4-propionyloxy-α-methylcinnamic acid (26.3 g), in a 80.0% yield. m.p. 107°-108° C.

Specific rotation $[\alpha]_D^{19} + 34.7°$ (C 1.00, CHCl$_3$)

Analysis Calcd. for C$_{44}$H$_{64}$O$_4$(M.W.656.95): C,80.44; H 9.82. Found: C,80.39; H 9.77.

IRν, KBr(cm$^{-1}$): 3400, 2920, 2850, 1860, 1710, 1630, 1260, 1200, 1165, 1120

PMR(CDCl$_3$)δ: 0.36(1H, ½ABq, 4.8 Hz), 0.61(1H, 1.2ABq, 4.8 Hz), 0.74-2.32(27H, m), 0.89(6H, s), 0.96 (6H, s), 1.26(3H, t, 7.2 Hz), 1.61(9H, s), 2.10 (3H, d, 1.2

Hz), 2.58(2H, q, 7.2 Hz), 4.46–4.86 (1H, m), 6.90–7.52(4H, m), 7.52–7.70(1H, m).

Example 126

Preparation of cyclobranyl ester of 4-hydroxy-α-methylcinnamic acid

Cyclobranyl ester of 4-propionyloxy-α-methylcinnamic acid (26.3 g, 0.040 mole) obtained according to the procedure of Example 125 was dissolved in dioxane (200 ml), and to the solution was added 25% aqueous ammonia dropwise. The mixture was heated to 50° C. and continued to stir for 2 hours. Then the solvent was removed by distillation under reduced pressure, and the residue was extracted with chloroform (200 ml). The extract was concentrated in vacuo, and the residue was recrystallized from acetone-methanol (1:1, v/v), giving cyclobranyl ester of 4-hydroxy-α-methylcinnamic acid (20.7 g), in a 83.1% yield. m.p. 203°–204° C.

Specific rotation $[\alpha]_D^{19}+46.0°$(C1.00, CHCl$_3$)

Analysis Calcd. for C$_{41}$H$_{60}$O$_3$(M.W.600.89): C,81.95; H,10,07. Found: C 81.99, H 10.07.

IRν, KBr(cm$^{-1}$): 3400, 2920, 2850, 1780, 1605, 1510, 1265, 1200, 1170, 1125.

PMR(CDCl$_3$)δ: 0.36(1H, ½ABq, 4.8 Hz), 0.61(1H, ½ABq, 4.8 Hz), 0.80–2.33(27H, m), 0.90(6H, s), 0.98 (6H, s), 1.60(9H, s), 2.12(3H, d, 1.2 Hz), 4.08–4.88(1H, m), 5.56–5.80(1H, m), 6.70–6.92 (2H, m), 7.12–7.44(2H, m), 7.58(1H, q, 1.2 Hz).

EXAMPLE 127

Preparation of 24-methylenecycloartanyl ester of 4-propionyloxy-α-methylcinnamic acid The title compound was prepared according to following the procedure of Example 125 but 24-methylenecycloartanol was used in place of cyclobranol. The yield was 25.8 g (78.5%). m.p. 94°–95° C.

Specific rotation $[\alpha]_D^{19}+44.2°$(C 1.00, CHCl$_3$)

Analysis Calcd. for C$_{44}$H$_{64}$O$_4$(M.W.656.95): C,80.44; H,9.82. Found: C,80.48; H 9.78.

EXAMPLE 128

Preparation of 24-metnylenecycloartanyl ester of 4-hydroxy-α-methylcinnamic acid 24-Methylenecycloartanyl ester of 4-propionyloxy-α-methylcinnamic acid (24.0 g, 0.036 mole) obtained according to the procedure of Example 127 was dissolved in dioxane (200 ml) and to the solution was added 25% aqueous ammonia dropwise. The mixture was heated to 50° C. and continued to stir for 2 hours. Then the solvent was removed by distillation under reduced pressure, and the residue was extracted with chloroform (200 ml). The extract was concentrated in vacuo and the residue was recrystallized from acetone-methanol (1:1,v/v), giving 24-methylenecycloartanyl ester of 4-hydroxy-α-methylcinnamic acid (19.4 g) in a 89.6% yield. m.p. 195°–196° C.

Specific rotation $[\alpha]_D^{19}+43.8°$(C 1.00, CHCl$_3$)

Analysis Calcd. for C$_{41}$H$_{60}$O$_3$(M.W.600.89): C,81.95; H 10.07. Found: C,81.90; H 10.14.

Example 129 Preparation of cycloartenyl ester of 4-butyryloxy-α-ethylcinnamic acid Thionyl chloride (4.8 ml, 5 equivalents) was added dropwise to a solution of 4-butyryloxy-α-ethylcinnamic acid (3.50 g, 0.0133 mole) in benzene (7 ml) at 0° C. The mixture was heated to 60° C. and continued to stir for 2 hours. Then the excess thionyl chloride and the solvent were removed by distillation under reduced pressure. After addition of pyridine (10 ml) to the residue, a solution of cycloartenol (2.85 g, 0.0067 mole) in pyridine (10 ml) was added to the mixture dropwise at 0° C. This mixture was warmed to 20° C. and continued to stir overnight. Then the solvent was removed by distillation under reduced pressure and the residue was extracted with chloroform (40 ml). The extract was concentrated in vacuo, and the residue was recrystallized from acetone-ethanol (1:1, v/v), giving cycloartenyl ester of 4-butyryloxy-α-ethylcinnamic acid (3.63 g) in a 80.7% in a yield. m.p. 88°–89° C.

Specific rotation $[\alpha]_D^{20}+41.2°$ (C 1.00, CHCl$_3$)

Analysis Calcd. for C$_{45}$H$_{66}$O$_4$(M W.670.98): C,80.55; H 9.92. Found: C,80.64; H,9.84.

IRν, KBr(cm$^{-1}$): 3400, 2940, 2860, 1760, 1710, 1240, 1200, 1170, 1125.

PMR(CDCl$_3$)δ: 0.36(1H, ½ABq, 4.2 Hz), 0.52–2.22(29H, m), 0.61(1H, ½ABq, 4.2 Hz), 0.90(6H, s), 0.96 (6H, s), 1.03(3H, t, 7.2 Hz), 1.18(3H, t, 7.2 Hz), 1.58(3H, s), 1.66(3H, s), 2.22–2.80(4H, m), 4.42–4.88(1H, m), 4.88–5.24(1H, m), 6.89–7.18 (2H, m), 7.18–7.46(2H, m), 7.46–7.64(1H, m).

EXAMPLE 130

Preparation of cycloartenyl ester of 4-hydroxy-α-ethylcinnamic acid

Cycloartenyl ester of 4-butyryloxy-α-ethylcinnamic acid (2.00 g, 0.003 mole) obtained according to the procedure of Example 129 was dissolved in dioxane (20 ml), and to the solution was added 25% aqueous ammonia (2 ml) dropwise. Then the mixture was warmed to 50° C. and continued to stir for 5 hours. The solvent was removed by distillation under reduced pressure, and the residue was extracted with chloroform (20 ml). The extract was concentrated in vacuo, and the residue was recrystallized from acetone, giving cycloartenyl ester of 4-hydroxy-α-ethylcinnamic acid (1.68 g), in a 93.2 % yield. m.p. 162.5°–163° C.

Specific rotation $[\alpha]_D^{20}+46.1°$ (C 1.00, CHCl$_3$)

Analysis Calcd. for C$_{41}$H$_{60}$O$_3$(M.W.600.89): C,81.95; H,10.07. Found: C,81.88; H 10.12.

IRν, KBr(cm$^{-1}$): 3300, 2920, 2800, 1760, 1710, 1625, 1500, 1280, 1240, 1200, 1165, 1120.

PMR(CDCl$_3$)δ: 0.36(1H, ½ABq, 4.2 Hz), 0.52–2.22(27H, m), 0.61(1H, ½ABq, 4.2 Hz), 0.90(6H, s), 0.96(6H, s), 1.19(3H, t, 7.2 Hz), 1.60(3H, s), 1.67(3H, s), 2.57(2H, bq, 7.2 Hz), 4.47–4.88(1H, m), 4.92–5.32(1H, m), 6.43–6.67(1H, m), 6.68–7.04(2H, m), 7.12–7.48(2H, m), 7.52–7.69(1H, m).

EXAMPLE 131

Preparation of cyclobranyl ester of 4-butyryloxy-α-ethylcinnamic acid

Thionyl chloride (7.3 ml, 5 equivalents) was added dropwise to a solution of 4-butyryloxy-α-ethylcinnamic acid (5.25 g, 0.02 mole) in benzene (10 ml) at 0° C. The mixture was heated to 60° C. and allowed to stir for 2 hours. Then the excess thionyl chloride and the solvent were removed by distillation under reduced pressure. After addition of pyridine (40 ml) to the residue, cyclobranol (4.41 g, 0.001 mole) was added while cooling the mixture at 0° C. The mixture was warmed to 20° C. and continued to stir overnight. Then the solvent was removed by distillation under reduced pressure, and the residue was extracted with chloroform (60 ml). The extract was concentrated in vacuo, and the residue was recrystallized from acetone-ethanol (1:1, v/v), giving cyclobranyl ester of 4-butyryloxy-α-ethylcinnamic acid (4.80 g), in a 70.1 % yield. m.p. 117.5°-118° C.

Specific rotation $[\alpha]_D^{20}+38.6°$ (C 1.00, CHCl$_3$)

Analysis Calcd. for C$_{46}$H$_{68}$O$_4$(M.W.685.00): C,80.65; H,10.01. Found: C,80.59; H 10.06.

IR$\nu$, KBr(cm$^{-1}$): 3400, 2900, 2850, 1770, 1710, 1625, 1510, 1230, 1120.

PMR(CDCl$_3$)δ: 0.36(1H, ½ABq, 4.8 Hz), 0.52-2.24(29H, m), 0.61(1H, ½ABq, 4.8 Hz), 0.90(6H, s), 0.96(6H, s), 1.03(3H, t, 7.2 Hz), 1.18(3H, t, 7.2 Hz), 1.59 (9H, s), 2.24-2.82(4H, m), 4.48-4.84(1H, m), 6.90-7.18(2H, m), 7.18-7.48(2H, m), 7.48-7.68(1H, m).

EXAMPLES 132

Preparation of cyclobranyl ester of 4-hydroxy-α-ethylcinnamic acid

Cyclobranyl ester of 4-butyryloxy-α-ethylcinnamic acid (4.11 g, 0.0060 mole) obtained according to the procedure of Example 131 was dissolved in dioxane (30 ml), and to the solution was added 25% aqueous ammonia (3 ml) dropwise. The mixture was heated to 50° C. and allowed to stir for 5 hours. Then, the solvent was removed by distillation under reduced pressure, and the residue was extracted with chloroform (40 ml). The 5 extract was concentrated in vacuo, and the residue was recrystallized from acetone, giving cyclobranyl ester of 4-hydroxy-α-ethylcinnamic acid (3.39 g), in a 91.9% yield. m.p. 202°-203° C.

Specific rotation $[\alpha]_D^{20}+44.0^5$ (C 1.00, CHCl$_3$)

Analysis Calcd. for C$_{42}$H$_{62}$O$_3$(M.W.614.92): C,82.03; H,10.16. Found: C,81.97; H,10.18.

IR$\nu$, KBr(cm$^{-1}$): 3350, 2920, 2860, 1680, 1600, 1510, 1275, 1245, 1200, 1170, 1130.

PMR(CDCl$_3$)δ: 0.36(1H, ½ABq, 4.8 Hz), 0.52-2.24 (27H, m), 0.61 (1H, ½ABq, 4.8 Hz), 0.90(6H, s), 0.97(6H, s), 1.19(3H, t, 7.2 Hz), 1.61(9H, s) 2.57(2H, bq, 7.2 Hz), 4.52-4.84(1H, m), 6.43-6.64(1H, m), 6.64-7.02(2H, m), 7.12-7.48(2H, m), 7.48-7.67(1H, m).

EXAMPLE 133

Preparation of cycloartenyl ester of 3-methoxy-4-valeryloxy-α-propylcinnamic acid The title compound was prepared according to following the procedure of Example 119 but 3-methoxy-4-valeryoxy-α-propylcinnamic acid (17.9 g, 0.056 mole) was used as a starting material, in place of 4-butyryloxy 3-methoxy-α-ethylcinnamic acid. The yield was 23.2 g (77.6%). m.p. 113°-114° C.

Specific rotation $[\alpha]_D^{20}+34.2°$ (C 1.00, CHCl$_3$)

Analysis Calcd. for C$_{48}$H$_{72}$O$_5$(M.W. 729.06): C,79.07; H 9.95. Found: C,79.13; H 9.88.

EXAMPLE 134

Preparation of cycloartenyl ester of 4-hydroxy-3-methoxy-α-propylcinnamic acid

The title compound was prepared according to following the procedure of Example 120 but cycloartenyl ester of 3-methoxy-4-valeryloxy-α-propyl-cinnamic acid (23.3 g, 0.032 mole) obtained according to the procedure of Example 133 was used as a starting material. The yield was 18.1 g (87.6 %). m.p. 122°-123° C.

Specific rotation $[\alpha]_D^{20}+41.2°$ (C 1.00, CHCl$_3$)

Analysis Calcd. for C$_{43}$H$_{64}$O$_4$(M.W.644.94): C,80.07; H,10.00. Found: C,80.14; H,9.97.

EXAMPLE 135

Preparation of cycloartenyl ester of 4-capryloxy-3-methoxy-α-butylcinnamic acid

The title compound was prepared according to following the procedure of Example 119 but 4-capryloxy-3-methoxy-α-butylcinnamic acid (19.2 g, 0.0551 mole) was used in place of 4-butyryloxy-3-methoxy-α-ethylcinnamic acid. The yield was 22.7 g(54.4 %). m.p. 100°-101° C.

Specific rotation $[\alpha]_D^{20}+33.5°$ (C 1.00, CHCl$_3$)

Analysis Calcd. for C$_{50}$H$_{76}$O$_5$(M.W.757.11): C,79.31; H,10.12. Found: C,79.38; H,10.05.

EXAMPLE 136

Preparation of cycloartenyl ester of 4-hydroxy-3-methoxy-α-butylcinnamic acid

The title compound was prepared according to following the procedure of Example 120 but cycroartenyl ester of 4-capryloxy-3-methoxy-α-butylcinnamic acid (24.4 g, 0.032 mole) was used as a starting material. The yield was 17.8 g (84.4 %). m.p. 110°-111° C.

Specific rotation $[\alpha]_D^{20}+40.6°$ (C 1.00, CHCl$_3$)

Analysis Calcd. for C$_{44}$H$_{66}$O$_4$(M.W.672.99): C,80.19; H,10.10. Found: C,80.24; H,10.05.

EXAMPLE 137

Preparation of cyclobranyl ester of 4-hydroxy-3-methoxy-α-butylcinnamic acid

The title compound was prepared according to following the procedure of Example 120 but cyclobranyl ester of 4-capryloxy-3-methoxy-α-butylcinnamic acid (26.2 g, 0.034 mole) was used as a starting material. The yield was 18.4 g ((80.4 %). m.p. 132°-133° C.

Specific rotation $[\alpha]_D^{20}+37.0°$ (C 1.00, CHCl$_3$)

Analysis Calcd. for C$_{45}$H$_{68}$O$_4$(M.W.672.99): C,80.31; H,10.18. Found: C,80 39; H,10.04

EXAMPLE 138

Preparation of 24-methylenecycloartanyl ester of 4-hydroxy-3-methoxy-α-butylcinnamic acid The title compound was prepared according to following the procedure of Example 120 but 24-methylenecycloartanyl ester of 4-capryloxy-3-methoxy-α-butylcinnamic acid (26.2 g, 0.034 mole) was used as a starting material. The yield was 18.1 g (79.1%). m.p. 124°-125° C.

Specific rotation $[\alpha]_D^{20}+39.8$(C 1.00, CHCl$_3$)

Analysis Calcd. for C$_{45}$H$_{68}$O$_4$(M.W.672.99): C,80.31; H,10.18. Found: C,80.25; H,10.22.

EXAMPLE 139

Preparation of cycloartenyl ester of 3-ethoxy-4-propionyloxy-α-methylcinnamic acid The title compound was prepared according to following the procedure of Example 120 but cycloartenyl ester of 3-ethoxy-4-propionyloxy-α-methylcinnamic acid (22.0 g, 0.032 mole) was used as a starting material. The yield was 15.8 g (78.2 %). m.p. 132°-133° C.

Specific rotation $[\alpha]_D^{20}+43.9°$ (C 1.00, CHCl$_3$)

Analysis Calcd. for C$_{42}$H$_{62}$O$_4$(M.W.630.92): C,79.95; H,9.91. Found: C,79.90; H 9.99.

EXAMPLE 140

Preparation of cyclobranyl ester of 3-ethoxy-4-hydroxy-α-methylcinnamic acid

The title compound was prepared according to following the procedure of Example 120 but cyclobranyl ester of 3-ethoxy-4-propionyloxy-α-methylcinnamic acid (21.7 g, 0.031 mole) was used as a starting material. The yield was 16.1 g (80.5%). m.p. 174°–175° C.

Specific rotation $[\alpha]_D^{20}+42.4°$ (C 1.00, CHCl$_3$)

Analysis Calcd. for C$_{43}$H$_{64}$O$_4$(M.W.644.94): C,80.07; H,10.00. Found: C,80.18; H,10.05.

EXAMPLE 141

Preparation of 24-methylenecycloartanyl ester of 3-ethoxy-4-hydroxy-α-methylcinnamic acid The title compound was prepared according to following the procedure of Example 120 but 24-methylenecycloartanyl ester of 3-ethoxy-4-propionyloxy-α-methylcinnamic acid (22.2 g, 0.0317 mole) was used as a starting material. The yield was 16.7 g (81.6 %). m.p. 134°–135° C.

Specific rotation $[\alpha]_D^{20}+40.2°$ (C 1.00, CHCl$_3$)

Analysis Calcd. for C$_{43}$H$_{64}$O$_4$(M.W.644.94): C,80.07; H,10.00. Found: C,80.13; H,9.92.

EXAMPLE 142

Preparation of cycloartenyl ester of 3-ethoxy-4-hydroxy-α-ethylcinnamic acid

The title compound was prepared according to following the procedure of Example 120 but cycloartenyl ester of 4-butyryloxy-3-ethoxy-α-methylcinnamic acid (21.5 g, 0.030 mole) was used as a starting material. The yield was 15.4 g (79.6 %). m.p. 124°–125° C.

Specific rotation $[\alpha]_D^{20}+41.2°$ (C 1.00, CHCl$_3$)

Analysis Calcd. for C$_{43}$H$_{64}$O$_4$(M.W.644.94): C,80.07; H,10.00. Found: C,80.04; H,10.08.

EXAMPLE 143

Preparation of cycloartenyl ester of 3-ethoxy-4-hydroxy-α-propylcinnamic acid

The title compound was prepared according to following the procedure of Example 120 but cycloartenyl ester of 3-ethoxy-4-valeryloxy-α-propylcinnamic acid (26.0 g, 0.035 mole) was used as a starting material. The yield was 16.8 g (72.8%). m.p. 111°–112° C.

Specific rotation $[\alpha]_D^{20}+40.7°$ (C 1.00, CHCl$_3$)

Analysis Calcd. for C$_{44}$H$_{66}$O$_4$(M.W.658.97): C,80.19; H,10.10. Found: C,80.26; H,10.02.

EXAMPLE 144

Preparation of cyclobranyl ester of 3-ethoxy-4-hydroxy-α-propylcinnamic acid

The title compound was prepared according to follwoing the procedure of Example 120 but cyclobranyl ester of 3-ethoxy-4-valeryloxy-α-propylcinnamic acid (24.2 g, 0.032 mole) was used as a starting material. The yield was 16.7 g(72.8%). m.p. 134°–135° C.

Specific rotation $[\alpha]_D^{20}+37.1°$ (C 1.00, CHCl$_3$)

Analysis Calcd. for C$_{45}$H$_{68}$O$_4$(M.W.672.99): C,80.31; H,10.18. Found: C,80.25; H,10.24.

EXAMPLE 145

Preparation of cycloartenyl ester of 3-ethoxy-4-hydroxy-α-butylcinnamic acid

The title compound was prepared according to following the procedure of Example 120 but cycloartenyl ester of 4-capryloxy-3-ethoxy-α-butylcinnamic acid (23.1 g, 0.030 mole) was used as a starting material. The yield was 16.2 g (80.2 %). m.p. 99°–100° C.

Specific rotation $[\alpha]_D^{20}+40.0°$ (C 1.00, CHCl$_3$)

Analysis Calcd. for C$_{45}$H$_{68}$O$_4$(M.W.672.99): C,80.31; H,10.18. Found: C,80.21; H,10.22.

EXAMPLE 146

Preparation of cycloartenyl ester of 4-hydroxy-3-propoxy-α-methylcinnamic acid

The title compound was prepared according to following the procedure of Example 120 but cycloartenyl ester of 4-propionyloxy-3-propoxy-α-methylcinnamic acid (23.1 g, 0.033 mole) was used as a starting material. The yield was 17.2 g (80.8 %). m.p. 138°–139° C.

Specific rotation $[\alpha]_D^{20}+43.7°$ (C 1.00, CHCl$_3$)

Analysis Calcd. for C$_{43}$H$_{64}$O$_4$(M.W.644.94): C,80.07; H,10.00. Found: C,80.19; H,10.04.

EXAMPLE 147

Preparation of cycloartenyl ester of 4-hydroxy-3-butoxy-α-methylcinnamic acid

The title compound was prepared according to following the procedure of Example 120 but cycloartenyl ester of 4-propionyloxy-3-butoxy-α-methylcinnamic acid (22.9 g, 0.032 mole) was used as a starting material. The yield was 16.5 g (78.2 %). m.p. 126°–127° C.

Specific rotation $[[]_D^{20}+39.7°$ (C 1.00, CHCl$_3$)

Analysis Calcd. for C$_{44}$H$_{66}$O$_4$(M.W.658.97): C,80.19; H,10.10. Found: C,80.24; H,10.03.

EXAMPLE 148

Preparation of 24-methylenecycloartanyl ester of 4-butyryloxy-3-methoxy-α-ethylcinnamic acid The title compound was prepared according to follwoing the procedure of Example 121 but 24-methylenecycloartanol (18.1 g, 0.041 mole) was used as a starting material. The yield was 22.8 g (77.8 %). m.p. 127°–128° C.

Specific rotation $[\alpha]_D^{20}+35.1°$ (C 1.00, CHCl$_3$)

Analysis Calcd. for C$_{47}$H$_{70}$O$_5$(M.W.715.03): C,78.94; H,9.87. Found: C,78.90; H,9.79.

EXAMPLE 149

Preparation of 24-methylenecycloartanyl ester of 4-hydroxy-3-methoxy-α-ethylcinnamic acid The title compound was prepared according to following the procedure of Example 122 but 24-methylenecycloartanyl ester of 4-butyryloxy-3-methoxy-α-ethylcinnamic acid (21.5 g, 0.0301 mole) was used as a starting material. The yield was 17.3 g (89.1%). m p. 137°–138° C.

Specific rotation $[\alpha]_D^{20}+40.7°$ (C 1.00, CHCl$_3$)

Analysis, for C$_{43}$H$_{64}$O$_4$(M.W.644.94): Calcd. (%): C 80.07, H 10.00. Found (%): C 80.11, H 9.93.

EXAMPLE 150

Preparation of cyclobranyl ester of 4-hydroxy-3-propoxy-α-ethylcinnamic acid The title compound was prepared according to following the procedure of Example 120 where cyclobranyl ester of 4-butyryloxy-3-propoxy-α-ethylcinnamic acid (22.1 g, 0.0297 mole) was used in place of cycloartenyl ester of 4-butyryloxy-3-methoxy-α-ethylcinnamic acid. The yield was 17.8 g (89.1%). m.p. 140°–141° C.

Specific rotation $[\alpha]_D^{20} +36.8°$ (C 1.00, CHCl$_3$)
Analysis. for C$_{45}$H$_{68}$O$_4$(M.W.672.99): Calcd. (%): C 80.31, H 10.18. Found (%): C 80.36, H 10.12.

EXAMPLE 151

Preparation of 24-methylenecycloartanyl ester of 4-hydroxy-3-propoxy-α-propylcinnamic acid The title compound was prepared according to following the procedure of Example 120 where 24-methylenecycloartanyl ester of 3-propoxy-4-valeryloxy-αpropylcinnamic acid (23.5 g, 0.0305 mole) was used in place of cycloartenyl ester of 4-butyryloxy-3-methoxy-α-ethylcinnamic acid. The yield was 17.2 g (82.1%). 121° C.

Specific rotation $[\alpha]_D^{20} +39.1°$ (C 1.00, CHCl$_3$)
Analysis, for C$_{46}$H$_{70}$O$_4$(M.W.687.02): Calcd. (%): C 80.41, H 10.27. Found (%): C 80.32, H 10.34.

EXAMPLES 152–154

Preparation of cycloartenyl, cyclobranyl, and 24-methylenecycloartanyl esters of 3-propionyloxy-α-methylcinnamic acid The title compounds were prepared according to following the procedure of Example 123 where cycloartenol (21.3 g, 0.050 mole), cyclobranol (22.0 g, 0.050 mole), and 24-methylenecycloartanol (22.0 g, 0.050 mole), respectively, and 3-propionyloxy-α-methyl-cinnamic acid (17.6 g, 0.075 mole) were used for each preparation. The yield (%), m.p. (°C.), and specific rotation $\{[\alpha]_D^{20}$(C 1.00, CHCl$_3$)$\}$ of each product were as follows:

| Example No. | Triterpenyl ester of 3-propionyloxy-α-methylcinnamic acid | Yield (%) | Melting point (°C.) | Specific rotation $[\alpha]_D^{20}$ |
|---|---|---|---|---|
| 152 | Cycloartenyl ester | 83.1 | 80–81 | +44.5° |
| 153 | Cyclobranyl ester | 82.4 | 100–101 | +34.3° |
| 154 | 24-Methylene cycloartanyl ester | 82.0 | 85–86 | +44.0° |

EXAMPLES 155–157

Preparation of cycloartenyl, cyclobranyl, and 24-methylene cycloartanyl ester of 3-hydroxy-α-methylcinnamic acid The title compounds were prepared according to following the procedure of Example 124 where the compounds (each 0.042 mole) of Examples 152–154 were used respectively. The yield (%), m.p. (°C.), and specific rotation $\{[\alpha]_D^{20}$ (C 1.00, CHCl$_3$)$\}$ of each produce were as follows:

| Example No. | Triterpenyl ester of 3-hydroxy-α-methyl-cinnamic acid | Yield (%) | Melting point (°C.) | Specific rotation $[\alpha]_D^{20}$ |
|---|---|---|---|---|
| 155 | Cycloartenyl ester | 86.2 | 178–179 | +44.3° |
| 156 | Cyclobranyl ester | 87.2 | 191–192 | +45.2° |
| 157 | 24-Methylene-cycloartanyl ester | 85.8 | 188–189 | +42.7° |

EXAMPLES 158–160

Preparation of cycloartenyl, cyclobranyl, and 24-methylenecycloartanyl ester of 3-butyryloxy-α-ethylcinnamic acid The title compounds were prepared according to following the procedure of Example 129 where 3-butyryloxy-α-ethylcinnamic acid (3.50 g, 0.0135 mole) and cycloartenol (2.85 g, 0.0067 mole), cyclobranol (2.95 g, 0.0067 mole), and 24-methylenecycloartanol (2.95 g, 0.0067 mole), respectively were used for each preparation. The yield (%), m.p. (°C.), and specific rotation $\{[\alpha]_D^{20}$(C 1.00, CHCl$_3$)$\}$ of each product were as follows:

| Example No. | Triterpenyl ester of 3-butyryloxy-α-ethylcinnamic acid | Yield (%) | Melting point (°C.) | Specific rotation $[\alpha]_D^{20}$ |
|---|---|---|---|---|
| 158 | Cycloartenyl ester | 81.4 | 82–83 | +41.4° |
| 159 | Cyclobranyl ester | 82.3 | 112–113 | +37.4° |
| 160 | 24-Methylene cycloartanyl ester | 79.4 | 89–90 | +40.8° |

EXAMPLES 161–163

Preparationof cycloartenol, cyclobranol, and 24-methylenecycloartanol ester of 3-hydroxy-α-ethylcinnamic acid The title compounds were prepared according to following the porcedure of Example 129 where the compounds (each 0.003 mole) of Examples 158–160 were used, respectively. The yield (%), m.p. (° C., and specific rotation $\{[\alpha]_D^{20}$ (C 1.00, CHCl$_3$)$\}$ of each product were as follows:

| Example No. | Triterpenyl ester of 3-hydroxy-α-ethyl-cinnamic acid | Yield (%) | Melting point (°C.) | Specific rotation $[\alpha]_D^{20}$ |
|---|---|---|---|---|
| 161 | Cycloartenyl ester | 92.4 | 161–162 | +44.8° |
| 162 | Cyclobranyl ester | 93.4 | 188–189 | +46.0° |
| 163 | 24-Methylene-cycloartanyl ester | 91.8 | 173–174 | +44.2° |

EXAMPLES 164–165

Preparation of cycloartenyl and cyclobranyl esters of 2-hydroxy-α-methylcinnamic acid Cycloartenyl and cyclobranyl esters of 2-propionyloxy-α-methylcinnamic acid (27.5 g, yield 85.5%; 27.5 g, yield 82.8%, respectively) were prepared according to following the procedure of Example 123 where cycloartenol (21.3 g, 0.050 mole) and cyclobranol (22.0 g, 0.050 mole), respectively, and 2-propionyloxy-α-methylcinnamic acid (17.6 g, 0.075 mole were used) for preparation. Using these esters (each 24.5 g), the title compounds were prepared according to following the procedure of Example 124. The yield (%), m.p. (°C.), and specific rotation {$[\alpha]_D^{20}$(C 1.00, CHCl$_3$)} of each product were as follows:

| Example No. | Triterpenyl ester of 2-hydroxy-α-methylcinnamic acid | Yield (%) | Melting point (°C.) | Specific rotation $[\alpha]_D^{20}$ |
|---|---|---|---|---|
| 164 | Cycloartenyl ester | 85.4 | 185–186 | +46.4° |
| 165 | Cyclobranyl ester | 86.2 | 197–198 | +48.7° |

EXAMPLE 166

Preparation of cycloartenyl ester of 3-methoxy-4-nitrobenzoic acid

To 3-methoxy-4-nitrobenzoic acid (15.0 g, 0.076 mole) were added thionyl chloride (34 ml, 6 equivalents) and dimethylformamide (0.5 ml), and the mixture was stirred at 60° C. for 2 hours. Then the reaction mixture was concentrated under reduced pressure and the residue was mixed with dioxane (75 ml) at 0° C. Thereto was added a solution of cycloartenol (25.0 g, 0.059 mole) in pyridine (110 ml). This reaction mixture was stirred at 70° C. for 20 minutes. After thus completing the reaction, the solvents were removed by distillation under reduced pressure. The resulting residue was dissolved in chloroform, and the chloroform layer was washed with saturated aqueous NaHCO$_3$ solution, and dried. The chloroform solution was concentrated under reduced pressure. The residual crystals were recrystallized from methylene chloride-methanol (1:2, v/v), giving cycloartenyl ester of 3-methoxy-4-nitrobenzoic acid (30.5 g) in a 85.3% yield. m.p. 182°–183° C.

Specific rotation $[\alpha]_D^{22.5}$ +57.7° (C 1.00, CHCl$_3$)

Analysis, for C$_{38}$H$_{55}$NO$_5$(M.W.605.82): Cald. (%): C 75.33, H 9.15, N 2.31. Found (%): C 75.42, H 9.07, N 2.36.

IR$\nu$, KBr(cm$^{-1}$): 2940, 1720, 1610, 1530, 1410, 1350, 1310, 1290, 1245.

PMR(CDCl$_3$)δ: 0.38(1H, ½ABq, 4.2 Hz), 0.62(1H, ½ABq, 4.2 Hz), 0.50–2.36(27H, m), 0.95(1H, s), 0.97 (3H, s), 1.04(3H, s), 1.60(3H, s), 1.69(3H, s), 4.00(3H, s), 4.50–5.32(2H, m), 7.42–8.01 (3H, m).

EXAMPLE 167

Preparation of cycloartenyl ester of 4-amino-3-methoxy benzoic acid

Acetic acid (400 ml) and dioxane (400 ml) were added to cycloartenyl ester of 3-methoxy-4-nitrobenzoic acid (40.0 g, 0.066 mole) prepared according to the procedure of Example 166. Thereto 6N-HCl-dioxane (22 ml, 2 equivalents) and zinc powder (40 g) were added at 0° C. and the mixture was stirred at 25° C. for 2 hours. After the reaction, zinc powder was removed by filtration. The filtrate was concentrated under reduced pressure, and the residue was extracted with chloroform. The chloroform extracts were washed successively with water and saturated aqueous NaHCO$_3$ solution, then dried, and concentrated. The residual crystals were recrystallized from methylene chloride-methanol (1:2, v/v), giving cycloartenyl ester 4-amino-3-methoxybenzoic acid (32 g) in a 84.1% yield. m.p. 186°–188° C.

Specific rotation $[\alpha]_D^{26.5}$ +64.3°(C 1.00, CHCl$_3$)

Analysis, for C$_{38}$H$_{57}$NO$_3$(M.W.575.83): Calcd. (%): C 79.26, H 9.98, N 2.43. Found (%): C 79.32, H 9.99, N 2.39.

IR$\nu$, KBr(cm$^{-1}$): 3450, 3350, 2930, 1700, 1620, 1520, 1460, 1305, 1285, 1260, 1220, 1180, 1105.

PMR(CDCl$_3$)δ: 0.36(1H, ½ABq, 4.2 Hz), 0.61(1H, ½ABq, 4.2 Hz), 0.48–2.39(27H, m), 1.61 (3H, s), 1.67 (3H, s), 3.88(3H, s), 4.20(2H, bs), 4.51–5.31 (2H, m), 6.46–6.77(1H, m), 7.30–7.71(2H, m).

EXAMPLE 168

Preparation of cyclobranyl ester of 3-methoxy-4-nitrobenzoic acid

3-Methoxy-4-nitrobenzoic acid (50.0 g, 0.254 mole) was allowed to react with thionyl chloride (60 ml, 3.2 equivalents) by adding dimethylformamide (0.5 ml) and the mixture was stirred at 60° C. for 2 hours. Then the reaction mixture was concentrated under reduced pressure. Dioxane (100 ml) was added thereto, and further a solution of cyclobranol (93 g, 0.211 mole) in pyridine (150 ml) was added at 0° C. The mixture was stirred at 70° C. for 30 minutes. After the reaction, the solvents were removed by distillation under reduced pressure. The resulting residue was dissolved in chloroform, and the chloroform layer was washed with saturated aqueous NaHCO$_3$ solution, and dried. This chloroform solution was concentrated under reduced pressure, and the residual crystals were recrystallized from chloroform-ethanol (1:3, v/v), giving cyclobranyl ester of 3-methoxy-4-nitrobenzoic acid (94.4 g) in a 72.1% yield. m.p. 213°–214° C.

Specific rotation $[\alpha]_D^{25.5}$ +53.9°(C 1.00, CHCl$_3$)

Analysis, for C$_{39}$H$_{57}$NO$_5$(M.W.619.85): Calcd. (%): C 75.57, H 9.27, N 2.26. Found (%): C 75.63, H 9.22, N 2.33.

IR$\nu$, KBr(cm$^{-1}$): 2930, 1715, 1610, 1530, 1410, 1360, 1310, 1285, 1240.

PMR(CDCl$_3$)δ: 0.39(1H, ½ABq, 4.8 Hz), 0.62(1H, ½ABq, 4 8 Hz), 0.50–2.28(27H, m), 0.92(6H, s), 0.99 (3H, s), 1.05(3H, s), 1.63(9H, s), 4.01(3H, s), 4.62–5.03(1H, m), 7.48–7.96(3H, m).

EXAMPLE 169

Preparation of cyclobranyl ester of 4-amino-3-methoxybenzoic acid

Cyclobranyl ester of 3-methoxy-4-nitrobenzoic acid (94.3 g, 0.152 mole) prepared according to the procedure of Example 168 was suspended in a mixture of acetic acid (1.2 l) and tetrahydrofuran (1.2 l), and thereto 6N-HCl-dioxane (100 ml) and zinc powder (94 g) were added, and the reaction mixture was stirred at 25° C. for 2 hours. After the reaction, zinc powder was removed by filtration. The filtrate was concentrated under reduced pressure and the residue was extracted with chloroform. The chloroform extracts were washed successively with water and saturated aqueous NaHCO$_3$ solution, then dried, and concentrated. The residual crystals were recrystallized from chloroform-ethanol (1:4, v/v), giving cyclobranyl ester of 4-amino-3-methoxybenzoic acid ester (64.2 g) in a 71.5% yield. m.p. 235°–236° C.

Specific rotation $[\alpha]_D^{25}$ +60.8°(C 1.00, CHCl$_3$)

Analysis, for C$_{39}$H$_{59}$NO$_3$(M.W.589.86): Calcd. (%): C 79.41, H 10.08, N 2.37. Found (%): C 79.49, H 10.12, N 2.42.

IR$\nu$, KBr(cm$^{-1}$): 3450, 3350, 2900, 1680, 1620, 1310, 1280, 1260, 1110.

PMR(CDCl$_3$)δ: 0.36(1H, ½ABq, 4.8 Hz), 0.61(1H, ½ABq, 4.8 Hz), 0.50–2.20(27H, m), 0.89(6H, s), 0.96 (3H, s), 1.01(3H, s), 3.85(3H, s), 3.92O4.36 (2H, bs), 4.51–4.91(1H, m), 6.42–6.72(1H, m), 7.26–7.72(2H, m).

EXAMPLE 170

Preparation of cycloartenyl ester of 2-methoxy-5-nitrobenzoic zcid 2-methoxy-5-nitrobenzoic acid (17,3 g, 0.088 mole) was allowed to react thionyl chloride (65 ml, 10 equivalents) by adding dimethylformamide (0.3 ml) and the mixture wa stirred at 50° C. for 1.5 hours. Then, the reaction mixture was concentrated under reduced pressure, dioxane (125 ml) was added thereto and further a solution of cycloartenol (25.0 g, 0.059 mole) in pyridine (125 ml) was added dropwise at 0° C. This reaction mixture was stirred at 60° C. for 1.5 hours. After the reaction, the solvents were removed by distillation under reduced pressure, the residue was extracted with chloroform, and the chloroform extracts were washed successively with water and saturated aqueous NaHCO$_3$ solution, then dried, and concentrated. The residue was recrystallized from methylene chloride-hexane (1:3, v/v), giving cycloartenyl ester of 2-methoxy-5-nitrobenzoic acid (31.5 g) in an 88.7% yield. m.p. 186°–187° C.

Specific rotation $[\alpha]_D^{25}+43.9°$(C 1.00, CHCl$_3$)

Analysis, for C$_{38}$H$_{55}$NO$_5$(M.W.605.82): Calcd. (%): C 75.33, H 9.15, N 2.31. Found (%) : C 75.30, H 9.22, N 2.29.

IR$\nu$, KBr(cm$^{-1}$): 2930, 1695, 1610, 1520, 1340, 1280, 1135.

PMR(CDCl$_3$)$\delta$: 0.39(1H, ½ABq, 4.2 Hz), 0.62(1H, ½ABq, 4.2 Hz), 0.50–2.40(27H, m), 0.90(3H, s), 0.96 (6H, s), 1.01(3H, s), 2.60(3H, bs), 2.68(3H, bs), 4.00(3H, s), 4.65–5.30(3H, m), 7.08(1H, d, 9.4 Hz) 8.34(1H, dd, 3.0 Hz, 9.4 Hz), 8.64(1H, d, 3.0 Hz).

EXAMPLE 171

Preparation of cycloartenyl ester of 5-amino-2-methoxybenzoic acid

Cycloartenyl ester of 2-methoxy-5-nitrobenzoic acid (34.0 g, 0.056 mole) prepared according to the procedure of Example 170 was suspended in acetic acid (1.2 l) at 20° C., and thereto 6N-HCl-dioxane (19 ml, 2 equivalent) and zinc powder (68 g) were added. The mixture was stirred at 30° C. for 1 hour. Then, zinc powder was removed by filtration, and the filtrate was concentrated under reduced pressure and the residue was extracted with chloroform. The chloroform extracts were washed successively with water and saturated aqueous NaHCO$_3$ solution, then dried, concentrated, and the residual crystals were recrystallized from methylene chloride-hexane (1:4, v/v), giving cycloartenyl ester of 5-amino-2-methoxybenzoic acid (27.2 g) in a 84.4% yield. m.p. 180°–182° C.

Specific rotation $[\alpha]_D^{26.5}+47.8°$(C 1.00, CHCl$_3$)

Analysis, for C$_{38}$H$_{57}$NO$_3$(M.W.575.83): Calcd. (%): C 79.26, H 9.98, N 2.43. Found (%): C 79.32, H 9.94, N 2.41.

IR$\nu$, KBr(cm$^{-1}$): 3450, 3350, 2900, 2860, 1690, 1630, 1500, 1440, 1300, 1270, 1245.

PMR(CDCl$_3$)$\delta$: 0.38(1H, ½ABq, 4.2 Hz), 0.59(1H, ½ABq, 4.2 Hz), 0.50–2.30(27H, m), 0.90(6H, s), 0.93 (6H, s), 1.59(3H, bs), 1.67(3H, bs), 3.55(2H, bs), 3.88(3H, s), 4.50–5.30(2H, m), 6.68–7.24(3H, m).

EXAMPLE 172

Preparation of cyclobranyl ester of 2-methoxy-5-nitrobenzoic acid

2-Methoxy-5-nitrobenzoic acid (11.6 g, 0.059 mole) was allowed to react with thionyl chloride (20 ml) and dimethylformamide (0.2 ml) and the mixture was stirred at 50° C. for 2 hours. Then the reaction mixture was concentrated under reduced pressure. Toluene (150 ml), pyridine (30 ml), and further cyclobranol (20 g, 0.045 mole) were added to the residue and the mixture was stirred at 60° C. for 2 hours. After the reaction, the solvents were removed by distillation under reduced pressure and the residue was extracted with chloroform. The chloroform extracts were washed successively with water and saturated aqueous NaHCO$_3$ solution, then dried, concentrated, and the residue was recrystallized from chloroform-ethanol (1:3, v/v),giving cyclobranyl ester of 2-methoxy-5-nitrobenzoic acid (25.9 g) in a 92.0% yield. m.p. 207°–208° C.

Specific rotaion $[\alpha]_D^{25}+32.5°$(C 1.00, CHCl$_3$)

Analysis, for C$_{39}$H$_{57}$NO$_5$(M.W. 619.85): Calcd. (%): C 75.57, H 9.27, N 2.26. Found (%): C 75.52, H 9.34, N 2.30.

IR$\nu$, KBr(cm$^{-1}$): 2390, 1700, 1610, 1520, 1345, 1280 1130.

PMR(CDCl$_3$)$\delta$: 0.39(1H, ½ABq, 4.8 Hz), 0.62(1H, ½ABq, 4.8 Hz), 0.76–2.24(27H, m), 0.91(3H, s), 0.96 (6H, s), 1.01(3H, s), 1.63(9H, s), 4.01(3H, s), 4.64–5.02(1H, m), 7.06(1H, d, 9.6 Hz), 8.34(1H, dd, 9.6 Hz, 3.6 Hz), 8.67(1H, d, 3.6 Hz).

EXAMPLE 173

Preparation of cyclobranyl ester of 5-amino-2-methoxybenzoic acid

Cyclobranyl ester of 2-methoxy-5-nitrobenzoic acid (25.0 g, 0.040 mole) prepared according to the procedure of Example 172 was suspended in acetic acid (1 l), and thereto 6N-HCl-dioxane (21 ml) and zinc powder (25.0 g) were added. The mixture was stirred at 30° C. for 2 hours. After the reaction, zinc powder was removed by filtration. The filtrate was concentrated under reduced pressure, and the residue was extracted with chloroform. The extracts were washed successively with water and saturated aqueous NaHCO$_3$ solution, then dried, concentrated, and the residue was recrystallized from chloroform-ethanol (1:2, v/v), giving cyclobranyl ester of 5-amino-2-methoxybenzoic acid (13.7 g) in a 57.5% yield. m.p. 193°–195° C.

Specific rotation $[\alpha]_D^{26.5}+41.5°$(C 1.00, CHCl$_3$)

Analysis, for C$_{39}$H$_{59}$NO$_3$(M.W.589.86): Calcd (%): C 79.41, H 10.08, N 2.37. Found (%): C 79.35, H 10.15, N 2.35.

IR$\nu$, KBr(cm$^{-1}$): 3430, 3350, 2930, 1690, 1500, 1460, 1430, 1310, 1270, 1245.

PMR(CDCl$_3$)$\delta$: 0.36(1H, ½ABq, 4.8 Hz), 0.61(1H, ½ABq, 4.8 Hz), 0.50–2.28(27H, m), 0.92(3H, s), 0.96 (6H, s), 1.00(3H, s), 1.64(9H, s), 2.88–3.26 (2H, m), 3.81(3H, s), 4.52–5.02(1H, m), 6.74–6.90(1H, m), 7.08–7.22(2H, m).

EXAMPLES 174–176

Preparation of cycloartenyl, cyclobranyl, and 24-methylenecycloartanyl esters of 3-methoxy-4-nitrocinnamic acid The title compounds were prepared according to following the procedure of Example 166 where 3-methoxy-4-nitrocinnamic acid (17.0 g, 0.076 mole) for each preparation and cycloartenol (25.0 g), cyclobranol (26.0 g), and 24-methylenecycloartanol (26.0 g), respectively were used. The yield (%), m.p. (°C.), and specific rotation $\{[\alpha]_D^{25}$ (C 1.00, CHCl$_3$)$\}$ of each product were as follows:

| Example No. | Triterpenyl ester of 3-methoxy-4-nitro-cinnamic acid | Yield (%) | Melting point (°C.) | Specific rotation $[\alpha]_D^{20}$ |
|---|---|---|---|---|
| 174 | Cycloartenyl ester | 86.2 | 190–194 | +43.6° |
| 175 | Cyclobranyl ester | 85.3 | 220–221 | +42.3° |
| 176 | 24-Methylene-cycloartanyl ester | 85.8 | 210–211 | +43.0° |

EXAMPLES 177–179

Preparation of cycloartenyl, cyclobranyl, and 24-methylenecycloartanyl ester of 4-amino-3-methoxycinnamic acid The title compounds were prepared according to following the procedure of Example 167 but where using cycloartenyl, cyclobranyl, and 24-methylenecycloartanyl esters of 3-methoxy-4-nitrocinnamic acid (41.7 g, 42.6 g and 42.6 g, respectively, each 0.066 mole) obtained in Examples 174–176 were used, respectively. The yield (%), m.p. (°C.), and specific rotation $\{[\alpha]_D^{25}$ (C 1.00, CHCl$_3$)$\}$ of each product were as follows:

| Example No. | Triterpenyl ester of 4-amino-3-methoxy-cinnamic acid | Yield (%) | Melting point (°C.) | Specific rotation $[\alpha]_D^{25}$ |
|---|---|---|---|---|
| 177 | Cycloartenyl ester | 85.2 | 194–195 | +42.3° |
| 178 | Cyclobranyl ester | 85.8 | 240–241 | +41.0° |
| 179 | 24-Methylene-cycloartanyl ester | 86.4 | 227–228 | +41.8° |

EXAMPLES 180–182

Preparation of cycloartenyl, cyclobranyl, and 24-methylenecycloartanyl esters of 2-ethoxy-5-nitrocinnamic acid The title compounds were prepared according to following the procedure of Example 170 where 2-ethoxy-5-nitrocinnamic acid (19.5 g, 0.082 mole) for each preparation and cycloartenol (25.0 g, 0.059 mole), cyclobranol (26.0 g, 0.059 mole), and 24-methylenecycloartanol (26.0 g, 0.059 mole), respectively were used. The yield (%), m.p. (°C.), and specific rotation $\{[\alpha]_D^{25}$(C 1.00, CHCl$_3$)$\}$ of each product were as follows:

| Example No. | Triterpenyl ester of 2-ethoxy-5-nitro-cinnamic acid | Yield (%) | Melting point (°C.) | Specific rotation $[\alpha]_D^{25}$ |
|---|---|---|---|---|
| 180 | Cycloartenyl ester | 87.8 | 182–183 | +42.7° |
| 181 | Cyclobranyl ester | 88.4 | 203–204 | +40.4° |
| 182 | 24-Methylene-cycloartanyl ester | 87.2 | 198–199 | +42.1° |

EXAMPLES 183–185

Preparation of cycloartenyl, cyclobranyl, and 24-methylenecycloartanyl esters of 5-amino-2-ethoxycinnamic acid The title compounds were prepared according to following the procedure of Example 171 where cycloartenyl, cyclobranyl, and 24-methylenecycloartanyl esters of 2-ethoxy-5-nitrocinnamic acid (36.2 g, 37.0 g, and 37.0 g, respectively, each 0.056 mole) obtained in Examples 180–182, respectively were used. The yield (%), m.p. (°C.), and specific rotation $\{[\alpha]_D^{25}$ (C 1.00, CHCl$_3$)$\}$ of each product were as follows:

| Example No. | Triterpenyl ester of 5-amino-2-ethoxy-cinnamic acid | Yield (%) | Melting point (°C.) | Specific rotation $[\alpha]_D^{25}$ |
|---|---|---|---|---|
| 183 | Cycloartenyl ester | 85.3 | 176–177 | +43.2° |
| 184 | Cyclobranyl ester | 84.8 | 190–191 | +41.0° |
| 185 | 24-Methylene-cycloartanyl ester | 85.8 | 181–182 | +42 2° |

EXAMPLE 186–188

Preparation of cycloartenyl, cyclobranyl, and 24-methylenecycloartanyl ester of 3-methoxy-4-nitro-α-methylcinnamic acid The title compounds were prepared according to following the procedure of Example 166 where 3-methoxy-4-nitro-α-methylcinnamic acid (17.3 g, 0.073 mole) for each preparation and cycloartenol (25.0 g, 0.059 mole), cyclobranol (26.0 g, 0.059 mole), and 24-methylenecycloartanol (26.0 g, 0.059 mole), respectively were used. The yield (%), m.p. (°C.), and specific rotation $\{[\alpha]_D^{25}$ (C 1.00, CHCl$_3$)$\}$ of each product were as follows:

| Example No. | Triterpenyl ester of 3-methoxy-4-nitro-α-methylcinnamic acid | Yield (%) | Melting point (°C.) | Specific rotation $[\alpha]_D^{25}$ |
|---|---|---|---|---|
| 186 | Cycloartenyl ester | 83.4 | 178–180 | +44.3° |
| 187 | Cyclobranyl ester | 84.2 | 208–209 | +43.7° |
| 188 | 24-Methylene-cycloartanyl ester | 82.5 | 199–200 | +44.1° |

EXAMPLES 189–191

Preparation of cycloartenyl, cyclobranyl, and 24-methylenecycloartanyl esters of 4-amino-3-methoxy-α-methylcinnamic acid The title compounds were prepared according to following the procedure of Example 167 where cycloartenyl, cyclobranyl, and 24-methylenecycloartanyl esters of 3-methoxy-4-nitro-α-methylcinnamic acid (43.6 g, 44.5 g, and 44.5 g, respectively, each 0.066 mole) obtained in Examples 186–188, respectively were used. The yield (%), m.p. (°C.), and specific rotation $\{[\alpha]_D^{25}$ (C 1.00, CHCl$_3$)$\}$ of each product were as follows:

| Example No. | Triterpenyl ester of 4-amino-3-methoxy-α-methylcinnamic acid | Yield (%) | Melting point (°C.) | Specific rotation $[\alpha]_D^{25}$ |
|---|---|---|---|---|
| 189 | Cycloartenyl ester | 85.6 | 183–184 | +43.0° |
| 190 | Cyclobranyl ester | 84.5 | 225–226 | +42.0° |
| 191 | 24-Methylene-cycloartanyl ester | 85.0 | 213–214 | +42.7° |

EXAMPLES 192–194

Preparation of cycloartenyl cyclobranyl, and 24-methylenecycloartanyl esters of 5-nitro-2-propoxy-α-methylcinnamic acid The title compounds were prepared according to following the procedure of Example 170 where 5-nitro-2-propoxy-α-methylcinnamic acid (21.2 g, 0.080 mole) for each preparation and cycloartenol (25.0 g, 0.059 mole), cyclobranol (26.0 g, 0.059 mole), and 24-methylenecycloartanol (26.0 g, 0.059 mole), respectively were used. The yield (%), m.p. (°C.), and specific rotation $\{[\alpha]_D^{25}$ (C 1.00, CHCl$_3$)$\}$ of each product were as follows:

| Example No. | Triterpenyl ester of 5-nitro-2-propoxy-α-methylcinnamic acid | Yield (%) | Melting point (°C.) | Specific rotation $[\alpha]_D^{25}$ |
|---|---|---|---|---|
| 192 | Cycloartenyl ester | 86.4 | 184–185 | +43.2° |
| 193 | Cyclobranyl ester | 88.4 | 204–205 | +41.3° |
| 194 | 24-Methylene cycloartanyl ester | 87.2 | 196–197 | +42.7° |

EXAMPLES 195–197

Preparation of cycloartenyl, cyclobranyl, and 24-methylenecycloartanyl esters of 5-amino-2-propoxy-α-methylcinnamic acid The title compounds were prepared according to following the procedure of Example 171 where cycloartenyl, cyclobranyl, and 24-methylenecycloartanyl esters of 5-nitro-2-propoxy-α-methylcinnamic acid (37.7 g, 38.5 g, and 38.5 g respectively, each 0.056 mole) obtained in Examples 192–194, respectively, were used. The yield (%), m.p. (°C.), and specific rotation $\{[\alpha]_D^{25}$ (C 1.00, CHCl$_3$)$\}$ of each product were as follows:

| Example No. | Triterpenyl ester of 5-amino-2-propoxy-α-methylcinnamic acid | Yield (%) | Melting point (°C.) | Specific rotation $[\alpha]_D^{25}$ |
|---|---|---|---|---|
| 195 | Cycloartenyl ester | 84.4 | 175–176 | +44.2° |
| 196 | Cyclobranyl ester | 83.5 | 194–195 | +41.7° |
| 197 | 24-Methylene-cycloartanyl ester | 84.2 | 187–188 | +43.6° |

EXAMPLES 198 AND 199

Preparation of cycloartenyl and cyclobranyl esters of 3-methoxy-4-nitro-α-isopropyl cinnamic acid The title compounds were prepared according to following the procedure of Example 166 where 3-methoxy 4-nitro-α-isopropylcinnamic acid (19.1 g, 0.072 mole) for each preparation and cycloartenol (25.0 g, 0.059 mole) and cyclobranol (26.0 g, 0.059 mole), respectively were used. The yield (%), m.p. (°C.), and specific rotation $\{[\alpha]_D^{25}$ (C 1.00, CHCl$_3$)$\}$ of each product were as follows:

| Example No. | Triterpenyl ester of 3-methoxy-4-nitro-α-isopropylcinnamic acid | Yield (%) | Melting point (°C.) | Specific rotation $[\alpha]_D^{25}$ |
|---|---|---|---|---|
| 198 | Cycloartenyl ester | 84.2 | 155–156 | +41.2° |
| 199 | Cuclobranyl ester | 84.6 | 190–191 | +40.5° |

EXAMPLES 200 AND 201

Preparation of cycloartenyl and cyclobranyl esters of 4-amino-3-methoxy-α-isopropylcinnamic acid The title compounds were prepared according to following the procedure of Example 167 where cycloartenyl and cyclobranyl esters of 3-methoxy-4-nitro-α-isopropylcinnamic acid (44.5 g and 45.4 g, respectively, each 0.066 mole) obtained in Examples 198 and 199, respectively were used. The yield (%), m.p. (°C.), and specific rotation $\{[\alpha]_D^{25}$ (C 1.00, CHCl$_3$)$\}$ of each product were as follows:

| Example No. | Triterpenyl ester of 4-amino-3-methoxy-α-isopropylcinnamic acid | Yield (%) | Melting point (°C.) | Specific rotation $[\alpha]_D^{25}$ |
|---|---|---|---|---|
| 200 | Cycloartenyl ester | 85.8 | 163–164 | +40.8° |
| 201 | Cyclobranyl ester | 84.2 | 201–202 | +39.7° |

EXAMPLES 202–204

Preparation of cycloartenyl, cyclobranyl and 24-methylenecycloartanyl esters of p-nitro-α-methylcinnamic acid Thionyl chloride (112 ml, 4 equivalents) and dimethylformamide (1 ml) were added to p-nitro-α-methylcinnamic acid (78.3 g, 0.378 mole) and the mixture was stirred at 60° C. for 2 hours. Then the resulting mixture was evaporated to dryness under reduced pressure, and the residue was mixed with dioxane (250 ml) and with pyridine (250 ml), and the mixture was allowed to react with cycloartenol (125.0 g, 0.293 mole), cyclobranol (129.1 g, 0.293 mole), or 24-methylenecycloartanol (129.1 g, 0.293 mole) at 60° C. for 2 hours. Then, the solvents were distilled off under reduced pressure, and the residue was extracted with chloroform. The extracts were washed successively with water and saturated aqueous solution of sodium bicarbonate, then dried, and evaporated to dryness under reduced pressure. The residual crystals were recrystallized from chloroformethanol (1:3, v/v), giving each of the title compounds. The yield (%), m.p. (°C.), and specific rotation $\{[\alpha]_D^{25}$ (C 1.00, CHCl$_3$)$\}$ of each product were as follows:

| Example No. | Triterpenyl ester of p-nitro--methyl-cinnamic acid | Yield (%) | Melting point (°C.) | Specific rotation $[\alpha]_D^{25}$ |
|---|---|---|---|---|
| 204 | Cycloartenyl ester | 88.7 | 188–189 | +44.2° |
| 205 | Cyclobranyl ester | 89.5 | 222–223 | +41.7° |
| 206 | 24-Methylene-cycloartanyl ester | 88.8 | 211–212 | +43.5° |

EXAMPLES 205–207

Preparation of cycloartenyl cyclobranyl, and 24-methylenecycloartanyl esters of p-amino-α-methylcinnamic acid Each of cycloartenyl, cyclobranyl, and 24-methylene-cycloartanyl esters of p-nitro-α-methylcinnamic acid (16.6 g, 17.0 g, and 17.0 g, respectively, 0.027 mole each) obtained in Examples 204–206, respectively, was suspended in a mixture of acetic acid (150 ml) and dioxane (150 ml), 6N-hydrochloric acid-dioxane (9.5 ml) and zinc powder (8 g) were added to the suspension and the mixture was stirred at 40° C. for 3 hours. After the reaction, zinc powder was removed by filtration. The filtrate was evaporated to dryness under reduced pressure. The residue was extracted with chloroform. The extracts were washed successively with water and saturated aqueous sodium bicarbonate solution, then dried, and evaporated to dryness. The residual crystals were recrystallized from chloroform-ethanol (1:3, v/v), giving each of the title compounds. The yield (%), m.p. (°C.), and specific rotation $\{[\alpha]_D^{25}$ (C 1.00, CHCl$_3$)$\}$ of each product were as follows:

| Example No. | Triterpenyl ester of p-amino-α-methyl-cinnamic acid | Yield (%) | Melting point (°C.) | Specific rotation $[\alpha]_D^{25}$ |
|---|---|---|---|---|
| 205 | Cycloartenyl ester | 91.2 | 168–169 | +42.6° |
| 206 | Cyclobranyl ester | 91.8 | 202–203 | +41.2° |
| 207 | 24-Methylene-cycloartanyl ester | 92.0 | 193–194 | +42.3° |

EXAMPLES 208–210

Preparation of cycloartenyl, cyclobranyl, and 24-methylenecycloartanyl esters of m-nitro-α-methylcinnamic acid Thionyl chloride (60 ml, 2.1 equivalent) and dimethylformamide (1 ml) were added to m-nitro-α-methylcinnamic acid (80.4 g, 0.388 mole) and the mixture was stirred at 60° C. for 2 hours. After concentration of the resulting mixture under reduced pressure, the residue was mixed with dioxane (300 ml) and with pyridine (200 ml), and the mixture was allowed to react with cycloartenol (125.9 g, 0.295 mole), cyclobranol (130.0 g, 0.295 mole), or 24-methylenecycloartanol (130.0 g, 0.295 mole) at 60° C. for 2 hours. Then the mixture was evaporated to dryness under reduced pressure, and the residue was extracted with chloroform. The extracts were washed successively with water and saturated aqueous solution of sodium bicarbonate, then dried, and evaporated to dryness under reduced pressure. The residual crystals were recrystallized from chloroformethanol (1:4, v/v), giving each of the title compounds. The yield (%), m.p. (°C.), and specific rotation $\{[\alpha]_D^{25}$ (C 1.00, $CHCl_3)\}$ of each product were as follows:

| Example No. | Triterpenyl ester of m-nitro-α-methyl-cinnamate | Yield (%) | Melting point (°C.) | Specific rotation $[\alpha]_D^{25}$ |
|---|---|---|---|---|
| 208 | Cycloartenyl ester | 92.4 | 161–162 | +43.0° |
| 209 | Cyclobranyl ester | 91.7 | 193–194 | +42.3° |
| 210 | 24-Methylene-cycloartanyl ester | 90.9 | 172–173 | +42.7° |

EXAMPLES 211–213

Preparation of cycloartenyl, cyclobranyl, and 24-methylenecycloartanyl esters of m-amino-α-methylcinnamic acid Each of cycloartenyl-, cyclobranyl-, and 24-methylenecycloartanyl esters of m-nitro-α-methylcinnamic acid (16.6 g, 17.0 g, and 17.0 g, respectively, 0.027 mole each) obtained in Examples 208–210, respectively, was suspended in a mixture of acetic acid (150 ml) and tetrahydrofuran (200 ml). 6N-hydrochloric acid-dioxane (12.5 ml) and zinc powder (16.5 g) were added to the suspension and the mixture was stirred at 20° C. for 2 hours. After the reaction, zinc powder was removed by filtration. The filtrate was concentrated under reduced pressure, and extracted with chloroform. The extracts were washed successively with water and saturated aqueous solution of sodium bicarbonate, then dried, and evaporated to dryness. The residual crystals were recrystallized from chloroform-ethanol (1:2, v/v), giving each of the title compounds. The yield (%), m.p. (°C.), and specific rotation $\{[\alpha]_D^{25}$ (C 1.00, $CHCl_3)\}$ of each product were as follows.

| Example No. | Triterpenyl ester of m-amino--methyl-cinnamic acid | Yield (%) | Melting point (°C.) | Specific rotation $[\alpha]_D^{25}$ |
|---|---|---|---|---|
| 211 | Cycloartenyl ester | 85.2 | 171–172 | +44.2° |
| 212 | Cyclobranyl ester | 86.3 | 198–199 | +42.8° |
| 213 | 24-Methylene-cycloartanyl ester | 84.2 | 177–178 | +43.4° |

EXAMPLES 214 AND 215

Preparation of cycloartenyl and cyclobranyl esters of p-nitro-α-ethylcinnamic acid Thionyl chloride (6 ml, 2.0 equivalent) and dimethylformamide (0.1 ml) were added to p-nitro-α-ethylcinnamic acid (8.9 g, 0.040 mole) and the mixture was stirred at 60° C. for 2 hours. Then the resulting mixture was concentrated under reduced pressure. The residue was mixed with dioxane (30 ml) and with pyridine (20 ml), and the mixture was allowed to react with cycloartenol (12.8 g, 0.030 mole) or cyclobranol (13.2 g, 0.030 mole) at 60° C. for 2 hours. Then the resulting mixture was concentrated under reduced pressure, and the residue was extracted with chloroform. The extracts were washed successively with water and saturated aqueous solution of sodium bicarbonate, then dried, and evaporated to dryness under reduced pressure. The residual crystals were recrystallized from chloroform-ethanol (1:3, v/v), giving each of the title compounds. The yield (%), m.p. (°C.), and specific rotation $\{[\alpha]_D^{25}$ (C 1.00, $CHCl_3)\}$ of each product were as follows:

| Example No. | Triterpenyl ester of p-nitro-α-ethyl-cinnamic acid | Yield (%) | Melting point (°C.) | Specific rotation $[\alpha]_D^{25}$ |
|---|---|---|---|---|
| 214 | Cycloartenyl ester | 92.1 | 178–179 | +44.8° |
| 215 | Cyclobranyl ester | 91.8 | 204–205 | +43.7° |

EXAMPLES 216 AND 217

Preparation of cycloartenyl and cyclobranyl esters of p-amino-α-ethylcinnamic acid Each of cycloartenyl and cyclobranyl esters of p-nitro-α-ethylcinnamic acid (17.0 g and 17.4 g, respectively, 0.027 mole each) obtained in Examples 214 and 215, respectively, was suspended in a mixture of acetic acid (150 ml) and tetrahydrofuran (200 ml). 6N-Hydrochloric acid-dioxane (12.5 ml) and zinc powder (16.5 g) were added to the suspension and the mixture was stirred at 22° C. for 2 hours. After the reaction, zinc powder was removed by filtration. The filtrate was evaporated to dryness under reduced pressure, and the residue was extracted with chloroform. The extracts were washed successively with water and saturated aqueous solution of sodium bicarbonate, then dried, and evaporated to dryness under reduced pressure. The residual crystals were recrystallized from chloroformethanol (1:3, v/v), giving each of the title compounds. The yield (%), m.p. (°C.), and specific rotation $\{[\alpha]_D^{25}$ (C 1.00, $CHCl_3)\}$ of each product were as follows:

| Example No. | Triterpenyl ester of p-amino-α-ethyl-cinnamic acid | Yield (%) | Melting point (°C.) | Specific rotation $[\alpha]_D^{25}$ |
|---|---|---|---|---|
| 216 | Cycloartenyl ester | 80.6 | 160–161 | +45.2° |

-continued

| Example No. | Triterpenyl ester of p-amino-α-ethyl-cinnamic acid | Yield (%) | Melting point (°C.) | Specific rotation $[\alpha]_D^{25}$ |
|---|---|---|---|---|
| 217 | Cyclobranyl ester | 79.3 | 200–201 | +44.3° |

EXAMPLE 218

Preparation of 24-methylenecycloartanyl ester of 3-methoxy-4-nitrobenzoic acid

The title compound was prepared according to following the procedure of Example 168 where 24-methylenecycloartanol (93.0 g, 0.211 mole) was used. The yield was 93.7 g (71.6%). m.p. 205°–206° C.

Specific rotation $[\alpha]_D^{25.5}$+56.5° (C 1.00, CHCl$_3$)

Analysis, Calcd. for C$_{39}$H$_{57}$NO$_5$ (M.W.619.85): C 75.57, H 9.27, N 2.26. Found: C 75.51, H 9.38, N 2.28.

EXAMPLE 219

Preparation of 24-methylenecycloartanyl ester of 4-amino-3-methoxybenzoic acid

The title compound was prepared according to the procedure of Example 169 where 24-methylenecycloartanyl ester of 3-methoxy-4-nitrobenzoic acid was used (92.2 g, 0.149 mole) obtained in Example 218. The yield was 62.8 g (71.5%). m.p. 222°–223° C.

Specific rotation $[\alpha]_D^{25}$+63.2° (C 1.00, CHCl$_3$)

Analysis, for C$_{39}$H$_{59}$NO$_3$ (M.W.589.86): Calcd. (%): C 79.41, H 10.08, N 2.37. Found (%): C 79.38, H 10.14, N 2.35.

EXAMPLE 220

Preparation of cycloartenyl ester of 4-amino-3-methoxybenzoic acid

4-Acetamido-3-methoxybenzoic acid (6.5 g, 0.031 mole) in dioxane (110 ml) was allowed to react with thionyl chloride (21.0 ml) and then pyridine (0.5 ml) at 20° C., and the mixture was stirred at 50° C. for 5 minutes. Then the resulting mixture was evaporated to dryness under reduced pressure, and to the residue a solution of cycloartenol (10.0 g, 0.023 mole) in a dioxane (50 ml)-benzene (50 ml) mixture was added and further pyridine (20 ml). After the mixture was heated at 70° C. for 3 hours, the solvents were distilled off under reduced pressure. The residue was dissolved in chloroform (100 ml), and the chloroform solution was washed with saturated aqueous solution of sodium bicarbonate. The aqueous solution was extracted with chloroform (5×10 ml). The whole chloroform solution was dried and concentrated under reduced pressure, and the residue was purified by silica gel column chromatography [solvent: chloroform-ethyl acetate (1:1, v/v)], giving cycloartenyl ester of 4-acetamido-3-methoxybenzoic acid (10.8 g) in a 76.5% yield. m.p. 224°–225° C.

Specific rotation $[\alpha]_D^{25}$+61.5° (C 1.00, CHCl$_3$).

Cycloartenyl ester of 4-acetamido-3-methoxybenzoic acid (10.0 g, 0.016 mole) thus obtained was allowed to react with 30% HCl (20 ml) in tetrahydrofuran (200 ml) under reflux for 2 hours. Then the solvent was distilled off under reduced pressure, and the residue was dissolved in chloroform (300 ml), and the chloroform layer was washed successively with 1N aqueous NaOH (200 ml) and saturated saline water. The aqueous solutions were extracted with chloroform 3 times. The combined chloroform solution was dried and concentrated and the residue was purified by silica gel column chromatography [solvent: ethyl acetate-hexane (1:4, v/v)], giving cycloartenyl ester of 4-amino-3-methoxybenzoic acid (5.4 g) in a 58.7% yield. m.p. 186°–187° C.

Specific rotation $[\alpha]_D^{26}$+64.4° (C 1.00, CHCl$_3$).

EXAMPLE 221

Preparation of cyclobranyl ester of 4-amino-3-methoxy-α-methylcinnamic acid

4-Acetamido-3-methoxy-α-methylcinnamic acid (21.93 g, 0.088 mole) dissolved in dioxane (150 ml) was allowed to react with thionyl chloride (25.7 ml) at 60° C. for 2 hours with stirring. Then the solvent was distilled off under reduced pressure. The residue was dissolved in dioxane (150 ml) and pyridine (50 ml), and allowed to react with cyclobranol (30 g, 0.068 mole) at 60° C. for 2 hours with stirring. The resulting mixture was concentrated under reduced pressure, and ethyl acetate (300 ml) was added to the residue. The resulting crystals were purified by silica gel column chromatography [solvent: chloroform-ethyl acetate (1:1, v/v)], giving cyclobranyl ester of 4-acetamido-3-methoxy-α-methylcinnamic acid (38.5 g) in a 84.2% yield, m.p. 248°–249° C.

Specific rotation $[\alpha]_D^{26}$+38.2° (C 1.00, CHCl$_3$).

Cyclobranyl ester of 4-acetamido-3-methoxy-α-methylcinnamic acid (34.4 g, 0.051 mole) thus obtained was dissolved in tetrahydrofuran (300 ml), and was allowed to react with 30% HCl (60 ml) at 70° C. for 2 hours with stirring. The resulting mixture was concentrated under reduced pressure, and the residue was purified by silica gel column chromatography [solvent: chloroform-ethyl acetate, (1:1, v/v)], giving cyclobranyl ester of 4-amino-3-methoxy-α-methylcinnamic acid (18.9 g) in a 58.8% yield. m.p. 225°–226° C.

Specific rotation $[\alpha]_D^{25}$+42.0° (C 1.00, CHCl$_3$).

EXAMPLE 222

Preparation of 24-methylenecycloartanyl ester of 4-amino-3-methoxycinnamic acid

24-Methylenecycloartanyl ester of 4-propionamido-3-methoxycinnamic acid was prepared according to the procedure of Example 221 where 4-propionamido-3-methoxycinnamic acid (21.93 g, 0.088 mole) and 24-methylenecycloartanol (30 g, 0.068 mole) were used in place of 4-acetamido-3-methoxy-α-methyl cinnamic acid and cyclobranol, respectively. The yield was 38.4 g (83.8%). m.p. 210°–211° C.

Specific rotation $[\alpha]_D^{26}$+39.4° (C 1.00, CHCl$_3$).

Then 24-methylenecycloartanyl ester of 4-amino-3-methoxycinnamic acid (18.7 g) was prepared according to the procedure of Example 221 where 24-methylenecycloartanyl ester of 4-propionamido-3-methoxycinnamic acid was used (35.2 g, 0.052 mole) in place of cyclobranyl ester of 4-acetamido-3-methoxy-α-methylcinnamic acid. The yield was 18.7 g (57.1%). m.p. 227°–228° C.

Specific rotation $[\alpha]_D^{25}$+41.8° (C 1.00, CHCl$_3$).

FORMULA EXAMPLE 1

| Tablets A | |
|---|---|
| Compound of Example 43: | |
| Cyclobranyl ester of p-aminobenzoic acid | 100 mg |
| Mannitol | 123 mg |
| Hydroxypropoxymethylcellulose | 7 mg |
| Talc | 5 mg |

|  |  |  |
|---|---|---|
| Microcrystalline cellulose | | 60 mg |
| Hydrogenated castor oil | | 5 mg |
| | Total | 300 mg |
| Tablets B | | |
| Compound of Example 86: | | |
| 24-Methylenecycloartanyl ester of 4-hydroxy-3-methoxybenzoic acid | | 150 mg |
| Corn starch | | 160 mg |
| Lactose | | 180 mg |
| Talc | | 7 mg |
| Magnesium stearate | | 3 mg |
| | Total | 500 mg |
| Tablets C | | |
| Compound of Example 100-2: | | |
| Cyclobranyl ester of 4-hydroxy-3-methoxycinnamic acid | | 100 mg |
| Soluble starch | | 20 mg |
| Corn starch | | 125 mg |
| Microcrystalline cellulose | | 45 mg |
| Silicon dioxide | | 6 mg |
| Magnesium stearate | | 4 mg |
| | Total | 300 mg |
| Tablets D | | |
| Compound of Example 60: | | |
| Cycloartenyl ester of 3-ethoxy-4-hydroxybenzoic acid | | 100 mg |
| Lactose | | 147 mg |
| Corn starch | | 62.1 mg |
| Microcrystalline cellulose | | 90 mg |
| Magnesium stearate | | 0.9 mg |
| | Total | 400 mg |
| Tablets E | | |
| Compound of Example 71: | | |
| Cyclobranyl ester of 3-ethoxy-4-hydroxycinnamic acid | | 50 mg |
| Lactose | | 10 mg |
| Microcrystalline cellulose | | 85.5 mg |
| Carboxymethyl cellulose calcium | | 2 mg |
| Magnesium stearate | | 1.5 mg |
| Stearic acid | | 1 mg |
| | Total | 150 mg |

According to the above prescriptions, various weights tablets were made of thoroughly uniformly mixed powders with a tableting machine.

In addition, tablets were prepared according to the recipe above but substituting, cycloartenyl ester of 4-hydroxy-3-methoxy-α-methylcinnamic acid of Example 114 for cyclobranyl ester of p-aminobenzoic acid of Example 43; 24-methylenecycloartanyl ester of 4-hydroxy-3-methoxy-α-methylcinnamic acid of Example 118 for 24-methylenecycloartanyl ester of 4-hydroxy-3-methoxybenzoic acid of Example 86; cyclobranyl ester of 4-hydroxy-3-methoxy-α-methylcinnamic acid of Example 116 for cyclobranyl ester of 4-hydroxy3-methoxycinnamic acid of Example 100-2; cycloartenyl ester of p-amino-α-methylcinnamic acid of Example 205 for cycloartenyl ester of 3-ethoxy-4-hydroxybenzoic acid of Example 60; and cyclobranyl ester of 5-amino-2-methoxybenzoic acid of Example 173 for cyclobranyl ester of 3-ethoxy-4-hydroxycinnamic acid of Example 71.

FORMULA EXAMPLE 2

|  |  |  |
|---|---|---|
| Granules A | | |
| Compound of Example 19: | | |
| Cycloartenyl ester of p-aminobenzoic acid | | 100 mg |
| Lactose | | 22 mg |
| Microcrystalline cellulose | | 60 mg |
| Corn starch | | 15 mg |
| Hydroxypropylcellulose | | 3 mg |
| | Total | 200 mg |

According to the above prescription, cycloartenyl ester of p-aminobenzoic acid, lactose, microcrystalline cellulose, and corn starch were mixed together. The mixture was sprayed with a 5% aqueous solution of hydroxypropylcellulose as a binder, dried and granulated by using a fluidized bed granulator.

Another granules were prepared in the same method as the above recipe but substituting cycloartenyl ester of 4-amino-3-methoxybenzoic acid of Example 167 for cycloartenyl ester of p-aminobenzoic acid of Example 19.

FORMULA EXAMPLE 3

|  |  |  |
|---|---|---|
| Granules B | | |
| Compound of Example 43: | | |
| Cyclobranyl ester of p-aminobenzoic acid | | 100 mg |
| Mannitol | | 38 mg |
| Microcrystalline cellulose | | 48 mg |
| Potato starch | | 10 mg |
| Polyvinylpyrrolidone | | 2 mg |
| Hydroxypropylcellulose | | 2 mg |
| | Total | 200 mg |

According to the above prescription, the cyclobranyl ester, mannitol, microcrystalline cellulose, potato starch and polyvinylpyrrolidone were mixed together, then the mixture was sprayed with 5% aqueous solution of hydroxypropylcellulose as a binder, dried and granulated, by using a fluidized bed granulator.

Another granules were prepared in the same method as the above recipe but substituting cycloartenyl ester of 5-amino-2-propoxy-α-methylcinnamic acid of Example 195 for cyclobranyl ester of p-aminobenzoic acid of Example 43.

FORMULA EXAMPLE 4

|  |  |  |
|---|---|---|
| Granules C | | |
| Cyclobranol | | 100 mg |
| Mannitol | | 10 mg |
| Microcrystalline cellulose | | 85 mg |
| Carboxymethyl cellulose calcium | | 2 mg |
| Magnesium stearate | | 1.5 mg |
| Hardened oil | | 1.5 mg |
| | Total | 200 mg |
| Granules D | | |
| Compound of Example 24: | | |
| Cycloartenyl ester of nicotinic acid | | 100 mg |
| Corn starch | | 29 mg |
| Microcrystalline cellulose | | 50 mg |
| Carboxymethyl cellulose calcium | | 21 mg |
| | Total | 200 mg |
| Granules E | | |
| Compound of Example 49: | | |
| Cyclobranyl ester of m-aminobenzoic acid | | 100 mg |
| Lactose | | 53 mg |
| Corn starch | | 39 mg |
| Potato starch | | 2 mg |
| Talc | | 3 mg |
| Magnesium stearate | | 3 mg |
| | Total | 200 mg |

According to the above prescriptions, the ingredients were mixed uniformly and granulated with an extruder.

In addition, another granules were prepared in the same method as the above recipe but substituting; cycloartenyl ester of 4-hydroxy-α-ethylcinnamic acid of Example 130 for cyclobranol; cycloartenyl ester of 4-amino-3-methoxycinnamic acid of Example 177 for cycloartenyl ester of nicotinic acid of Example 24 and cycloartenyl ester of 5-amino-2-methoxybenzoic acid of Example 171 for cyclobranyl ester of m-aminobenzoic acid of Example 49.

FORMULA EXAMPLE 5

| Capsules A<br>Compound of Example 100-2: | |
|---|---|
| Cyclobranyl ester of 4-hydroxy-3-methoxy-cinnamic acid | 100 mg |
| Lactose | 28 mg |
| Microcrystalline cellulose | 47 mg |
| Mannitol | 10 mg |
| Corn starch | 10 mg |
| Polyvinylpyrrolidone | 2 mg |
| Hydroxypropylcellulose | 3 mg |
| Total | 200 mg |

According to the above prescription, cyclobranyl ester of 4-hydroxy-3-methoxycinnamic acid, lactose, microcrystalline cellulose, mannitol, corn starch and polyvinylpyrrolidone were mixed together, then the mixture was sprayed with a 5% aqueous solution of hydroxypropylcellulose as a binder, dried and granulated, by using a fluidized bed granulator. No. 3 hard capsules were each filled with 200 mg of these granules.

Another hard capsules were prepared in the same method as the above recipe but substituting cycloartenyl ester of 4-hydroxy-3-methoxy-α-methylcinnamic acid of Example 114 for cyclobranyl ester of 4-hydroxy-3-methoxycinnamic acid of Example 100-2.

FORMULA EXAMPLE 6

Capsules B

Hard capsules were prepared by filling each of No. 3 hard capsules with 160 mg of granules A prepared according to Formula Example 2.

FORMULA EXAMPLE 7

Capsules C

Hard capsules were prepared by the following procedure. No. 2 hard capsules were filled with 200 mg of granules D prepared in Formula Example 4.

FORMULA EXAMPLE 8

| Capsules D<br>Compound of Example 12: | |
|---|---|
| Cycloartenyl ester of m-hydroxybenzoic acid | 100 mg |
| Mannitol | 98 mg |
| Carboxymethyl cellulose calcium | 2 mg |
| Total | 200 mg |

According to the above prescription, the ingredients were mixed uniformly. Gelatin capsules of No. 2 were filled with 200 mg of the mixed powder each. Then the capsules were enteric-coated to give enteric capsules.

Another enteric capsules were prepared by the same method as the above recipe but substituting cyloartenyl ester of 4-hydroxy-3-propoxy-α-methylcinnamic acid of Example 146 for cycloartenyl ester of m-hydroxybenzoic acid of Example 12.

FORMULA EXAMPLE 9

| Capsules E<br>Compound of Example 58: | |
|---|---|
| Cyclobranyl ester of p-hydroxybenzoic acid | 200 g |
| Sodium laurylsulfate | 9 mg |
| Disodium hydrogen phosphate | 1 mg |
| Mannitol | 188 mg |
| Magnesium stearate | 2 mg |
| Total | 400 g |

According to the above prescription, ingredients were uniformly mixed. Gelatin capsules of No. 1 were filled with 300 mg of the mixture each. Another capsules were prepared by the same method as the above recipe but substituting cyclobranyl ester of m-amino-α-methylcinnamic acid of Example 212 for cyclobranyl ester of p-hydroxybenzoic acid.

FORMULA EXAMPLE 10

| Enteric granules<br>Compound of Example 25: | |
|---|---|
| Cycloartenyl ester of linoleic acid | 100 g |
| Mannitol | 16 mg |
| Microcrystalline cellulose | 65 mg |
| Corn starch | 15 mg |
| Hydroxypropylmethylcellulose | 3 mg |
| Vinylpyrrolidone-vinyl acetate copolymer (supplied by General Aniline & Film Corp.) | 1 mg |
| Total | 200 g |

According to the above prescription, the ingredients were uniformly mixed and then granulated into spherical granules by an extruder. These granules were coated with material composed of hydroxypropylmethylcellulose phthalate (74%), glyceryl triacetate (11.6%), stearic acid (11.6%) and light silicon dioxide (2.8%), to give enteric granules.

Another enteric granules were prepared in the same method as the above recipe but substituting cycloartenyl ester of 5-amino-2-methoxybenzoic acid of Example 171 for cycloartenyl ester of linoleic acid of Example 25.

FORMULA EXAMPLE 11

| Enteric tablets<br>Compound of Example 54: | |
|---|---|
| Cyclobranyl ester of m-hydroxybenzoic acid | 100 mg |
| Mannitol | 10 mg |
| Microcrystalline cellulose | 85 mg |
| Carboxymethyl cellulose calcium | 2 mg |
| Magnesium stearate | 1.5 mg |
| Hardened oil | 1.5 mg |
| Total | 200 mg |

According to the above prescription, the ingredients were mixed uniformly. The mixture was compressed into tablets with a tabletting machine, followed by coating with the substance for enteric coating below.

| Coating substance: | |
|---|---|
| Hydroxypropylmethylcellulose phthalate | 14.8 mg |

| Coating substance: | | |
|---|---|---|
| Dioctyl phthalate | | 2.3 mg |
| Stearic acid | | 2.3 mg |
| Light silicon dioxide | | 0.6 mg |
| | Total | 20 mg |

In addition, enteric tablets were prepared in the same method as the above recipe but substituting cycloartenyl ester of 5-amino-2-ethoxycinnamic acid of Example 183 for cyclobranyl ester of m-hydroxybenzoic acid of Example 54.

FORMULA EXAMPLE 12

| Granules Compound of Example 16: | | |
|---|---|---|
| Cycloartenyl ester of o-nitrobenzoic acid | | 100 mg |
| Corn starch | | 32.5 mg |
| Hydroxypropylcellulose | | 3.5 mg |
| | Total | 136 mg |

According to the above prescription, the ingredients were uniformly mixed, the mixture was nucleated by tumbling or centrifugal methods. Then these nuclei were diluted with the uniformly mixed excipient below. The diluted nuclei were allowed to adhere each other with a usual binder; then coated and granulated. The granules (230 mg) were coated with the same enteric coating substance (30 mg) as shown in Formula Example 11. No. 3 gelatin capsules were each filled with 260 mg of the enteric granules.

| Excipient: | | |
|---|---|---|
| sugar | | 33.0 mg |
| Corn starch | | 58.5 mg |
| Hydroxypropylcellulose | | 2.5 mg |
| | Total | 94 mg |

FORMULA EXAMPLE 13

| Powders A Compound of Example 100-1: | | |
|---|---|---|
| Cycloartenyl ester of 4-hydroxy-3-methoxycinnamic acid | | 100 mg |
| Mannitol | | 50 mg |
| Corn starch | | 50 mg |
| | Total | 200 mg |
| Powders B Compound of Example 46: | | |
| Cyclopranyl ester of o-aminobenzoic acid | | 100 mg |
| Corn starch | | 100 mg |
| | Total | 200 mg |

Powders were prepared by mixing the above ingredients uniformly in a double cone type blender.

FORMULA EXAMPLE 14

| Capsules Compound of Example 93: | |
|---|---|
| 24-Methylenecycloartanyl ester of linoleic acid | 260 g |
| Vitamin C | 10 mg |
| Citric acid | 5 mg |
| Carboxymethyl cellulose calcium | 20 mg |
| Sodium laurylsulfate | 10 mg |
| Polyoxyethylene monostearate | 5 mg |
| Methylene chloride | 300 ml |

The above ingredients were thoroughly mixed to make a suspension. Aerosil 200 - 400 (tradename) (180 g) was added to the suspension, then the mixture was stirred and dried. The resulting solid mass was ground to a powder, and a chlorothene-ethanol solution (300 ml) which contains 20 g of vinylpyrrolidone and 2-methyl-5-vinylpyridine-methacrylic acid - methyl acrylate copolymer as a binder was added to the powder. The mixture was kneaded and granulated with a pelleter according to the ordinary method, and the granules were dried at about 50° C. (containing about 51% 24-methylenecycloartanyl ester of linoleic acid). Hard capsules were filled with 200 mg of the granules with mixing a small amount of magnesium stearate each by using an automatic capsule-filling machine.

FORMULA EXAMPLE 15

| Suppositorys A Compound of Example 74: | | |
|---|---|---|
| Cycloartenyl ester of 4-hydroxy-3-propoxycinnamic acid | | 200 mg |
| Witepsol E-85 | | 540 mg |
| Witepsol W-35 | | 1454 mg |
| Methyl-p-hydroxybenzoate | | 3 mg |
| Butyl-p-hydroxybenzoate | | 3 mg |
| | Total | 2200 mg |
| Suppositorys B Compound of Example 29: | | |
| Cycloartenyl ester of 4-hydroxy-3-methoxybenzoic acid | | 200 mg |
| Ascorbic acid | | 20 mg |
| Polyethylene glycol | | 2080 mg |
| | Total | 2300 mg |
| Suppositorys C Compound of Example 39: | | |
| Cyclobranyl ester of 3,4-dihydroxybenzoic acid | | 200 mg |
| Butylhydroxyanisole | | 6 mg |
| Semisythetic glyceride | | 2900 mg |
| | Total | 3106 mg |
| Suppositorys D Compound of Example 27: | | |
| Cycloartenyl ester of 3,4-dihydroxybenzoic acid | | 200.0 mg |
| Gelatin | | 1152.0 mg |
| Glycerol | | 454.0 mg |
| Methyl-p-hydroxybenzoate | | 2.0 mg |
| Propyl-p-hydroxybenzoate | | 0.4 mg |
| Ethylvanillin | | 2.8 mg |
| Titanium dioxide | | 24.0 mg |
| DC yellow lake No. 5 | | 12.0 mg |
| Distilled water | | 352.8 mg |
| | Total | 2200.0 mg |

According to the above prescriptions, the ingredients were thoroughly mixed and melted. And the melts were cast in aluminum molds, and cooled to give suppository.

FORMULA EXAMPLE 16

Emulsion

Polysolvate 80 (tradename, 1 g) and DK Ester F-160 (tradename, 1 g) were dissolved in a 50% aqueous solution of (100 ml) sorbitol. Cyclobranyl ester of 4-acetoxy-3-methoxycinnamic acid (50 g) was added thereto and the mixture was emulsified by stirring at 80° C. for 30 minutes. Sodium benzoate (0.25 g) and citric acid (1 g) were dissolved therein, then the volume was adjusted to 500 ml with distilled water. The whole was stirred again, giving the emulsion (containing about 10% cyclobranyl ester of 4-acetoxy-3-methoxycinnamic acid).

FORMULA EXAMPLE 17

| Tablets F Compound of Example 102: | | |
|---|---|---|
| Cycloartenyl ester of p-aminocinnamic acid | | 100 mg |
| Mannitol | | 123 mg |
| Hydroxypropoxymethylcellulose | | 7 mg |
| Talc | | 5 mg |
| Microcrystalline cellulose | | 61 mg |
| Magnesium stearate | | 4 mg |
| | Total | 300 mg |
| Tablets G Compound of Example 104: | | |
| Cyclobranyl ester of p-aminocinnamic acid | | 100 mg |
| Lactose | | 147 mg |
| Corn starch | | 62 mg |
| Microcrystalline cellulose | | 86 mg |
| Magnesium stearate | | 5 mg |
| | Total | 400 mg |
| Tablets H Compound of Example 108: | | |
| Cycloartenyl ester of m-aminocinnamic acid | | 100 mg |
| Soluble starch | | 20 mg |
| Corn starch | | 125 mg |
| Microcrystalline cellulose | | 45 mg |
| Silicon dioxide | | 6 mg |
| Magnesium stearate | | 4 mg |
| | Total | 300 mg |

According to the each prescription above, the ingredients were uniformly mixed and compressed into the tablets of each weight by using a tabletting machine.

FORMULA EXAMPLE 18

| Granules F Compound of Example 112: | | |
|---|---|---|
| 24-Methylenecycloartanyl ester of m-aminocinnamic acid | | 100 mg |
| Lactose | | 22 mg |
| Microcrystalline cellulose | | 60 mg |
| Corn starch | | 15 mg |
| Hydroxypropylcellulose | | 3 mg |
| | Total | 200 mg |

According to the prescription, 24-methylenecycloartanyl ester of m-aminocinnamic acid, lactose, microcrystalline cellulose, and corn starch were mixed. The mixture sprayed with a 5% aqueous hydroxypropylcellulose solution as a binder was dried and granulated with a fluidized bed granulator.

FORMULA EXAMPLE 19

| Granules G Compound of Example 102: | |
|---|---|
| Cycloartenyl ester of p-aminocinnamic acid | 100 mg |

| —continued Granules G Compound of Example 102: | |
|---|---|
| Lactose | 53 mg |
| Corn starch | 39 mg |
| Potato starch | 2 mg |
| Talc | 3 mg |
| Magnesium stearate | 3 mg |
| Total | 200 mg |

According to the above prescription, the ingredients were uniformly mixed and granulated with an extruder.

FORMULA EXAMPLE 20

Capsules F

Hard capsules of No. 2 were filled with granules G prepared according to Formula Example 19. One capsule contained 200 mg of granules G.

FORMULA EXAMPLE 21

| Capsules G Compound of Example 102: | |
|---|---|
| Cycloartenyl ester of p-aminocinnamic acid | 150 mg |
| Sodium laurylsulfate | 4 mg |
| Disodium hydrogen phosphate | 1 mg |
| Mannitol | 93 mg |
| Magnesium stearate | 2 mg |
| Total | 250 mg |

According to the above prescription, the ingredients were uniformly mixed. No. 1 gelatin capsules were filled with 250 mg of the mixed powder each.

What we claim is:

1. A triterpenyl ester derived from triterpenyl alcohol and organic acid other than ferulic acid and monobasic and dibasic saturated fatty acids, wherein
(a) the triterpenyl alcohol is selected from the group consisting of cycloartenol, cyclobranol, 24-methylenecycloartanol, lanosterol, lanostenol, agnosterol, cyclosadol, dihydroagnosterol, cyclolaudenol, cycloartanol, cycloeucalenol, euphol, butyrospermol, tirucallol, euphorbol and dammerdienol and
(b) the organic acid is nicotinic acid, linoleic acid, or an organic acid of the formula $$Ar(CH=CR)_n-COOH$$

wherein R is hydrogen or a $C_{1-4}$-alkyl group and Ar is aminophenyl, nitrophenyl, hydroxyphenyl, a $C_{1-4}$-alkoxyphenyl, $C_{1-4}$-alkyl-CONH-phenyl, ($C_{1-5}$-alkyl)COO-phenyl, $C_{1-4}$-alkoxyhydroxyphenyl, hydroxy-($C_{1-5}$-akyl)COO-phenyl, $C_{1-4}$-alkoxy-($C_{1-5}$-alkyl)COO-phenyl, $C_{1-4}$-alkoxynitrophenyl, $C_{1-4}$-alkoxyaminophenyl, $C_{1-4}$-alkyl-CONH-$C_{1-4}$-alkxyphenyl, di-($C_{1-4}$-alkoxyphenyl), di-($C_{1-5}$-alkyl-COO)phenyl and dihydroxyphenyl and n is 0 or 1.

2. The ester according to claim 1, wherein the organic acid is a substituted cinnamic acid, benzoic acid, or α-($C_1$–$C_4$ alkyl) cinnamic acid substituted by one member selected from the group consisting of amino, nitro, hydroxyl, $C_1$–$C_4$ alkoxy, $C_2$–$C_5$ acylamino, and $C_2$–$C_6$ alkylcarboxyl groups on the benzene ring.

3. The ester according to claim 1, wherein the organic acid is a substituted cinnamic acid, benzoic acid, or α(C₁–C₄ alkyl) cinnamic acid having two substituents on the benzene ring, said substituents being one pair selected from the group consisting of hydroxyl and C₁–C₄ alkoxy groups, hydroxyl and C₂–C₆ alkylcarboxyl groups, C₁–C₄ alkoxy and C₂–C₆ alkylcarboxyl groups, C₁–C₄ alkoxy and nitro groups, C₁–C₄ alkoxy and amino groups, C₁–C₄ alkoxy and C₂–C₅ acylamino groups, two C₁–C₄ alkoxy groups, two C₂–C₆ alkyl carboxyl groups, and two hydroxyl groups.

4. The ester according to claim 1, wherein the organic acid is nicotinic acid or linoleic acid.

5. The ester according to claim 2, which is a cycloartenyl ester or cyclobranyl ester of p-acetoxycinnamic acid, p-hydroxycinnamic acid, m-, or p-nitrocinnamic acid, m-, or p-aminocinnamic acid, m-, o-, or p-acetoxybenzoic acid, m-, o-, or p-hydroxybenzoic acid, m-, o-, or p-methoxybenzoic acid, m-,o-, or p-nitrobenzoic acid, m-, o-, or p-aminobenzoic acid, p-acetamidobenzoic acid, m- or p-nitro-α-methylcinnamic acid, m- or p-amino-α-methylcinnamic acid, 3- or 4-propionyloxy-α-methylcinnamic acid, 3- or 4-hydroxy-α-methylcinnamic acid, 3- or 4-butyryloxy-α-ethylcinnamic acid, 3- or 4-hydroxy-α-ethylcinnamic acid, 2-hydroxy-α-methylcinnamic acid, p-nitro-α-ethylcinnamic acid, or p-amino-α-ethylcinnamic acid.

6. The ester according to claim 3, which is a cycloartenyl ester or cyclobranyl ester of 3,4-diacetoxycinnamic acid, 3,4-dihydroxycinnamic acid, 3,4-dipropionyloxycinnamic acid, 3,4-dimethoxycinnamic acid, 4-acetoxy-3-methoxycinnamic acid, 4-acetoxy-3-ethoxycinnamic acid, 3-ethoxy-4-hydroxycinnamic acid, 4-hydroxy-3-n-propoxycinnamic acid, 3-methoxy-4-nitrocinnamic acid, 4-amino-3-methoxycinnamic acid, 2-ethoxy-5-nitrocinnamic acid, 5-amino-2-ethoxycinnamic acid, 3,4-diacetoxybenzoic acid, 3,4-dihydroxybenzoic acid, 3,4-dimethoxybenzoic acid, 4-acetoxy-3-methoxybenzoic acid, 4-hydroxy-3-methoxybenzoic acid, 4-acetoxy-3-ethoxybenzoic acid, 3-ethoxy-4-hydroxybenzoic acid, 3-methoxy-4-nitrobenzoic acid, 4-amino-3-methoxybenzoic acid, 2-methoxy-5-nitrobenzoic acid, 5-amino-2-methoxybenzoic acid, 3-methoxy-4-propionyloxy-α-methylcinnamic acid, 4-hydroxy-3-methoxy-α-methylcinnamic acid, 4-butyryloxy-3-methoxy-α-ethylcinnamic acid, 4-hydroxy-3-methoxy-α-ethylcinnamic acid, 4-hydroxy-3-methoxy-α-butylcinnamic acid, 3-ethoxy-4-hydroxy-α-methylcinnamic acid, 3-ethoxy-4-hydroxy-α-propylcinnamic acid, 3-methoxy-4-nitro-α-methylcinnamic acid, 4-amino-3-methoxy-α-methylcinnamic acid, 5-nitro-2-propoxy-α-methylcinnamic acid, 5-amino-2-propoxy-α-methylcinnamic acid, 3-methoxy-4-nitro-α-isopropylcinnamic acid, or 4-amino-3-methoxy-α-isopropylcinnamic acid.

7. The ester according to claim 2, which is the 24-methylenecycloartanyl ester of p-acetoxycinnamic acid, p-hydroxycinnamic acid, m- or p-nitrocinnamic acid, m- or p-aminocinnamic acid, m-, o- or p-hydroxybenzoic acid, m-, o-, or p-nitrobenzoic acid, m-, o-, or p-aminobenzoic acid, m-acetoxybenzoic acid, m- or p-nitro-α-methylcinnamic acid, m- or p-amino-α-methylcinnamic acid, 3- or 4-propionyloxy-α-methylcinnamic acid, 3- or 4-hydroxy-α-methylcinnamic acid, 3-butyryloxy-α-ethylcinnamic acid, or 3-hydroxy-α-ethylcinnamic acid.

8. The ester according to claim 3, which is the 24-methylenecycloartanyl ester of 4-acetoxy-3-methoxycinnamic acid, 4-acetoxy-3-ethyoxycinnamic acid, 3-ethoxy-4-hydroxycinnamic acid, 3,4-diacetoxycinnamic acid, 3,4-dihydroxycinnamic acid, 3-methoxy-4-nitrocinnamic acid, 4-amino-3-methoxycinnamic acid, 2-ethoxy-5-nitrocinnamic acid, 5-amino-2-ethoxycinnamic acid, 4-acetoxy-3-methoxybenzoic acid, 4-hydroxy-3-methoxybenzoic acid, 4-acetoxy-3-ethoxybenzoic acid, 3-ethoxy-4-hydroxybenzoic acid, 3,4-diacetoxybenzoic acid, 3,4-dihydroxybenzoic acid, 3-methoxy-4-nitrobenzoic acid, 4-amino-3-methoxybenzoic acid, 3-methoxy-4-propionyloxy-α-methylcinnamic acid, 4-hydroxy-3-methoxy-α-methylcinnamic acid, 4-butyryloxy-3-methoxy-α-ethylcinnamic acid, 4-hydroxy-3-methoxy-α-ethylcinnamic acid, 4-hydroxy-3-methoxy-α-butylcinnamic acid, 3-ethoxy-4-hydroxy-α-methylcinnamic acid, 4-hydroxy-3-propoxy-α-propylcinnamic acid, 3-methoxy-4-nitro-α-methylcinnamic acid, 4-amino-3-methoxy-α-methylcinnamic acid, 5-nitro-2-propoxy-α-methylcinnamic acid, or 5-amino-2-propoxy-α-methylcinnamic acid.

9. The ester according to claim 3, which is the cycloartenyl ester of 3-methoxy-4-propionyloxycinnamic acid, 3-methoxy-4-valeryloxy-α-propylcinnamic acid, 4-hydroxy-3-methoxy-α-propylcinnamic acid, 4-capryloxy-3-methoxy-α-butylcinnamic acid, 3-ethoxy-4-hydroxy-α-ethylcinnamic acid, 3-ethoxy-4-hydroxy-α-butylcinnamic acid, 4-hydroxy-3-propoxy-α-methylcinnamic acid, or 4-hydroxy-3-butoxy-α-methylcinnamic acid.

10. The ester according to claim 3, which is the cyclobranyl ester of 4-hydroxy-3-propoxy-α-ethylcinnamic acid.

11. A pharmaceutical composition for the treatment of hyperlipidemia comprising a pharmaceutical carrier and an effective amount of a triterpenyl ester derived from triterpenyl alcohol and organic acid other than ferulic acid and monobasic and dibasic saturated fatty acids, wherein
(a) the triterphenyl alcohol is selected from the group consisting of cycloartenol, cyclobranol, 24-methylenecycloartanol, lanosterol, lanostenol, agnosterol, cyclosadol, dihydroagnosterol, cyclolaudenol, cycloartanol, cycloeucalenol, euphol, butyrospermol, tirucallol, euphorbol and dammerdienol and
(b) the organic acid is nicotinic acid, linoleic acid, or an organic acid of the formula

wherein R is hydrogen or a C₁₋₄-alkyl group and Ar is aminophenyl, nitrophenyl, hydroxyphenyl, a C₁₋₄-alkoxyphenyl, C₁₋₄-alkyl-CONH-phenyl, (C₁₋₅-alkyl)COO-phenyl, C₁₋₄-alkoxyhydroxyphenyl hydroxy-(C₁₋₅-alkyl)COO-phenyl, C₁₋₄-alkoxy-(C₁₋₅-alkyl)COO-phenyl, C₁₋₄-alkoxynitrophenyl, C₁₋₄-alkoxyaminophenyl, C₁₋₄-alkyl-CONH-C₁₋₄-alkoxyphenyl, di(C₁₋₄-alkoxyphenyl), di-(C₁₋₅-alkyl-COO)phenyl and dihydroxyphenyl and n is 0 or 1.

12. The pharmaceutical composition according to claim 11, wherein the organic acid is a substituted cinnamic acid, benzoic acid, or α-(C₁–C₄ alkyl) cinnamic acid substituted by one member selected from the group consisting of amino, nitro, hydroxyl, C₁–C₄ alkoxy, C₂–C₅ acylamino, and C₂–C₆ alkylcarboxyl groups on the benzene ring.

13. The pharmaceutical composition according to claim 11, wherein the organic acid is a substituted cinnamic acid, benzoic acid, or α-(C₁–C₄ alkyl)cinnamic acid having two substituents on the benzene ring, said substituents being one pair selected from the group consisting of hydroxyl and $C_1$-$C_4$ alkoxy groups, hydroxyl and $C_2$-$C_6$ alkylcarboxyl groups, $C_1$-$C_4$ alkoxy and $C_2$-$C_6$ alkylcarboxyl groups, $C_1$-$C_4$ alkoxy and nitro groups, $C_1$-$C_4$ alkoxy and amino groups, $C_1$-$C_4$ alkoxy and $C_2$-$C_5$ acylamino groups, two $C_1$-$C_4$ alkoxy groups, two $C_2$-$C_6$ alkylcarboxyl groups, and two hydroxyl groups.

14. The pharmaceutical composition according to claim 11, wherein the organic acid is nicotinic acid or linoleic acid.

15. The pharmaceutical compositin according to claim 12, wherein the triterpenyl ester is a cycloartenyl ester or a cyclobranyl ester of p-acetoxycinnamic acid, p-hydroxycinnamic acid, m- or p-nitrocinnamic acid, m- or p-aminocinnamic acid, m-, o-, or p-acetoxybenzoic acid, m-, o-, or p-hydroxybenzoic acid, m-, o-, or p-methoxybenzoic acid, m-, o-, or p-nitrobenzoic acid, m-, o-, or p-acetamidobenzoic acid, p-acetamidobenzoic acid, m- or p-nitro-α-methylcinnamic acid, m- or p-amino-α-methylcinnamic acid, 3- or 4-propionyloxy-α-methylcinnamic acid, 3- or 4-hydroxy-α-methylcinnamic acid, 3- or 4-butyryloxy-α-ethylcinnamic acid, 3- or 4-hydroxy-α-ethylcinnamic, 2-hydroxy-α-methylcinnamic acid, p-nitro-α-ethylcinnamic acid, or p-amino-α-ethylcinnamic acid.

16. The pharmaceutical composition according to claim 13, wherein the triterpenyl ester is a cycloartenyl ester or a cyclobranyl ester of 3,4-diacetoxycinnamic acid, 3,4-dihydroxycinnamic acid, 3,4-dipropionyloxycinnamic acid, 3,4-dimethoxycinnamic acid, 4-acetoxy-3-methoxycinnamic acid, 4-acetoxy-3-ethoxycinnamic acid, 4-hydroxy-3-methoxycinnamic acid, 3-ethoxy-4-hydroxycinnamic acid, 4-hydroxy-3-propoxycinnamic acid, 3-methoxy-4-nitrocinnamic acid, 4-amino-3-methoxycinnamic acid, 2-ethoxy-5-nitrocinnamic acid, 5-amino-2-ethoxycinnamic acid, 3,4-diacetoxybenzoic acid, 3,4-dihydroxybenzoic acid, 3,4-dimethoxybenzoic acid, 4-acetoxy-3-methoxybenzoic acid, 4-hydroxy-3-methoxybenzoic acid, 4-acetoxy-3-ethoxybenzoic acid, 3-ethoxy-4-hydroxybenzoic acid, 3-methoxy-4 nitrobenzoic acid, 4-amino-3-methoxybenzoic acid, 2-methoxy-5-nitrobenzoic acid, 5-amino-2-mcthoxybenzoic acid, 3-methoxy-4-propionyloxy-α-methylcinnamic acid, 4-hydroxy-3-methoxy-α-methylcinnamic acid, 4-butyryloxy-3-methoxy-α-ethylcinnamic acid, 4-hydroxy-3-methoxy-α-ethylcinnamic acid, 4-hydroxy-3-methoxy-α-butylcinnamic acid, 3-ethoxy-4-hydroxy-α-methylcinnamic acid, 3-ethoxy-4-hydroxy-α-propylcinnamic acid, 3-methoxy-4-nitro-α-methylcinnamic acid, 4-amino-3-methoxy-α-methylcinnamic acid, 5-nitro-2-propoxy-α-methylcinnamic acid, 5-amino-2-propoxy-α-methylcinnamic acid, 3-methoxy-4-nitro-α-isopropylcinnamic acid, or 4-amino-3-methoxy-α-isopropylcinnamic acid.

17. The pharmaceutical composition according to claim 12, wherein the triterpenyl ester is the 24-methylenecycloartanyl ester of p-acetoxycinnamic acid, p-hydroxycinnamic acid, m- or p-nitrocinnamic acid, m- or p-aminocinnamic acid, m-, o-, or p-hydroxybenzoic acid, m-, o-, or p-nitrobenzoic acid, m-, o-, or p-aminobenzoic acid, m-acetoxybenzoic acid, m- or p-nitro-α-methylcinnamic acid, m- or p-amino-α-methylcinnamic acid, 3- or 4-propionyloxy-α-methylcinnamic acid, 3- or 4-hydroxy-α-methylcinnamic acid, 3-butyryloxy-α-ethylcinnamic acid, or 3-hydroxy-α-ethylcinnamic acid.

18. The pharmaceutical composition according to claim 13, wherein the triterpenyl ester is the 24-methylene cycloartanyl ester of 4-acetoxy-3-methoxycinnamic acid, 4-acetoxy-3-ethoxycinnamic acid, 4-hydroxy-3-methoxycinnamic acid, 3-ethoxy-4-hydroxycinnamic acid, 3,4-diacetoxycinnamic acid, 3,4-dihydroxycinnamic acid, 3-methoxy-4-nitrocinnamic acid, 4-amino-3-methoxycinnamic acid, 2-ethoxy-5-nitrocinnamic acid, 5-amino-2-ethoxycinnamic acid, 4-acetoxy-3-methoxybenzoic acid, 4-hydroxy-3-methoxybenzoic acid, 4-acetoxy-3-ethoxybenzoic acid, 3-ethoxy-4-hydroxybenzoic acid, 3,4-diacetoxybenzoic acid, 3,4-dihydroxybenzoic acid, 3-methoxy-4-nitrobenzoic acid, 4-amino-3-methoxybenzoic acid, 3-methoxy-4-propionyloxy-α-methylcinnamic acid, 4-hydroxy-3-methoxy-α-methylcinnamic acid, 4-butyryloxy-3-methoxy-α-ethylcinnamic acid, 4-hydroxy-3-methoxy-α-ethylcinnamic acid, 4-hydroxy-3-methoxy-α-butylcinnamic acid, 3-ethoxy-4-hydroxy-α-methylcinnamic acid, 4-hydroxy-3-propoxy-α-propylcinnamic acid, 3-methoxy-4-nitro-α-methylcinnamic acid, 4-amino-3-methoxy-α-methylcinnamic acid, 5-nitro-2-propoxy-α-methylcinnamic acid, or 5-amino-2-propoxy-α-methylcinnamic acid.

19. The pharmaceutical composition according to claim 13, wherein the triterpenyl ester is the cycloartenyl ester of 3-methoxy-4-propionyloxycinnamic acid, 3-methoxy-4-valeryloxy-α-propylcinnamic acid, 4-hydroxy-3-methoxy-α-propylcinnamic acid, 4-capryloxy-3-methoxy-α-butylcinnamic acid, 3-ethoxy-4-hydroxy-α-ethylcinnamic acid, 3-ethoxy-4-hydroxy-α-butylcinnamic acid, 4-hydroxy-3-propoxy-α-methylcinnamic acid, or 4-hydroxy-3-butoxy-α-methylcinnamic acid.

20. The pharmaceutical composition according to claim 13, wherein the triterpenyl ester is cyclobranyl ester of 4-hydroxy-3-propoxy-α-ethylcinnamic acid.

21. A method of treating hyperlipidemia comprising administrating to a patient in need of such treatment, a therapeutically effective amount of cyclobranol, or of a triterpenyl ester of organic acid other than dibasic saturated fatty acid.

* * * * *

REEXAMINATION CERTIFICATE (1571st)

United States Patent [19]
Kimura et al.

[11] B1 4,748,161
[45] Certificate Issued Oct. 15, 1991

[54] TRITERPENYL ESTERS OF ORGANIC ACIDS AND HYPOLIPIDEMIC AGENTS COMPOSED OF THEM

[75] Inventors: Goro Kimura, Kamakura; Yoshihiko Hirose, Ohgaki; Kumi Yoshida, Sayamachi; Fumio Kuzuya, Nagoya; Katsunari Fujita, Aichi, all of Japan

[73] Assignee: Amano Pharmaceutical Co., Ltd.

Reexamination Request:
No. 90/001,980, Apr. 4, 1990

Reexamination Certificate for:
Patent No.: 4,748,161
Issued: May 31, 1988
Appl. No.: 739,183
Filed: May 30, 1985

[30] Foreign Application Priority Data

Jun. 4, 1984 [JP] Japan ............................... 59-115306
Jun. 4, 1984 [JP] Japan ............................... 59-115307
Apr. 19, 1985 [JP] Japan ............................... 60-85254
Apr. 19, 1985 [JP] Japan ............................... 60-85255

[51] Int. Cl.$^5$ .......................... A61K 31/56; C07J 9/00
[52] U.S. Cl. ...................................... 514/182; 552/544
[58] Field of Search ........................ 514/182; 552/544

[56] References Cited
FOREIGN PATENT DOCUMENTS 46-23060  7/1971  Japan .
52-18809  2/1977  Japan .
55-162740 12/1980 Japan .
55-162800 12/1980 Japan .

*Primary Examiner*—Leonard Schenkman

[57] ABSTRACT

A triterpenyl ester of organic acid other than triterpenyl esters of ferulic acid and of monobasic and dibasic saturated fatty acids. A process for producing a triterpenyl ester of organic acid other than esters of ferulic acid and of monobasic and dibasic saturated fatty acids, which comprises the reaction of a triterpenyl alcohol with an acid halide of the corresponding organic acid. A pharmaceutical composition for treatment of hyperlipidemia comprising a pharmaceutical carrier and an effective amount of a triterpenyl ester of organic acid other than triterpenyl esters of dibasic saturated fatty acids. A pharmaceutical composition for treating hyperlipidemia which comprises a pharmaceutical carrier and an effective amount of cyclobranol as an active ingredient.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 21 is confirmed.

Claims 1–9 and 11–19 are determined to be patentable as amended.

Claims 10 and 20, dependent on an amended claim, are determined to be patentable.

New claims 22–33 are added and determined to be patentable.

1. A triterpenyl ester derived from triterpenyl alcohol and organic acid other than ferulic acid and monobasic and dibasic saturated fatty acids, wherein
(a) the triterpenyl alcohol is selected from the group consisting of cycloartenol, cyclobranol, *and* 24-methylenecycloartanol, [lanosterol, lanostenol, agnosterol, cyclosadol, dihydroagnosterol, cyclolaudenol, cycloartanol, cycloeucalenol, euphol, butyrospermol, tirucallol, euphorbol and dammerdienol] and
(b) the organic acid is [nicotinic acid,] linoleic acid[,] or an organic acid of the formula

[Ar(CH=CR)$_n$—COOH] *Ar(CH=CR)—COOH*

wherein R is [hydrogen or] or $C_{1\text{-}4}$-alkyl group and Ar is aminophenyl, nitrophenyl, hydroxyphenyl, a $C_{1\text{-}4}$-alkoxyphenyl, $C_{1\text{-}4}$-alkyl-CONH-phenyl, ($C_{1\text{-}5}$-alkyl)-COO-phenyl, $C_{1\text{-}4}$-alkoxyhydroxyphenyl, hydroxy-($C_{1\text{-}5}$-[alkyl]*alkyl*)COO-phenyl, $C_{1\text{-}4}$-alkoxy-($C_{1\text{-}5}$-alkyl)-COO-phenyl, $C_{1\text{-}4}$-alkoxynitrophenyl, $C_{1\text{-}4}$-alkoxyaminophenyl, [$C_{1\text{-}4}$-alkyl-CONH-$C_{1\text{-}4}$-alkxyphenyl] *$C_{1\text{-}4}$-alkyl-CONH-$C_{1\text{-}4}$-alkoxyphenyl*, di-($C_{1\text{-}4}$-alkoxyphenyl), di-($C_{1\text{-}5}$-alkyl-COO)phenyl and dihydroxyphenyl [and n is 0 or 1].

2. The ester according to claim 1, wherein the organic acid is a substituted [cinnamic acid, benzoic acid, or] α-($C_1$-$C_4$ alkyl) cinnamic acid substituted by one member selected from the group consisting of amino, nitro, hydroxyl, $C_1$-$C_4$ alkoxy, $C_2$-$C_5$ acylamino, and $C_2$-$C_6$ alkylcarboxyl groups on the benzene ring.

3. The ester according to claim 1, wherein the organic acid is a substituted [cinnamic acid, benzoic acid, or] α($C_1$-$C_4$ alkyl) cinnamic acid having two substituents on the benzene ring, said substituents being one pair selected from the group consisting of hydroxyl and $C_1$-$C_4$ alkoxy groups, hydroxyl and $C_2$-$C_6$ alkylcarboxyl groups, $C_1$-$C_4$ alkoxy and $C_2$-$C_6$ alkylcarboxyl groups, $C_1$-$C_4$ alkoxy and nitro groups, $C_1$-$C_4$ alkoxy and amino groups, $C_1$-$C_4$ alkoxy and $C_2$-$C_5$ acylamino groups, two $C_1$-$C_4$ alkoxy groups, two $C_2$-$C_6$ alkyl carboxyl groups, and two hydroxyl groups.

4. The ester according to claim 1, wherein the organic acid is [nicotinic acid or] linoleic acid.

5. The ester according to claim 2, which is a cycloartenyl ester or cyclobranyl ester of [p-acetoxycinnamic acid, p-hydroxycinnamic acid, m-, or p-nitrocinnamic acid, m-, or p-aminocinnamic acid, m-, o-, or p-acetoxybenzoic acid, m-, o-, or p-hydroxybenzoic acid, m-, o-, or p-methoxybenzoic acid, m-, o-, or p-nitrobenzoic acid, m-, o-, or p-aminobenzoic acid, p-acetamidobenzoic acid,] m- or p-nitro-α-methylcinnamic acid, m- or p-amino-α-methylcinnamic acid, 3- or 4-propionyloxy-α-methylcinnamic acid, 3- or 4-hydroxy-α-methylcinnamic acid, 3- or 4-butyryloxy-α-ethylcinnamic acid, 3- or 4-hydroxy-α-ethylcinnamic acid, 2-hydroxy-α-methylcinnamic acid, p-nitro-α-ethylcinnamic acid, or p-amino-α-ethylcinnamic acid.

6. The ester according to claim 3, which is a cycloartenyl ester or cyclobranyl ester of [3,4-diacetoxycinnamic acid, 3,4-dihydroxycinnamic acid, 3,4-dipropionyloxycinnamic acid, 3,4-dimethoxycinnamic acid, 4-acetoxy-3-methoxycinnamic acid, 4-acetoxy-3-ethoxycinnamic acid, 3-ethoxy-4-hydroxycinnamic acid, 4-hydroxy-3-n-propoxycinnamic acid, 3-methoxy-4-nitrocinnamic acid, 4-amino-3-methoxycinnamic acid, 2-ethoxy-5-nitrocinnamic acid, 5-amino-2-ethoxycinnamic acid, 3,4-diacetoxybenzoic acid, 3,4-dihydroxybenzoic acid, 3,4-dimethoxybenzoic acid, 4-acetoxy-3-methoxybenzoic acid, 4-hydroxy-3-methoxybenzoic acid, 4-acetoxy-3-ethoxybenzoic acid, 3-ethoxy-4-hydroxybenzoic acid, 3-methoxy-4-nitrobenzoic acid, 4-amino-3-methoxybenzoic acid, 2-methoxy-5-nitrobenzoic acid, 5-amino-2-methoxybenzoic acid,] 3-methoxy-4-propionyloxy-α-methylcinnamic acid, 4-hydroxy-3-methoxy-α-methylcinnamic acid, 4-butyryloxy-3-methoxy-α-ethylcinnamic acid, 4-hydroxy-3-methoxy-α-ethylcinnamic acid, 4-hydroxy-3-methoxy-α-butylcinnamic acid, 3-ethoxy-4-hydroxy-α-methylcinnamic acid, 3-ethoxy-4-hydroxy-α-propylcinnamic acid, 3-methoxy-4-nitro-α-methylcinnamic acid, 4-amino-3-methoxy-α-methylcinnamic acid, 5-nitro-2-propoxy-α-methylcinnamic acid, 5-amino-2-propoxy-α-methylcinnamic acid, 3-methoxy-4-nitro-α-isopropylcinnamic acid, or 4-amino-3-methoxy-α-isopropylcinnamic acid.

7. The ester according to claim 2, which is the 24-methylenecycloartanyl ester of [p-acetoxycinnamic acid, p-hydroxycinnamic acid, m- or p-nitrocinnamic acid, m- or p-aminocinnamic acid, m-, o- or p-hydroxybenzoic acid, m-, o-, or p-nitrobenzoic acid, m-, o-, or p-aminobenzoic acid, m-acetoxybenzoic acid,] m- or p-nitro-α-methylcinnamic acid, m- or p-amino-α-methylcinnamic acid, 3- or 4-propionyloxy-α-methylcinnamic acid, 3- or 4-hydroxy-α-methylcinnamic acid, 3-butyryloxy-α-ethylcinnamic acid, or 3-hydroxy-α-ethylcinnamic acid.

8. The ester according to claim 3, which is the 24-methylenecycloartanyl ester of [4-acetoxy-3-methoxycinnamic acid, 4-acetoxy-3-ethoxycinnamic acid, 3-ethoxy-4-hydroxycinnamic acid, 3,4-diacetoxycinnamic acid, 3,4-dihydroxycinnamic acid, 3-methoxy-4-nitrocinnamic acid, 4-amino-3-methoxycinnamic acid, 2-ethoxy-5-nitrocinnamic acid, 5-amino-2-ethoxycinnamic acid, 4-acetoxy-3-methoxybenzoic acid, 4-hydroxy-3-methoxybenzoic acid, 4-acetoxy-3-ethoxybenzoic acid, 3-ethoxy-4-hydroxybenzoic acid, 3,4-diacetoxybenzoic acid, 3,4-dihydroxybenzoic acid, 3- methoxy-4-nitrobenzoic acid, 4-amino-3-methoxybenzoic acid,] 3-methoxy-4-propionyloxy-α-methylcinnamic acid, 4-hydroxy-3-methoxy-α-methylcinnamic acid, 4-butyryloxy-3-methoxy-α-ethylcinnamic acid, 4-hydroxy-3-methoxy-α-ethylcinnamic acid, 4-hydroxy-3-methoxy-α-butylcinnamic acid, 3-ethoxy-4-hydroxy-α-methylcinnamic acid, 4-hydroxy-3-propoxy-α-propylcinnamic acid, 3-methoxy-4-nitro-α-methylcinnamic acid, 4-amino-3-methoxy-α-methylcinnamic acid, 5-nitro-2-propoxy-α-methylcinnamic acid, or 5-amino-2-propoxy-α-methylcinnamic acid.

9. The ester according to claim 3, which is the cycloartenyl ester of [3-methoxy-4-propionyloxycinnamic acid,] 3-methoxy-4-valeryloxy-α-propylcinnamic acid, 4-hydroxy-3-methoxy-α-propylcinnamic acid, 4-capryloxy-3-methoxy-α-butylcinnamic acid, 3-ethoxy-4-hydroxy-α-ethylcinnamic acid, 3-ethoxy-4-hydroxy-α-butylcinnamic acid, 4-hydroxy-3-propoxy-α-methylcinnamic acid, or 4-hydroxy-3-butoxy-α-methylcinnamic acid.

11. A pharmaceutical composition for the treatment of hyperlipidemia comprising a pharmaceutical carrier and an effective amount of a triterpenyl ester derived from triterpenyl alcohol and organic acid other than ferulic acid and monobasic and dibasic saturated fatty acids, wherein
(a) the triterpenyl alcohol is selected from the group consisting of cycloartenol, cyclobranol, and 24-methylenecycloartanol, [lanosterol, lanostenol, agnosterol, cyclosadol, dihydroagnosterol, cyclolaudenol, cycloartanol, cycloeucalenol, euphol, butyrospermol, tirucallol, euphorbol and dammerdienol] and
(b) the organic acid is [nicotinic acid,] linoleic acid[,] or an organic acid of the formula

[Ar(CH=CR)$_n$—COOH]  Ar(CH=CR)—COOH wherein R is [hydrogen or] a $C_{1-4}$-alkyl group and Ar is aminophenyl, nitrophenyl, hydroxyphenyl, a $C_{1-4}$-alkoxyphenyl, $C_{1-4}$-alkyl-CONH-phenyl, $(C_{1-5}$-alkyl)-COO-phenyl, $C_{1-4}$-alkoxyhydroxyphenyl, hydroxy-$(C_{1-5}$-alkyl)COO-phenyl, $C_{1-4}$-alkoxy-$(C_{1-5}$-alkyl)COO-phenyl, $C_{1-4}$-alkoxynitrophenyl, $C_{1-4}$-alkoxyaminophenyl, $C_{1-4}$-alkyl-CONH-$C_{1-4}$-alkoxyphenyl, di-$(C_{1-4}$-alkoxyphenyl), di-$(C_{1-5}$-alkyl-COO)phenyl and dihydroxyphenyl [and n is 0 or 1].

12. The pharmaceutical composition according to claim 11, wherein the organic acid is a substituted [cinnamic acid, benzoic acid, or] α-$(C_1-C_4$ alkyl) cinnamic acid substituted by one member selected from the group consisting of amino, nitro, hydroxyl, $C_1-C_4$ alkoxy, $C_2-C_5$ acylamino, and $C_2-C_6$ alkylcarboxyl groups on the benzene ring.

13. The pharmaceutical composition according to claim 11, wherein the organic acid is a substituted [cinnamic acid, benzoic acid, or] α$(C_1-C_4$ alkyl) cinnamic acid having two substituents on the benzene ring, said substituents being one pair selected from the group consisting of hydroxyl and $C_1-C_4$ alkoxy groups, hydroxyl and $C_2-C_6$ alkylcarboxyl groups, $C_1-C_4$ alkoxy and $C_2-C_6$ alkylcarboxyl groups, $C_1-C_4$ alkoxy and nitro groups, $C_1-C_4$ alkoxy and amino groups, $C_1-C_4$ alkoxy and $C_2-C_5$ acylamino groups, two $C_1-C_4$ alkoxy groups, two $C_2-C_6$ alkylcarboxyl groups, and two hydroxyl groups.

14. The pharmaceutical composition according to claim 11, wherein the organic acid is [nicotinic or] linoleic acid.

15. The pharmaceutical composition according to claim 12, wherein the triterpenyl ester is a cycloartenyl ester or a cyclobranyl ester of [p-acetoxycinnamic acid, p-hydroxycinnamic acid, m- or p-nitrocinnamic acid, m- or p-aminocinnamic acid, m-, o-, or p-acetoxybenzoic acid, m-, o-, or p-hydroxybenzoic acid, m-, o-, or p-methoxybenzoic acid, m-, o-, or p-nitrobenzoic acid, m-, o-, or p-acetamidobenzoic acid, p-acetamidobenzoic acid,] m- or p-nitro-α-methylcinnamic acid, m- or p-amino-α-methylcinnamic acid, 3- or 4-propionyloxy-α-methylcinnamic acid, 3- or 4-hydroxy-α-methylcinnamic acid, 3- or 4-butyryloxy-α-ethylcinnamic acid, 3- or 4-hydroxy-α-ethylcinnamic acid, 2-hydroxy-α-methylcinnamic acid, p-nitro-α-ethylcinnamic acid, or p-amino-α-ethylcinnamic acid.

16. The pharmaceutical composition according to claim 13, wherein the triterpenyl ester is a cycloartenyl ester or a cyclobranyl ester of [3,4-diacetoxycinnamic acid, 3,4-dihydroxycinnamic acid, 3,4-dipropionyloxycinnamic acid, 3,4-dimethoxycinnamic acid, 4-acetoxy-3-methoxycinnamic acid, 4-acetoxy-3-ethoxycinnamic acid, 4-hydroxy-3-methoxycinnamic acid, 3-ethoxy-4-hydroxycinnamic acid, 4-hydroxy-3-propoxycinnamic acid, 3-methoxy-4-nitrocinnamic acid, 4-amino-3-methoxycinnamic acid, 2-ethoxy-5-nitrocinnamic acid, 5-amino-2-ethoxycinnamic acid, 3,4-diacetoxybenzoic acid, 3,4-dihydroxybenzoic acid, 3,4-dimethoxybenzoic acid, 4-acetoxy-3-methoxybenzoic acid, 4-hydroxy-3-methoxybenzoic acid, 4-acetoxy-3-ethoxybenzoic acid, 3-ethoxy-4-hydroxybenzoic acid, 3-methoxy-4-nitrobenzoic acid, 4-amino-3-methoxybenzoic acid, 2-methoxy-5-nitrobenzoic acid, 5-amino-2-methoxybenzoic acid,] 3-methoxy-4-propionyloxy-α-methylcinnamic acid, 4-hydroxy-3-methoxy-α-methylcinnamic acid, 4-butyryloxy-3-methoxy-α-ethylcinnamic acid, 4-hydroxy-3-methoxy-α-ethylcinnamic acid, 4-hydroxy-3-methoxy-α-butylcinnamic acid, 3-ethoxy-4-hydroxy-α-methylcinnamic acid, 3-ethoxy-4-hydroxy-α-propylcinnamic acid, 3-methoxy-4-nitro-α-methylcinnamic acid, 4-amino-3-methoxy-α-methylcinnamic acid, 5-nitro-2-propoxy-α-methylcinnamic acid, 5-amino-2-propoxy-α-methylcinnamic acid, 3-methoxy-4-nitro-α-isopropylcinnamic acid, or 4-amino-3-methoxy-α-isopropylcinnamic acid.

17. The pharmaceutical composition according to claim 12, wherein the triterpenyl ester is the 24-methylenecycloartanyl ester of [p-acetoxycinnamic acid, p-hydroxycinnamic acid, m- or p-nitrocinnamic acid, m- or p-aminocinnamic acid, m-, o- or p-hydroxybenzoic acid, m-, o-, or p-nitrobenzoic acid, m-, o-, or p-aminobenzoic acid, m-acetoxybenzoic acid,] m- or p-nitro-α-methylcinnamic acid, m- or p-amino-α-methylcinnamic acid, 3- or 4-propionyloxy-α-methylcinnamic acid, 3- or 4-hydroxy-α-methylcinnamic acid, 3-butyryloxy-α-ethylcinnamic acid, or 3-hydroxy-α-ethylcinnamic acid.

18. The pharmaceutical composition according to claim 13, wherein the triterpenyl ester is the 24-methylene cycloartanyl ester of [4-acetoxy-3-methoxycinnamic acid, 4-acetoxy-3-ethoxycinnamic acid, 4-hydroxy-3-methoxycinnamic acid, 3-ethoxy-4-hydroxycinnamic acid, 3,4-diacetoxycinnamic acid, 3,4-dihydroxycinnamic acid, 3-methoxy-4-nitrocinnamic acid, 4-amino-3-methoxycinnamic acid, 2-ethoxy-5-nitrocinnamic acid, 5-amino-2-ethoxycinnamic acid, 4-acetoxy- 3-methoxybenzoic acid, 4-hydroxy-3-methoxybenzoic acid, 4-acetoxy-3-ethoxybenzoic acid, 3-ethoxy-4-hydroxybenzoic acid, 3,4-diacetoxybenzoic acid, 3,4-dihydroxybenzoic acid, 3-methoxy-4-nitrobenzoic acid, 4-amino-3-methoxybenzoic acid,] 3-methoxy-4-propionyloxy-α-methylcinnamic acid, 4-hydroxy-3-methoxy-α-methylcinnamic acid, 4-butyryloxy-3-methoxy-α-ethylcinnamic acid, 4-hydroxy-3-methoxy-α-ethylcinnamic acid, 4-hydroxy-3-methoxy-α-butylcinnamic acid, 3-ethoxy-4-hydroxy-α-methylcinnamic acid, 4-hydroxy-3-propoxy-α-propylcinnamic acid, 3-methoxy-4-nitro-α-methylcinnamic acid, 4-amino-3-methoxy-α-methylcinnamic acid, 5-nitro-2-propoxy-α-methylcinnamic acid, or 5-amino-2-propoxy-α-methylcinnamic acid.

19. The pharmaceutical composition according to claim 13, wherein the triterpenyl ester is the cycloartenyl ester of [3-methoxy-4-propionyloxycinnamic acid,] 3-methoxy-4-valeryloxy-α-propylcinnamic acid, 4-hydroxy-3-methoxy-α-propylcinnamic acid, 4-capryloxy-3-methoxy-α-butylcinnamic acid, 3-ethoxy-4-hydroxy-α-ethylcinnamic acid, 3-ethoxy-4-hydroxy-α-butylcinnamic acid, 4-hydroxy-3-propoxy-α-methylcinnamic acid, or 4-hydroxy-3-butoxy-α-methylcinnamic acid.

22. A method of treating hyperlipidemia according to claim 21, wherein the organic acid is nicotinic acid, linoleic acid, or an organic acid of the formula

[Ar(CH=CR)$_n$-COOH]

wherein R is hydrogen or a $C_{1-4}$-alkyl group and Ar is aminophenyl, nitrophenyl, hydroxyphenyl, a $C_{1-4}$-alkoxyphenyl, $C_{1-4}$-alkyl-CONH-phenyl, ($C_{1-5}$-alkyl)COO-phenyl, $C_{1-4}$-alkoxyhydroxyphenyl, hydroxy-($C_{1-5}$-alkyl)COO-phenyl, $C_{1-4}$-alkoxy-($C_{1-5}$-alkyl)COO-phenyl, $C_{1-4}$-alkoxynitrophenyl, $C_{1-4}$-alkoxyaminophenyl, $C_{1-4}$-alkyl-CONH-$C_{1-4}$-alkoxyphenyl, di-($C_{1-4}$-alkoxyphenyl), di-($C_{1-5}$-alkyl-COO)phenyl and dihydroxyphenyl and n is 0 or 1.

23. The method according to claim 22, wherein the organic acid is a substituted cinnamic acid, benzoic acid, or α-($C_1$-$C_4$ alkyl) cinnamic acid substituted by one member selected from the group consisting of amino, nitro, hydroxyl, $C_1$-$C_4$ alkoxy, $C_2$-$C_5$ acylamino, and $C_2$-$C_6$ alkylcarboxyl groups on the benzene ring.

24. The method according to claim 22, wherein the organic acid is a substituted cinnamic acid, benzoic acid, or α($C_1$-$C_4$ alkyl) cinnamic acid having two substituents on the benzene ring, said substituents being one pair selected from the group consisting of hydroxyl and $C_1$-$C_4$ alkoxy groups, hydroxyl and $C_2$-$C_6$ alkylcarboxyl groups, $C_1$-$C_4$ alkoxy and $C_2$-$C_6$ alkylcarboxyl groups, $C_1$-$C_4$ alkoxy and nitro groups, $C_1$-$C_4$ alkoxy and amino groups, $C_1$-$C_4$ alkoxy and $C_2$-$C_5$ acylamino groups, two $C_1$-$C_4$ alkoxy groups, two $C_2$-$C_6$ alkyl carboxyl groups, and two hydroxyl groups.

25. The method according to claim 22, wherein the organic acid is nicotinic or linoleic acid.

26. The method according to claim 23, wherein the triterpenyl ester is a cycloartenyl ester or cyclobranyl ester of p- acetoxycinnamic acid, p-hydroxycinnamic acid, m- or p-nitrocinnamic acid, m- or p-aminocinnamic acid, m-, o- or p-acetoxybenzoic acid, m-, o-, or p-hydroxybenzoic acid, m-, -o, or p-methoxybenzoic acid, m-, o-, or p-nitrobenzoic acid, m-, o-, or p-aminobenzoic acid, p-acetamidobenzoic acid, m-or -nitro-α-methylcinnamic acid, m- or p-amino-α-methylcinnamic acid, 3- or 4-propionyloxy-α-methylcinnamic acid, 3- or 4-hydroxy-α-methylcinnamic acid, 3- or 4-butyryloxy-α-ethylcinnamic acid, 3- or 4-hydroxy-α-ethylcinnamic acid, 2-hydroxy-α-methylcinnamic acid, p-nitro-α-ethylcinnamic acid, or p-amino-α-ethylcinnamic acid.

27. The method according to claim 24, wherein the triterpenyl ester is a cycloartenyl ester or cyclobranyl ester of 3,4-diacetoxycinnamic acid, 3,4-dihydroxycinnamic acid, 3,4-dipropionyloxycinnamic acid, 3,4-dimethoxycinnamic acid, 4-acetoxy-3-methoxycinnamic acid, 4-acetoxy-3-ethoxycinnamic acid, 4-hydroxy-3-methoxycinnamic acid, 3-ethoxy-4-hydroxycinnamic acid, 4-hydroxy-3-propoxycinnamic acid, 3-methoxy-4-nitrocinnamic acid, 4-amino-3-methoxycinnamic acid, 2-ethoxy-5-nitrocinnamic acid, 5-amino-2-ethoxycinnamic acid, 3,4-diacetoxybenzoic acid, 3,4-dihydroxybenzoic acid, 3,4-dimethoxybenzoic acid, 4-acetoxy-3-methoxybenzoic acid, 4-hydroxy-3-methoxybenzoic acid, 4-acetoxy-3-ethoxybenzoic acid, 3-ethoxy-4-hydroxybenzoic acid, 3-methoxy-4-nitrobenzoic acid, 4-amino-3-methoxybenzoic acid, 2-methoxy-5-nitrobenzoic acid, 5-amino-2-methoxybenzoic acid, 3-methoxy-4-propionyloxy-α-methylcinnamic acid, 4-hydroxy-3-methoxy-α-methylcinnamic acid, 4-butyryloxy-3-methoxy-α-ethylcinnamic acid, 4-hydroxy-3-methoxy-α-ethylcinnamic acid, 4-hydroxy-3-methoxy-α-butylcinnamic acid, 3-ethoxy-4-hydroxy-α-methylcinnamic acid, 3-ethoxy-4-hydroxy-α-propylcinnamic acid, 3-methoxy-4-nitro-α-methylcinnamic acid, 4-amino-3-methoxy-α-methylcinnamic acid, 5-nitro-2-propoxy-α-methylcinnamic acid, 5-amino-2-propoxy-α-methylcinnamic acid, 3-methoxy-4-nitro-α-isopropylcinnamic acid, or 4-amino-3-methoxy-α-isopropylcinnamic acid.

28. The method according to claim 23, wherein the triterpenyl ester is the 24-methylenecycloartanyl ester of p-acetoxycinnamic acid, p-hydroxycinnamic acid, m- or p-nitrocinnamic acid, m- or p-aminocinnamic acid, m-, o- or p-hydroxybenzoic acid, m-, o-, or p-nitrobenzoic acid, m-, o-, or p-aminobenzoic acid, m-acetoxybenzoic acid, m- or p-nitro-α-methylcinnamic acid, m- or p-amino-α-methylcinnacmic acid, 3- or 4-propionyloxy-α-methylcinnamic acid, 3- or 4-hydroxy-α-methylcinnamic acid, 3-butyryloxy-α-ethylcinnamic acid, or 3-hydroxy-α-ethylcinnamic acid.

29. The method according to claim 24, wherein the triterpenyl ester is the 24-methylenecycloartanyl ester of 4-acetoxy-3-methoxycinnamic acid, 4-acetoxy-3-ethoxycinnamic acid, 4-hydroxy-3-methoxycinnamic acid, 3-ethoxy-4-hydroxycinnamic acid, 3,4-diacetoxycinnamic acid, 3,4-dihydroxycinnamic acid, 3-methoxy-4-nitrocinnamic acid, 4-amino-3-methoxycinnamic acid, 2-ethoxy-5-nitrocinnamic acid, 5-amino-2-ethoxycinnamic acid, 4-acetoxy-3-methoxybenzoic acid, 4-hydroxy-3-methoxybenzoic acid, 4-acetoxy-3-ethoxybenzoic acid, 3-ethoxy-4-hydroxybenzoic acid, 3,4-di-acetoxybenzoic acid, 3,4-dihydroxybenzoic acid, 3-methoxy-4-nitrobenzoic acid, 4-amino-3-methoxybenzoic acid, 3-methoxy-4-propionyloxy-α-methylcinnamic acid, 4-hydroxy-3-methoxy-α-methylcinnamic acid, 4-butyryloxy-3-methoxy-α-ethylcinnamic acid, 4-hydroxy-3-methoxy-α-ethylcinnamic acid, 4-hydroxy-3-methoxy-α-butylcinnamic acid, 3-ethoxy-4-hydroxy-α-methylcinnamic acid, 4-hydroxy-3-propoxy-α-propylcinnamic acid, 3-methoxy-4-nitro-α-methylcinnamic acid, 4-amino-3-methoxy-α-methylcinnamic acid, 5-nitro-2-propoxy-α-methylcinnamic acid, or 5-amino-2-propoxy-α-methylcinnamic acid.

30. The method according to claim 24, wherein the triterpenyl ester is the cycloartenyl ester of 3-methoxy-4-propionyloxycinnamic acid, 3-methoxy-4-valeryloxy-α-propylcinnamic acid, 4-hydroxy-3-methoxy-α-propylcinnamic acid, 4-capryloxy-3-methoxy-α-butylcinnamic acid, 3-ethoxy-4-hydroxy-α-ethylcinnamic acid, 3-ethoxy-4-hydroxy-α-butylcinnamic acid, 4-hydroxy-3-propoxy-α-methylcinnamic acid, or 4-hydroxy-3-butoxy-α-methylcinnamic acid.

31. The method according to claim 24, wherein the triterpenyl ester is cyclobranyl ester of 4-hydroxy-3-propoxy-α-ethylcinnamic acid.

32. The ester according to claim 1, wherein Ar is $C_{1-4}$-alkoxyhydroxyphenyl.

33. The ester according to claim 32, which is a 4-hydroxy-3-$C_{1-4}$-alkoxy-α-($C_{1-4}$ alkyl)cinnamic acid.

* * * * *